(12) United States Patent
Sharma

(10) Patent No.: US 11,607,329 B2
(45) Date of Patent: Mar. 21, 2023

(54) INTRAGASTRIC DEVICE FOR TREATING OBESITY

(71) Applicant: SynerZ Medical, Inc., Newark, DE (US)

(72) Inventor: Virender K. Sharma, Paradise Valley, AZ (US)

(73) Assignee: SynerZ Medical, Inc., Newark, DE (US)

( * ) Notice: Subject to any disclaimer, the term of this patent is extended or adjusted under 35 U.S.C. 154(b) by 442 days.

(21) Appl. No.: 16/725,771

(22) Filed: Dec. 23, 2019

(65) Prior Publication Data

US 2020/0206006 A1 Jul. 2, 2020

Related U.S. Application Data

(63) Continuation of application No. 15/353,219, filed on Nov. 16, 2016, now Pat. No. 10,512,557, which is a
(Continued)

(51) Int. Cl.
*A61F 5/00* (2006.01)
(52) U.S. Cl.
CPC .......... *A61F 5/0036* (2013.01); *A61F 5/0076* (2013.01); *A61F 5/0079* (2013.01); *A61F 5/0089* (2013.01)
(58) Field of Classification Search
CPC .... A61F 5/0036; A61F 5/0076; A61F 5/0079; A61F 5/0089
See application file for complete search history.

(56) References Cited

U.S. PATENT DOCUMENTS

| 1,899,781 A | 2/1933 | Twiss |
| 2,464,933 A | 3/1949 | Kaslow |

(Continued)

FOREIGN PATENT DOCUMENTS

| AU | 2010271294 A1 | 2/2012 |
| AU | 2011203951 A1 | 7/2012 |

(Continued)

OTHER PUBLICATIONS

US 8,668,662 B2, 03/2014, Levine (withdrawn)
(Continued)

*Primary Examiner* — Richard G Louis

(57) ABSTRACT

A gastrointestinal device for treating obesity includes a three-dimensional porous structure configurable between a compressed pre-deployment configuration to facilitate delivery and an expanded post-deployment configuration. The porous structure includes a first opening at its proximal end and a larger second opening at its distal end. The porous structure also includes a sleeve coupled to its distal end. Optionally, the device further includes a suture at the proximal end of the wire mesh structure to facilitate retrieval and an anti-migration component positioned at the junction of the porous structure with the sleeve. The porous structure is deployed in a patient's stomach such that the anti-migration component sits proximal to the patient's pylorus and prevents migration of the entirety of the device into and through the pylorus. The sleeve extends through the pylorus, into the duodenum and ends in the duodenum or jejunum. Food enters the device from the first opening at the proximal end of the porous structure, passes through the porous structure and sleeve, and exits at the distal end of the sleeve. The device treats obesity by providing a relatively immovable volume occupying structure in the stomach and a bypass for food past the pylorus and proximal portion of the small intestine. Optionally, the device further acts to slow the
(Continued)

passage of food through the digestive tract. Patients with the device experience satiety more quickly and have a prolonged sensation of satiety.

17 Claims, 109 Drawing Sheets

Related U.S. Application Data continuation of application No. 14/214,609, filed on Mar. 14, 2014, now Pat. No. 9,526,648, which is a continuation-in-part of application No. 14/096,505, filed on Dec. 4, 2013, now Pat. No. 10,413,436, which is a continuation of application No. 12/814,481, filed on Jun. 13, 2010, now Pat. No. 8,628,554.

(60) Provisional application No. 61/884,981, filed on Sep. 30, 2013, provisional application No. 61/782,564, filed on Mar. 14, 2013.

(56) References Cited

U.S. PATENT DOCUMENTS

| | | | |
|---|---|---|---|
| 3,780,740 A | 12/1973 | Rhea | |
| 4,133,315 A | 1/1979 | Berman et al. | |
| 4,134,405 A | 1/1979 | Smit | |
| 4,246,893 A | 1/1981 | Berson | |
| 4,270,542 A | 6/1981 | Plumley | |
| 4,279,251 A | 7/1981 | Heinz | |
| 4,315,509 A | 2/1982 | Smit | |
| 4,403,604 A | 9/1983 | Wilkinson et al. | |
| 4,416,267 A | 11/1983 | Garren et al. | |
| 4,441,215 A | 4/1984 | Kaster | |
| 4,501,264 A | 2/1985 | Rockey | |
| 4,580,568 A | 4/1986 | Gianturco | |
| 4,607,618 A | 8/1986 | Angelchik | |
| 4,617,932 A | 10/1986 | Kornberg | |
| 4,641,653 A | 2/1987 | Rockey | |
| 4,648,383 A | 3/1987 | Angelchik | |
| 4,694,827 A | 9/1987 | Weiner et al. | |
| 4,723,547 A | 2/1988 | Kullas et al. | |
| 4,738,667 A | 4/1988 | Galloway | |
| 4,763,653 A | 8/1988 | Rockey | |
| 4,767,627 A | 8/1988 | Caldwell et al. | |
| 4,823,808 A | 4/1989 | Clegg et al. | |
| 4,846,836 A | 7/1989 | Reich | |
| 4,878,905 A | 11/1989 | Blass | |
| 4,899,747 A | 2/1990 | Garren et al. | |
| 4,913,141 A | 4/1990 | Hillstead | |
| 5,035,706 A | 7/1991 | Giantureo et al. | |
| 5,037,387 A | 8/1991 | Quinn et al. | |
| 5,041,126 A | 8/1991 | Gianturco | |
| 5,057,091 A | 10/1991 | Andersen | |
| 5,104,399 A | 4/1992 | Lazarus | |
| 5,152,756 A | 10/1992 | Quinn et al. | |
| 5,163,952 A | 11/1992 | Froix | |
| 5,188,104 A | 2/1993 | Wernicke et al. | |
| 5,211,658 A | 5/1993 | Clouse | |
| 5,234,454 A | 8/1993 | Bangs | |
| 5,236,423 A | 8/1993 | Mix et al. | |
| 5,246,456 A | 9/1993 | Wilkinson | |
| 5,259,399 A | 11/1993 | Brown | |
| 5,279,553 A | 1/1994 | Winkler et al. | |
| 5,282,824 A | 2/1994 | Gianturco | |
| 5,290,217 A | 3/1994 | Campos | |
| 5,306,300 A | 4/1994 | Berry | |
| 5,314,444 A | 5/1994 | Gianturco | |
| 5,314,472 A | 5/1994 | Fontaine | |
| 5,314,473 A | 5/1994 | Godin | |
| 5,318,530 A | 6/1994 | Nelson, Jr. | |
| 5,327,914 A | 7/1994 | Shlain | |
| 5,345,949 A | 9/1994 | Shlain | |
| 5,364,353 A | 11/1994 | Corfitsen et al. | |
| 5,387,235 A | 2/1995 | Chuter | |
| 5,401,241 A | 3/1995 | Delany | |
| 5,405,377 A | 4/1995 | Cragg | |
| 5,405,378 A | 4/1995 | Strecker | |
| 5,423,872 A | 6/1995 | Cigaina | |
| 5,432,872 A | 7/1995 | Stewart et al. | |
| 5,443,498 A | 8/1995 | Fontaine | |
| 5,456,713 A | 10/1995 | Chuter | |
| 5,480,423 A | 1/1996 | Ravenscroft et al. | |
| 5,507,767 A | 4/1996 | Maeda et al. | |
| 5,507,771 A | 4/1996 | Gianturco | |
| 5,514,176 A | 5/1996 | Bosley, Jr. | |
| 5,536,274 A | 7/1996 | Neuss | |
| 5,562,697 A | 10/1996 | Christiansen | |
| 5,569,219 A | 10/1996 | Hakki et al. | |
| 5,593,434 A | 1/1997 | Williams | |
| 5,611,787 A | 3/1997 | Demeter et al. | |
| 5,624,430 A | 4/1997 | Eton et al. | |
| 5,630,797 A | 5/1997 | Diedrich et al. | |
| 5,637,699 A | 6/1997 | Dorn et al. | |
| 5,653,743 A | 8/1997 | Martin | |
| 5,658,322 A | 8/1997 | Fleming | |
| 5,662,713 A | 9/1997 | Andersen et al. | |
| 5,665,064 A | 9/1997 | Bodicky et al. | |
| 5,668,263 A | 9/1997 | Hoyer et al. | |
| 5,674,241 A | 10/1997 | Bley et al. | |
| 5,690,692 A | 11/1997 | Fleming | |
| 5,693,084 A | 12/1997 | Chuter | |
| 5,700,272 A | 12/1997 | Gordon et al. | |
| 5,709,657 A | 1/1998 | Zimmon | |
| 5,713,910 A | 2/1998 | Gordon et al. | |
| 5,715,832 A | 2/1998 | Koblish et al. | |
| 5,720,776 A | 2/1998 | Chuter et al. | |
| 5,733,325 A | 3/1998 | Robinson et al. | |
| 5,741,277 A | 4/1998 | Gordon et al. | |
| 5,741,279 A | 4/1998 | Gordon et al. | |
| 5,749,918 A | 5/1998 | Hogendijk et al. | |
| 5,755,777 A | 5/1998 | Chuter | |
| 5,771,903 A | 6/1998 | Jakobsson et al. | |
| 5,800,456 A | 9/1998 | Maeda et al. | |
| 5,800,526 A | 9/1998 | Anderson et al. | |
| 5,817,466 A | 10/1998 | Hoyer et al. | |
| 5,820,584 A | 10/1998 | Crabb | |
| 5,830,229 A | 11/1998 | Konya et al. | |
| 5,835,897 A | 11/1998 | Dang | |
| 5,843,164 A | 12/1998 | Frantzen et al. | |
| 5,861,036 A | 1/1999 | Godin | |
| 5,868,141 A | 2/1999 | Ellias | |
| 5,876,445 A | 3/1999 | Andersen et al. | |
| 5,887,594 A | 3/1999 | Locicero, III | |
| 5,891,845 A | 4/1999 | Myers | |
| 5,922,019 A | 7/1999 | Hankh et al. | |
| 5,955,579 A | 9/1999 | Leonard et al. | |
| 5,965,396 A | 10/1999 | Pan et al. | |
| 5,993,483 A | 11/1999 | Gianotti | |
| 6,027,508 A | 2/2000 | Ren et al. | |
| 6,048,351 A | 4/2000 | Gordon et al. | |
| 6,087,129 A | 7/2000 | Newgard et al. | |
| 6,099,552 A | 8/2000 | Adams | |
| 6,102,922 A | 8/2000 | Jakobsson et al. | |
| 6,113,609 A | 9/2000 | Adams | |
| 6,117,911 A | 9/2000 | Grainger et al. | |
| 6,132,471 A | 10/2000 | Johlin, Jr. | |
| 6,146,416 A | 11/2000 | Andersen et al. | |
| 6,159,238 A | 12/2000 | Killion et al. | |
| 6,180,082 B1 | 1/2001 | Woltering et al. | |
| 6,183,461 B1 | 2/2001 | Matsuura et al. | |
| 6,184,254 B1 | 2/2001 | Bukoski et al. | |
| 6,200,336 B1 | 3/2001 | Pavcnik et al. | |
| 6,200,600 B1 | 3/2001 | Rashid | |
| 6,241,738 B1 | 6/2001 | Dereume | |
| 6,245,761 B1 | 6/2001 | Britton et al. | |
| 6,251,132 B1 | 6/2001 | Ravenscroft et al. | |
| 6,254,642 B1 | 7/2001 | Taylor | |
| 6,258,120 B1 | 7/2001 | McKenzie et al. | |
| 6,264,700 B1 | 7/2001 | Kilcoyne et al. | |
| 6,302,891 B1 | 10/2001 | Nadal | |
| 6,302,917 B1 | 10/2001 | Dua et al. | |
| 6,303,637 B1 | 10/2001 | Bao et al. | |
| 6,322,538 B1 | 11/2001 | Elbert et al. | |

(56) References Cited

U.S. PATENT DOCUMENTS

| | | |
|---|---|---|
| 6,331,190 B1 | 12/2001 | Shokoohi et al. |
| 6,332,877 B1 | 12/2001 | Michels |
| 6,364,868 B1 | 4/2002 | Ikeguchi |
| 6,370,511 B1 | 4/2002 | Dang |
| 6,387,114 B2 | 5/2002 | Adams |
| 6,406,840 B1 | 6/2002 | Li et al. |
| 6,410,587 B1 | 6/2002 | Grainger et al. |
| 6,424,864 B1 | 7/2002 | Matsuura |
| 6,450,989 B2 | 9/2002 | Dubrul et al. |
| 6,454,785 B2 | 9/2002 | De Hoyos Garza |
| 6,485,409 B1 | 11/2002 | Voloshin et al. |
| 6,494,888 B1 | 12/2002 | Laufer et al. |
| 6,503,264 B1 | 1/2003 | Birk |
| 6,508,833 B2 | 1/2003 | Pavcnik et al. |
| 6,524,335 B1 | 2/2003 | Hartley et al. |
| 6,524,336 B1 | 2/2003 | Papazolgou et al. |
| 6,530,951 B1 | 3/2003 | Bates et al. |
| 6,531,491 B1 | 3/2003 | Kania et al. |
| 6,534,524 B1 | 3/2003 | Kania et al. |
| 6,537,247 B2 | 3/2003 | Shannon |
| 6,540,789 B1 | 4/2003 | Silverman et al. |
| 6,544,291 B2 | 4/2003 | Taylor |
| 6,547,801 B1 | 4/2003 | Dargent et al. |
| 6,558,400 B2 | 5/2003 | Deem et al. |
| 6,558,429 B2 | 5/2003 | Taylor |
| 6,565,597 B1 | 5/2003 | Fearnot et al. |
| 6,571,127 B1 | 5/2003 | Ben-Haim et al. |
| 6,572,627 B2 | 6/2003 | Gabbay |
| 6,572,629 B2 | 6/2003 | Kalloo et al. |
| 6,575,896 B2 | 6/2003 | Silverman et al. |
| 6,589,213 B2 | 7/2003 | Reydel |
| 6,589,275 B1 | 7/2003 | Ivancev et al. |
| 6,596,023 B1 | 7/2003 | Nunez et al. |
| 6,623,518 B2 | 9/2003 | Thompson et al. |
| 6,630,123 B1 | 10/2003 | Woltering et al. |
| 6,635,079 B2 | 10/2003 | Unsworth et al. |
| 6,656,194 B1 | 12/2003 | Gannoe et al. |
| 6,663,639 B1 | 12/2003 | Laufer et al. |
| 6,666,848 B2 | 12/2003 | Stone |
| 6,675,809 B2 | 1/2004 | Stack et al. |
| 6,676,692 B2 | 1/2004 | Rabkin et al. |
| 6,685,962 B2 | 2/2004 | Friedman et al. |
| 6,695,875 B2 | 2/2004 | Stelter et al. |
| 6,696,575 B2 | 2/2004 | Schmidt et al. |
| 6,699,263 B2 | 3/2004 | Cope |
| 6,733,512 B2 | 5/2004 | McGhan |
| 6,734,208 B2 | 5/2004 | Grainger et al. |
| 6,740,121 B2 | 5/2004 | Geitz |
| 6,743,198 B1 | 6/2004 | Tihon |
| 6,755,869 B2 | 6/2004 | Geitz |
| 6,761,733 B2 | 7/2004 | Chobotov et al. |
| 6,764,518 B2 | 7/2004 | Godin |
| 6,773,440 B2 | 8/2004 | Gannoe et al. |
| 6,773,441 B1 | 8/2004 | Laufer et al. |
| 6,776,791 B1 | 8/2004 | Stallings et al. |
| 6,776,999 B1 | 8/2004 | Krumme |
| 6,802,846 B2 | 10/2004 | Hauschild et al. |
| 6,802,868 B2 | 10/2004 | Silverman et al. |
| 6,844,349 B2 | 1/2005 | Kath et al. |
| 6,845,776 B2 | 1/2005 | Stack et al. |
| 6,855,153 B2 | 2/2005 | Saadat |
| 6,884,890 B2 | 4/2005 | Kania et al. |
| 6,890,924 B2 | 5/2005 | Kath et al. |
| 6,891,044 B2 | 5/2005 | Kania et al. |
| 6,911,198 B2 | 6/2005 | Shachar et al. |
| 6,932,838 B2 | 8/2005 | Schwartz et al. |
| 6,939,370 B2 | 9/2005 | Hartley et al. |
| 6,947,792 B2 | 9/2005 | Ben-Haim et al. |
| 6,950,707 B2 | 9/2005 | Whitehurst |
| 6,994,095 B2 | 2/2006 | Burnett |
| 7,019,147 B1 | 3/2006 | Barth et al. |
| 7,025,791 B2 | 4/2006 | Levine et al. |
| 7,033,373 B2 | 4/2006 | De et al. |
| 7,033,384 B2 | 4/2006 | Gannoe et al. |
| 7,037,344 B2 | 5/2006 | Kagan et al. |
| 7,041,120 B2 | 5/2006 | Li et al. |
| 7,044,979 B2 | 5/2006 | Silverman et al. |
| 7,056,305 B2 | 6/2006 | Garza Alvarez |
| 7,060,080 B2 | 6/2006 | Bachmann |
| 7,063,860 B2 | 6/2006 | Chancellor et al. |
| 7,066,945 B2 | 6/2006 | Hashiba et al. |
| 7,071,337 B2 | 7/2006 | Kath et al. |
| 7,083,629 B2 | 8/2006 | Weller et al. |
| 7,084,171 B2 | 8/2006 | Grainger et al. |
| 7,090,699 B2 | 8/2006 | Geitz |
| 7,097,665 B2 | 8/2006 | Stack et al. |
| 7,111,627 B2 | 9/2006 | Stack et al. |
| 7,120,497 B2 | 10/2006 | Ben-Haim et al. |
| 7,121,283 B2 | 10/2006 | Stack et al. |
| 7,122,058 B2 | 10/2006 | Levine et al. |
| 7,128,750 B1 | 10/2006 | Stergiopulos |
| 7,141,581 B2 | 11/2006 | Bender et al. |
| 7,141,587 B2 | 11/2006 | Kania et al. |
| 7,145,008 B2 | 12/2006 | Kath et al. |
| 7,146,984 B2 | 12/2006 | Stack et al. |
| 7,148,380 B2 | 12/2006 | Wang et al. |
| 7,152,607 B2 | 12/2006 | Stack et al. |
| 7,153,314 B2 | 12/2006 | Laufer et al. |
| 7,172,613 B2 | 2/2007 | Wazne |
| 7,189,750 B2 | 3/2007 | Assaf et al. |
| 7,196,093 B2 | 3/2007 | Yuan |
| 7,208,499 B2 | 4/2007 | Kath et al. |
| 7,211,114 B2 | 5/2007 | Bessler et al. |
| 7,220,284 B2 | 5/2007 | Kagan et al. |
| 7,221,978 B2 | 5/2007 | Ben-Haim et al. |
| 7,230,098 B2 | 6/2007 | Cui et al. |
| 7,235,562 B2 | 6/2007 | Kath et al. |
| 7,238,191 B2 | 7/2007 | Bachmann |
| 7,267,694 B2 | 9/2007 | Levine et al. |
| 7,271,262 B2 | 9/2007 | La et al. |
| 7,273,451 B2 | 9/2007 | Sekine et al. |
| 7,288,099 B2 | 10/2007 | Deem et al. |
| 7,288,101 B2 | 10/2007 | Deem et al. |
| 7,306,614 B2 | 12/2007 | Weller et al. |
| 7,309,858 B2 | 12/2007 | Pappin et al. |
| 7,314,443 B2 | 1/2008 | Jordan et al. |
| 7,316,716 B2 | 1/2008 | Egan |
| 7,320,696 B2 | 1/2008 | Gazi et al. |
| 7,329,285 B2 | 2/2008 | Levine et al. |
| 7,330,747 B2 | 2/2008 | Maier |
| 7,330,753 B2 | 2/2008 | Policker et al. |
| 7,332,493 B2 | 2/2008 | Kath et al. |
| 7,332,513 B2 | 2/2008 | Assaf et al. |
| 7,335,210 B2 | 2/2008 | Smit |
| 7,335,646 B2 | 2/2008 | Kieffer et al. |
| 7,338,433 B2 | 3/2008 | Coe |
| 7,347,868 B2 | 3/2008 | Burnett et al. |
| 7,347,875 B2 | 3/2008 | Levine et al. |
| 7,354,454 B2 | 4/2008 | Stack et al. |
| 7,364,591 B2 | 4/2008 | Silverman et al. |
| 7,368,577 B2 | 5/2008 | Assaf et al. |
| 7,371,862 B2 | 5/2008 | Vanotti et al. |
| 7,410,988 B2 | 8/2008 | Dickson et al. |
| 7,416,885 B2 | 8/2008 | Freeman et al. |
| 7,427,415 B2 | 9/2008 | Scharp et al. |
| 7,435,739 B2 | 10/2008 | Chen et al. |
| 7,462,487 B2 | 12/2008 | Tsao |
| 7,468,355 B2 | 12/2008 | Hamdi et al. |
| 7,476,256 B2 | 1/2009 | Meade et al. |
| 7,483,746 B2 | 1/2009 | Lee et al. |
| 7,498,445 B2 | 3/2009 | Assaf et al. |
| 7,503,922 B2 | 3/2009 | Deem et al. |
| 7,510,559 B2 | 3/2009 | Deem et al. |
| 7,511,070 B2 | 3/2009 | Grainger et al. |
| 7,513,914 B2 | 4/2009 | Schurr |
| 7,530,985 B2 | 5/2009 | Takemoto et al. |
| 7,547,312 B2 | 6/2009 | Bauman et al. |
| 7,579,477 B2 | 8/2009 | Assaf et al. |
| 7,582,313 B2 | 9/2009 | Faustman |
| 7,585,869 B2 | 9/2009 | Bhattacharya et al. |
| 7,594,926 B2 | 9/2009 | Linder et al. |
| 7,601,525 B2 | 10/2009 | Batich et al. |
| 7,604,649 B2 | 10/2009 | McGuckin et al. |
| 7,608,114 B2 | 10/2009 | Levine et al. |

(56) References Cited

U.S. PATENT DOCUMENTS

| | | |
|---|---|---|
| 7,620,454 B2 | 11/2009 | Dinsmoor et al. |
| 7,620,560 B2 | 11/2009 | Dang |
| 7,625,939 B2 | 12/2009 | Heiser et al. |
| 7,628,821 B2 | 12/2009 | Stack et al. |
| 7,628,988 B2 | 12/2009 | Faustman |
| 7,637,905 B2 | 12/2009 | Saadat et al. |
| 7,637,919 B2 | 12/2009 | Ishikawa et al. |
| 7,654,951 B2 | 2/2010 | Ishikawa |
| 7,662,929 B2 | 2/2010 | Brown et al. |
| 7,674,396 B2 | 3/2010 | Sterling et al. |
| 7,674,457 B2 | 3/2010 | Borlongan et al. |
| 7,678,068 B2 | 3/2010 | Levine et al. |
| 7,682,330 B2 | 3/2010 | Meade et al. |
| 7,691,152 B2 | 4/2010 | Silverman et al. |
| 7,695,446 B2 | 4/2010 | Levine et al. |
| 7,696,213 B2 | 4/2010 | Cheng et al. |
| 7,699,863 B2 | 4/2010 | Marco et al. |
| 7,725,333 B2 | 5/2010 | Dang |
| 7,727,143 B2 | 6/2010 | Birk et al. |
| 7,731,757 B2 | 6/2010 | Taylor et al. |
| 7,736,373 B2 | 6/2010 | Laufer et al. |
| 7,741,336 B2 | 6/2010 | Kath et al. |
| 7,742,818 B2 | 6/2010 | Dinsmoor et al. |
| 7,749,254 B2 | 7/2010 | Sobelman et al. |
| 7,758,535 B2 | 7/2010 | Levine et al. |
| 7,765,008 B2 | 7/2010 | Ben-Haim et al. |
| 7,766,861 B2 | 8/2010 | Levine et al. |
| 7,766,973 B2 | 8/2010 | Levine et al. |
| 7,771,382 B2 | 8/2010 | Levine et al. |
| 7,774,216 B2 | 8/2010 | Dang |
| 7,780,590 B2 | 8/2010 | Birk et al. |
| 7,794,447 B2 | 9/2010 | Dann et al. |
| 7,795,290 B2 | 9/2010 | Dickson et al. |
| 7,798,954 B2 | 9/2010 | Birk et al. |
| 7,799,088 B2 | 9/2010 | Geitz |
| 7,803,177 B2 | 9/2010 | Hartley et al. |
| 7,803,195 B2 | 9/2010 | Levy et al. |
| 7,811,298 B2 | 10/2010 | Birk |
| 7,811,299 B2 | 10/2010 | Bachmann et al. |
| 7,815,589 B2 | 10/2010 | Meade et al. |
| 7,815,591 B2 | 10/2010 | Levine et al. |
| 7,819,836 B2 | 10/2010 | Levine et al. |
| 7,833,280 B2 | 11/2010 | Stack et al. |
| 7,837,643 B2 | 11/2010 | Levine et al. |
| 7,837,669 B2 | 11/2010 | Dann et al. |
| 7,838,524 B2 | 11/2010 | Lee et al. |
| 7,840,269 B2 | 11/2010 | Policker et al. |
| 7,846,138 B2 | 12/2010 | Dann et al. |
| 7,850,704 B2 | 12/2010 | Burnett et al. |
| 7,862,574 B2 | 1/2011 | Deem et al. |
| 7,867,283 B2 | 1/2011 | Krueger et al. |
| 7,881,797 B2 | 2/2011 | Griffin et al. |
| 7,883,524 B2 | 2/2011 | Chen |
| 7,892,214 B2 | 2/2011 | Kagan et al. |
| 7,892,827 B2 | 2/2011 | Matschiner et al. |
| 7,901,419 B2 | 3/2011 | Bachmann et al. |
| 7,909,838 B2 | 3/2011 | Deem et al. |
| 7,922,684 B2 | 4/2011 | Weitzner et al. |
| 7,928,109 B2 | 4/2011 | Luzzio et al. |
| 7,935,073 B2 | 5/2011 | Levine et al. |
| 7,945,323 B2 | 5/2011 | Jaax et al. |
| 7,959,552 B2 | 6/2011 | Jordan et al. |
| 7,959,640 B2 | 6/2011 | Kantsevoy et al. |
| 7,960,345 B2 | 6/2011 | Kim |
| 7,966,071 B2 | 6/2011 | Ben-Haim et al. |
| 7,968,575 B2 | 6/2011 | Assaf et al. |
| 7,972,346 B2 | 7/2011 | Bachmann et al. |
| 7,976,488 B2 | 7/2011 | Levine et al. |
| 7,979,290 B2 | 7/2011 | Dang |
| 7,981,162 B2 | 7/2011 | Stack et al. |
| 7,981,163 B2 | 7/2011 | Meade et al. |
| 7,985,844 B2 | 7/2011 | Brown et al. |
| 7,998,220 B2 | 8/2011 | Murphy |
| 7,998,966 B2 | 8/2011 | Bearss et al. |
| 8,002,731 B2 | 8/2011 | Weitzner et al. |
| 8,003,806 B2 | 8/2011 | Bloxham et al. |
| 8,006,701 B2 | 8/2011 | Bilotti et al. |
| 8,007,507 B2 | 8/2011 | Waller |
| 8,008,449 B2 | 8/2011 | Korman et al. |
| 8,012,135 B2 | 9/2011 | Dann et al. |
| 8,012,140 B1 | 9/2011 | Kagan et al. |
| 8,012,162 B2 | 9/2011 | Bachmann |
| 8,012,966 B2 | 9/2011 | Tang et al. |
| 8,021,693 B2 | 9/2011 | Faustman |
| 8,043,206 B2 | 10/2011 | Birk |
| 8,043,248 B2 | 10/2011 | Pasricha |
| 8,048,169 B2 | 11/2011 | Burnett et al. |
| 8,048,170 B2 | 11/2011 | Silverman et al. |
| 8,057,420 B2 | 11/2011 | Meade et al. |
| 8,057,494 B2 | 11/2011 | Laufer et al. |
| 8,062,656 B2 | 11/2011 | Oh-Lee et al. |
| 8,066,689 B2 | 11/2011 | Mitelberg et al. |
| 8,070,743 B2 | 12/2011 | Kagan et al. |
| 8,070,824 B2 | 12/2011 | Burnett et al. |
| 8,075,577 B2 | 12/2011 | Deem et al. |
| 8,079,974 B2 | 12/2011 | Stergiopulos |
| 8,080,022 B2 | 12/2011 | Deem et al. |
| 8,080,025 B2 | 12/2011 | Deem et al. |
| 8,084,457 B2 | 12/2011 | Choidas et al. |
| 8,084,484 B2 | 12/2011 | Frank et al. |
| 8,092,482 B2 | 1/2012 | Gannoe et al. |
| 8,095,219 B2 | 1/2012 | Lee et al. |
| 8,096,966 B2 | 1/2012 | Levine et al. |
| 8,105,392 B2 | 1/2012 | Durgin |
| 8,106,197 B2 | 1/2012 | Cui et al. |
| 8,109,895 B2 | 2/2012 | Williams et al. |
| 8,114,045 B2 | 2/2012 | Surti |
| 8,114,893 B2 | 2/2012 | Baell et al. |
| 8,116,883 B2 | 2/2012 | Williams et al. |
| 8,118,774 B2 | 2/2012 | Dann et al. |
| 8,121,869 B2 | 2/2012 | Dang |
| 8,123,765 B2 | 2/2012 | Deem et al. |
| 8,123,766 B2 | 2/2012 | Bauman et al. |
| 8,123,767 B2 | 2/2012 | Bauman et al. |
| 8,134,010 B2 | 3/2012 | Assaf |
| 8,137,301 B2 | 3/2012 | Levine et al. |
| 8,137,662 B2 | 3/2012 | Freeman et al. |
| 8,142,469 B2 | 3/2012 | Sosnowski et al. |
| 8,142,514 B2 | 3/2012 | Geitz |
| 8,147,561 B2 | 4/2012 | Binmoeller |
| 8,162,871 B2 | 4/2012 | Levine et al. |
| 8,173,129 B2 | 5/2012 | Faustman |
| 8,177,853 B2 | 5/2012 | Stack et al. |
| 8,182,441 B2 | 5/2012 | Swain et al. |
| 8,182,459 B2 | 5/2012 | Dann et al. |
| 8,182,543 B2 | 5/2012 | Schurr |
| 8,187,289 B2 | 5/2012 | Tacchino et al. |
| 8,207,166 B2 | 6/2012 | Lee et al. |
| 8,211,186 B2 | 7/2012 | Belhe et al. |
| 8,216,266 B2 | 7/2012 | Hively |
| 8,216,268 B2 | 7/2012 | Haller et al. |
| 8,219,201 B2 | 7/2012 | Ben-Haim et al. |
| 8,226,593 B2 | 7/2012 | Graham et al. |
| 8,226,602 B2 | 7/2012 | Quijana et al. |
| 8,232,273 B2 | 7/2012 | Baell et al. |
| 8,236,023 B2 | 8/2012 | Birk et al. |
| 8,247,411 B2 | 8/2012 | Luzzio et al. |
| 8,252,816 B2 | 8/2012 | Frank et al. |
| 8,268,821 B2 | 9/2012 | Nadeson et al. |
| 8,273,755 B2 | 9/2012 | Cheng et al. |
| 8,277,468 B2 | 10/2012 | Laufer et al. |
| 8,282,598 B2 | 10/2012 | Belhe et al. |
| 8,282,666 B2 | 10/2012 | Birk |
| 8,290,582 B2 | 10/2012 | Lin et al. |
| 8,292,800 B2 | 10/2012 | Stone et al. |
| 8,296,165 B2 | 10/2012 | Dang |
| 8,299,022 B2 | 10/2012 | Dong |
| 8,303,669 B2 | 11/2012 | Meade et al. |
| 8,308,630 B2 | 11/2012 | Birk et al. |
| 8,308,813 B2 | 11/2012 | Krueger et al. |
| 8,317,677 B2 | 11/2012 | Bertolote et al. |
| 8,323,180 B2 | 12/2012 | Birk et al. |
| 8,323,229 B2 | 12/2012 | Shin et al. |
| 8,334,263 B2 | 12/2012 | Nadeson et al. |

(56) References Cited

U.S. PATENT DOCUMENTS

| | | |
|---|---|---|
| 8,337,567 B2 | 12/2012 | Stack et al. |
| 8,337,829 B2 | 12/2012 | Freeman et al. |
| 8,357,501 B2 | 1/2013 | Jackson et al. |
| 8,362,251 B2 | 1/2013 | Tang et al. |
| 8,366,602 B2 | 2/2013 | Birk et al. |
| 8,376,929 B2 | 2/2013 | Birk et al. |
| 8,377,081 B2 | 2/2013 | Bachmann et al. |
| 8,382,780 B2 | 2/2013 | Birk |
| 8,398,654 B2 | 3/2013 | Franklin et al. |
| 8,399,223 B2 | 3/2013 | Park et al. |
| 8,403,877 B2 | 3/2013 | Priplata et al. |
| 8,409,221 B2 | 4/2013 | Franklin et al. |
| 8,409,226 B2 | 4/2013 | Kantsevoy et al. |
| 8,414,559 B2 | 4/2013 | Gross |
| 8,425,451 B2 | 4/2013 | Levine et al. |
| 8,430,894 B2 | 4/2013 | Brooks et al. |
| 8,430,895 B2 | 4/2013 | Brooks et al. |
| 8,431,597 B2 | 4/2013 | Munchhof et al. |
| 8,436,011 B2 | 5/2013 | Bellevergue et al. |
| 8,440,822 B2 | 5/2013 | Luzzio et al. |
| 8,465,447 B2 | 6/2013 | Krueger et al. |
| 8,470,815 B2 | 6/2013 | Saulnier et al. |
| 8,475,401 B2 | 7/2013 | Priplata et al. |
| 8,486,153 B2 | 7/2013 | Levine et al. |
| 8,491,472 B2 | 7/2013 | Mitelberg et al. |
| 8,491,519 B2 | 7/2013 | Chin |
| 8,496,931 B2 | 7/2013 | Pogue et al. |
| 8,506,517 B2 | 8/2013 | Stergiopulos |
| 8,506,532 B2 | 8/2013 | Olroyd et al. |
| 8,507,274 B2 | 8/2013 | Melton et al. |
| 8,515,542 B2 | 8/2013 | Jaax et al. |
| 8,517,915 B2 | 8/2013 | Perron et al. |
| 8,518,970 B2 | 8/2013 | Baell et al. |
| 8,529,943 B2 | 9/2013 | Kliger et al. |
| 8,556,918 B2 | 10/2013 | Bauman et al. |
| 8,556,925 B2 | 10/2013 | Makower et al. |
| 8,556,934 B2 | 10/2013 | Godin |
| 8,568,488 B2 | 10/2013 | Stack et al. |
| 8,579,988 B2 | 11/2013 | Burnett et al. |
| 8,585,628 B2 | 11/2013 | Harris et al. |
| 8,585,753 B2 | 11/2013 | Scanlon et al. |
| 8,585,771 B2 | 11/2013 | Binmoeller et al. |
| 8,591,452 B2 | 11/2013 | Priplata et al. |
| 8,591,533 B2 | 11/2013 | Needleman et al. |
| 8,591,598 B2 | 11/2013 | Silverman et al. |
| 8,597,224 B2 | 12/2013 | Vargas |
| 8,603,186 B2 | 12/2013 | Binmoeller |
| 8,613,749 B2 | 12/2013 | Deem et al. |
| 8,623,893 B2 | 1/2014 | Lassalle et al. |
| 8,628,554 B2 | 1/2014 | Sharma |
| 8,628,583 B2 | 1/2014 | Meade et al. |
| 8,633,204 B2 | 1/2014 | Cheng et al. |
| 8,636,683 B2 | 1/2014 | Chin et al. |
| 8,636,751 B2 | 1/2014 | Albrecht et al. |
| 8,642,623 B2 | 2/2014 | Frank et al. |
| 8,652,083 B2 | 2/2014 | Weitzner et al. |
| 8,657,885 B2 | 2/2014 | Burnett et al. |
| 8,663,301 B2 | 3/2014 | Riina et al. |
| 8,663,338 B2 | 3/2014 | Burnett et al. |
| 8,678,993 B2 | 3/2014 | Stroumpoulis |
| 8,679,137 B2 | 3/2014 | Bauman et al. |
| 8,683,881 B2 | 4/2014 | Bouasaysy et al. |
| 8,691,271 B2 | 4/2014 | Burnett et al. |
| 8,698,373 B2 | 4/2014 | Augarten et al. |
| 8,702,641 B2 | 4/2014 | Belhe et al. |
| 8,702,642 B2 | 4/2014 | Belhe et al. |
| 8,708,979 B2 | 4/2014 | Honaryar et al. |
| 8,715,158 B2 | 5/2014 | Honaryar et al. |
| 8,725,435 B2 | 5/2014 | Snow et al. |
| 8,753,369 B2 | 6/2014 | Murature et al. |
| 8,758,221 B2 | 6/2014 | Snow et al. |
| 8,764,624 B2 | 7/2014 | Snow et al. |
| 8,771,219 B2 | 7/2014 | Meade et al. |
| 8,795,301 B2 | 8/2014 | Burnett et al. |
| 8,801,597 B2 | 8/2014 | Franklin et al. |
| 8,801,647 B2 | 8/2014 | Melanson et al. |
| 8,808,270 B2 | 8/2014 | Dann et al. |
| 8,821,373 B2 | 9/2014 | Schwab et al. |
| 8,821,429 B2 | 9/2014 | Vargas |
| 8,821,430 B2 | 9/2014 | Stergiopulos |
| 8,821,521 B2 | 9/2014 | Burnett |
| 8,821,584 B2 | 9/2014 | Burnett et al. |
| 8,834,405 B2 | 9/2014 | Meade et al. |
| 8,834,553 B2 | 9/2014 | Melanson et al. |
| 8,840,541 B2 | 9/2014 | Snow et al. |
| 8,840,679 B2 | 9/2014 | Durgin |
| 8,840,952 B2 | 9/2014 | Ashby et al. |
| 8,845,513 B2 | 9/2014 | Coe |
| 8,845,672 B2 | 9/2014 | Alverdy |
| 8,858,421 B2 | 10/2014 | Honaryar |
| 8,864,840 B2 | 10/2014 | Dominguez et al. |
| 8,870,806 B2 | 10/2014 | Levine et al. |
| 8,870,966 B2 | 10/2014 | Schwab et al. |
| 8,876,694 B2 | 11/2014 | Honaryar et al. |
| 8,882,655 B2 | 11/2014 | Nitka et al. |
| 8,882,698 B2 | 11/2014 | Levine et al. |
| 8,882,728 B2 | 11/2014 | Harders et al. |
| 8,882,798 B2 | 11/2014 | Schwab et al. |
| 8,888,732 B2 | 11/2014 | Raven et al. |
| 8,888,797 B2 | 11/2014 | Burnett et al. |
| 8,894,568 B2 | 11/2014 | Kwok et al. |
| 8,900,117 B2 | 12/2014 | Birk |
| 8,900,118 B2 | 12/2014 | Birk et al. |
| 8,905,915 B2 | 12/2014 | Birk |
| 8,905,916 B2 | 12/2014 | Jacobs et al. |
| 8,920,358 B2 | 12/2014 | Levine et al. |
| 8,920,447 B2 | 12/2014 | Dominguez |
| 8,932,247 B2 | 1/2015 | Stergiopulos |
| 8,939,888 B2 | 1/2015 | Augarten et al. |
| 8,956,318 B2 | 2/2015 | Miller et al. |
| 8,956,380 B2 | 2/2015 | Dominguez et al. |
| 8,961,393 B2 | 2/2015 | Rion et al. |
| 8,961,394 B2 | 2/2015 | Honaryar et al. |
| 8,968,177 B2 | 3/2015 | Silverman et al. |
| 8,968,270 B2 | 3/2015 | Kagan et al. |
| 8,979,735 B2 | 3/2015 | Augarten |
| 8,992,415 B2 | 3/2015 | Deuel et al. |
| 8,992,559 B2 | 3/2015 | Weitzner et al. |
| 9,017,358 B2 | 4/2015 | Schwab et al. |
| 9,023,062 B2 | 5/2015 | Franklin et al. |
| 9,023,063 B2 | 5/2015 | Franklin et al. |
| 9,028,394 B2 | 5/2015 | Honaryar et al. |
| 9,039,649 B2 | 5/2015 | Neisz et al. |
| 9,044,298 B2 | 6/2015 | Franklin et al. |
| 9,044,300 B2 | 6/2015 | Belhe et al. |
| 9,050,165 B2 | 6/2015 | Perron |
| 9,050,168 B2 | 6/2015 | Neisz et al. |
| 9,050,174 B2 | 6/2015 | Pecor et al. |
| 9,060,844 B2 | 6/2015 | Kagan et al. |
| 9,066,780 B2 | 6/2015 | Weber |
| 9,072,579 B2 | 7/2015 | Birk et al. |
| 9,084,669 B2 | 7/2015 | Meade et al. |
| 9,089,395 B2 | 7/2015 | Honaryar |
| 9,095,405 B2 | 8/2015 | Babkes et al. |
| 9,095,416 B2 | 8/2015 | Meade et al. |
| 9,526,648 B2 | 12/2016 | Sharma |
| 10,010,439 B2 | 7/2018 | Sharma et al. |
| 10,413,436 B2 | 9/2019 | Sharma |
| 10,420,665 B2 | 9/2019 | Sharma et al. |
| 10,512,557 B2 | 12/2019 | Sharma |
| 10,779,980 B2 | 9/2020 | Sharma et al. |
| 11,351,050 B2 | 6/2022 | Sharma |
| 2001/0011543 A1 | 8/2001 | Forsell |
| 2002/0006962 A1 | 1/2002 | Wang et al. |
| 2002/0071857 A1 | 6/2002 | Kararli et al. |
| 2002/0091439 A1 | 7/2002 | Baker et al. |
| 2002/0137086 A1 | 9/2002 | Olek et al. |
| 2002/0143387 A1 | 10/2002 | Soetikno et al. |
| 2002/0155100 A1 | 10/2002 | Kieffer et al. |
| 2002/0165572 A1 | 11/2002 | Saadat |
| 2002/0165738 A1 | 11/2002 | Dang |
| 2002/0169165 A1 | 11/2002 | Kath et al. |
| 2002/0173987 A1 | 11/2002 | Dang |
| 2002/0173988 A1 | 11/2002 | Dang |

(56) References Cited

U.S. PATENT DOCUMENTS

| | | |
|---|---|---|
| 2002/0173989 A1 | 11/2002 | Dang |
| 2002/0173992 A1 | 11/2002 | Dang |
| 2002/0183768 A1 | 12/2002 | Deem et al. |
| 2002/0193816 A1 | 12/2002 | Laufer et al. |
| 2002/0193828 A1 | 12/2002 | Griffin et al. |
| 2002/0197656 A1 | 12/2002 | Li et al. |
| 2003/0018299 A1 | 1/2003 | Stone |
| 2003/0040804 A1 | 2/2003 | Stack et al. |
| 2003/0040808 A1 | 2/2003 | Stack et al. |
| 2003/0050684 A1 | 3/2003 | Abrams et al. |
| 2003/0053985 A1 | 3/2003 | Shachar et al. |
| 2003/0055465 A1 | 3/2003 | Ben-Haim et al. |
| 2003/0055466 A1 | 3/2003 | Ben-Haim et al. |
| 2003/0055467 A1 | 3/2003 | Ben-Haim et al. |
| 2003/0064970 A1 | 4/2003 | Grainger et al. |
| 2003/0065359 A1 | 4/2003 | Weller et al. |
| 2003/0066987 A1 | 4/2003 | Schmidt et al. |
| 2003/0086975 A1 | 5/2003 | Ringeisen |
| 2003/0108597 A1 | 6/2003 | Chancellor et al. |
| 2003/0109892 A1 | 6/2003 | Deem et al. |
| 2003/0109935 A1 | 6/2003 | Geitz |
| 2003/0120265 A1 | 6/2003 | Deem et al. |
| 2003/0153905 A1 | 8/2003 | Edwards et al. |
| 2003/0158217 A1 | 8/2003 | Kath et al. |
| 2003/0171261 A1 | 9/2003 | Livingston et al. |
| 2003/0171386 A1 | 9/2003 | Connell et al. |
| 2003/0190368 A1 | 10/2003 | Stoughton et al. |
| 2003/0191476 A1 | 10/2003 | Smit |
| 2003/0191492 A1 | 10/2003 | Gellman et al. |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208260 A1 | 11/2003 | Lau et al. |
| 2003/0232752 A1 | 12/2003 | Freeman et al. |
| 2004/0024386 A1 | 2/2004 | Deem et al. |
| 2004/0028658 A1 | 2/2004 | Faustman |
| 2004/0039350 A1 | 2/2004 | McKittrick |
| 2004/0039452 A1 | 2/2004 | Bessler |
| 2004/0044357 A1 | 3/2004 | Gannoe et al. |
| 2004/0045045 A1 | 3/2004 | Mather et al. |
| 2004/0062778 A1 | 4/2004 | Shefer et al. |
| 2004/0073278 A1 | 4/2004 | Pachys |
| 2004/0087876 A1 | 5/2004 | Eskuri |
| 2004/0092892 A1 | 5/2004 | Kagan et al. |
| 2004/0097428 A1 | 5/2004 | Hamdi et al. |
| 2004/0106892 A1 | 6/2004 | Stone |
| 2004/0107004 A1 | 6/2004 | Levine et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0122456 A1 | 6/2004 | Saadat et al. |
| 2004/0127800 A1 | 7/2004 | Kimball et al. |
| 2004/0133147 A1 | 7/2004 | Woo |
| 2004/0138529 A1 | 7/2004 | Wiltshire et al. |
| 2004/0138760 A1 | 7/2004 | Schurr |
| 2004/0143342 A1 | 7/2004 | Stack et al. |
| 2004/0147816 A1 | 7/2004 | Policker et al. |
| 2004/0147871 A1 | 7/2004 | Burnett |
| 2004/0148034 A1 | 7/2004 | Kagan et al. |
| 2004/0158331 A1 | 8/2004 | Stack et al. |
| 2004/0170631 A1 | 9/2004 | Yacoby-Zeevi et al. |
| 2004/0171634 A1 | 9/2004 | Kania et al. |
| 2004/0172143 A1 | 9/2004 | Geitz |
| 2004/0180086 A1 | 9/2004 | Ramtoola et al. |
| 2004/0181242 A1 | 9/2004 | Stack et al. |
| 2004/0192598 A1 | 9/2004 | Kragie |
| 2004/0193184 A1 | 9/2004 | Laufer et al. |
| 2004/0204429 A1 | 10/2004 | Yuan |
| 2004/0220177 A1 | 11/2004 | Kath et al. |
| 2004/0220248 A1 | 11/2004 | Kania et al. |
| 2004/0220682 A1 | 11/2004 | Levine et al. |
| 2004/0225191 A1 | 11/2004 | Sekine et al. |
| 2004/0236381 A1 | 11/2004 | Dinsmoor et al. |
| 2004/0236382 A1 | 11/2004 | Dinsmoor et al. |
| 2004/0242604 A1 | 12/2004 | Bhattacharya et al. |
| 2004/0243152 A1 | 12/2004 | Taylor et al. |
| 2004/0254204 A1 | 12/2004 | Kath et al. |
| 2004/0267378 A1 | 12/2004 | Gazi et al. |
| 2005/0004430 A1 | 1/2005 | Lee et al. |
| 2005/0004681 A1 | 1/2005 | Stack et al. |
| 2005/0009840 A1 | 1/2005 | Cui et al. |
| 2005/0020667 A1 | 1/2005 | Grainger et al. |
| 2005/0037999 A1 | 2/2005 | La et al. |
| 2005/0038097 A1 | 2/2005 | Bender et al. |
| 2005/0049718 A1 | 3/2005 | Dann et al. |
| 2005/0055039 A1 | 3/2005 | Burnett et al. |
| 2005/0075354 A1 | 4/2005 | Li et al. |
| 2005/0085923 A1 | 4/2005 | Levine et al. |
| 2005/0089577 A1 | 4/2005 | Yokoyama et al. |
| 2005/0101011 A1 | 5/2005 | Tsao |
| 2005/0101618 A1 | 5/2005 | Connell et al. |
| 2005/0124599 A1 | 6/2005 | Kath et al. |
| 2005/0124662 A1 | 6/2005 | Kania et al. |
| 2005/0125020 A1* | 6/2005 | Meade ............... A61F 2/848 606/191 |
| 2005/0125075 A1 | 6/2005 | Meade et al. |
| 2005/0130994 A1 | 6/2005 | Chen et al. |
| 2005/0143765 A1 | 6/2005 | Bachmann et al. |
| 2005/0143766 A1 | 6/2005 | Bachmann et al. |
| 2005/0158288 A1 | 7/2005 | Faustman |
| 2005/0159435 A1 | 7/2005 | Kath et al. |
| 2005/0159769 A1 | 7/2005 | Alverdy |
| 2005/0164388 A1 | 7/2005 | Son et al. |
| 2005/0169902 A1 | 8/2005 | Borlongan et al. |
| 2005/0171556 A1 | 8/2005 | Murphy |
| 2005/0192614 A1 | 9/2005 | Binmoeller |
| 2005/0196423 A1 | 9/2005 | Batich et al. |
| 2005/0197714 A1 | 9/2005 | Sayet |
| 2005/0251182 A1 | 11/2005 | Bachmann |
| 2005/0256111 A1 | 11/2005 | Kath et al. |
| 2005/0256125 A1 | 11/2005 | Kath et al. |
| 2005/0256144 A1 | 11/2005 | Kath et al. |
| 2005/0256587 A1 | 11/2005 | Egan |
| 2005/0267595 A1 | 12/2005 | Chen et al. |
| 2005/0273060 A1 | 12/2005 | Levy et al. |
| 2005/0277975 A1 | 12/2005 | Saadat et al. |
| 2006/0002899 A1 | 1/2006 | Rice et al. |
| 2006/0009858 A1 | 1/2006 | Levine et al. |
| 2006/0015125 A1 | 1/2006 | Swain |
| 2006/0015151 A1 | 1/2006 | Aldrich |
| 2006/0020278 A1 | 1/2006 | Burnett et al. |
| 2006/0025799 A1 | 2/2006 | Basu |
| 2006/0052416 A1 | 3/2006 | Dickson et al. |
| 2006/0064120 A1 | 3/2006 | Levine et al. |
| 2006/0069138 A1 | 3/2006 | Assaf et al. |
| 2006/0069139 A1 | 3/2006 | Assaf et al. |
| 2006/0069400 A1 | 3/2006 | Burnett et al. |
| 2006/0074073 A1 | 4/2006 | Steinfeldt et al. |
| 2006/0078993 A1 | 4/2006 | Phan et al. |
| 2006/0084696 A1 | 4/2006 | Grainger et al. |
| 2006/0089571 A1 | 4/2006 | Gertner |
| 2006/0089627 A1 | 4/2006 | Burnett et al. |
| 2006/0105454 A1 | 5/2006 | Son et al. |
| 2006/0116383 A1 | 6/2006 | Bloxham et al. |
| 2006/0127437 A1 | 6/2006 | Kennedy et al. |
| 2006/0134109 A1 | 6/2006 | Gaitanaris et al. |
| 2006/0134186 A1 | 6/2006 | Carlton et al. |
| 2006/0142731 A1 | 6/2006 | Brooks |
| 2006/0142787 A1 | 6/2006 | Weller et al. |
| 2006/0161187 A1 | 7/2006 | Levine et al. |
| 2006/0161265 A1 | 7/2006 | Levine et al. |
| 2006/0183718 A1 | 8/2006 | Assaf et al. |
| 2006/0183912 A1 | 8/2006 | Assaf et al. |
| 2006/0183913 A1 | 8/2006 | Assaf et al. |
| 2006/0228775 A1 | 10/2006 | Collier et al. |
| 2006/0241130 A1 | 10/2006 | Keinan et al. |
| 2006/0241748 A1 | 10/2006 | Lee et al. |
| 2006/0271088 A1 | 11/2006 | Alfrhan |
| 2006/0276713 A1 | 12/2006 | Maier |
| 2007/0003610 A1 | 1/2007 | Chancellor et al. |
| 2007/0021382 A1 | 1/2007 | Assaf et al. |
| 2007/0021988 A1 | 1/2007 | Dang |
| 2007/0027548 A1 | 2/2007 | Levine et al. |
| 2007/0032879 A1 | 2/2007 | Levine et al. |

(56) References Cited

U.S. PATENT DOCUMENTS

| | | |
|---|---|---|
| 2007/0037883 A1 | 2/2007 | Dusting et al. |
| 2007/0060940 A1 | 3/2007 | Brazzini et al. |
| 2007/0072874 A1 | 3/2007 | Cui et al. |
| 2007/0072885 A1 | 3/2007 | Bhattacharya et al. |
| 2007/0078435 A1 | 4/2007 | Stone et al. |
| 2007/0083224 A1 | 4/2007 | Hively |
| 2007/0083271 A1 | 4/2007 | Levine et al. |
| 2007/0088389 A1 | 4/2007 | Dunkin et al. |
| 2007/0100367 A1 | 5/2007 | Quijano et al. |
| 2007/0100368 A1 | 5/2007 | Quijano et al. |
| 2007/0104754 A1 | 5/2007 | Sterling et al. |
| 2007/0105861 A1 | 5/2007 | Lee et al. |
| 2007/0112020 A1 | 5/2007 | Vanotti et al. |
| 2007/0118158 A1 | 5/2007 | Deem et al. |
| 2007/0118159 A1 | 5/2007 | Deem et al. |
| 2007/0118168 A1 | 5/2007 | Lointier et al. |
| 2007/0135335 A1 | 6/2007 | Collier et al. |
| 2007/0135825 A1 | 6/2007 | Binmoeller |
| 2007/0135829 A1 | 6/2007 | Paganon |
| 2007/0135831 A1 | 6/2007 | Burnett |
| 2007/0148129 A1 | 6/2007 | Shortman et al. |
| 2007/0149994 A1 | 6/2007 | Sosnowski et al. |
| 2007/0156248 A1 | 7/2007 | Marco et al. |
| 2007/0167963 A1 | 7/2007 | Deem et al. |
| 2007/0173881 A1 | 7/2007 | Birk et al. |
| 2007/0178160 A1 | 8/2007 | Burnett |
| 2007/0185176 A1 | 8/2007 | Van et al. |
| 2007/0185540 A1 | 8/2007 | Ben-Haim et al. |
| 2007/0191344 A1 | 8/2007 | Choidas et al. |
| 2007/0198039 A1 | 8/2007 | Jones et al. |
| 2007/0198074 A1 | 8/2007 | Dann et al. |
| 2007/0207186 A1 | 9/2007 | Scanlon et al. |
| 2007/0210018 A1 | 9/2007 | Wallwiener et al. |
| 2007/0213740 A1 | 9/2007 | Deem et al. |
| 2007/0213748 A1 | 9/2007 | Deem et al. |
| 2007/0219570 A1 | 9/2007 | Deem et al. |
| 2007/0250083 A1 | 10/2007 | Deem et al. |
| 2007/0250132 A1 | 10/2007 | Burnett |
| 2007/0255379 A1 | 11/2007 | Williams et al. |
| 2007/0265598 A1 | 11/2007 | Karasik |
| 2007/0265709 A1 | 11/2007 | Rajan et al. |
| 2007/0275902 A1 | 11/2007 | Gonda et al. |
| 2007/0275962 A1 | 11/2007 | Koul et al. |
| 2007/0276428 A1 | 11/2007 | Haller et al. |
| 2007/0282349 A1 | 12/2007 | Deem et al. |
| 2007/0282452 A1 | 12/2007 | Weitzner et al. |
| 2007/0282453 A1 | 12/2007 | Weitzner et al. |
| 2007/0286856 A1 | 12/2007 | Brown et al. |
| 2007/0293716 A1 | 12/2007 | Baker et al. |
| 2007/0293885 A1 | 12/2007 | Binmoeller |
| 2007/0299320 A1 | 12/2007 | Policker et al. |
| 2008/0021742 A1 | 1/2008 | Dang |
| 2008/0026072 A1 | 1/2008 | Nakayama et al. |
| 2008/0027469 A1 | 1/2008 | Bachmann |
| 2008/0039463 A1 | 2/2008 | Nadeson et al. |
| 2008/0051849 A1 | 2/2008 | Ben-Haim et al. |
| 2008/0058887 A1 | 3/2008 | Griffin et al. |
| 2008/0058889 A1 | 3/2008 | Ben-Haim et al. |
| 2008/0058891 A1 | 3/2008 | Ben-Haim et al. |
| 2008/0059231 A1 | 3/2008 | Dang |
| 2008/0065136 A1 | 3/2008 | Young |
| 2008/0065421 A1 | 3/2008 | Dang |
| 2008/0071383 A1 | 3/2008 | Levine et al. |
| 2008/0090801 A1 | 4/2008 | Cheng et al. |
| 2008/0097466 A1 | 4/2008 | Levine et al. |
| 2008/0097513 A1 | 4/2008 | Kaji et al. |
| 2008/0097788 A1 | 4/2008 | Dang |
| 2008/0120734 A1 | 5/2008 | Kieffer et al. |
| 2008/0154129 A1 | 6/2008 | Mizunuma |
| 2008/0161838 A1 | 7/2008 | D et al. |
| 2008/0175828 A1 | 7/2008 | Freeman et al. |
| 2008/0187575 A1 | 8/2008 | Klebl et al. |
| 2008/0194574 A1 | 8/2008 | Eikhoff et al. |
| 2008/0194596 A1 | 8/2008 | Letrent |
| 2008/0195226 A1 | 8/2008 | Williams et al. |
| 2008/0207677 A1 | 8/2008 | Muller et al. |
| 2008/0208241 A1 | 8/2008 | Weiner et al. |
| 2008/0208355 A1 | 8/2008 | Stack et al. |
| 2008/0208356 A1 | 8/2008 | Stack et al. |
| 2008/0208357 A1 | 8/2008 | Melanson et al. |
| 2008/0214545 A1 | 9/2008 | Lee et al. |
| 2008/0221595 A1 | 9/2008 | Surti |
| 2008/0228030 A1 | 9/2008 | Godin |
| 2008/0228066 A1 | 9/2008 | Waitzman |
| 2008/0233163 A1 | 9/2008 | Assaf |
| 2008/0234718 A1 | 9/2008 | Paganon et al. |
| 2008/0234834 A1 | 9/2008 | Meade et al. |
| 2008/0243071 A1 | 10/2008 | Quijano et al. |
| 2008/0243166 A1 | 10/2008 | Paganon et al. |
| 2008/0243167 A1 | 10/2008 | Paganon et al. |
| 2008/0249533 A1 | 10/2008 | Godin |
| 2008/0249635 A1 | 10/2008 | Weitzner et al. |
| 2008/0255587 A1 | 10/2008 | Cully et al. |
| 2008/0255594 A1 | 10/2008 | Cully et al. |
| 2008/0255678 A1 | 10/2008 | Cully et al. |
| 2008/0260797 A1 | 10/2008 | Oh-Lee et al. |
| 2008/0261258 A1 | 10/2008 | Smith et al. |
| 2008/0262529 A1 | 10/2008 | Jacques |
| 2008/0269289 A1 | 10/2008 | Frank et al. |
| 2008/0269555 A1 | 10/2008 | Paganon et al. |
| 2008/0281257 A1 | 11/2008 | Waller |
| 2008/0281375 A1 | 11/2008 | Chen |
| 2008/0293618 A1 | 11/2008 | Heiser et al. |
| 2008/0293733 A1 | 11/2008 | Bearss et al. |
| 2008/0300234 A1 | 12/2008 | Kath et al. |
| 2008/0302855 A1 | 12/2008 | Bilotti et al. |
| 2008/0319471 A1 | 12/2008 | Sosnowski et al. |
| 2009/0005867 A1 | 1/2009 | Lefranc et al. |
| 2009/0012544 A1 | 1/2009 | Thompson et al. |
| 2009/0042785 A1 | 2/2009 | Matschiner et al. |
| 2009/0048313 A1 | 2/2009 | Dickson et al. |
| 2009/0053182 A1 | 2/2009 | Ichim et al. |
| 2009/0054395 A1 | 2/2009 | Luzzio et al. |
| 2009/0062401 A1 | 3/2009 | Odermatt et al. |
| 2009/0088676 A1 | 4/2009 | Murata |
| 2009/0093839 A1 | 4/2009 | Kelleher |
| 2009/0105562 A1 | 4/2009 | Chiou et al. |
| 2009/0111805 A1 | 4/2009 | Morris et al. |
| 2009/0138094 A1 | 5/2009 | Schurr |
| 2009/0142413 A1 | 6/2009 | Allen et al. |
| 2009/0149849 A1 | 6/2009 | Lin et al. |
| 2009/0156590 A1 | 6/2009 | Frank et al. |
| 2009/0164028 A1 | 6/2009 | Chen |
| 2009/0171383 A1 | 7/2009 | Cole et al. |
| 2009/0178153 A1 | 7/2009 | Gaitanaris et al. |
| 2009/0182303 A1 | 7/2009 | Walak et al. |
| 2009/0182424 A1 | 7/2009 | Marco et al. |
| 2009/0187197 A1 | 7/2009 | Roeber et al. |
| 2009/0187200 A1 | 7/2009 | Burnett et al. |
| 2009/0187201 A1 | 7/2009 | Burnett et al. |
| 2009/0196912 A1 | 8/2009 | Eickhoff et al. |
| 2009/0198254 A1 | 8/2009 | Laufer et al. |
| 2009/0214474 A1 | 8/2009 | Jennings |
| 2009/0216262 A1 | 8/2009 | Burnett et al. |
| 2009/0217401 A1 | 8/2009 | Korman et al. |
| 2009/0226907 A1 | 9/2009 | Nice et al. |
| 2009/0227641 A1 | 9/2009 | Bhattacharya et al. |
| 2009/0259240 A1 | 10/2009 | Graham et al. |
| 2009/0264345 A1 | 10/2009 | McAlpine et al. |
| 2009/0275511 A1 | 11/2009 | Dong |
| 2009/0276055 A1 | 11/2009 | Harris et al. |
| 2009/0287231 A1 | 11/2009 | Brooks et al. |
| 2009/0299486 A1 | 12/2009 | Shohat et al. |
| 2009/0299487 A1 | 12/2009 | Stack et al. |
| 2009/0306186 A1 | 12/2009 | Jackson et al. |
| 2009/0317374 A1 | 12/2009 | Park et al. |
| 2010/0004239 A1 | 1/2010 | Tang et al. |
| 2010/0016353 A1 | 1/2010 | Henne et al. |
| 2010/0029615 A1 | 2/2010 | Munchhof et al. |
| 2010/0036481 A1 | 2/2010 | Dubrul et al. |
| 2010/0048471 A1 | 2/2010 | Kim |
| 2010/0049224 A1 | 2/2010 | Vargas |
| 2010/0068177 A1 | 3/2010 | Faustman |
| 2010/0114150 A1 | 5/2010 | Magal |

(56) References Cited

U.S. PATENT DOCUMENTS

| | | |
|---|---|---|
| 2010/0121371 A1 | 5/2010 | Brooks et al. |
| 2010/0136114 A1 | 6/2010 | Mao |
| 2010/0137279 A1 | 6/2010 | Cheng et al. |
| 2010/0145301 A1 | 6/2010 | Magal |
| 2010/0150893 A1 | 6/2010 | Faustman |
| 2010/0152765 A1 | 6/2010 | Haley |
| 2010/0158896 A1 | 6/2010 | Brown et al. |
| 2010/0158902 A1 | 6/2010 | Pogue et al. |
| 2010/0168563 A1 | 7/2010 | Braver |
| 2010/0179584 A1 | 7/2010 | Carpenter et al. |
| 2010/0190782 A1 | 7/2010 | Baell et al. |
| 2010/0204093 A1 | 8/2010 | Kaushal et al. |
| 2010/0204221 A1 | 8/2010 | Vankayalapati et al. |
| 2010/0204688 A1 | 8/2010 | Hoey et al. |
| 2010/0209488 A1 | 8/2010 | Wrasidlo et al. |
| 2010/0210622 A1 | 8/2010 | Baell et al. |
| 2010/0221233 A1 | 9/2010 | Borlongan et al. |
| 2010/0222381 A1 | 9/2010 | Vankayalapati et al. |
| 2010/0234435 A1 | 9/2010 | Bhattacharya et al. |
| 2010/0234886 A1 | 9/2010 | Godin |
| 2010/0235197 A1 | 9/2010 | Dang |
| 2010/0247691 A1 | 9/2010 | Kim |
| 2010/0249822 A1 | 9/2010 | Nihalani |
| 2010/0249825 A1 | 9/2010 | Nihalani |
| 2010/0255087 A1 | 10/2010 | Coulter |
| 2010/0256654 A1 | 10/2010 | Pasricha |
| 2010/0256775 A1 | 10/2010 | Belhe et al. |
| 2010/0261162 A1 | 10/2010 | Nice et al. |
| 2010/0266675 A1 | 10/2010 | Gerwick et al. |
| 2010/0268260 A1 | 10/2010 | Riina et al. |
| 2010/0286628 A1 | 11/2010 | Gross |
| 2010/0286660 A1 | 11/2010 | Gross |
| 2010/0298631 A1 | 11/2010 | Stack et al. |
| 2010/0298741 A1 | 11/2010 | Gross et al. |
| 2010/0305590 A1 | 12/2010 | Holmes et al. |
| 2010/0324572 A1 | 12/2010 | Needleman et al. |
| 2010/0324928 A1 | 12/2010 | Dang |
| 2011/0004146 A1 | 1/2011 | Priplata et al. |
| 2011/0004320 A1 | 1/2011 | Priplata et al. |
| 2011/0009801 A1 | 1/2011 | Blaeser et al. |
| 2011/0040230 A1 | 2/2011 | Laufer |
| 2011/0040232 A1 | 2/2011 | Magal |
| 2011/0066175 A1 | 3/2011 | Gross |
| 2011/0068143 A1 | 3/2011 | Laufer et al. |
| 2011/0082535 A1 | 4/2011 | Shin et al. |
| 2011/0087146 A1* | 4/2011 | Ryan ............... A61F 2/04 604/8 |
| 2011/0092482 A1 | 4/2011 | Nadeson et al. |
| 2011/0097280 A1 | 4/2011 | Dees et al. |
| 2011/0098730 A1 | 4/2011 | Kelleher |
| 2011/0118650 A1 | 5/2011 | Nihalani |
| 2011/0124643 A1 | 5/2011 | Bellevergue et al. |
| 2011/0125211 A1 | 5/2011 | Griffin et al. |
| 2011/0130775 A1 | 6/2011 | Tacchino et al. |
| 2011/0136809 A1 | 6/2011 | Lee et al. |
| 2011/0137428 A1 | 6/2011 | Terliuc |
| 2011/0142905 A1 | 6/2011 | Bar-Shalom et al. |
| 2011/0152608 A1 | 6/2011 | Bachmann et al. |
| 2011/0152899 A1 | 6/2011 | Deem et al. |
| 2011/0166120 A1 | 7/2011 | Luzzio et al. |
| 2011/0172585 A1 | 7/2011 | Weitzner et al. |
| 2011/0185439 A1 | 7/2011 | Gaitanaris et al. |
| 2011/0190905 A1 | 8/2011 | Behan |
| 2011/0206760 A1 | 8/2011 | Kliger et al. |
| 2011/0213469 A1 | 9/2011 | Chin et al. |
| 2011/0214189 A1 | 9/2011 | Gaitanaris et al. |
| 2011/0218143 A1 | 9/2011 | Kaushal et al. |
| 2011/0218563 A1 | 9/2011 | Brooks et al. |
| 2011/0245752 A1 | 10/2011 | Levine et al. |
| 2011/0256123 A1 | 10/2011 | Ilan et al. |
| 2011/0257580 A1 | 10/2011 | Meade et al. |
| 2011/0263504 A1 | 10/2011 | Cerami et al. |
| 2011/0269772 A1 | 11/2011 | Bearss et al. |
| 2011/0270405 A1 | 11/2011 | Geitz et al. |
| 2011/0270410 A1 | 11/2011 | Stack et al. |
| 2011/0275891 A1 | 11/2011 | Shemi |
| 2011/0276091 A1 | 11/2011 | Melanson et al. |
| 2011/0288080 A1 | 11/2011 | Saulnier et al. |
| 2011/0295054 A1 | 12/2011 | Aldridge et al. |
| 2011/0295055 A1 | 12/2011 | Albrecht et al. |
| 2011/0295151 A1 | 12/2011 | Bakos et al. |
| 2011/0295286 A1 | 12/2011 | Harris et al. |
| 2011/0301156 A1 | 12/2011 | Frank et al. |
| 2011/0301353 A1 | 12/2011 | Tang et al. |
| 2011/0307075 A1 | 12/2011 | Sharma |
| 2011/0320219 A1 | 12/2011 | Dang |
| 2012/0003204 A1 | 1/2012 | Park et al. |
| 2012/0003634 A1 | 1/2012 | Frumkin et al. |
| 2012/0004676 A1 | 1/2012 | Vargas |
| 2012/0029550 A1 | 2/2012 | Forsell |
| 2012/0029635 A1 | 2/2012 | Schoenhoeffer et al. |
| 2012/0041465 A1 | 2/2012 | Shalon |
| 2012/0046718 A1 | 2/2012 | Singh |
| 2012/0058107 A1 | 3/2012 | Tang et al. |
| 2012/0059431 A1 | 3/2012 | Williams et al. |
| 2012/0065571 A1 | 3/2012 | Thompson et al. |
| 2012/0083819 A1 | 4/2012 | Wang et al. |
| 2012/0087910 A1 | 4/2012 | Trieu et al. |
| 2012/0088300 A1 | 4/2012 | Melton et al. |
| 2012/0088967 A1 | 4/2012 | Laufer et al. |
| 2012/0089170 A1 | 4/2012 | Dominguez |
| 2012/0095384 A1 | 4/2012 | Babkes et al. |
| 2012/0095385 A1 | 4/2012 | Dominguez et al. |
| 2012/0095483 A1 | 4/2012 | Babkes et al. |
| 2012/0095494 A1 | 4/2012 | Dominguez et al. |
| 2012/0095495 A1 | 4/2012 | Babkes et al. |
| 2012/0095497 A1 | 4/2012 | Babkes et al. |
| 2012/0108590 A1 | 5/2012 | Birtalan et al. |
| 2012/0110682 A1 | 5/2012 | Mather et al. |
| 2012/0116285 A1* | 5/2012 | Duggirala ............. A61F 5/0079 604/8 |
| 2012/0116286 A1 | 5/2012 | Williams et al. |
| 2012/0121594 A1 | 5/2012 | Smith |
| 2012/0142760 A1 | 6/2012 | Kieffer et al. |
| 2012/0148540 A1 | 6/2012 | Freeman et al. |
| 2012/0157470 A1 | 6/2012 | Catron et al. |
| 2012/0157495 A1 | 6/2012 | Munchhof et al. |
| 2012/0158026 A1 | 6/2012 | Behan |
| 2012/0179086 A1 | 7/2012 | Shank et al. |
| 2012/0184541 A1 | 7/2012 | Baell et al. |
| 2012/0184893 A1 | 7/2012 | Thompson et al. |
| 2012/0184967 A1 | 7/2012 | Levine et al. |
| 2012/0208786 A1 | 8/2012 | Lyles et al. |
| 2012/0209400 A1 | 8/2012 | Schurr |
| 2012/0213731 A1 | 8/2012 | Faustman |
| 2012/0214848 A1 | 8/2012 | Zhang et al. |
| 2012/0215152 A1 | 8/2012 | Levine et al. |
| 2012/0232460 A1 | 9/2012 | Raven et al. |
| 2012/0232577 A1 | 9/2012 | Birk et al. |
| 2012/0245087 A1 | 9/2012 | Jackson et al. |
| 2012/0245553 A1 | 9/2012 | Raven et al. |
| 2012/0253259 A1 | 10/2012 | Belhe et al. |
| 2012/0253260 A1 | 10/2012 | Belhe et al. |
| 2012/0253529 A1 | 10/2012 | Carlson et al. |
| 2012/0258126 A1 | 10/2012 | Schoeller et al. |
| 2012/0263781 A1 | 10/2012 | Chancellor et al. |
| 2012/0271217 A1 | 10/2012 | Stack et al. |
| 2012/0277210 A1 | 11/2012 | Catron et al. |
| 2012/0277271 A1 | 11/2012 | Nadeson et al. |
| 2012/0296365 A1 | 11/2012 | Nguyen |
| 2012/0301475 A1 | 11/2012 | Shemesh et al. |
| 2012/0302602 A1 | 11/2012 | Frank et al. |
| 2012/0309775 A1 | 12/2012 | Cheng et al. |
| 2013/0005724 A1 | 1/2013 | Lassalle et al. |
| 2013/0005964 A1 | 1/2013 | Luzzio et al. |
| 2013/0006382 A1 | 1/2013 | Behan |
| 2013/0006672 A1 | 1/2013 | Dang |
| 2013/0011332 A1 | 1/2013 | Boyden et al. |
| 2013/0013084 A1 | 1/2013 | Birk |
| 2013/0030350 A1 | 1/2013 | Albrecht et al. |
| 2013/0030351 A1 | 1/2013 | Belhe et al. |
| 2013/0034844 A1 | 2/2013 | Boyle et al. |
| 2013/0035576 A1 | 2/2013 | O'Grady et al. |
| 2013/0041424 A1 | 2/2013 | Neisz |

(56) References Cited

U.S. PATENT DOCUMENTS

| | | |
|---|---|---|
| 2013/0071466 A1 | 3/2013 | Chancellor et al. |
| 2013/0079329 A1 | 3/2013 | Hood et al. |
| 2013/0079345 A1 | 3/2013 | Eickhoff et al. |
| 2013/0079603 A1 | 3/2013 | Vargas |
| 2013/0133091 A1 | 5/2013 | Korman et al. |
| 2013/0156726 A1 | 6/2013 | Ichim et al. |
| 2013/0164371 A1 | 6/2013 | Imran |
| 2013/0164372 A1 | 6/2013 | Imran |
| 2013/0164373 A1 | 6/2013 | Imran |
| 2013/0165372 A1 | 6/2013 | Imran |
| 2013/0165373 A1 | 6/2013 | Imran |
| 2013/0165772 A1 | 6/2013 | Traverso et al. |
| 2013/0165859 A1 | 6/2013 | Imran |
| 2013/0171244 A1 | 7/2013 | Imran |
| 2013/0171245 A1 | 7/2013 | Imran |
| 2013/0171246 A1 | 7/2013 | Imran |
| 2013/0171247 A1 | 7/2013 | Imran |
| 2013/0172257 A1 | 7/2013 | Imran |
| 2013/0177527 A1 | 7/2013 | Imran |
| 2013/0177550 A1 | 7/2013 | Imran |
| 2013/0178472 A1 | 7/2013 | Bellevergue et al. |
| 2013/0189240 A1 | 7/2013 | Cho et al. |
| 2013/0189353 A1 | 7/2013 | Imran |
| 2013/0190675 A1 | 7/2013 | Sandoski |
| 2013/0195970 A1 | 8/2013 | Imran |
| 2013/0197421 A1 | 8/2013 | Sharvit et al. |
| 2013/0204208 A1 | 8/2013 | Olson et al. |
| 2013/0210800 A1 | 8/2013 | Nair et al. |
| 2013/0218289 A1 | 8/2013 | Gao et al. |
| 2013/0245068 A1 | 9/2013 | Kwon et al. |
| 2013/0247233 A1 | 9/2013 | Gaitanaris et al. |
| 2013/0253408 A1 | 9/2013 | Krueger et al. |
| 2013/0273061 A1 | 10/2013 | Huang et al. |
| 2013/0274659 A1 | 10/2013 | Imran et al. |
| 2013/0274789 A1 | 10/2013 | Brooks et al. |
| 2013/0281911 A1 | 10/2013 | Babkes et al. |
| 2013/0289139 A1 | 10/2013 | Radford et al. |
| 2013/0289466 A1 | 10/2013 | Babkes et al. |
| 2013/0296764 A1 | 11/2013 | Stack et al. |
| 2013/0296913 A1 | 11/2013 | Foote et al. |
| 2013/0310727 A1 | 11/2013 | Stack et al. |
| 2013/0310833 A1 | 11/2013 | Brown et al. |
| 2013/0324902 A1 | 12/2013 | Miller et al. |
| 2013/0324906 A1 | 12/2013 | Neisz et al. |
| 2013/0324907 A1 | 12/2013 | Huntley et al. |
| 2013/0331359 A1 | 12/2013 | Yun et al. |
| 2013/0331383 A1 | 12/2013 | Saulnier et al. |
| 2013/0331759 A1 | 12/2013 | Neisz et al. |
| 2013/0337563 A1 | 12/2013 | Phan et al. |
| 2013/0338741 A1 | 12/2013 | Singh |
| 2013/0344173 A1 | 12/2013 | Fogelman et al. |
| 2013/0345670 A1 | 12/2013 | Rajagopalan et al. |
| 2014/0004175 A1 | 1/2014 | Kliger et al. |
| 2014/0005190 A1 | 1/2014 | Baell et al. |
| 2014/0018719 A1 | 1/2014 | Chamorro et al. |
| 2014/0024114 A1 | 1/2014 | Melton et al. |
| 2014/0024991 A1 | 1/2014 | Chin |
| 2014/0039250 A1 | 2/2014 | Bachmann et al. |
| 2014/0044641 A1 | 2/2014 | Toporik et al. |
| 2014/0044736 A1 | 2/2014 | Hammers |
| 2014/0045815 A1 | 2/2014 | Hood et al. |
| 2014/0051645 A1 | 2/2014 | Matschiner et al. |
| 2014/0081416 A1 | 3/2014 | Clerc et al. |
| 2014/0094734 A1 | 4/2014 | Stack et al. |
| 2014/0121585 A1 | 5/2014 | Baker et al. |
| 2014/0142720 A1 | 5/2014 | Stack et al. |
| 2014/0180188 A1 | 6/2014 | Chin et al. |
| 2014/0180192 A1 | 6/2014 | Ortiz et al. |
| 2014/0194806 A1 | 7/2014 | Belhe et al. |
| 2014/0194917 A1 | 7/2014 | Sharma |
| 2014/0200502 A1 | 7/2014 | Belhe et al. |
| 2014/0213960 A1 | 7/2014 | Belhe et al. |
| 2014/0221899 A1 | 8/2014 | Vargas |
| 2014/0236064 A1* | 8/2014 | Binmoeller ........... A61F 5/0076 604/8 |
| 2014/0243992 A1 | 8/2014 | Walsh et al. |
| 2014/0276336 A1 | 9/2014 | Sharma |
| 2014/0277345 A1 | 9/2014 | Havel et al. |
| 2015/0196412 A1 | 7/2015 | Roselauf et al. |
| 2015/0196419 A1 | 7/2015 | Roselauf et al. |
| 2016/0095733 A1 | 4/2016 | Sharma et al. |
| 2017/0312111 A1 | 11/2017 | Sharma et al. |
| 2018/0263803 A1 | 9/2018 | Sharma et al. |
| 2019/0365552 A1 | 12/2019 | Sharma |
| 2020/0015990 A1 | 1/2020 | Sharma et al. |
| 2020/0206006 A1 | 7/2020 | Sharma |
| 2021/0015645 A1 | 1/2021 | Sharma et al. |
| 2022/0000648 A1 | 1/2022 | Sharma et al. |

FOREIGN PATENT DOCUMENTS

| | | |
|---|---|---|
| AU | 2012211067 A1 | 8/2013 |
| AU | 2010232570 B2 | 11/2013 |
| AU | 2014200766 A1 | 3/2014 |
| AU | 2012315575 A1 | 4/2014 |
| CA | 2756991 A1 | 10/2010 |
| CN | 1575155 A | 2/2005 |
| CN | 1713870 A | 12/2005 |
| CN | 2756991 Y | 2/2006 |
| CN | 102014763 A | 4/2011 |
| CN | 102387762 A | 3/2012 |
| CN | 102470038 A | 5/2012 |
| CN | 102551938 A | 7/2012 |
| CN | 102824239 A | 12/2012 |
| CN | 103635212 A | 3/2014 |
| CN | 105263439 A | 1/2016 |
| EP | 0278937 B1 | 10/1993 |
| EP | 0480667 B1 | 3/1996 |
| EP | 0774571 A1 | 5/1997 |
| EP | 0754017 B1 | 6/2002 |
| EP | 0843538 B1 | 6/2002 |
| EP | 1420730 A2 | 5/2004 |
| EP | 1492477 A1 | 1/2005 |
| EP | 1492478 A1 | 1/2005 |
| EP | 2451411 A2 | 5/2012 |
| EP | 2512386 A1 | 10/2012 |
| EP | 2521513 A1 | 11/2012 |
| EP | 2667910 A2 | 12/2013 |
| EP | 2413849 B1 | 7/2014 |
| EP | 2760502 A1 | 8/2014 |
| JP | 04-212348 A | 8/1992 |
| JP | 2005-500127 A | 1/2005 |
| JP | 2010-523262 A | 7/2010 |
| JP | 2011-152425 A | 8/2011 |
| JP | 2012-501812 A | 1/2012 |
| JP | 2012-522595 A | 9/2012 |
| JP | 2015-534887 A | 12/2015 |
| JP | 6725691 B2 | 7/2020 |
| KR | 10-1065368 B1 | 9/2011 |
| KR | 2012-0008492 A | 1/2012 |
| WO | 88/00027 A1 | 1/1988 |
| WO | 91/01117 A1 | 2/1991 |
| WO | 94/01165 A1 | 1/1994 |
| WO | 00/12027 A1 | 3/2000 |
| WO | 00/32137 A1 | 6/2000 |
| WO | 00/42949 A2 | 7/2000 |
| WO | 01/45485 A2 | 6/2001 |
| WO | 01/49359 A1 | 7/2001 |
| WO | 02/96327 A2 | 12/2002 |
| WO | 03/17882 A2 | 3/2003 |
| WO | 03/86246 A1 | 10/2003 |
| WO | 03/86247 A1 | 10/2003 |
| WO | 03/86360 A1 | 10/2003 |
| WO | 03/94784 A2 | 11/2003 |
| WO | 03/94785 A1 | 11/2003 |
| WO | 2004/049982 A2 | 6/2004 |
| WO | 2004/064680 A1 | 8/2004 |
| WO | 2004/064685 A1 | 8/2004 |
| WO | 2004/069331 A2 | 8/2004 |
| WO | 2004/069332 A1 | 8/2004 |
| WO | 2004/087014 A2 | 10/2004 |
| WO | 2004/087233 A2 | 10/2004 |
| WO | 2006/064503 A2 | 6/2006 |
| WO | 2007/007339 A2 | 1/2007 |

(56) References Cited

FOREIGN PATENT DOCUMENTS

| WO | 2007/072469 | A2 | 6/2007 |
|---|---|---|---|
| WO | 2008/023374 | A2 | 2/2008 |
| WO | 2008/112894 | A1 | 9/2008 |
| WO | 2008/121409 | A1 | 10/2008 |
| WO | 2008/121831 | A1 | 10/2008 |
| WO | 2008/154450 | A1 | 12/2008 |
| WO | 2010/115011 | A1 | 10/2010 |
| WO | 2010/128495 | A1 | 11/2010 |
| WO | 2011/006098 | A2 | 1/2011 |
| WO | 2011/073970 | A1 | 6/2011 |
| WO | 2011/085234 | A1 | 7/2011 |
| WO | 2011/159271 | A1 | 12/2011 |
| WO | 2012/068377 | A1 | 5/2012 |
| WO | 2012/103531 | A2 | 8/2012 |
| WO | 2013/049779 | A1 | 4/2013 |
| WO | 2014/113483 | A1 | 7/2014 |
| WO | 2014/153267 | A2 | 9/2014 |
| WO | 2015/071496 | A1 | 5/2015 |
| WO | 2015/200554 | A1 | 12/2015 |
| WO | 2016/049149 | A2 | 3/2016 |
| WO | 2017/013266 | A1 | 1/2017 |
| WO | 2017/132676 | A1 | 8/2017 |
| WO | 2017/189682 | A1 | 11/2017 |

OTHER PUBLICATIONS

International Preliminary Report on Patentability received for PCT Patent Application No. PCT/US2014/029846, dated Sep. 24, 2015, 16 pages.
International Preliminary Report on Patentability received for PCT Patent Application No. PCT/US2015/051668, dated Apr. 6, 2017, 10 pages.
International Preliminary Report on Patentability received for PCT Patent Application No. PCT/US2016/028509, dated Apr. 5, 2018, 7 pages.
International Preliminary Report on Patentability received for PCT Patent Application No. PCT/US2017/029571, dated Nov. 8, 2018, 12 pages.
International Search Report—Application No. PCT/US2017/029571 dated Sep. 11, 2017.
International Search Report and Written Opinion received for PCT Patent Application No. PCT/US2016/028509, dated Aug. 12, 2016, 8 pages.
International Search Report for PCT/US2014/029846, dated Apr. 2, 2015.
International Search Report for PCT/US2015/051668, dated Apr. 19, 2016.
International Written Opinion received for PCT Patent Application No. PCT/US2014/029846, dated Apr. 2, 2015, 14 pages.
International Written Opinion received for PCT Patent Application No. PCT/US2015/051668, dated Apr. 19, 2016, 8 pages.
International Written Opinion received for PCT Patent Application No. PCT/US2017/029571, dated Sep. 11, 2017, 10 pages.
Klausner et al., "Expandable gastroretentive dosage forms", Journal of Controlled Release 90:143-162 (2003).
Sun et al., "Intestinal electric stimulation decreases fat absorption in rats: Therapeutic potential for obesity", Obes Res. Aug. 2004; 12(8):1235-42.

* cited by examiner

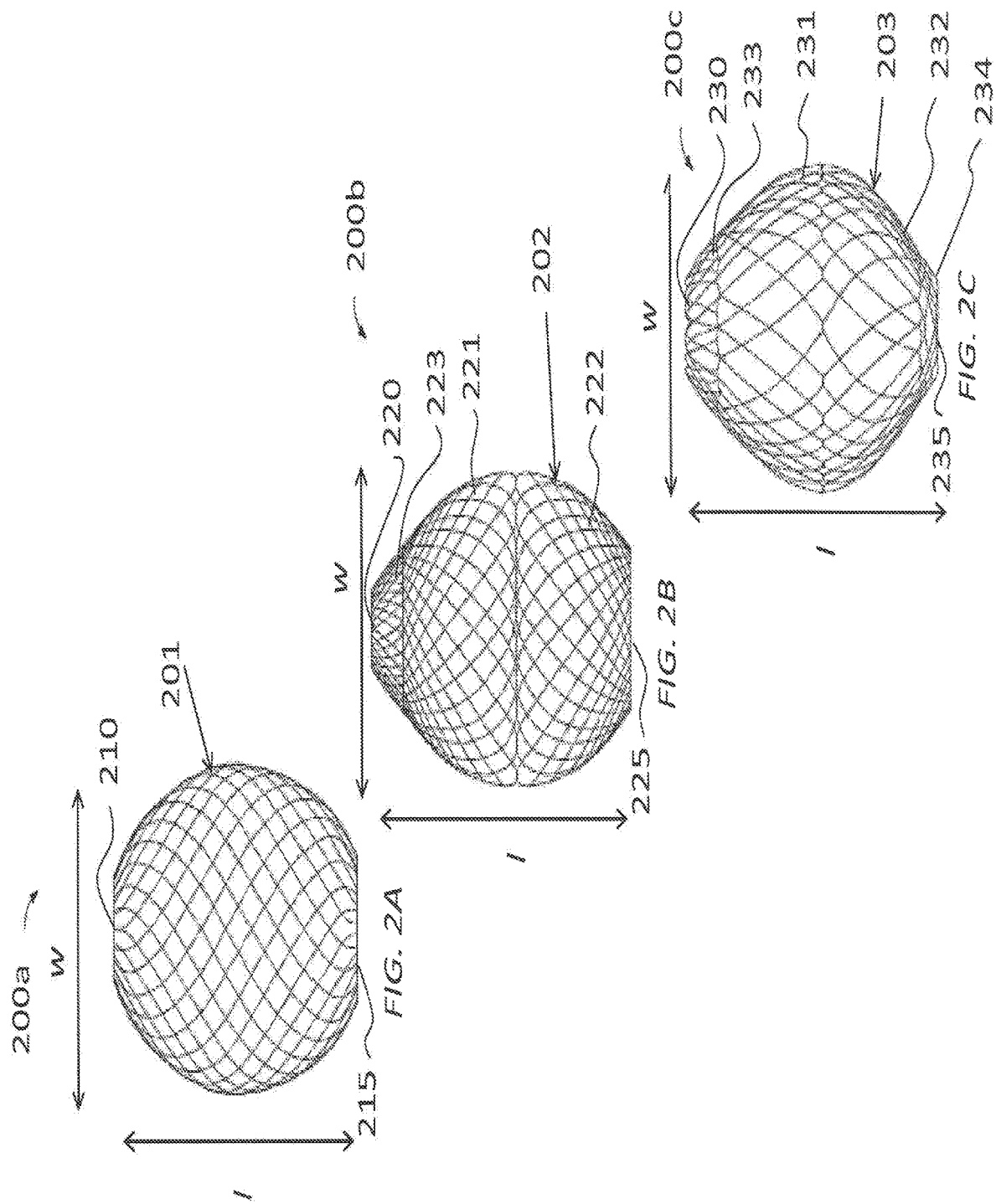

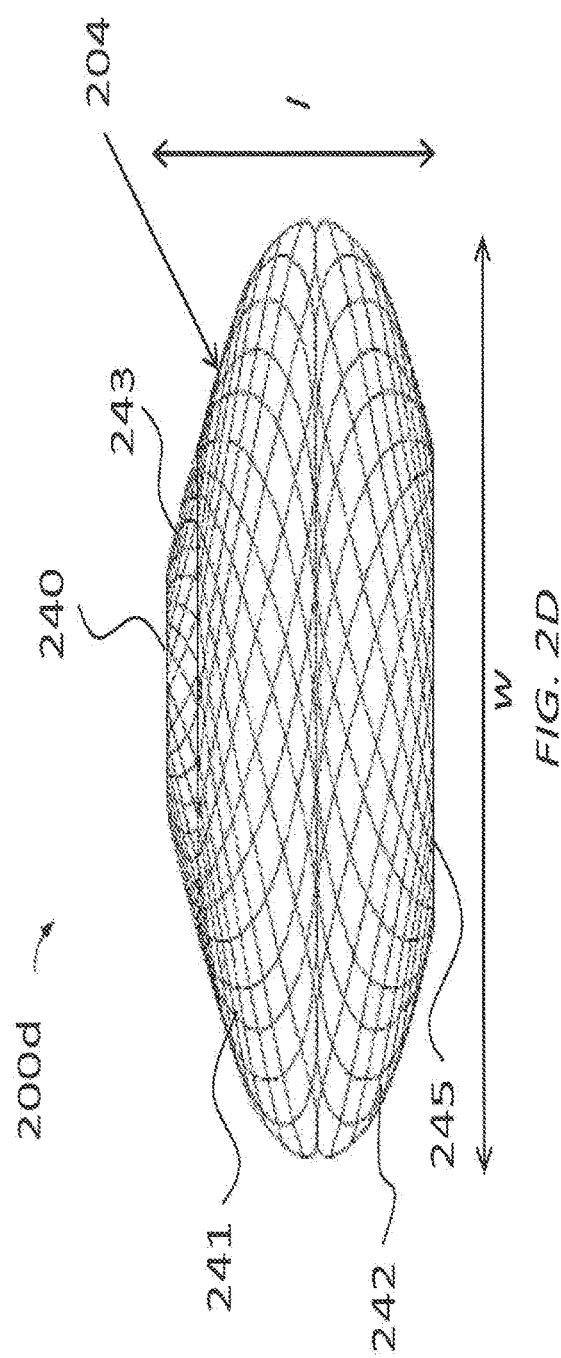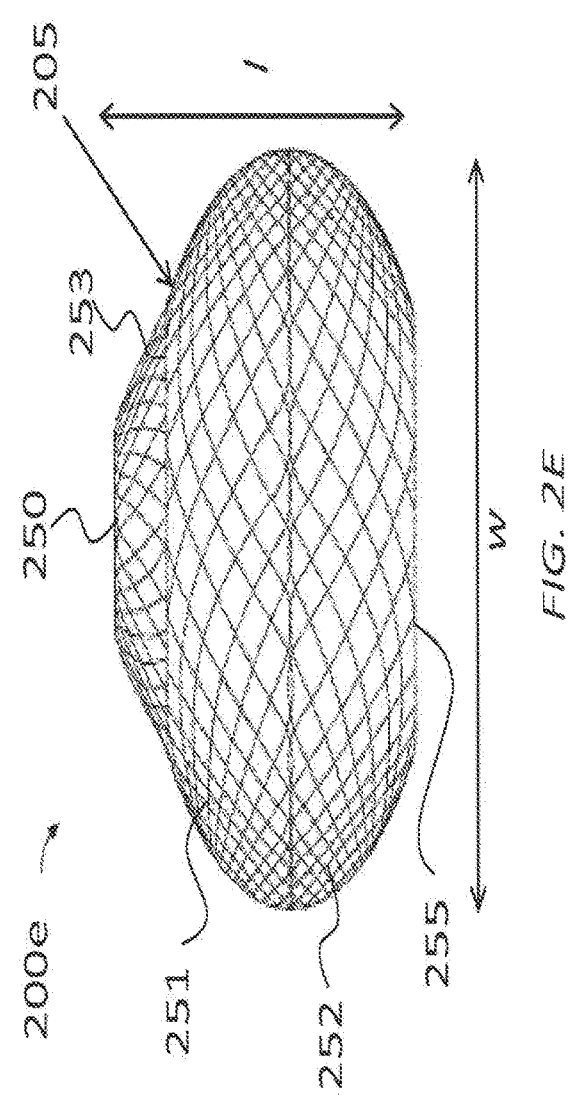

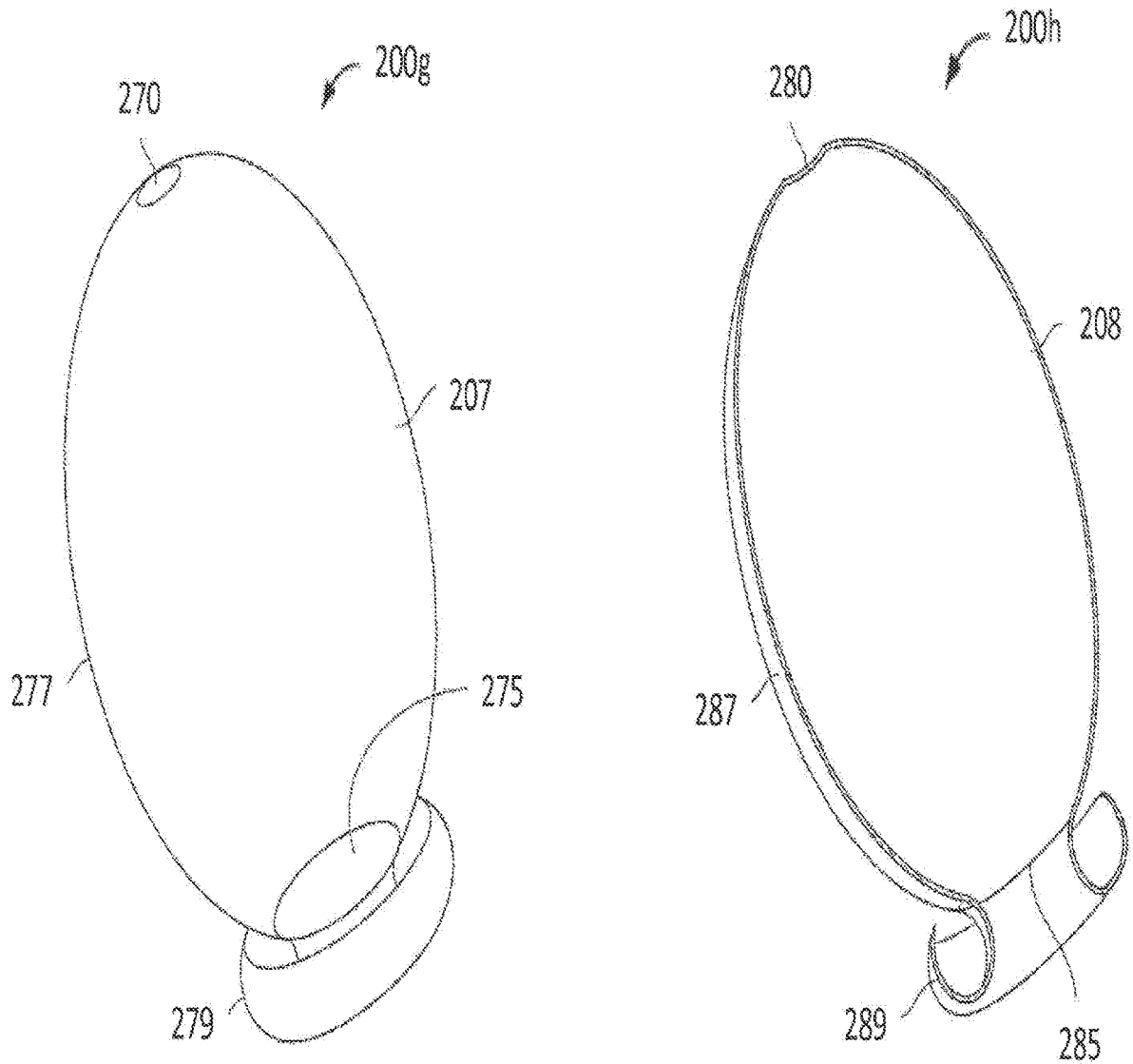

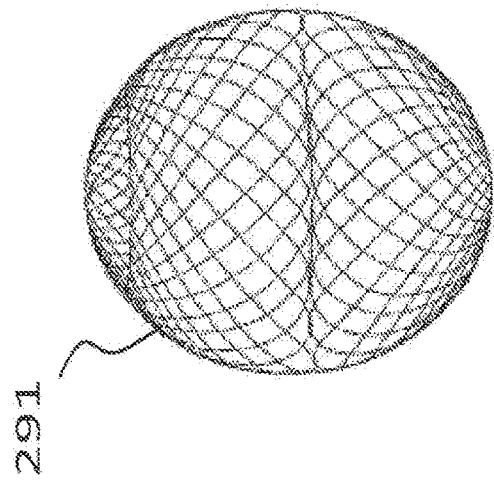
*FIG. 2Q*
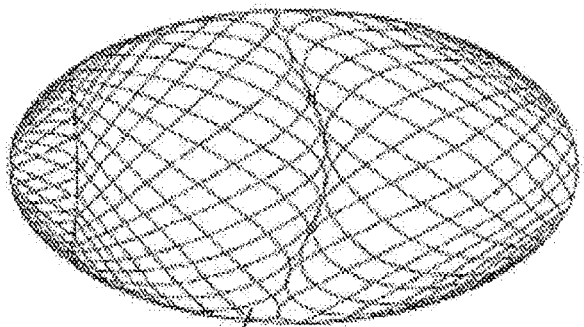
*FIG. 2R*
*FIG. 2S*
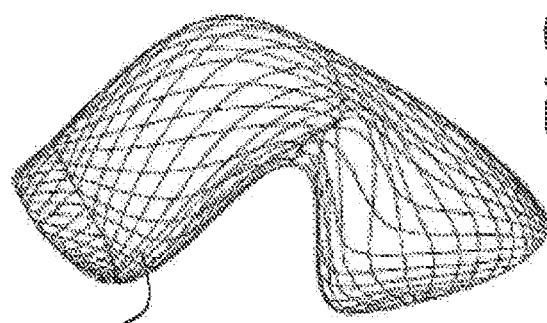
*FIG. 2T*
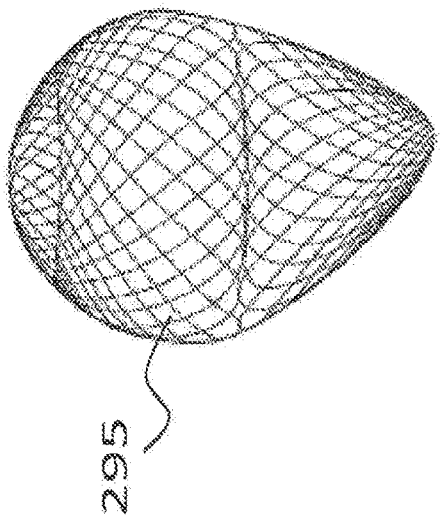
*FIG. 2U*
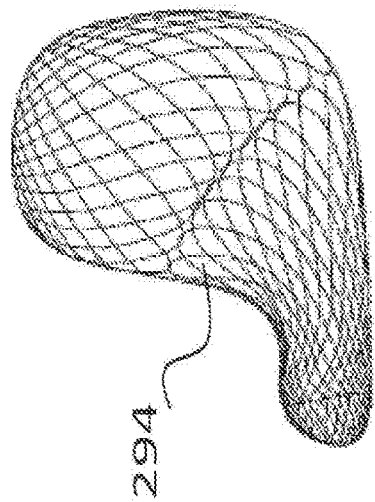

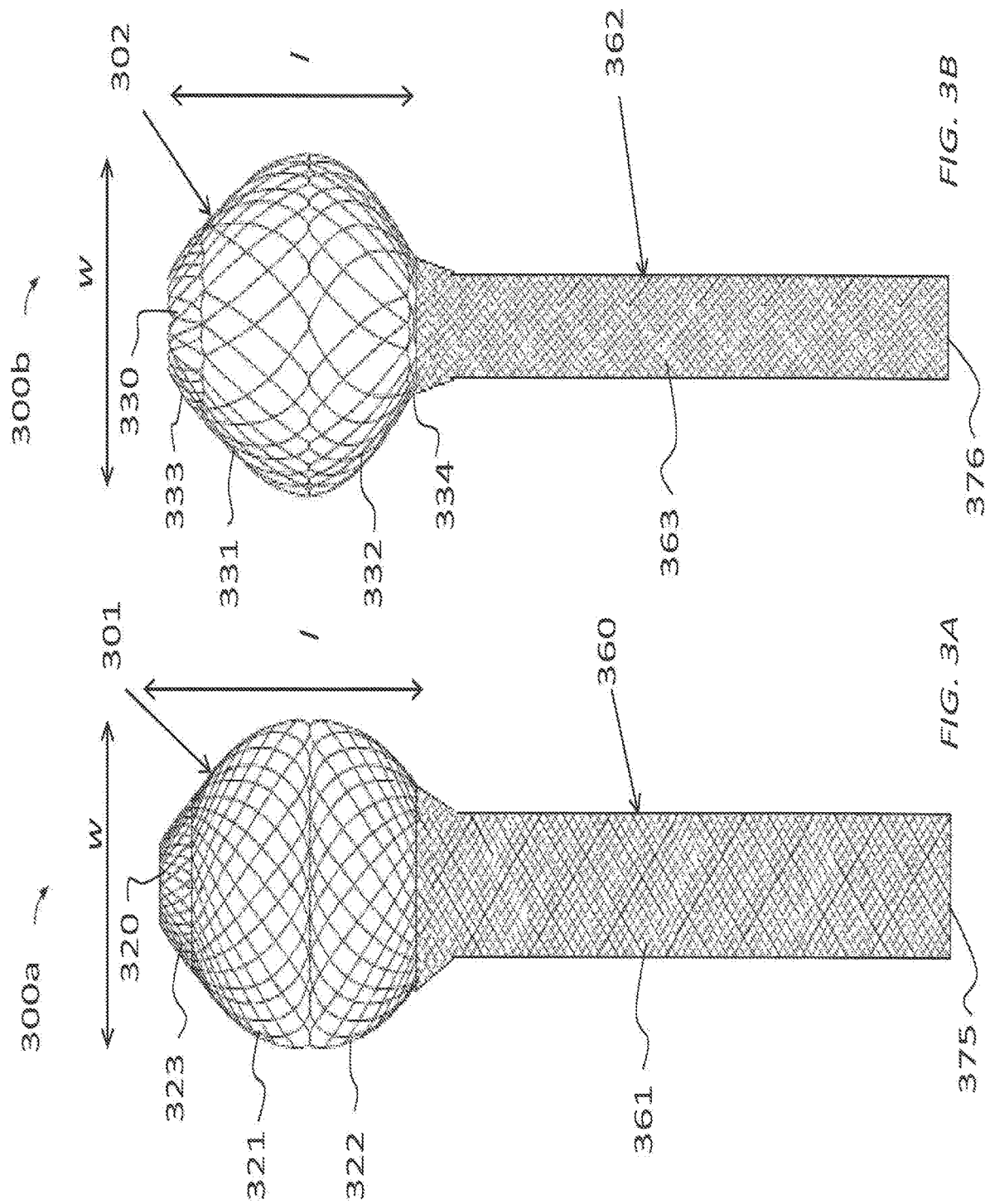

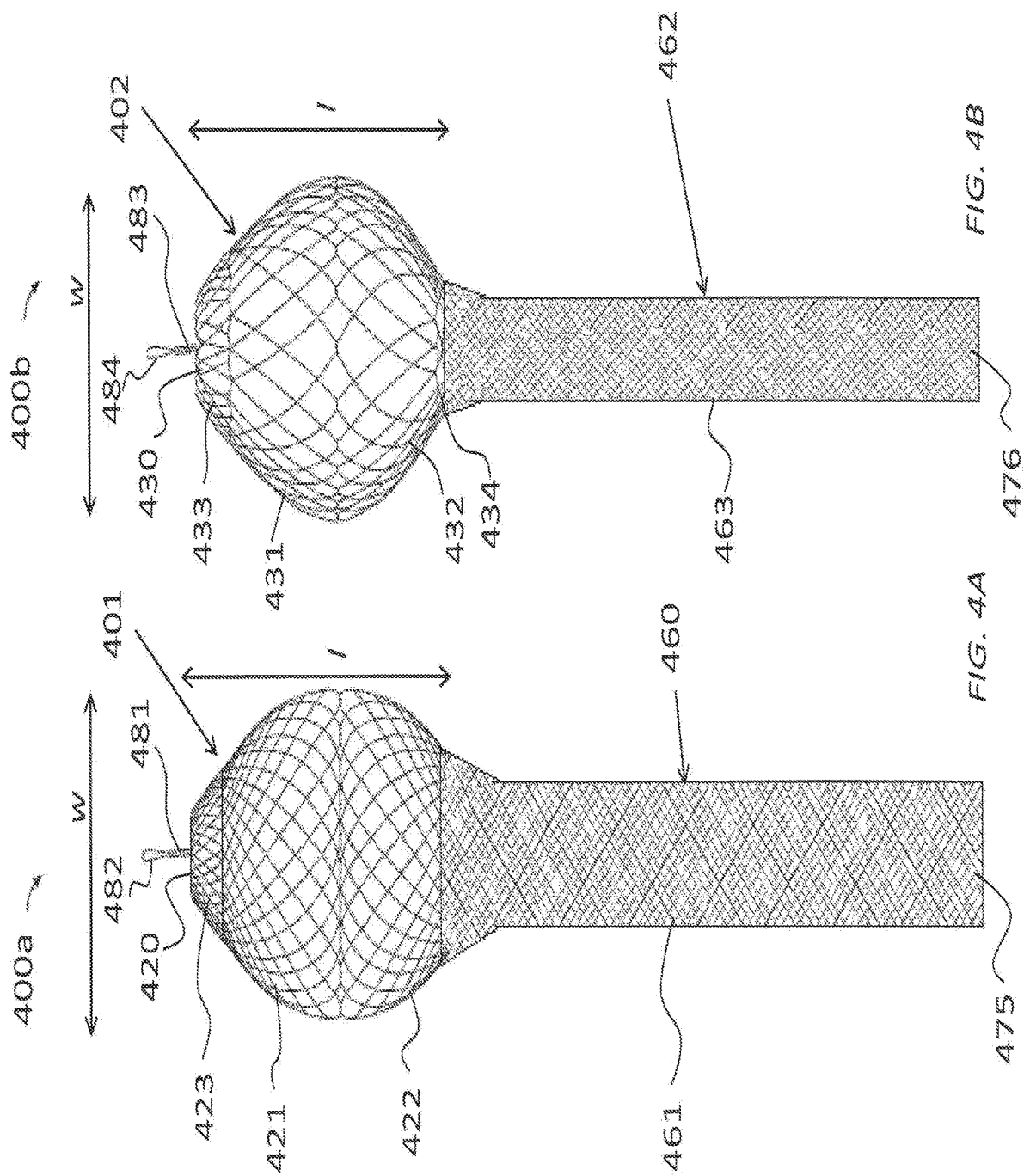

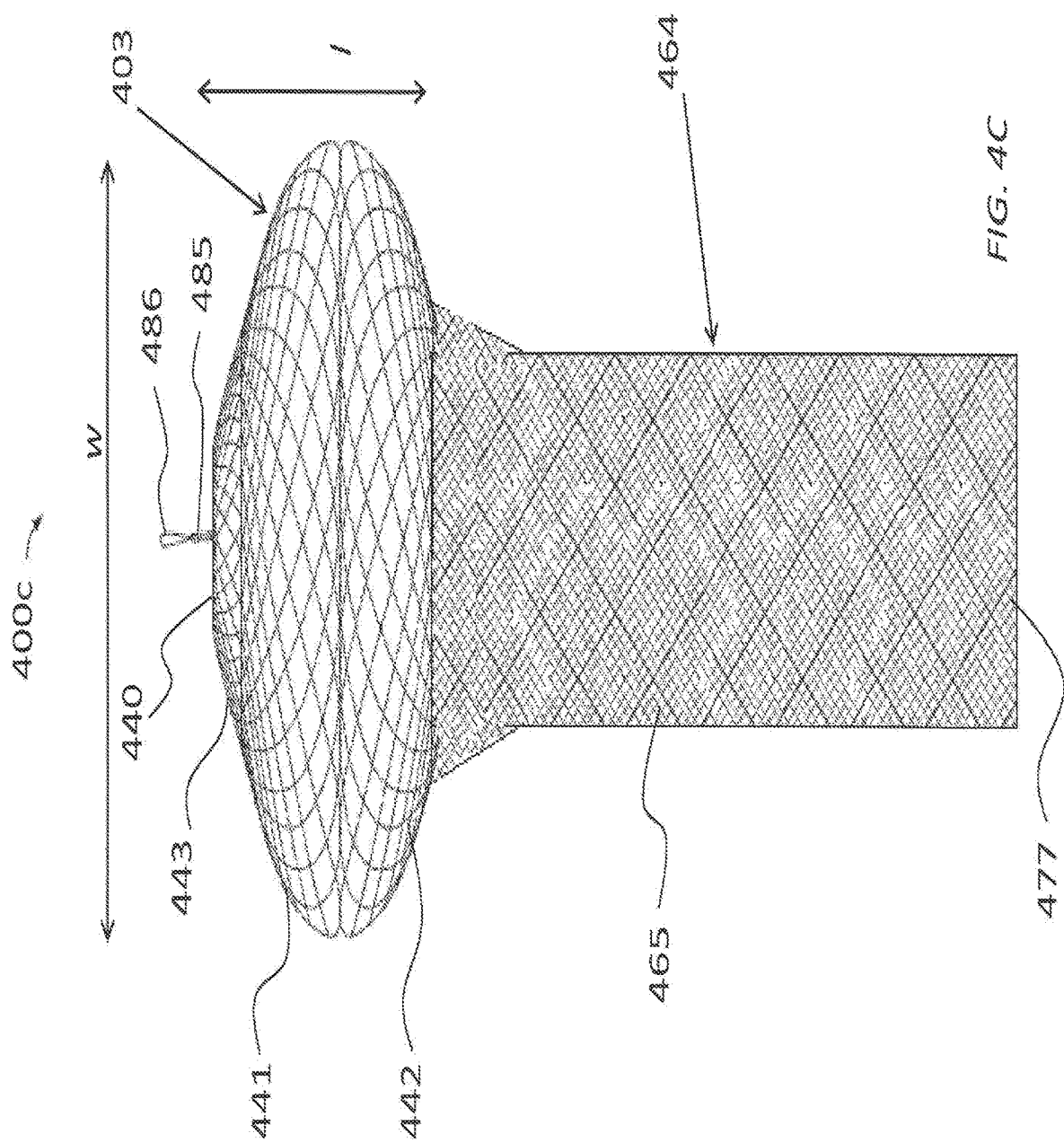

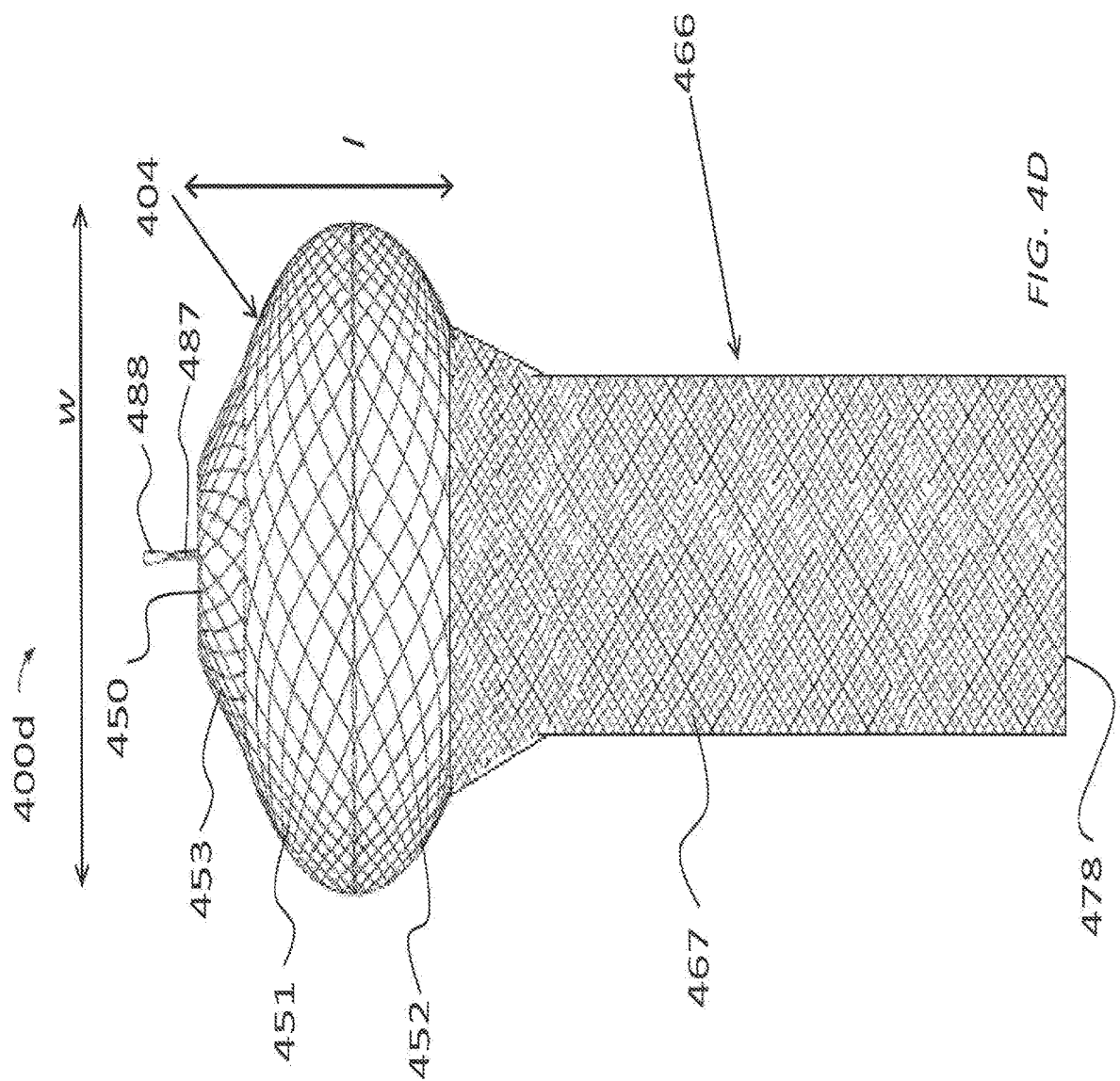

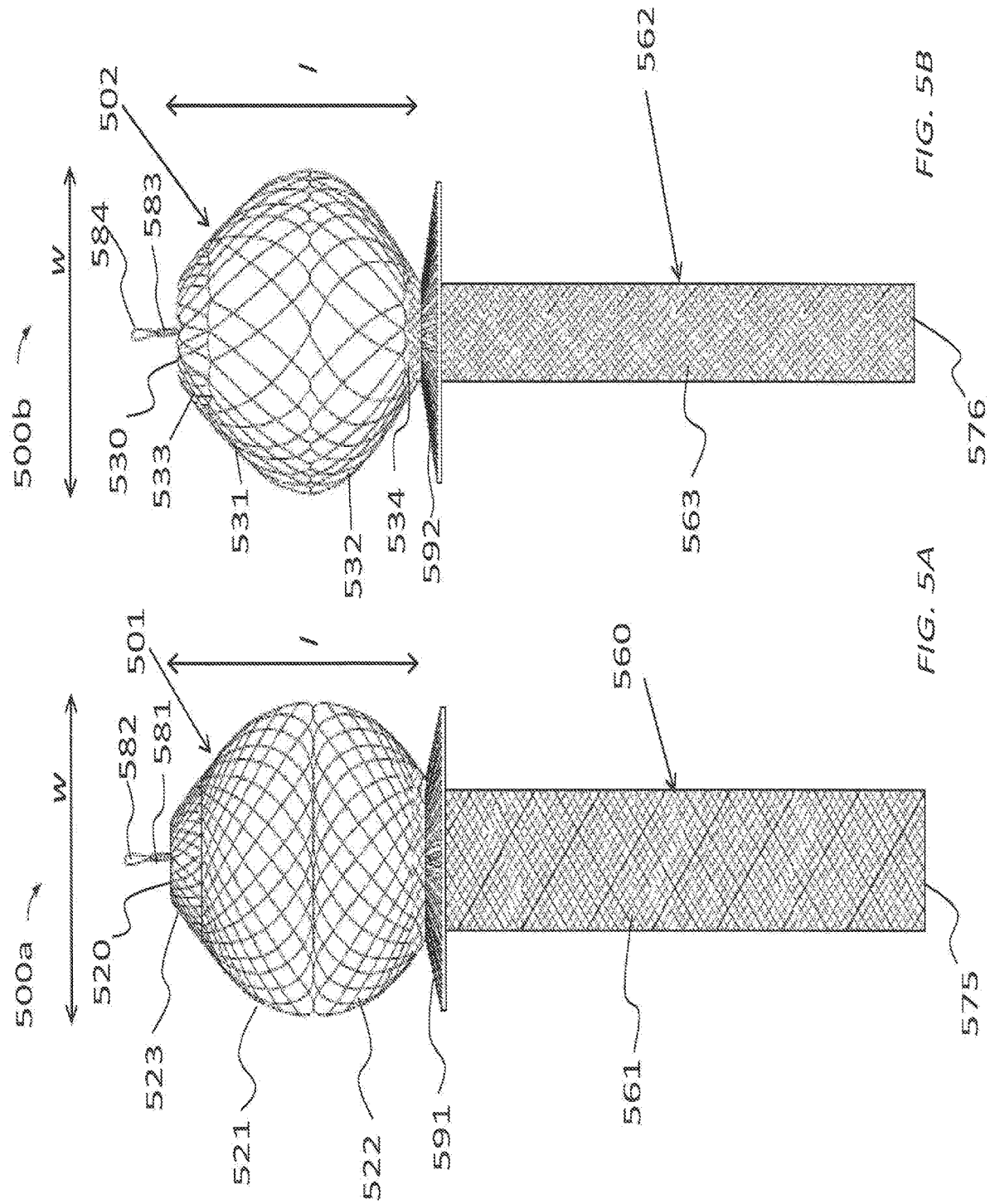

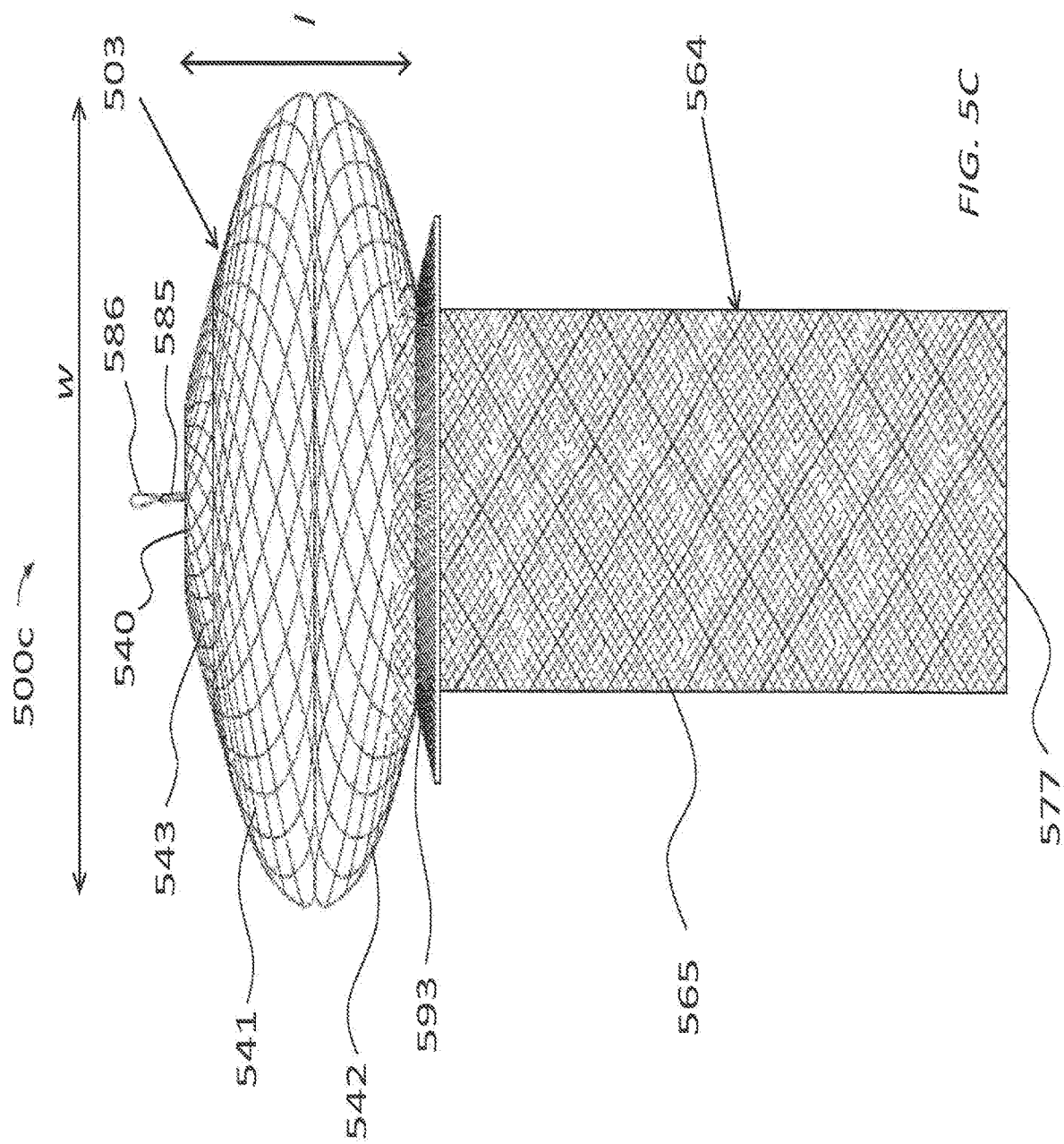

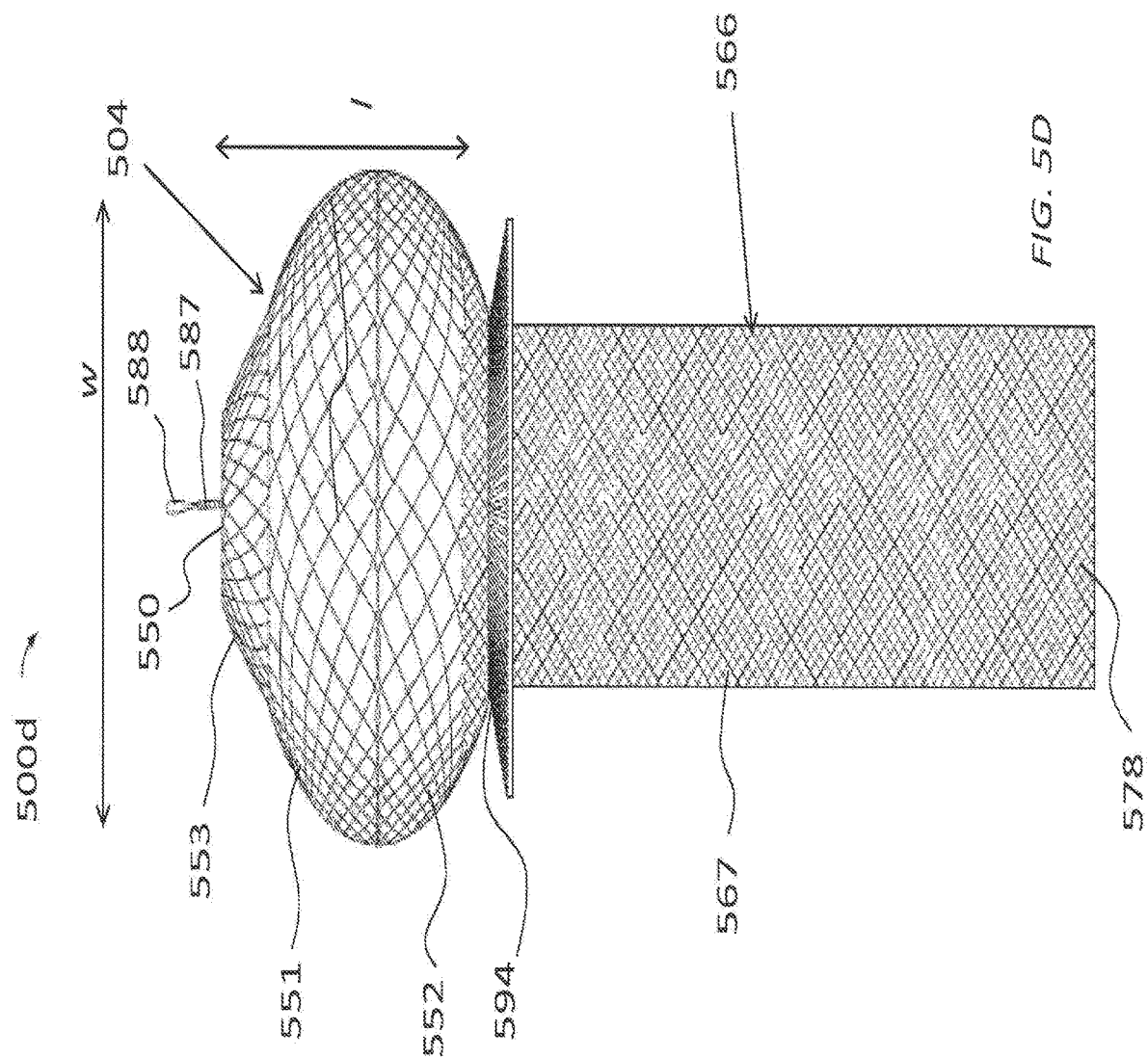

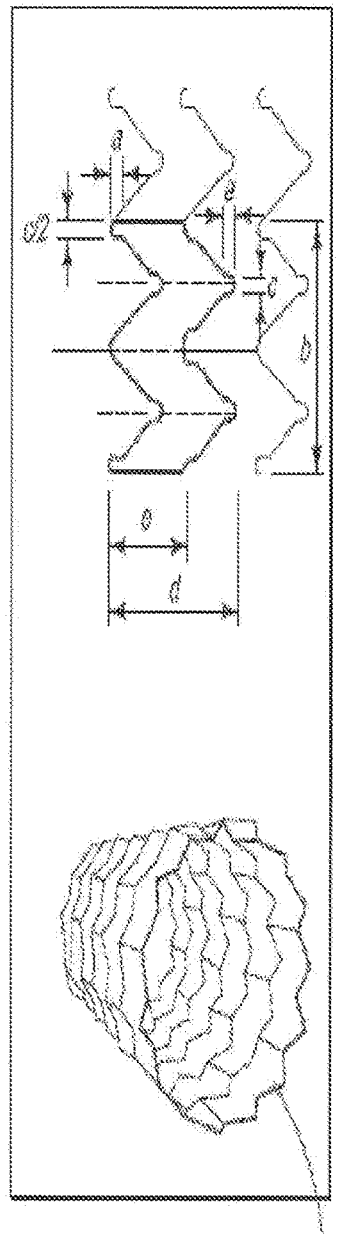 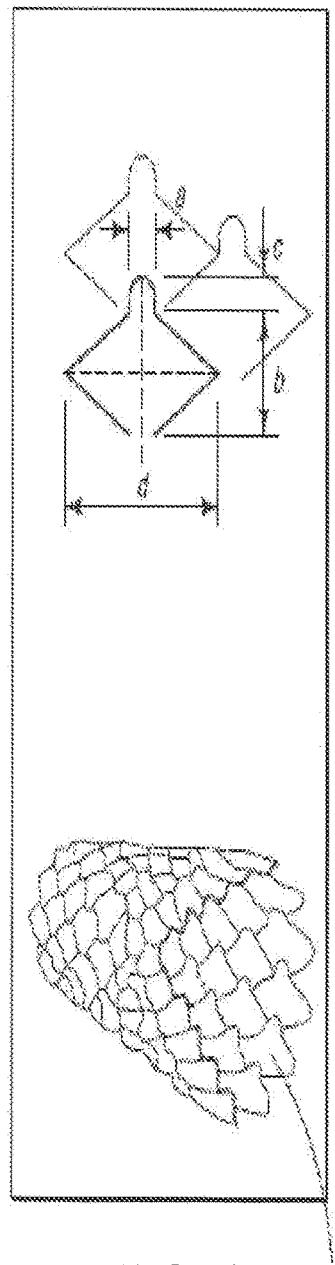 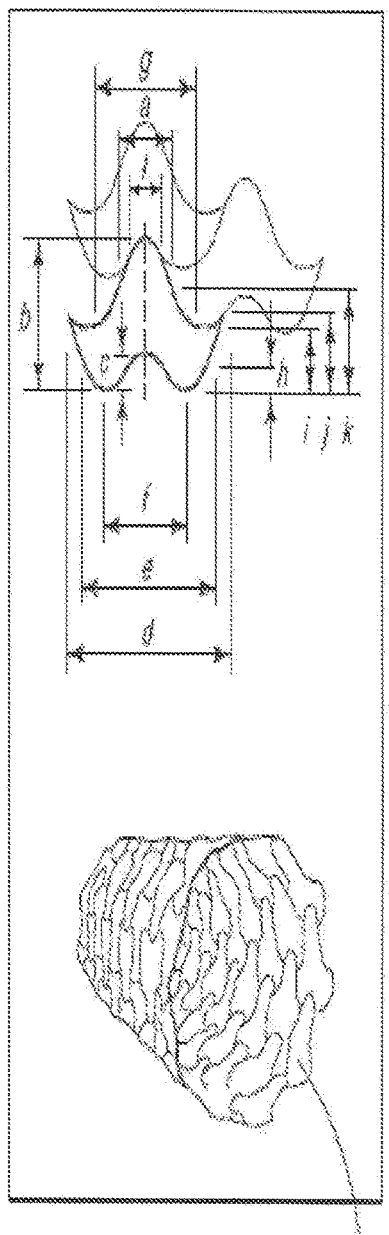
FIG. 6A  600a    FIG. 6B  600b    FIG. 6C  600c

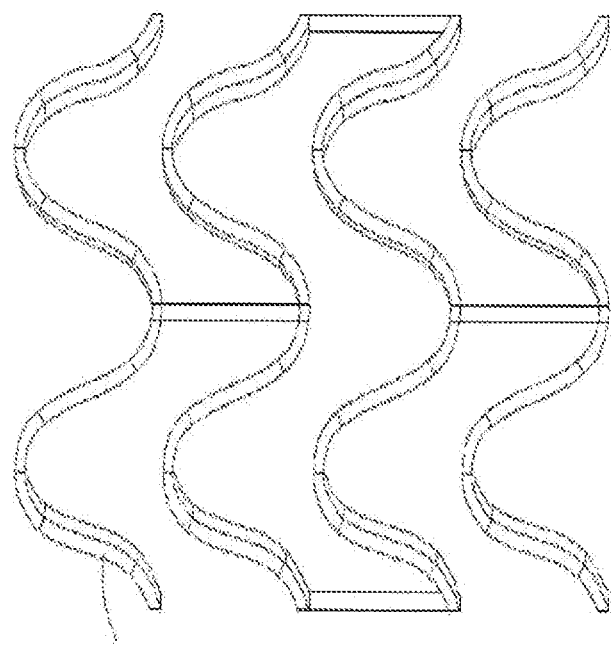
*600d*
*FIG. 6D*
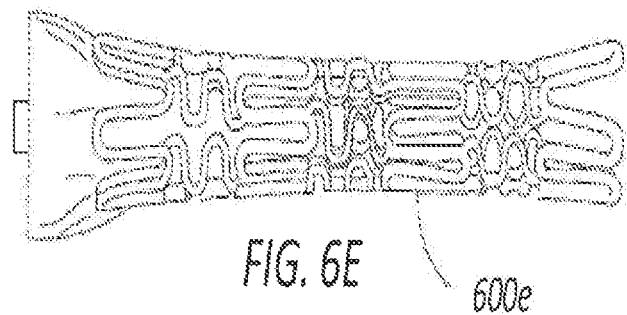
*FIG. 6E*  *600e*
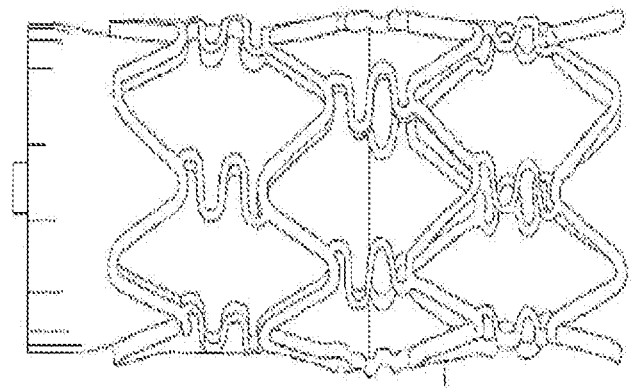
*FIG. 6F*  *600f*

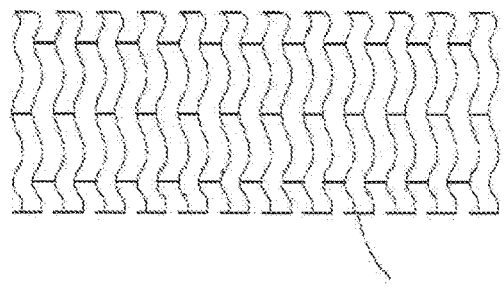
FIG. 6G    600g
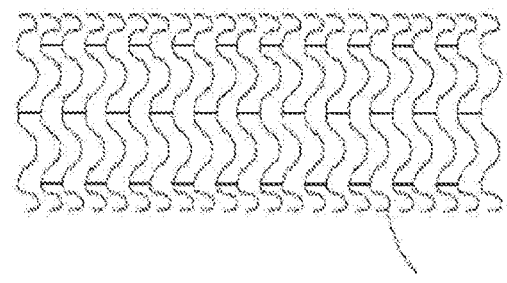
FIG. 6H    600h
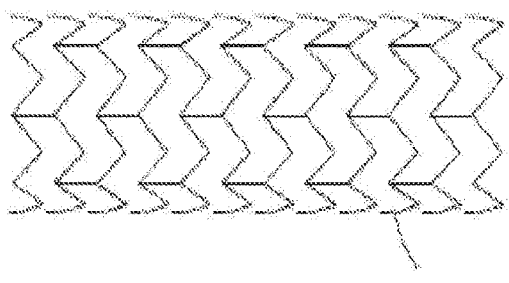
FIG. 6I    600i
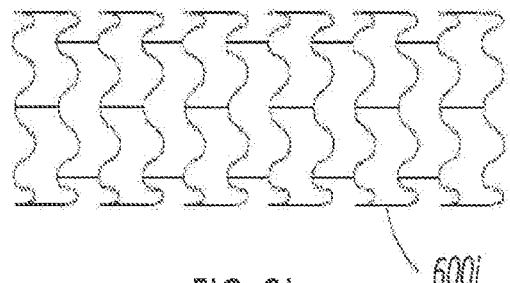
FIG. 6J    600j

FIG. 1.1

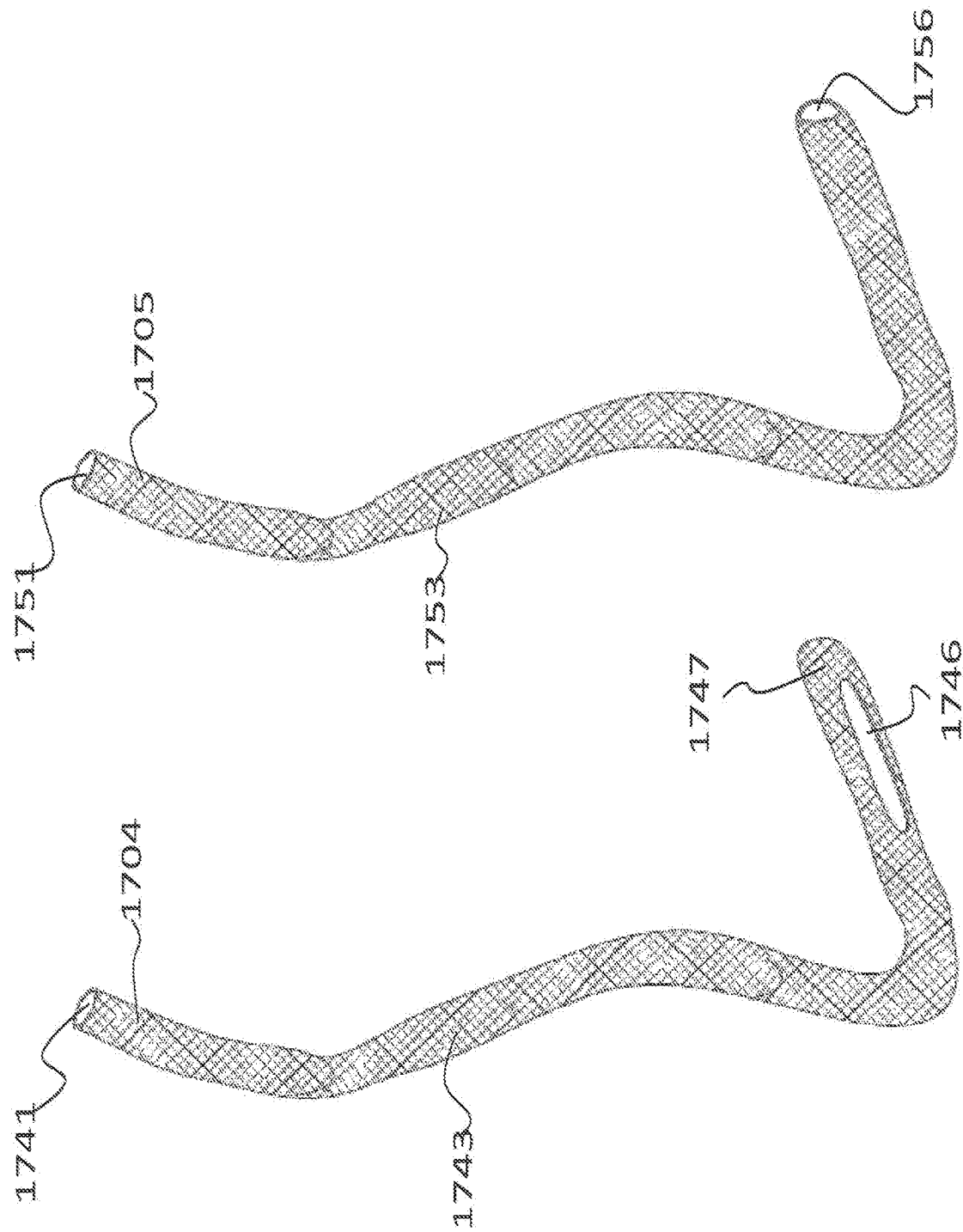

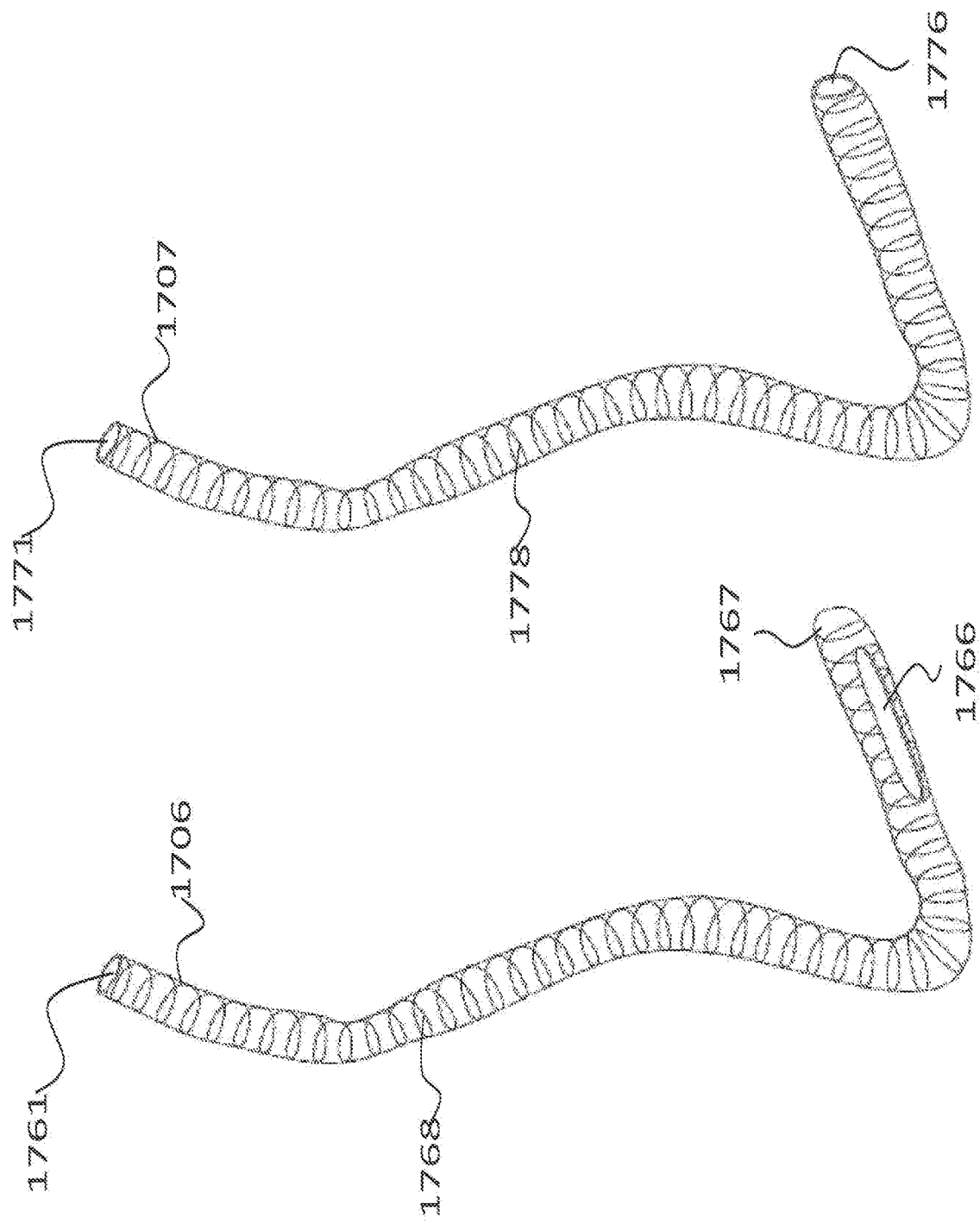

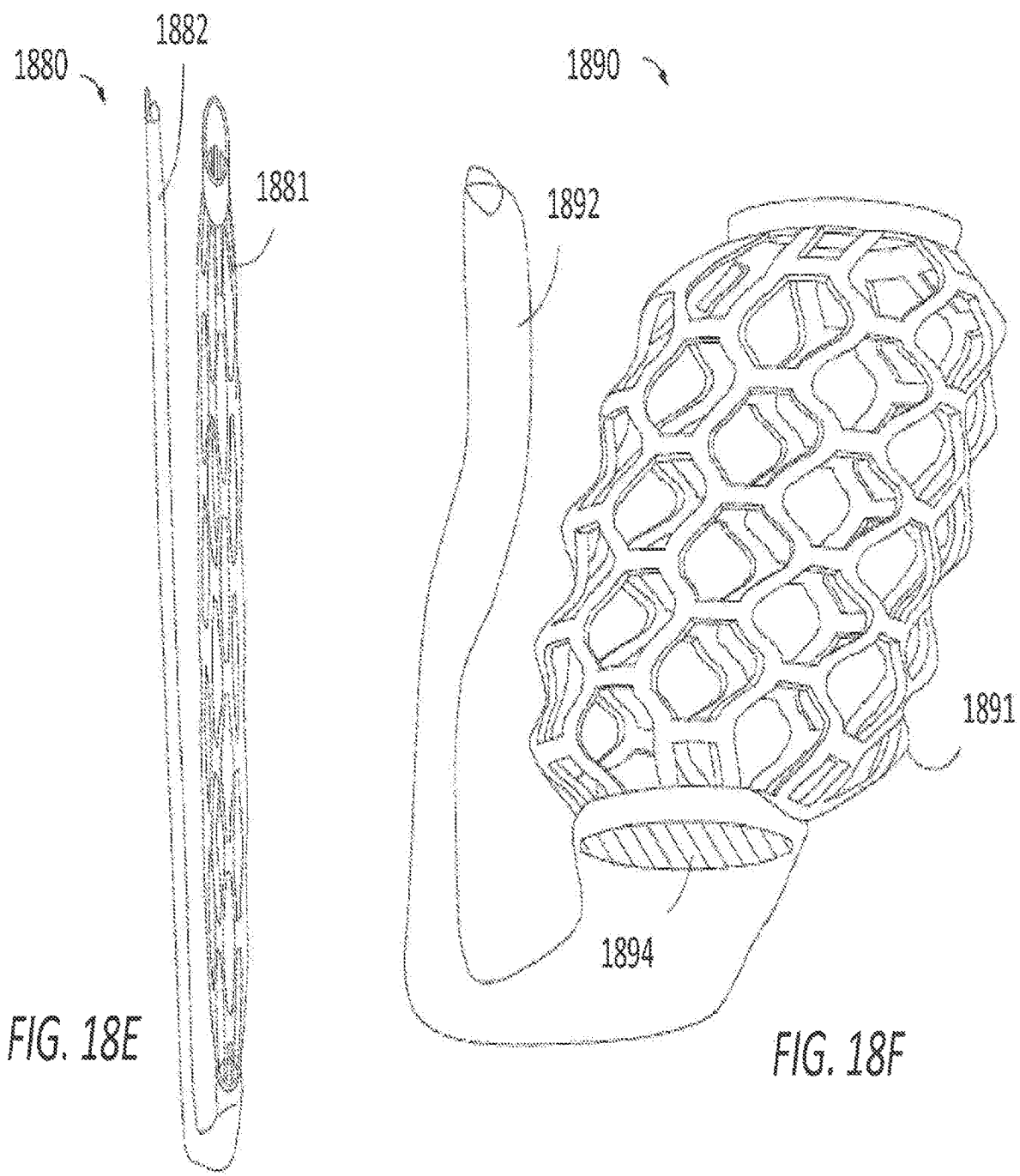

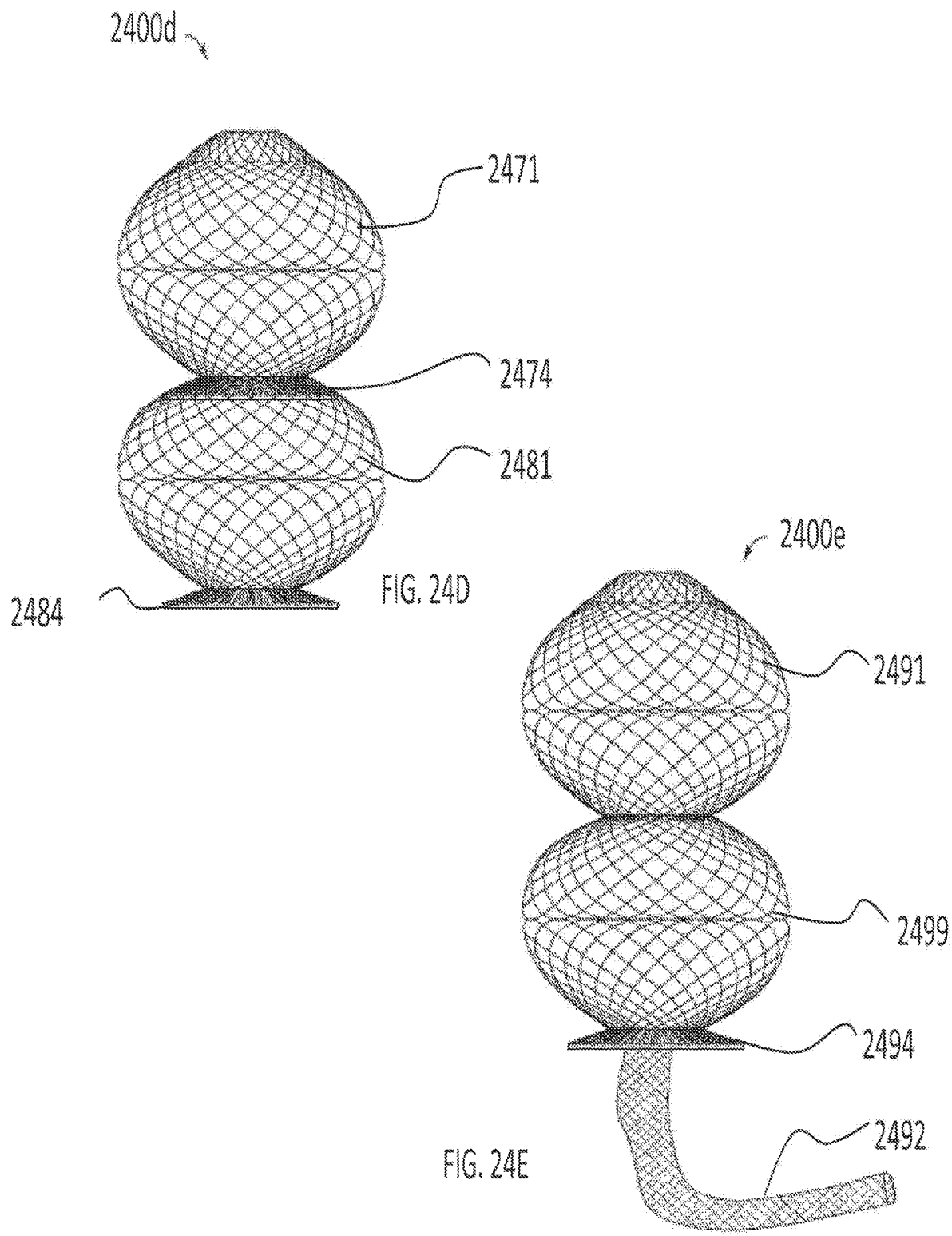

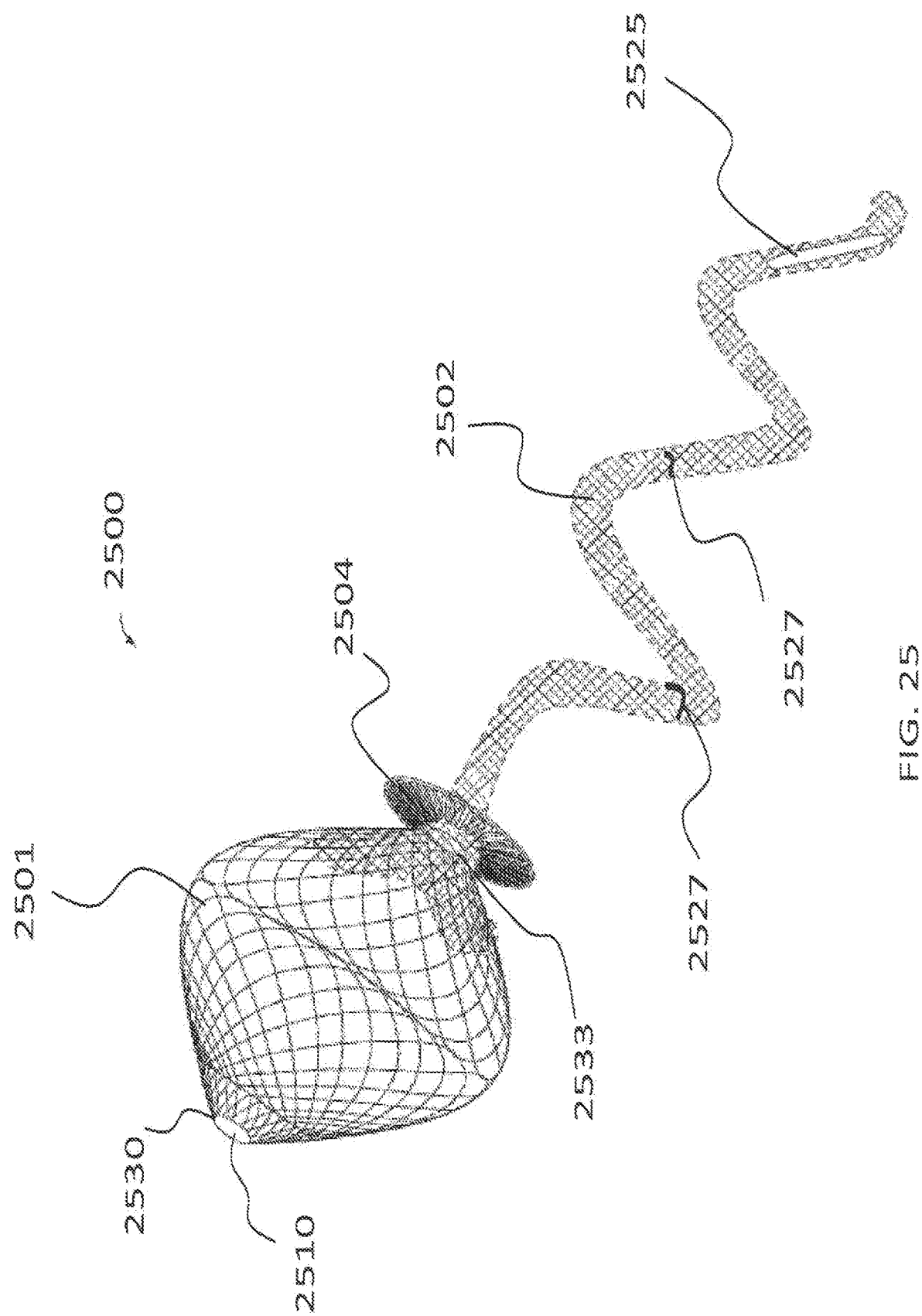

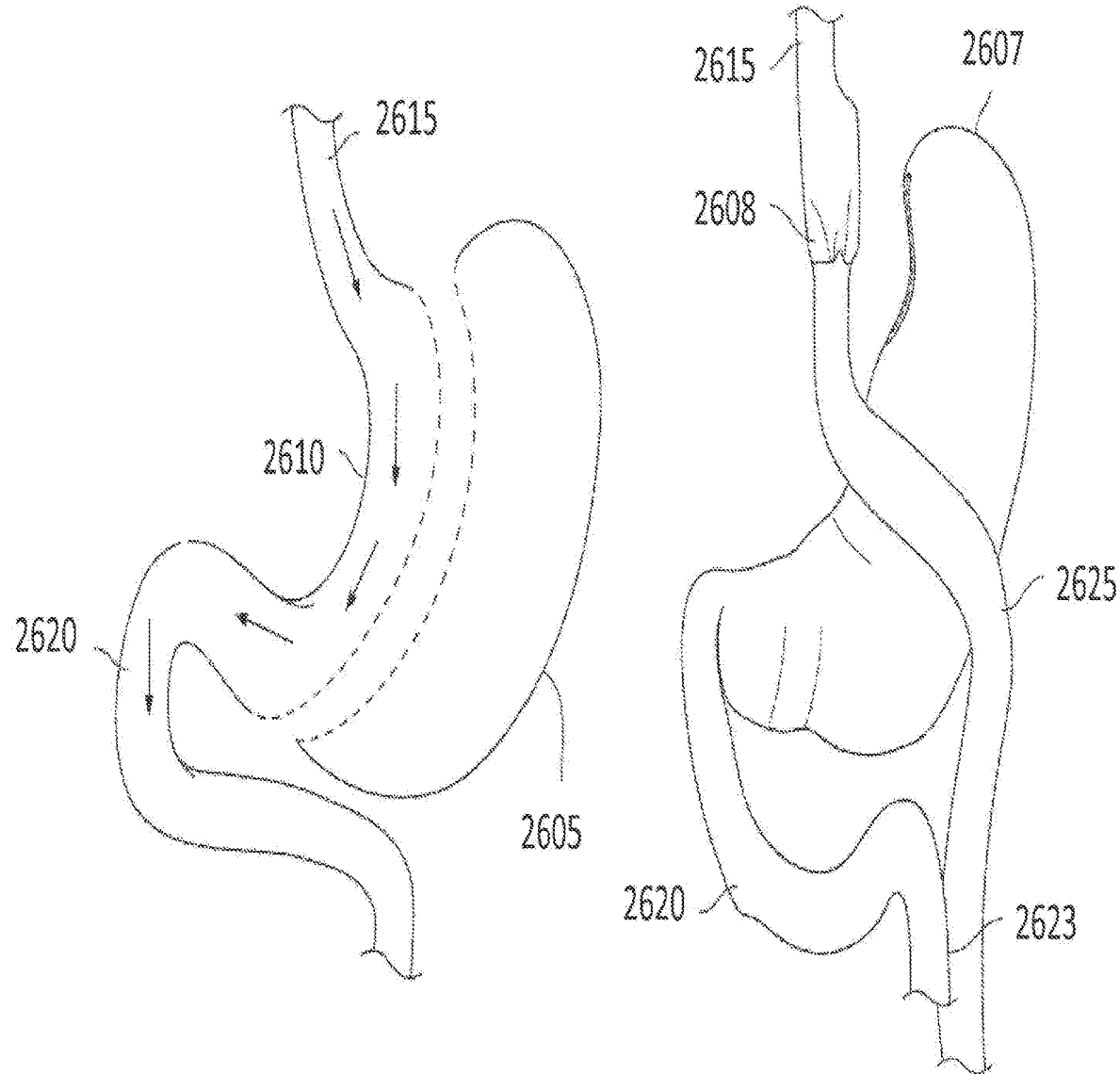
FIG. 26A – PRIOR ART   FIG. 26B – PRIOR ART

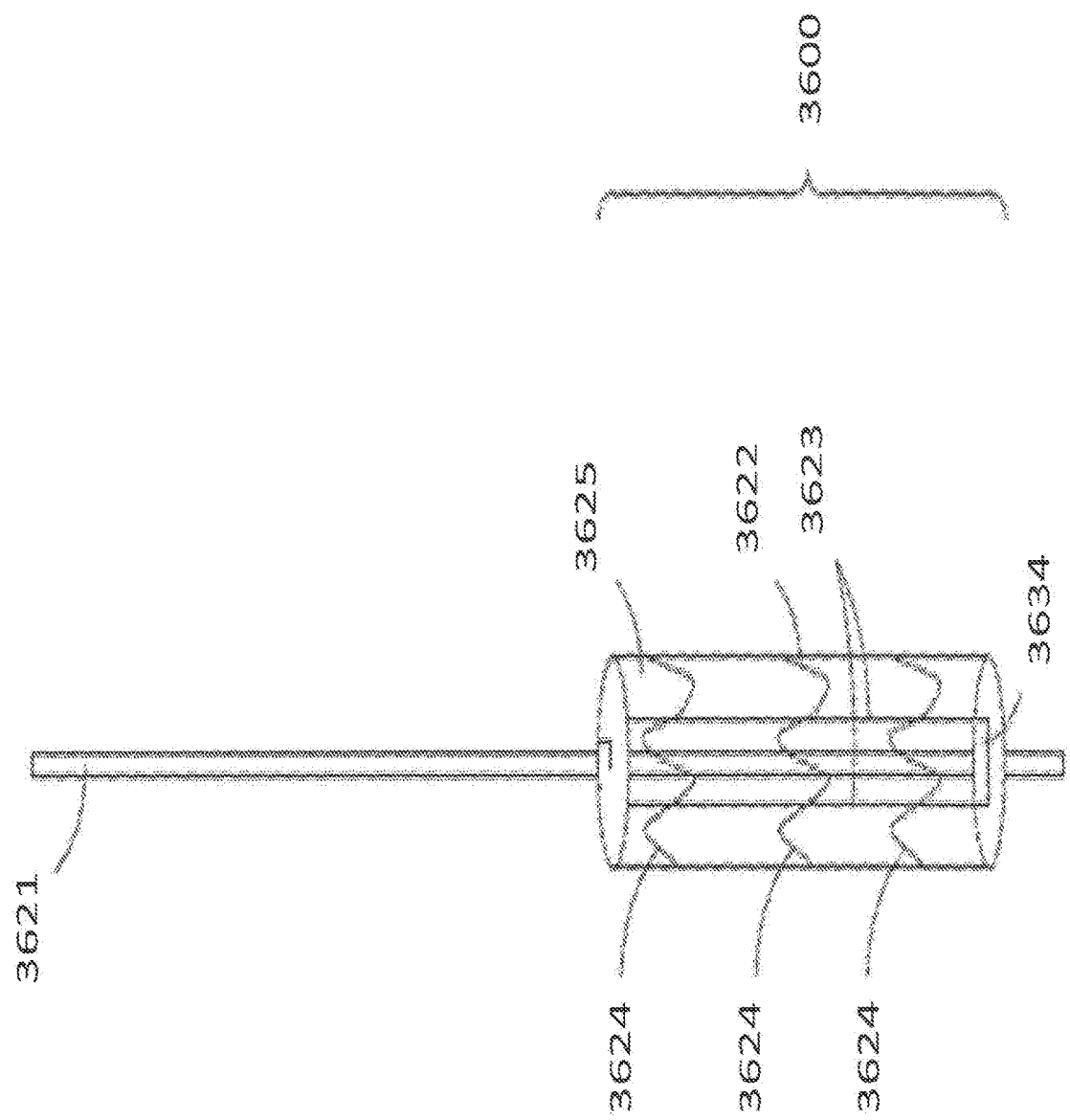

INTRAGASTRIC DEVICE FOR TREATING OBESITY

CROSS-REFERENCE

The present application relies on U.S. Provisional Patent Application Ser. Nos. 61/884,981, entitled "Gastrointestinal Device for Treating Obesity" and filed on Sep. 30, 2013, and 61/782,564, entitled "Intragastric Device for Treating Obesity" and filed on Mar. 14, 2013, for priority.

The present application is also a continuation of U.S. patent application Ser. No. 15/353,219, entitled "INTRAGASTRIC DEVICE FOR TREATING OBESITY," filed on Nov. 16, 2016, which is a continuation of Ser. No. 14/214,609, of the same title, filed on Mar. 14, 2014, now U.S. Pat. No. 9,526,648, which is a continuation-in-part of U.S. patent application Ser. No. 14/096,505, of the same title, filed on Dec. 4, 2013, now U.S. Pat. No. 10,413,436, which is a continuation application of U.S. patent application Ser. No. 12/814,481, of the same title, filed on Jun. 13, 2010, now U.S. Pat. No. 8,628,554.

All of the above applications are herein incorporated by reference in their entirety.

FIELD

The present specification relates generally to medical devices useful in the treatment of obesity. More particularly, the present specification relates to intragastric and gastrointestinal devices of dynamic weight that reduce gastric volume, slow gastric emptying, and/or bypass portions of the small intestine, thereby leading to patient weight loss.

BACKGROUND

Obesity is a common condition and growing public health problem in developed nations including the United States. As of 2009, more than two thirds of American adults, approximately 127 million people, were either overweight or obese. Over one third of American adults are obese. Data suggest that 300,000 Americans die prematurely from obesity-related complications each year. Many children in the United States are also either overweight or obese. Hence, the overall number of overweight Americans is expected to rise in the future. It has been estimated that obesity costs the United States over $100 billion annually in direct and indirect health care expenses and in lost productivity. This trend is also apparent in many other developed nations.

For adults, the body mass index (BMI) is used to determine if one is overweight or obese. A person's BMI is calculated by multiplying body weight in pounds by 703 and then dividing the total by height in inches squared. A person's BMI is expressed as kilograms per meter squared. An adult is considered overweight if his or her BMI is between 25 and 30 kg/m2. Obesity is defined as possessing a BMI between 30 and 40 kg/m2. A BMI greater than 30 kg/m2 is associated with significant co-morbidities. Morbid obesity is defined as possessing either a body weight more than 100 pounds greater than ideal or a BMI greater than 40 kg/m2. Approximately 5% of the U.S. population meets at least one of the criteria for morbid obesity. Morbid obesity is associated with many diseases and disorders including, for example: diabetes; hypertension; heart attack; stroke; dyslipidemia; sleep apnea; pickwickian syndrome; asthma; lower back and disc disease; weight-bearing osteoarthritis of the hips, knees, ankles and feet; thrombophlebitis and pulmonary emboli; intertriginous dermatitis; urinary stress incontinence; gastroesophageal reflux disease (GERD); gallstones; and, sclerosis and carcinoma of the liver. In women, infertility, cancer of the uterus, and cancer of the breast are additionally associated with morbid obesity. Taken together, the diseases associated with morbid obesity markedly reduce the odds of attaining an average lifespan. The sequelae raise annual mortality rates in affected people by a factor of 10 or more.

Current treatments for obesity include diet, exercise, behavioral treatments, medications, surgery (open and laparoscopic), and endoscopic devices. New drug treatments for obesity are currently being evaluated in clinical trials. However, a high efficacy pharmaceutical treatment has not yet been developed. Further, short-term and long-term side effects of current pharmaceutical treatments often concern consumers, pharmaceutical providers, and/or their insurers. Generally, diet or drug therapy programs have been consistently disappointing, failing to bring about significant, sustained weight loss in the majority of morbidly obese people.

Currently, most operations used to treat morbid obesity include gastric restrictive procedures, involving the creation of a small (e.g., 15-35 ml) upper gastric pouch that drains through a small outlet (e.g., 0.75-1.2 cm), setting in motion the body's satiety mechanism. About 15% of operations used to treat morbid obesity performed in the United States involve combining a gastric restrictive procedure with a malabsorptive procedure. Typical malabsorptive procedures divide small intestinal flow into a biliary-pancreatic conduit and a food conduit. Potential long-term side effects associated with abdominal surgical procedures include herniation and small bowel obstruction. In addition, long-term problems specific to bariatric procedures also include gastric outlet obstruction, marginal ulceration, protein malnutrition, and vitamin deficiency.

Other surgical strategies for treating obesity include endoscopic procedures, many of which are still in development. Endoscopic procedures and devices to produce gastric pouch and gastrojejunal anastomosis are used to replicate laparoscopic procedures. Endoscopically placed gastric balloons restrict gastric volume and result in satiety with smaller meals. For example, U.S. patent application Ser. No. 10/221,562, now issued as U.S. Pat. No. 7,172,613 and assigned to Districlass Medical SA, describes an "intragastric device inserted by endoscopic path into a patient's stomach. The device includes a balloon or envelope having a specific nominal volume. The balloon is sealingly connected to connecting elements consisting of a disc forming a support base for the balloon against an inner wall of the stomach. The device also includes a flexible tube or catheter for connecting the balloon to a filling device and catching element integral with the tube or catheter. The connection elements enable a doctor to set and/or remove the balloon and to fix, either inside the patient's body, or subcutaneously the filling device and to be able to bring the balloon or envelope to its predetermined nominal volume."

The silicone intragastric balloon (IGB) has been developed as a temporary aid to achieve weight loss specifically for people who weigh 40% or more of their ideal weight and who have had unsatisfactory results in their treatment of obesity, despite being cared for by a multidisciplinary team. This treatment is also indicated for morbidly obese patients who have a high morbidity and mortality risk for surgery. The placement and removal of the IGB is an endoscopic procedure and the balloon is designed to float freely inside the stomach. The IGB technique reduces the volume of the stomach and leads to a premature feeling of satiety. However, use of IGBs did not show convincing evidence of a greater weight loss. The relative risks for minor complications, for example, gastric ulcers and erosions, were significantly raised. All inflatable IGB devices suffer from the problem of deterioration of the balloon over time. This deterioration can result in deflation with loss of efficacy and complications such as small bowel obstruction secondary to balloon migration. Due to loss of efficacy over time, IGB devices are recommended only for short (<6 month) durations. In addition, rapid inflation of the balloon poses the risk of esophageal or gastric perforations, both of which are surgical emergencies. Deaths have been reported in patients using IGB treatment.

Endoscopic procedures are also used to deploy mesh structures into the stomach in an effort to occupy stomach volume and create the artificial sensation of being full. For example, U.S. patent application Ser. No. 11/657,231, assigned to Wilson-Cook Medical, Inc., describes an "intragastric device generally compris[ing] a strip digestive-resistant mesh material that is operable between a first configuration and a second configuration. The first configuration is sufficiently small to permit introduction of the digestive-resistant mesh material into a gastric lumen of the mammal. The second configuration is sufficiently large to prevent the digestive-resistant mesh material from passing through the mammal's pylorus, thereby permitting the mesh member to act as an artificial bezoar."

Although endoscopically placed balloon structures can be effective, they are not without their associated risks and complications. Mesh structures are effective in occupying available gastric volume but they do not address gastric emptying. Migration and small bowel obstruction from such devices continue to remain a significant problem. Therefore, a need exists for an intragastric device to treat obesity that combines the benefits obtained through reducing stomach volume, slowing gastric emptying, and providing a bypass for food past the pylorus and a portion of the small intestine, while remaining relatively safe. The device should also include a component for preventing migration of the entire device out of the stomach. This device should limit side effects and be able to be deployed and removed in a non-invasive manner with relative ease. In addition, this device should have the option of further treating obesity by including the benefits obtained by malabsorptive diversion procedures. The addition of this optional benefit would make the device effective in treating not only obesity, but type II diabetes as well.

Typical metal structures cannot survive the hostile environment, particularly with respect to the high acidity, of the stomach. Intragastric devices comprising acid-sensitive components, such as metal wires, are typically covered or coated in an acid-resistant material (i.e. silicone) to prevent degradation of these components by acidic gastric contents. Conventional manufacturing processes for creating these coated intragastric devices first coat the metal wires of the device and then form the wires into the desired end shape of the device. As the shapes and structures of intragastric devices become more complicated, these conventional processes are unable to properly create the desired end product. A shape memory metal, such as Nitinol, is heat-set at temperatures in excess of 400° C. Coating the metal with an acid-resistant material and then heat-setting into the final shape would result in destruction of the coating during exposure to the high temperatures. Therefore, a method of manufacture is needed wherein the wires of the intragastric device are first formed into the desired end shape and are then coated with a corrosion-resistant material. Such a method will take care to prevent the coating and covering or clogging of the spaces or openings between the wires of the wire mesh. Such a method will also produce a finished device that is still flexible enough to be converted from a compressed, first pre-deployment shape to an expanded, post-deployment shape.

Specific surgical options for the treatment of obesity also include laparoscopic sleeve gastrectomy (LSG) and laparoscopic roux-en-y-gastric bypass (RGB) surgery. Gastrectomy refers to a partial or full surgical removal of the stomach. LSG is a restrictive treatment, surgical weight-loss procedure in which the stomach is reduced to approximately 25% of its original size by surgical removal of a large portion following the major curve. The open edges are then attached together (often with surgical staples) to form a sleeve or tube with a banana shape. The procedure permanently reduces the size of the stomach. The procedure is performed laparoscopically and is not reversible. Following the operation, the stomach empties its contents rapidly into the small intestine, but with little or no vomiting (characteristic of other restrictive procedures).

LSG involves a longitudinal resection of the stomach on the greater curvature from the antrum starting opposite the nerve of Latarjet up to the angle of His. The first step of the procedure is the division of the vascular supply of the greater curvature of the stomach which is achieved with the section of the gastro-colic and gastro-splenic ligaments close to the stomach. The greater curvature is completely freed up to the left crus of the diaphragm to resect the gastric fundus that harbors the ghrelin secreting cells of the stomach. The second step of the procedure is the longitudinal gastrectomy that "sleeves" the stomach to reduce its shape to a narrow tube. The pylorus and part of the antrum are preserved, resulting in a lesser curvature-based "restrictive" gastric sleeve.

Sleeve gastrectomy (also called gastric sleeve) is usually performed on extremely obese patients, with a body mass index of 40 or more, where the risk of performing a gastric bypass or duodenal switch procedure may be too large. A two-stage procedure is performed: the first is a sleeve gastrectomy; the second is a conversion into a gastric bypass or duodenal switch. Patients usually lose a large quantity of their excess weight after the first sleeve gastrectomy procedure but, if weight loss ceases, the second step is performed.

For patients that are obese but not extremely obese, sleeve gastrectomy alone is a suitable operation with minimal risks. The sleeve gastrectomy is currently an acceptable weight loss surgery option for obese patients as a single procedure. Most surgeons prefer to use a bougie (tapering cylindrical instrument) having an outer diameter between 32-60 French (the optimal bougie size is 32 Fr-36 Fr) with the procedure. The ideal approximate remaining capacity of the stomach after the procedure is 15 ml.

One of the mechanisms involved in weight loss observed after the LSG is the dramatic reduction of the capacity of the stomach. The concept of restriction has been widely used in bariatric surgery in vertical banded gastroplasty (VBG) and laparoscopic adjustable gastric banding (LAGB). The distension of the small gastric pouch in the LAGB procedure or VBG is intended to account for the feeling of early fullness, enhanced satiety and decreased hunger experienced by a patient after the ingestion of small quantities of food.

The hormonal modifications induced by LSG differ from those found after a purely restrictive procedure such as LAGB. Ghrelin, a peptide hormone mainly produced in the fundus of the stomach, is believed to be involved in the mechanisms regulating hunger. There is a significant reduction in ghrelin associated with resection of the gastric fundus.

What makes LSG a preferable option lies in the fact that the operation is a straightforward procedure that can generally be completed laparoscopically, even in the case of an extremely obese patient. It does not involve any digestive anastomosis and no mesenteric defects are created, eliminating the risk of internal hernia. In addition, no foreign material is used as in the case of gastric banding, the whole digestive tract remains accessible to endoscopy, and it is not associated with Dumping syndrome. Also, the risk of peptic ulcer is low and the absorption of nutrients, vitamins, minerals and drugs is not altered.

Early reports of LSG have shown it to be safe and effective with marked weight loss and significant reduction of major obesity-related comorbidities. The question whether LSG may work as a sole bariatric procedure in the long term cannot yet be answered. For this reason, LSG is proposed as the first step of a staged approach in patients for whom a biliopancreatic diversion with duodenal switch (BPD-DS) or RGB seems too hazardous because of a very high BMI (super obesity=BMI>50 or super-super obesity=BMI>60) and/or associated diseases whether related or not to obesity.

Laparoscopic roux-en-y-gastric bypass (RGB) involves the creation of a small (20-30 ml) gastric pouch and a Roux limb (typically 75-105 cm) that reroutes a portion of the alimentary tract to bypass the distal stomach and proximal small bowel. Following RGB, a pleiotropic endocrine response may contribute to improved glycemic control, appetite reduction, and long-term changes in body weight. RGB also has a profoundly positive impact on obesity-related comorbidities and quality of life. Other advantages include established long-term effectiveness for sustained weight loss, reduction of comorbidities, minimal risk for long-term nutritional sequelae, and effective relief of gastroesophageal reflux disease (GERD). RGB is not without risks. Common causes of death include pulmonary embolism and anastomotic leaks. Nonfatal perioperative complications include anastomotic leaks, venous thromboembolism, wound infections, small bowel obstruction, and bleeding. Postoperative gastrointestinal complications include nausea and vomiting, micronutrient deficiencies, and possible weight regain.

Failures after these bariatric procedures are common and patients start regaining weight or the progressive weight loss stops at a sub-therapeutic level. Therefore, there is a need for salvage therapy after one or more failed bariatric procedures. What is needed is a device to be used following bariatric surgery that will combine the benefits of gastric volume reduction, bilio-pancreatic diversion and/or intestinal bypass to enhance the weight loss effects of the device. What is also needed is a device that will further reduce the volume of a surgically restricted stomach to reduce the amount of calories that can be consumed. The device will also bypass the proximal small intestine or the roux limb of the intestine in order to produce intestinal mal absorption, bilio-pancreatic diversion or both. The device can further act to delay gastric emptying, release the gastric hormones associated with satiety, and stimulate the gastric nerves associated with sensation of satiety. The device could be combined with other therapeutic agents such as electrical stimulation, magnetic stimulation, or pharmaceutical agents.

The device can be used as a primary therapeutic procedure for weight loss or as a bridge to surgery for a definitive weight loss procedure. The device may also be used in the treatment of other conditions including, but not limited to, metabolic syndrome, diabetes mellitus, dyslipidemias and cardiovascular disease.

SUMMARY

The present specification discloses an intragastric device comprising: a porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom such that food enters said porous structure through said at least one first opening, passes through said interior, and exits said porous structure through said at least one second opening; and a sleeve having a flexible elongate body, a proximal end with a third opening, a distal end with a fourth opening, and a sleeve interior, wherein said sleeve is coupled to said porous structure such that food exiting said at least one second opening enters said sleeve through said third opening, passes through said sleeve interior, and exits said sleeve through said fourth opening.

In one embodiment, said at least one first opening does not direct food into said sleeve interior such that food exiting said interior of said porous structure through said at least one first opening does not enter said sleeve and said at least one second opening does direct food into said sleeve interior such that food exiting said interior of said porous structure through said at least one second opening does enter said sleeve. In one embodiment, a first surface area defined by said at least one first opening is greater than a second surface area defined by said at least one second opening. In another embodiment, a first surface area defined by said at least one first opening is less than a second surface area defined by said at least one second opening. In yet another embodiment, a first surface area defined by said at least one first opening is substantially equal to a second surface area defined by said at least one second opening.

In various embodiments, said at least one first opening has a diameter of 50 mm or less.

In various embodiments, said at least one second opening has a diameter of 100 mm or less.

In various embodiments, said pre-deployment shape is at least one of linear, cylindrical, or conical.

In various embodiments, when in said pre-deployment configuration, said device has a diameter or 25 mm or less.

In various embodiments, said post-deployment shape of said porous structure is at least one of an expanded cylinder, ovoid, sphere, bean, stomach shape, football, cube or cuboid.

In various embodiments, when in said post-deployment configuration, said porous structure occupies at least 10% of a patient's stomach volume.

In various embodiments, when is said post-deployment configuration, said porous structure has a volume of at least 100 mL.

In various embodiments, when in said post-deployment configuration, the diameter of said porous structure is greater than the diameter of an open pylorus.

In various embodiments, when in said post-deployment configuration, said device is capable of moving no more than 15 inches proximally, distally, and laterally within a patient's stomach.

In various embodiments, when in said post-deployment configuration, said porous structure has a width within a range of 1 cm to 25 cm and a length within a range of 1 cm to 25 cm.

In various embodiments, the porous structure comprises at least one of a wire mesh structure, a spiral wire structure, a spiral strip structure, or a lattice structure. In one embodiment, said wire mesh structure comprises mesh openings between the wires of said wire mesh structure wherein the average size of said mesh openings is greater than 1 mm in diameter. In various embodiments, when in said post-deployment configuration, the wires of said wire mesh structure comprise 50% or less of the surface area of said wire mesh structure and openings between said wires comprise the remaining surface area. In various embodiments, said wire mesh has a plurality of vertical and horizontal elements which, when expanded, create the at least one first opening and the at least one second opening. In various embodiments, said wire mesh vertical and horizontal elements comprise at least one of a metal, an alloy, a polymer, a shape memory metal, or a shape memory polymer.

In one embodiment, when in said post-deployment configuration, the wire mesh structure has a length from its proximal end to its distal end that is greater than a width of the wire mesh structure that extends, at the midpoint between said proximal end and said distal end, from one side of said wire mesh structure to the opposite side of said wire mesh structure. In another embodiment, when in said post-deployment configuration, the wire mesh structure has a length from its proximal end to its distal end that is equal to a width of the wire mesh structure that extends, at the midpoint between said proximal end and said distal end, from one side of said wire mesh structure to the opposite side of said wire mesh structure. In yet another embodiment, when in said post-deployment configuration, the wire mesh structure has a length from its proximal end to its distal end that is less than a width of the wire mesh structure that extends, at the midpoint between said proximal end and said distal end, from one side of said wire mesh structure to the opposite side of said wire mesh structure.

In one embodiment, when in said post-deployment configuration, said wire mesh structure comprises a wire mesh weave pattern which makes the wire mesh structure more easily compressible along the vertical axis. In another embodiment, when in said post-deployment configuration, said wire mesh structure comprises a wire mesh weave pattern which makes the wire mesh structure more easily compressible along the horizontal axis.

In one embodiment, when in said post-deployment configuration, said wire mesh structure comprises a wire mesh weave pattern which provides a consistent radial strength throughout said wire mesh structure, further wherein said radial strength is greater than the compressive force of a patient's stomach.

In various embodiments, when in said post-deployment configuration, said wire mesh structure comprises an upper portion extending from said proximal end to a middle point halfway between said proximal end and said distal end and a lower portion extending from said distal end to a middle point halfway between said proximal end and said distal end. Optionally, in one embodiment, said upper portion comprises a first wire mesh weave pattern which provides said upper portion with a radial strength greater than the radial strength provided to the lower portion by a second wire mesh weave pattern of said lower portion. Optionally, in another embodiment, said upper portion comprises a wire mesh weave pattern which provides said upper portion with a radial strength greater than the compressive force of a patient's stomach and said lower portion comprises a flexible membrane.

In one embodiment, said wire mesh structure further comprises a mechanism which is designed to be manually engaged when said device is in said post-deployment configuration wherein said mechanism provides said wire mesh structure with a radial strength greater than the compressive force of a patient's stomach. In various embodiments, said mechanism comprises any one or combination of a rod, radial spokes, a disc, or a separate device within said wire mesh structure.

In one embodiment, said device is self-expanding and said expansion is effectuated through the use of a shape memory metal. In one embodiment, said shape memory metal is Nitinol.

In one embodiment, said device is self-expanding and said expansion is effectuated through the use of a temperature sensitive material.

In one embodiment, the shape of said device is changed from said pre-deployment shape to said post-deployment shape by the use of an expansion tool.

In various embodiments, said porous structure in enveloped by a partially perforated membrane having a membrane surface area. In various embodiments, said membrane comprises at least one of silicone, latex, parylene, polyurethane, polytetrafluoroethylene (PTFE), expanded polytetrafluoroethylene (PTFE), fluorinated ethylene-propylene, Dacron, or Polyethylene terephthalate (PET). In one embodiment, said membrane is substantially non-porous. In other embodiments, said membrane has a specific level of porosity.

In various embodiments, said membrane has at least one first membrane opening positioned proximate said top of said porous structure and defining a first membrane opening surface area and at least one second membrane opening positioned proximate said bottom of said porous structure and defining a second membrane opening surface area. In one embodiment, said first membrane opening surface area is greater than said second membrane opening surface area. In another embodiment, said first membrane opening surface area is less than said second membrane opening surface area. In yet another embodiment, said first membrane opening surface area is substantially equal to said second membrane opening surface area.

In various embodiments, a sum of said first membrane opening surface area and said second membrane opening surface area is between one and ninety-nine percent of the membrane surface area.

In various embodiments, said at least one first membrane opening and/or at least one said second membrane opening has at least one valve that controls a directionality of flow of food or nutrients in and out of the porous structure.

In various embodiments, said at least one first membrane opening is positioned to align with said at least one first opening of said porous structure and said at least one second membrane opening is positioned to align with said at least one second opening of said porous structure.

Optionally, in one embodiment, said device is attached to a catheter, wherein said catheter is configured to induce a change from the pre-deployment shape to said post-deployment shape.

Optionally, in various embodiments, the intragastric device further comprises a second porous structure attached to said top of said existing porous structure. In one embodiment, said second porous structure is smaller than said existing porous structure. In another embodiment, said second porous structure is larger than said existing porous structure. In yet another embodiment, said second porous structure is substantially the same size as said existing porous structure.

Optionally, in various embodiments, said porous structure is coated with a corrosion-resistant material preventing exposure of said porous structure to gastric acid, wherein said corrosion-resistant material covers said porous structure and does not cover said openings of said porous structure. In various embodiments, said corrosion-resistant material comprises any one or combination of silicone, polyester, polyether ether ketone (PEEK), a medical grade epoxy, ceramic, or metal.

Optionally, in various embodiments, the intragastric device further comprises at least one circumferential constricting mechanism positioned about said porous structure.

Optionally, in various embodiments, said porous structure further includes a radiopaque marker to facilitate delivery using radiographic visualization.

Optionally, in various embodiments, the intragastric device further comprises at least one sensor. In various embodiments, said sensor comprises any one or combination of a flow or impedance sensor, a glucose sensor, a temperature sensor, a pH sensor, and an accelerometer.

In various embodiments, said sleeve has a length sufficient to extend from said bottom of said porous structure, through a patient's pylorus and duodenum, and into the patient's jejunum.

In various embodiments, said sleeve is comprised of a corrosive resistant and biocompatible material. In various embodiments, said sleeve comprises at least one of silicone, latex, parylene, polyurethane, polytetrafluoroethylene (PTFE), expanded polytetrafluoroethylene (PTFE), fluorinated ethylene-propylene, Dacron, or Polyethylene terephthalate (PET).

Optionally, in one embodiment, said fourth opening of said sleeve is positioned on said elongate body proximal to said distal end and said sleeve further comprises a pouch at said distal end beyond said fourth opening.

Optionally, in one embodiment, said fourth opening of said sleeve is positioned at said distal end of said sleeve.

In various embodiments, said sleeve has a length within a range of 6 inches to 120 inches. In one embodiment, said sleeve has a length of 24 inches.

In various embodiments, said sleeve has a diameter within a range of 1 cm to 10 cm. In one embodiment, said sleeve has a diameter of 3 cm.

In one embodiment, said distal end of sleeve is weighted to maintain sleeve in an elongate shape.

In various embodiments, said sleeve is coupled to said porous structure via sutures or glue or is thermally fused to said porous structure. In one embodiment, said device further includes an adapter coupling said sleeve with said porous structure.

In one embodiment, said sleeve is coupled via at least one coupling mechanism to said porous structure at a distance distally away from said porous structure.

In one embodiment, the intragastric device further comprises a second sleeve wherein said second sleeve comprises a flexible elongate body having a proximal end, a distal end, and a lumen within, a fifth opening at said proximal end, and a sixth opening proximate said distal end wherein said fifth opening of said second sleeve and a diameter of said second sleeve are greater than or equal to the diameter of said first sleeve, further wherein said first sleeve is coupled directly to said porous structure and said second sleeve is coupled via at least one coupling mechanism to said porous structure at a distance distally away from said porous structure, further wherein said distal end of said first sleeve extends through said fifth opening of said second sleeve such that said fourth opening of said first sleeve opens into said lumen of said second sleeve.

In various embodiments, said sleeve comprises a flexible coil or mesh having a weave pattern which provides the sleeve with anti-torsional properties and structural support such that said sleeve remains in an elongate shape.

In various embodiments, said sleeve comprises a membrane having a plurality of horizontal and vertical support elements which provide the sleeve with anti-torsional properties and structural support such that said sleeve remains in an elongate shape. In various embodiments, said horizontal support elements are spaced between 1 inch and 24 inches apart from one another and said vertical support elements are between 1 inch and 60 inches in length.

In various embodiments, said horizontal support elements are spaced 6 inches apart from one another and said vertical support elements are 6 inches in length.

In various embodiments, said sleeve comprises a membrane having a spiral metal wire extending its entire length which provides the sleeve with anti-torsional properties and structural support such that said sleeve remains in an elongate shape.

In one embodiment, said sleeve is capable of telescoping into itself.

In one embodiment, said sleeve comprises a membrane and said membrane of said sleeve extends onto a portion of said porous structure.

In one embodiment, said sleeve further comprises a radiopaque marker to facilitate delivery using radiographic visualization.

In one embodiment, the intragastric device further comprises a retrieval mechanism fixedly attached to the top of said porous structure. In various embodiments, said retrieval mechanism comprises a suture or wire having a loop shape.

Optionally, in various embodiments, the intragastric device further comprises an anti-migration component positioned at the junction of said porous structure and said sleeve and attached to said porous structure or said sleeve or both, wherein said anti-migration component comprises a compressed pre-deployment configuration and an expanded post-deployment configuration and is designed to sit proximal to a patient's pylorus and prevent migration of the porous structure into and through said pylorus.

In various embodiments, when in said pre-deployment configuration, said anti-migration component has a shape comprising any one of linear, cylindrical, or conical.

In various embodiments, when in said post-deployment configuration, said anti-migration component has a shape comprising any one of donut, discoid sloping proximally, discoid sloping proximally, flat discoid or circular, a half bumper, a full bumper, a flower shape, or a saucer shape.

In one embodiment, when in said post-deployment configuration, said anti-migration component has a width that is greater than the diameter of the porous structure.

In one embodiment, when in said post-deployment configuration, said anti-migration component has a radial strength that is greater than the compressive force of a patient's stomach.

In one embodiment, said anti-migration component is comprised of metal. In one embodiment, said metal is a shape memory metal. In one embodiment, said shape memory metal is Nitinol. In another embodiment, said metal is temperature sensitive.

Optionally, in one embodiment, anti-migration component is coated with a corrosive resistant material. In various embodiments, said corrosive resistant material is any one or combination of silicone, polyester, a medical grade epoxy, ceramic, or metal.

In one embodiment, said anti-migration component further includes a radiographic marker to facilitate delivery using radiographic visualization.

The present specification also discloses a method for manufacturing a porous structure for an intragastric device, said porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom, said method comprising the steps of: heat-setting at least one flexible metal wire or strip having memory shape properties into said porous structure having said post-deployment shape; dipping the entirety of said porous structure into a corrosion-resistant material that has been heated to a liquid state; removing said porous structure from said corrosion-resistant material; allowing corrosion-resistant material present on said porous structure after said dipping and removing to air dry into a solid state; and, repeating the steps of dipping said porous structure into said corrosion-resistant material, removing said porous structure from said corrosion-resistant material, and allowing corrosion resistant-material to air dry, until a corrosion-resistant material coating having a desired thickness has been deposited onto said porous structure.

In various embodiments, when in said post-deployment configuration, a plurality of spaces create in said porous structure each has a diameter of 2-20 mm.

In various embodiments, said corrosion-resistant material comprises a specific weight ratio of silicone to methylbenzene. In various embodiments, said weight ratio of silicone to methylbenzene is in a range of 1:100-25:100. In one embodiment, said weight ratio of silicone to methylbenzene is 8:100.

In various embodiments, said desired thickness is in a range of 0.001-0.010 inches.

The present specification also discloses a method for manufacturing a porous structure for an intragastric device, said porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom, said method comprising the steps of: heat-setting at least one flexible metal wire or strip having memory shape properties into said porous structure having said post-deployment shape; spraying said porous structure with a vapor deposition of a corrosion-resistant material; allowing corrosion-resistant material present on said porous structure after said spraying to air dry into a solid state; and, repeating the steps of spraying said porous structure with said corrosion-resistant material and allowing corrosion resistant-material to air dry until a corrosion-resistant material coating having a desired thickness has been deposited onto said porous structure.

In various embodiments, when in said post-deployment configuration, a plurality of spaces create in said porous structure each has a diameter of 2-20 mm.

In one embodiment, said corrosion-resistant material comprises parylene.

In various embodiments, said desired thickness is in a range of 0.001-0.010 inches.

The present specification also discloses a method for manufacturing a porous structure for an intragastric device, said porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom, said method comprising the steps of: heat-setting at least one flexible metal wire or strip having memory shape properties into said porous structure having said post-deployment shape; dipping the entirety of said porous structure into a first corrosion-resistant material that has been heated to a liquid state; removing said porous structure from said first corrosion-resistant material; allowing first corrosion-resistant material present on said porous structure after said dipping and removing to air dry into a solid state; and, repeating the steps of dipping said porous structure into said first corrosion-resistant material, removing said porous structure from said first corrosion-resistant material, and allowing first corrosion resistant-material to air dry, until a first corrosion-resistant material coating having a first desired thickness has been deposited onto said porous structure; spraying said porous structure having said first corrosion-resistant material coating with a vapor deposition of a second corrosion-resistant material; allowing second corrosion-resistant material present on said porous structure after said spraying to air dry into a solid state; and, repeating the steps of spraying said porous structure with said second corrosion-resistant material and allowing second corrosion resistant-material to air dry until a second corrosion-resistant material coating having a second desired thickness has been deposited onto said porous structure.

In various embodiments, when in said post-deployment configuration, a plurality of spaces create in said porous structure each has a diameter of 2-20 mm.

In various embodiments, said first corrosion-resistant material comprises a specific weight ratio of silicone to methylbenzene. In various embodiments, said weight ratio of silicone to methylbenzene is in a range of 1:100-25:100. In one embodiment, said weight ratio of silicone to methylbenzene is 8:100.

In various embodiments, said first desired thickness is in a range of 0.001-0.005 inches.

In one embodiment, said second corrosion-resistant material comprises parylene.

In various embodiments, said second desired thickness is in a range of 0.001-0.005 inches.

The present specification also discloses a delivery device for endoscopically delivering an intragastric device into a gastrointestinal tract of a patient, said intragastric device comprising a porous structure configurable between a compressed pre-deployment configuration and an expanded post-deployment configuration and an elongate sleeve coupled to a distal end of said porous structure, said delivery device comprising: an elongate body having a proximal end and a distal end; and, a restraining mechanism for constricting said device in said pre-deployment configuration coaxially over said distal end of said elongate body.

In one embodiment, the delivery device further comprises a locking mechanism for locking said delivery device in a specific position.

In one embodiment, said distal end comprises a most distal portion and a proximal distal portion, wherein said most distal portion is more flexible than said proximal distal portion.

In one embodiment, the delivery device further comprises a thread pull port on said proximal end, wherein said restraining mechanism comprises a thread wrapped about said device in said pre-deployment configuration.

In one embodiment, said restraining mechanism comprises a zipped sheath coaxially covering said device in said pre-deployment configuration. In another embodiment, said restraining mechanism comprises a tear away sheath coaxially covering said device in said pre-deployment configuration.

The present specification also discloses a retrieval device for endoscopically removing an intragastric device from a gastrointestinal tract of a patient, said intragastric device comprising a porous structure configurable between a compressed pre-deployment configuration and an expanded post-deployment configuration and including at least one circumferential constricting mechanism positioned about said porous structure and a retrieval mechanism at its proximal end and, an elongate sleeve coupled to a distal end of said porous structure, said retrieval device comprising: an elongate body having a proximal end and a distal end and a lumen within; an elongate metal wire disposed within said lumen and having a proximal end and a distal end; a grasping mechanism formed from said distal end of said wire for grasping a free end of said at least one circumferential constricting mechanism and said retrieval mechanism of said porous structure; and, an actuator attached to said proximal end of said wire.

In one embodiment, the retrieval device further comprises a grasper having two opposing jaws attached to said distal end of said elongate body and operatively connected to said actuator at said proximal end of said wire and at least one clamp positioned between said jaws of said grasper.

The present specification also discloses a method of delivering an intragastric device into the gastrointestinal tract of a patient using a delivery device, wherein said intragastric device comprises a porous structure configurable between a compressed pre-deployment configuration and an expanded post-deployment configuration and an elongate sleeve coupled to a distal end of said porous structure, said method comprising the steps of: using said delivery device to position said porous structure in a stomach of said patient proximate a pylorus and to position said sleeve extending through said pylorus and into a duodenum or through said pylorus, through said duodenum, and into a jejunum of said patient; deploying said intragastric device such that said porous structure remains free-floating in said stomach and said sleeve remains in said patient's small intestine.

In one embodiment, said delivery device comprises an elongate body having a proximal end, a distal end, a thread pull port on said body, and a thread for wrapping about said intragastric device for constricting said intragastric device in said pre-deployment configuration coaxially over said distal end of said body of said delivery device, and said method further comprises the steps of: coaxially placing said constricted intragastric device in said pre-deployment configuration over said distal end of said body of said delivery device; endoscopically inserting said delivery device into a patient and advancing said distal end of said body of said delivery device to a duodenum or jejunum of said patient; once intragastric device is positioned, pulling on said thread from said thread pull port to remove said thread from said constricted intragastric device, allowing said intragastric device to automatically expand into said post-deployment configuration; and, sliding said distal end of said body of said delivery device coaxially away from said expanded intragastric device and removing said delivery device from said patient.

In one embodiment, the method further comprises the step of applying a cooling element to said compressed intragastric device to slow the expansion of said porous structure during the removal of said thread, facilitating the removal of said delivery device.

In another embodiment, said delivery device comprises an elongate body having a proximal end, a distal end, and a zipped sheath for coaxially sliding over said intragastric device for constricting said intragastric device in said pre-deployment configuration coaxially over said distal end of said body of said delivery device, and said method further comprises the steps of: coaxially placing said constricted intragastric device in said pre-deployment configuration over said distal end of said body of said delivery device; endoscopically inserting said delivery device into a patient and advancing said distal end of said body of said delivery device to a duodenum or jejunum of said patient; once intragastric device is positioned, using a working tool to unzip said zipped sheath to remove said sheath from said constricted intragastric device, allowing said intragastric device to automatically expand into said post-deployment configuration; and, sliding said distal end of said body of said delivery device coaxially away from said expanded intragastric device and removing said delivery device from said patient.

In one embodiment, the method further comprises the step of applying a cooling element to said compressed intragastric device to slow the expansion of said porous structure during removal of said sheath, facilitating the removal of said delivery device.

In another embodiment, said delivery device comprises an elongate body having a proximal end, a distal end, and a tear away sheath for coaxially sliding over said intragastric device for constricting said intragastric device in said pre-deployment configuration coaxially over said distal end of said body of said delivery device, and said method further comprises the steps of: coaxially placing said constricted intragastric device in said pre-deployment configuration over said distal end of said body of said delivery device; endoscopically inserting said delivery device into a patient and advancing said distal end of said body of said delivery device to a duodenum or jejunum of said patient; once intragastric device is positioned, using a working tool to tear said tear away sheath to remove said sheath from said constricted intragastric device, allowing said intragastric device to automatically expand into said post-deployment configuration; and, sliding said distal end of said body of said delivery device coaxially away from said expanded intragastric device and removing said delivery device from said patient.

In one embodiment, the method further comprises the step of applying a cooling element to said compressed intragastric device to slow the expansion of said porous structure during removal of said sheath, facilitating the removal of said delivery device.

The present specification also discloses a method of delivering an intragastric device into the gastrointestinal tract of a patient using a delivery device, wherein said intragastric device comprises a porous structure configurable between a compressed pre-deployment configuration and an expanded post-deployment configuration and an elongate sleeve coupled to a distal end of said porous structure, said method comprising the steps of: deploying said porous structure without said sleeve and allowing said porous structure to expand into said post-deployment configuration in a first procedure; deploying said sleeve within said expanded porous structure in a second procedure; and coupling a proximal end of said sleeve to a distal end of said porous structure during said second procedure.

The present specification also discloses a method of retrieving a device from a gastrointestinal tract of a patient using a retrieval device, wherein said device comprises a porous structure configurable between a compressed pre-deployment configuration and an expanded post-deployment configuration and includes at least one circumferential constricting mechanism positioned about said porous structure and a retrieval mechanism at its proximal end and, an elongate sleeve coupled to a distal end of said porous structure, and said retrieval device comprises an elongate body having a proximal end and a distal end and a lumen within, an elongate metal wire disposed within said lumen and having a proximal end and a distal end, a grasping mechanism formed from said distal end of said wire for grasping a free end of said at least one circumferential constricting mechanism and said retrieval mechanism of said porous structure, and an actuator attached to said proximal end of said wire, said method comprising the steps of: endoscopically inserting said retrieval device into said patient and advancing said distal end of said body of said retrieval device to a proximal end of said device; manipulating said grasping mechanism of said retrieval device to engage a free end of said at least one circumferential constricting mechanism positioned about said porous structure; pulling on said actuator of said retrieval device to constrict and automatically lock said at least one circumferential constricting mechanism, thereby compressing said porous structure into said pre-deployment shape; manipulating said grasping mechanism of said retrieval device to disengage said free end of said at least one circumferential constricting mechanism; manipulating said grasping mechanism to engage said retrieval mechanism at said proximal end of said porous structure; pulling said actuator to withdraw a proximal portion of said device into said lumen of said retrieval device; and, removing said retrieval device and said device from said patient.

In one embodiment, the method further comprises the step of applying a cooling element to said compressed device to prevent the re-expansion of said porous structure during removal of said retrieval device and said device.

The present specification also discloses a method of retrieving a device from a gastrointestinal tract of a patient using a retrieval device, wherein said device comprises a porous structure configurable between a compressed pre-deployment configuration and an expanded post-deployment configuration and includes at least one circumferential constricting mechanism positioned about said porous structure and, an elongate sleeve coupled to a distal end of said porous structure, and said retrieval device comprises an elongate body having a proximal end and a distal end and a lumen within, an elongate metal wire disposed within said lumen and having a proximal end and a distal end, an engaging or grasping mechanism formed from said distal end of said wire for grasping a free end of said at least one circumferential constricting mechanism, an actuator attached to said proximal end of said wire, a grasper having two opposing jaws attached to said distal end of said elongate body and operatively connected to said actuator at said proximal end of said wire, and at least one clamp positioned between said jaws of said grasper, said method comprising the steps of: endoscopically inserting said retrieval device into said patient and advancing said distal end of said body of said retrieval device to a proximal end of said device; manipulating said grasping mechanism of said retrieval device to engage a free end of said at least one circumferential constricting mechanism positioned about said porous structure; pulling on said actuator of said retrieval device to constrict said at least one circumferential constricting mechanism, thereby compressing said porous structure into said pre-deployment shape; manipulating said grasper of said retrieval device to apply said at least one clamp to said free end of said at least one circumferential constricting mechanism proximate said compressed porous structure; pulling said actuator to withdraw a proximal portion of said device into said lumen of said retrieval device; and, removing said retrieval device and said device from said patient.

In one embodiment, the method further comprises the step of applying a cooling element to said compressed device to prevent the re-expansion of said porous structure during removal of said retrieval device and said device.

The present specification also discloses a method of treating a condition of a patient, said method comprising the steps of: delivering an intragastric device, comprising a porous structure configurable between a compressed pre-deployment configuration and an expanded post-deployment configuration and an elongate sleeve coupled to a distal end of said porous structure, into a gastrointestinal tract of a patient; allowing said porous structure to expand into said post-deployment shape; leaving said intragastric device in said gastrointestinal tract for a sufficient duration to have a therapeutic effect; constraining said porous structure into said pre-deployment shape; removing said intragastric device from said gastrointestinal tract of said patient while said device is constrained in said pre-deployment configuration.

In various embodiments, said condition is any one or combination of obesity and type II diabetes.

The present specification also discloses a method of treatment comprising the steps of: deploying a freely floating device having a proximal and a distal end and comprising a porous structure coupled to a proximal portion of an unsupported flexible sleeve, said device having openings at said proximal and distal ends, into a stomach to receive partially digested food from said stomach; and extending said unsupported flexible sleeve distally into a small intestine to deliver said received partially digested food into said small intestine.

The present specification also discloses a method of treatment comprising the steps of: deploying a freely floating device with a porous structure into a stomach; coupling a proximal portion of an unsupported sleeve, open at a proximal end and a distal end, to said porous structure; and extending said unsupported flexible sleeve distally into a small intestine.

The present specification also discloses an intragastric device having a top and a bottom comprising: a structure having a pre-deployment shape with a first volume and a post-deployment shape with a second volume, wherein said first volume is less than said second volume; wherein, in said post-deployment shape, said device comprises at least one first opening proximate to the top of said device, each first opening defined by an area where a sum of the areas of the first openings is equal to a first area; wherein, in said post-deployment shape, said device comprises at least one second opening proximate to the bottom of said device, each second opening defined by an area where a sum of the areas of the second openings is equal to a second area; and wherein said first area is equal or larger than said second area. Optionally, the pre-deployment shape is linear, cylindrical, conical, a non-linear cylinder, spherical, a cube or a cuboid. Optionally, the structure comprises at least one of a mesh structure, a spiral structure, or a lattice structure. The device on deployment spontaneously assumes the post-deployment shape and volume without the need of fillers. Alternatively, a balloon could be used to assist the transition from the pre-deployment shape to the post-deployment shape but following that the device maintains the post-deployment shape and volume without the need of fillers.

Optionally, the wire mesh has a plurality of vertical and horizontal elements which, when expanded, create the at least one first opening and the at least one second opening. The wire mesh vertical and horizontal elements comprise at least one of a metal, an alloy, a polymer, a shape memory metal, or a shape memory polymer. The structure is enveloped by a partially perforated membrane having a surface area. The membrane comprises at least one of silicone, latex, parylene, polyurethane, polytetrafluoroethylene (PTFE), expanded polytetrafluoroethylene (ePTFE), fluorinated ethylene-propylene, Dacron, or Polyethylene terephthalate (PET). The membrane has at least one first membrane opening, each first membrane opening having a first membrane opening area where a sum of said first membrane opening areas is equal to a third area, wherein said at least one first membrane opening is proximate to the top of the device.

The membrane has at least one second membrane opening, each second membrane opening having a second membrane opening area where a sum of said second membrane opening areas is equal to a fourth area, wherein said at least one second membrane opening is proximate to the bottom of the device and wherein the third area is equal or larger than the fourth area. The sum of said third area and fourth area is between one and ninety-nine percent of the membrane surface area. The membrane comprises at least one opening wherein said opening has at least one valve that controls a directionality of flow of food or nutrients in and out of the device.

Optionally, the device is attached to a catheter, wherein said catheter is configured to induce a change from the pre-deployment shape to said post-deployment shape. A sleeve is attached to the bottom of said device, wherein said sleeve has a length sufficient to extend from the bottom of the device, through a patient's pylorus and duodenum, and into the patient's jejunum. The sleeve comprises at least one of silicone, latex, parylene, polyurethane, polytetrafluoroethylene (PTFE), expanded polytetrafluoroethylene (ePTFE), fluorinated ethylene-propylene, Dacron, or Polyethylene terephthalate (PET). Optionally, in one embodiment, the device is configured to receive a second intragastric device.

In another embodiment, the present specification discloses an intragastric device having a top and a bottom comprising: a structure having a pre-deployment shape with a first volume and a post-deployment shape with a second volume, wherein said first volume is less than said second volume; wherein, in said post-deployment shape, said device comprises a plurality of first openings, each of said plurality of first openings defined by an area where a sum of the areas of the plurality of first openings is equal to a first area; wherein, in said post-deployment shape, said device comprises a plurality of second openings, each of said plurality of second openings defined by an area where a sum of the areas of the plurality of second openings is equal to a second area; wherein said first area is equal to larger than said second area; wherein said first area is closer to the top of device relative to the second area; and wherein said structure is enveloped by a membrane that does not cover said first area or said second area.

In another embodiment, the present specification discloses an intragastric device having a top and a bottom comprising: a structure having a pre-deployment shape with a first volume and a post-deployment shape with a second volume, wherein said first volume is less than said second volume; wherein, in said post-deployment shape, said device comprises at least one first opening to allow for entry of food into the device and at least one second opening to allow for exit of food from the device, wherein the device has a first weight when a patient is in a pre-feeding stage and a second weight when a patient is in a feeding or a post-feeding stage, and wherein the second weight is greater than the first weight. A patient is in a feeding stage when a patient is actively ingesting food or nutrients. This stage typically lasts between 1 minute and 1 hour. A patient is in a post-feeding stage after the patient has stopped ingesting food or nutrients and until most of the food or nutrients have exited the stomach. This stage normally lasts between 15 minutes and 4 hours and depends upon the amount and type of food or nutrients ingested. This state is also affected by the health of patient and can be significantly prolonged in patients having gastric emptying abnormalities such as gastroparesis. A patient is in a pre-feeding stage between the end of the post-feeding stage and the beginning of the feeding stage. In one embodiment, the first opening is the same as the second opening. In other embodiments, the first opening is different from the second opening. In various embodiments, the device has a top half with a first weight and a bottom half with a second weight wherein the first weight is different from the second weight.

The present specification also discloses an intragastric device comprising: a structure having a pre-deployment shape with a first volume and a post-deployment shape with a second volume, wherein said first volume is less than said second volume, further wherein, when in said post-deployment shape, said structure approximates a lower hemisphere shape, said structure having a top and a bottom, said top comprising a first opening and said bottom comprising a second opening wherein said first opening is larger than said second opening; an elongate tubular member having a proximal end, a distal end, and a lumen within, said tubular member further comprising a third opening at its proximal end and a fourth opening proximate its distal end, said proximal end of said tubular member attached to said bottom of said structure; and wherein, when said device is rotated about a horizontal axis, contents within said structure that are too large to pass through said second opening exit said structure via said first opening.

The present specification also discloses an intragastric device having a top and a bottom comprising: a structure having a pre-deployment shape with a first volume and a post-deployment shape with a second volume, wherein said first volume is less than said second volume; wherein, in said post-deployment shape, said device comprises at least one first opening proximate to the top of said device, further wherein said top of said device has a first radial force; wherein, in said post-deployment shape, said device comprises at least one second opening proximate to the bottom of said device, further wherein said bottom of said device has a second radial force; and wherein said first radial force is greater than said second radial force.

The present specification also discloses an intragastric device having a top and a bottom comprising: a structure having a pre-deployment shape with a first volume and a post-deployment shape with a second volume, wherein said first volume is less than said second volume; wherein, in said post-deployment shape, said device comprises at least one first opening proximate to the top of said device, further wherein said top of said device comprises a wire structure having a radial force; and wherein, in said post-deployment shape, said device comprises at least one second opening proximate to the bottom of said device, further wherein said bottom of said device comprises a compressible membranous member.

The present specification also discloses an intragastric device for use following bariatric surgery, comprising: a structure having a pre-deployment shape with a first volume and a post-deployment shape with a second volume, wherein said first volume is less than said second volume, further wherein said structure approximates a sphere, ovoid, or anatomy conforming shape when in said post-deployment shape, said structure having a proximal end and a distal end, said proximal end having one or more openings and said distal end having one opening; an elongate tubular member having a proximal end, a distal end, and a lumen within, wherein said proximal end of said tubular member is attached to and partially covers said distal end of said structure, further wherein said lumen of said tubular member is in fluid communication with said opening at said distal end of said structure; and wherein said structure and said tubular member are configured to be positioned within a gastric remnant and small intestine of a patient following bariatric surgery.

In one embodiment, the intragastric device further comprises at least one valve at said one or more openings at said proximal end of said structure.

In one embodiment, the intragastric device further comprises at least one anchoring mechanism for anchoring said device following implantation.

In one embodiment, the intragastric device further comprises at least one weighting mechanism proximate said distal end of said tubular member.

In one embodiment, the intragastric device has a wire mesh collar attached to one of its ends, said collar having a pre-deployment shape with a first volume and a post-deployment shape with a second volume, wherein said first volume is less than said second volume, further wherein said structure approximates a disc, donut, sphere, ovoid, or anatomy conforming shape when in said post-deployment shape. The collar serves an anti-migration function, preventing the migration of the device out of the stomach. Alternatively, the collar may serve to preferentially add weight to one of the end of the device.

In one embodiment, the distal end of the tubular member extends further distally beyond the distal opening.

In one embodiment, the intragastric device further comprises at least one constricting mechanism for returning said device to said pre-deployment shape.

The present specification also discloses an intragastric device for use following bariatric surgery, comprising: a structure having a pre-deployment shape with a first volume and a post-deployment shape with a second volume, wherein said first volume is less than said second volume, said structure having a proximal end and a distal end, said proximal end having one or more openings and said distal end having one opening, wherein a first diameter of said proximal end of said structure is less than a second diameter of said distal end of said structure when in said post-deployment shape; an elongate tubular member having a proximal end, a distal end, and a lumen within, wherein said proximal end of said tubular member is attached to and partially covers said distal end of said structure, further wherein said lumen of said tubular member is in fluid communication with said opening at said distal end of said structure; and wherein said structure and said tubular member are configured to be positioned within a gastric remnant and small intestine of a patient following bariatric surgery.

In one embodiment, the intragastric device further comprises at least one valve at said one or more openings at said proximal end of said structure.

In one embodiment, the intragastric device further comprises at least one valve at said one or more openings at said distal end of said structure.

In one embodiment, the intragastric device further comprises at least one anchoring mechanism for anchoring said device following implantation.

In one embodiment, the intragastric device further comprises at least one weighting mechanism proximate said distal end of said tubular member.

In one embodiment, the distal end of the tubular member extends further distally beyond the distal opening.

In one embodiment, the intragastric device further comprises at least one constricting mechanism for returning said device to said pre-deployment shape.

The present specification also discloses an intragastric device for use following bariatric surgery, comprising: a structure having a pre-deployment shape with a first volume and a post-deployment shape with a second volume, wherein said first volume is less than said second volume, further wherein said structure approximates a sphere, ovoid, or anatomy conforming shape when in said post-deployment shape, said structure having a proximal end and a distal end, said proximal end having one or more openings and said distal end having one opening; an elongate tubular member having a proximal end, a distal end, and a lumen within, wherein said proximal end of said tubular member is attached to and partially covers said distal end of said structure, further wherein said lumen of said tubular member is in fluid communication with said opening at said distal end of said structure; and wherein said structure and said tubular member are configured to be positioned within a gastric pouch and jejunum of a patient following bariatric surgery.

In one embodiment, the intragastric device further comprises at least one valve at said one or more openings at said proximal end of said structure.

In one embodiment, the valve at said one or more openings at said proximal end of said structure is a flap valve or a tubular membrane valve.

In one embodiment, the intragastric device further comprises at least one anchoring mechanism for anchoring said device following implantation.

In one embodiment, the intragastric device further comprises at least one weighting mechanism proximate said distal end of said tubular member.

In one embodiment, the distal end of the tubular member extends further distally beyond the distal opening.

In one embodiment, the intragastric device further comprises at least one constricting mechanism for returning said device to said pre-deployment shape.

The present specification also discloses a method for retrieving an implanted intragastric device, said method comprising the steps of: inserting an endoscope into the esophagus of a patient having an intragastric device implanted, said device comprising a proximal end, a distal end, and at least one constricting mechanism for converting said device from a post-deployment configuration to approximate a pre-deployment configuration, wherein said pre-deployment configuration approximates an elongate slender cylinder having a diameter smaller than that of a gastric overtube (<20 mm); advancing a grasping device through a working channel of an endoscope; grasping a portion of each of said at least one constricting mechanism; pulling on said portion to tighten said constricting mechanism, thereby causing said device to return substantially to said pre-deployment configuration; grasping said proximal end of said device; and, pulling on said device to remove it from said patient through said overtube or an endoscope.

The present specification also discloses an intragastric device having a wire mesh structure wherein said wire mesh structure comprises: a three-dimensional structure having a proximal end, a distal end, and a volume defined within; a compressed pre-deployment configuration and an expanded post-deployment configuration wherein the volume of said post-deployment configuration is greater than the volume of said pre-deployment configuration; and, at least one first opening proximate the proximal end of said wire mesh structure and at least one second opening proximate the distal end of said wire mesh structure wherein said at least one second opening is larger than said at least one first opening. The device on deployment spontaneously transitions from the pre-deployment configuration to the post-deployment configuration. Alternatively, an inflatable balloon could be used to create the post-deployment configuration. The device then maintains the post-deployment configuration without the need for a balloon or fillers.

In one embodiment, when in said post-deployment configuration, said device occupies at least 10% of a patient's stomach volume. In one embodiment, when in said post-deployment configuration, the wires of said wire mesh structure comprise 50% or less of the surface area of said wire mesh structure and openings between said wires comprise the remaining surface area. In one embodiment, when in said post-deployment configuration, the diameter of said device is greater than the diameter of an open pylorus. In one embodiment, when in said post-deployment configuration, said device is capable of moving no more than 15 inches proximally and distally within a patient's stomach. In one embodiment, the device freely floats inside the stomach and any portion of the device is free to move relative to any portion of the gastrointestinal tract.

In one embodiment, when in said pre-deployment configuration, said device has a shape comprising any one of linear, cylindrical, or conical. In one embodiment, when in said pre-deployment configuration, said device has a diameter or 25 mm or less.

In one embodiment, when in said post-deployment configuration, said device has a shape comprising any one of spherical, oval, ovoid, bean, stomach shaped, or football shaped. In various embodiments, when in said post-deployment configuration, said device has a width within a range of 1 cm to 25 cm and a length within a range of 1 cm to 25 cm.

In one embodiment, when in said post-deployment configuration, the wire mesh structure has a length from its proximal end to its distal end that is greater than a width of the wire mesh structure that extends, at the midpoint between said proximal end and said distal end, from one side of said wire mesh structure to the opposite side of said wire mesh structure. In another embodiment, when in said post-deployment configuration, the wire mesh structure has a length from its proximal end to its distal end that is equal to a width of the wire mesh structure that extends, at the midpoint between said proximal end and said distal end, from one side of said wire mesh structure to the opposite side of said wire mesh structure. In another embodiment, when in said post-deployment configuration, the wire mesh structure has a length from its proximal end to its distal end that is less than a width of the wire mesh structure that extends, at the midpoint between said proximal end and said distal end, from one side of said wire mesh structure to the opposite side of said wire mesh structure.

In one embodiment, said wire mesh structure is comprised of metal. In one embodiment, said metal is coated with a corrosive resistant material. In one embodiment, said corrosive resistant material comprises any one of silicone, polyester, polyether ether ketone (PEEK), a medical grade epoxy, ceramic, or an additional metal. In one embodiment, the coating metal is tantalum. Tantalum provides corrosive resistance and radiopacity. In one embodiment, wherein the coating is ceramic, the ceramic coating has a thickness of several angstroms. In various embodiments, any one or combination of the above corrosive resistant materials is used to coat the metal of the wire mesh structure.

In one embodiment, said metal of said wire mesh structure is a shape memory metal. In one embodiment, said shape memory metal is Nitinol. In one embodiment, said shape memory metal is temperature sensitive.

In one embodiment, said wire mesh structure is comprised of a polymer. In one embodiment, said polymer is polyether ether ketone (PEEK) or a bioresorbable polymer. In another embodiment, said wire mesh structure is made of carbon fibers.

In one embodiment, said at least one first opening has a diameter of 50 mm or less. In one embodiment, said at least one second opening has a diameter of 4 inches or less.

In one embodiment, when in said post-deployment configuration, said wire mesh structure comprises a wire mesh weave pattern which makes the wire mesh structure more easily compressible along the vertical axis. In another embodiment, when in said post-deployment configuration, said wire mesh structure comprises a wire mesh weave pattern which makes the wire mesh structure more easily compressible along the horizontal axis.

In one embodiment, when in said post-deployment configuration, said wire mesh structure comprises a wire mesh weave pattern which provides a consistent radial strength throughout said wire mesh structure, wherein said radial strength is greater than the compressive force of a patient's stomach.

In one embodiment, when in said post-deployment configuration, said wire mesh structure comprises an upper portion extending from said proximal end to a middle point halfway between said proximal end and said distal end and a lower portion extending from said distal end to a middle point halfway between said proximal end and said distal end. In one embodiment, said upper portion comprises a first wire mesh weave pattern which provides said upper portion with a radial strength greater than the radial strength provided to the lower portion by a second wire mesh weave pattern of said lower portion. In another embodiment, said upper portion comprises a wire mesh weave pattern which provides said upper portion with a radial strength greater than the compressive force of a patient's stomach and said lower portion comprises a flexible, compressible membrane.

In one embodiment, said wire mesh structure further comprises a mechanism which is designed to be manually engaged when said device is in said post-deployment configuration wherein said mechanism provides said wire mesh structure with a radial strength greater than the compressive force of a patient's stomach. In one embodiment, said mechanism comprises any one of a rod, spoke, disc, or separate device deployed within said wire mesh structure.

In one embodiment, the intragastric device further comprises a membrane covering a portion of said wire mesh structure, wherein said portion comprises 1% to 100% of the surface area of said wire mesh structure which excludes said first and second openings. In one embodiment, said membrane is substantially non-porous. In another embodiment, said membrane has a specific level of porosity. In one embodiment, said membrane comprises at least one opening wherein said at least one opening is positioned to align with at least one opening between the wires of said wire mesh structure. In one embodiment, said membrane includes a unidirectional valve or flap at said at least one opening in said membrane to allow the passage of food into but not out of said device.

In one embodiment, the intragastric device further comprises at least one circumferential constricting mechanism positioned about said wire mesh structure.

In one embodiment, said wire mesh structure further includes a radiopaque marker to facilitate delivery using radiographic visualization.

In one embodiment, the intragastric device further comprises at least one sensor. In one embodiment, said sensor comprises any one or combination of a flow or impedance sensor, a glucose sensor, a temperature sensor, a pH sensor and an accelerometer.

In one embodiment, the intragastric device further comprises a sleeve coupled to a distal portion of said wire mesh structure, wherein said sleeve comprises: a flexible elongate body having a proximal end, a distal end, and a lumen within; a first opening at said proximal end; and, a second opening proximate said distal end.

In one embodiment, said proximal end of said sleeve is positioned in the antrum of a patient's stomach, said body of said sleeve extends through a pylorus of a patient and into a patient's duodenum, and said second opening of said sleeve opens into said duodenum. In another embodiment, said proximal end of said sleeve is positioned in the antrum of a patient's stomach, said body of said sleeve extends through a pylorus and duodenum of a patient and into a patient's jejunum, and said second opening of said sleeve opens into said jejunum.

In one embodiment, said second opening of said sleeve is positioned on said elongate body proximal to said distal end and said sleeve further comprises a pouch at said distal end. In another embodiment, said second opening of said sleeve is positioned at said distal end of sleeve.

In various embodiments, said sleeve has a length within a range of 6 inches to 120 inches. In one embodiment, said sleeve has a length of 24 inches. In another embodiment, said sleeve has a length of 30 inches.

In various embodiments, said sleeve has a diameter within a range of 1 cm to 10 cm. In one embodiment, said sleeve has a diameter of 3 cm.

In one embodiment, said distal end of sleeve is weighted to maintain sleeve in an elongate shape.

In one embodiment, said sleeve is coupled to said wire mesh structure via sutures. In another embodiment, said device further includes a wire mesh adapter coupling said sleeve with said wire mesh structure. In another embodiment, said sleeve is coupled via at least two coupling mechanisms to said wire mesh structure at a distance distally away from said wire mesh structure.

In one embodiment, the intragastric device further comprises a second sleeve wherein said second sleeve comprises a flexible elongate body having a proximal end, a distal end, and a lumen within, a first opening at said proximal end, and a second opening proximate said distal end wherein said first opening of said second sleeve and a diameter of said second sleeve are the same size or greater in size than a diameter of said first sleeve, further wherein said first sleeve is coupled directly to said wire mesh structure and said second sleeve is coupled via at least two coupling mechanisms to said wire mesh structure at a distance distally away from said wire mesh structure, still further wherein said distal end of said first sleeve extends through said first opening of said second sleeve such that said second opening of said first sleeve opens into said lumen of said second sleeve. Alternatively, the second sleeve is attached directly to the first sleeve at one or more points.

In one embodiment, said sleeve is comprised of a corrosive resistant material.

In one embodiment, said sleeve is comprised of a biocompatible material.

In one embodiment, said sleeve comprises a flexible coil or mesh having a weave pattern which provides the sleeve with anti-torsional properties and structural support such that said sleeve remains in an elongate shape. In another embodiment, said sleeve comprises a membrane having a plurality of horizontal and vertical support elements which provide the sleeve with anti-torsional properties and structural support such that said sleeve remains in an elongate shape. In various embodiments, said horizontal support elements are spaced between 1 inch and 24 inches apart from one another and said vertical support elements are between 1 inch and 60 inches in length. In one embodiment, said horizontal support elements are spaced 6 inches apart from one another and said vertical support elements are 6 inches in length. In another embodiment, said sleeve comprises a membrane having a spiral metal wire extending its entire length which provides the sleeve with anti-torsional properties and structural support such that said sleeve remains in an elongate shape.

In one embodiment, said sleeve is capable of telescoping into itself. In the embodiment with two or more sleeves, the distal sleeve(s) telescopes into or over the proximal sleeve (s).

In one embodiment, said sleeve comprises a membrane and said membrane of said sleeve extends onto a portion of said wire mesh structure.

In one embodiment, said sleeve further comprises a radiopaque marker to facilitate delivery using radiographic visualization.

In one embodiment, the intragastric device further comprises a retrieval mechanism fixedly attached to the proximal end of said wire mesh structure. In one embodiment, said retrieval mechanism comprises a retrieval suture having a loop shape.

In one embodiment, the intragastric device further comprises an anti-migration component attached to the distal end of said wire mesh structure, wherein said anti-migration component comprises a compressed pre-deployment configuration and an expanded post-deployment configuration and is designed to sit proximal to a patient's pylorus and prevent migration of the wire mesh structure into and through said pylorus.

In one embodiment, when in said pre-deployment configuration, said anti-migration component has a shape comprising any one of linear, cylindrical, or conical.

In one embodiment, when in said post-deployment configuration, said anti-migration component has a shape comprising any one of discoid sloping proximally, discoid sloping proximally, flat discoid or circular, a half bumper, a full bumper, a flower shape, a donut shape or a saucer shape. In another embodiment, the anti-migration collar is spherical in shape. In another embodiment, the weave of the anti-migration collar is different than the weave of the mesh to provide it with different compressibility than the mesh.

In one embodiment, when in said post-deployment configuration, said anti-migration component has a width that is greater than the diameter of the wire mesh structure.

In another embodiment, when in said post-deployment configuration, said anti-migration component has a width that is less than the diameter of the wire mesh structure.

In another embodiment, when in said post-deployment configuration, said anti-migration component has a width that is similar to the diameter of the wire mesh structure.

In one embodiment, when in said post-deployment configuration, said anti-migration component has a radial strength that is greater than the compressive force of a patient's stomach.

In one embodiment, said anti-migration component is comprised of metal. In one embodiment, said metal is a shape memory metal. In one embodiment, said shape memory metal is Nitinol. In one embodiment, said metal is temperature sensitive. In one embodiment, said anti-migration component is coated with a corrosive resistant material. In one embodiment, said corrosive resistant material is silicone, polyester, polyether ether ketone (PEEK), parylene, a medical grade epoxy, ceramic, or an additional metal. In one embodiment, the coating metal is tantalum. Tantalum provides corrosive resistance and radiopacity. In one embodiment, wherein the coating is ceramic, the ceramic coating has a thickness of several angstroms. In various embodiments, any one or combination of the above corrosive resistant materials is used to coat the metal of the wire mesh structure. In one embodiment, said anti-migration component further includes a radiographic marker to facilitate delivery using radiographic visualization.

In one embodiment, the intragastric device further comprises a second wire mesh structure having a proximal end and a distal end and a volume within, wherein said proximal end of said second wire mesh structure is removably attached to said distal end of said first wire mesh structure, further wherein said second wire mesh structure is also configurable between a compressed pre-deployment configuration and a post-deployment configuration. In one embodiment, the intragastric device having first and second wire mesh structures further comprises a first anti-migration component attached to the distal end of said first wire mesh structure and extending into the volume of said second wire mesh structure and a second anti-migration component attached to the distal end of said second wire mesh structure, wherein said first wire mesh structure functions to couple said first wire mesh structure and said second wire mesh together and maintain the expanded configuration of said second wire mesh structure and said second anti-migration component functions to prevent said device from being passed into and through a patient's pylorus. In one embodiment, the intragastric device having first and second wire mesh structures further comprises a sleeve coupled to the distal end of said second wire mesh structure.

The present specification also discloses a delivery device for endoscopically delivering an intragastric device into a gastrointestinal tract of a patient, said intragastric device comprising a wire mesh structure configurable between a compressed pre-deployment configuration and an expanded post-deployment configuration and an elongate sleeve coupled to a distal end of said wire mesh structure, said delivery device comprising: an elongate body having a proximal end and a distal end; and, a restraining mechanism for constricting said device in said pre-deployment configuration coaxially over said distal end of said elongate body.

In one embodiment, the delivery device further comprises a locking mechanism for locking said delivery device in a specific position. In one embodiment, said distal end of said delivery device comprises a most distal portion and a proximal distal portion, wherein said most distal portion is more flexible than said proximal distal portion. In one embodiment, the delivery device has a lumen for passage over a guidewire. In one embodiment, the most distal portion has a spherical shape to end to help track the catheter over a guidewire.

In one embodiment, the delivery device further comprises a thread pull port on said proximal end, wherein said restraining mechanism comprises a thread wrapped about said device in said pre-deployment configuration. In another embodiment, said restraining mechanism comprises a zipped sheath coaxially covering said device in said pre-deployment configuration. In another embodiment, said restraining mechanism comprises a tear away sheath coaxially covering said device in said pre-deployment configuration.

The present specification also discloses a retrieval device for endoscopically removing an intragastric device from a gastrointestinal tract of a patient, said intragastric device comprising a wire mesh structure configurable between a compressed pre-deployment configuration and an expanded post-deployment configuration and including at least one circumferential constricting mechanism positioned about said wire mesh structure and a retrieval mechanism at its proximal end and, an elongate sleeve coupled to a distal end of said wire mesh structure, said retrieval device comprising: an elongate body having a proximal end and a distal end and a lumen within; an elongate metal wire disposed within said lumen and having a proximal end and a distal end; a grasping or hooking mechanism formed from said distal end of said wire for grasping or hooking a free end of said at least one circumferential constricting mechanism and said retrieval mechanism of said wire mesh structure; and, an optional actuator attached to said proximal end of said wire.

In one embodiment, the retrieval device further comprises a grasper having two opposing jaws attached to said distal end of said elongate body and operatively connected to said actuator at said proximal end of said wire and at least one clamp positioned between said jaws of said grasper.

The present specification also discloses a method of delivering an intragastric device into the gastrointestinal tract of a patient using a delivery device, wherein said intragastric device comprises a wire mesh structure configurable between a compressed pre-deployment configuration and an expanded post-deployment configuration and an elongate sleeve coupled to a distal end of said wire mesh structure, and said delivery device comprises an elongate body having a proximal end, a distal end, a thread pull port on said body, and a thread for wrapping about said intragastric device for constricting said intragastric device in said pre-deployment configuration coaxially over said distal end of said body of said delivery device, said method comprising the steps of: coaxially placing said constricted intragastric device in said pre-deployment configuration over said distal end of said body of said delivery device; endoscopically inserting said delivery device into a patient and advancing said distal end of said body of said delivery device to a duodenum and/or jejunum of said patient; positioning said body of said delivery device in said intragastric tract of said patient such that said wire mesh structure is positioned in a stomach of said patient proximate a pylorus and said sleeve is positioned extending through said pylorus and into said duodenum and/or jejunum; pulling on said thread from said thread pull port to remove said thread from said constricted intragastric device, allowing said intragastric device to automatically expand into said post-deployment configuration; and, sliding said distal end of said body of said delivery device coaxially away from said expanded intragastric device and removing said delivery device from said patient.

The present specification also discloses a method of delivering an intragastric device into the gastrointestinal tract of a patient using a delivery device, wherein said intragastric device comprises a wire mesh structure configurable between a compressed pre-deployment configuration and an expanded post-deployment configuration and an elongate sleeve coupled to a distal end of said wire mesh structure, and said delivery device comprises an elongate body having a proximal end, a distal end, and a zipped sheath for coaxially sliding over said intragastric device for constricting said intragastric device in said pre-deployment configuration coaxially over said distal end of said body of said delivery device, said method comprising the steps of: coaxially placing said constricted intragastric device in said pre-deployment configuration over said distal end of said body of said delivery device; endoscopically inserting said delivery device into a patient and advancing said distal end of said body of said delivery device to a duodenum and/or jejunum of said patient; positioning said body of said delivery device in said gastrointestinal tract of said patient such that said wire mesh structure is positioned in a stomach of said patient proximate a pylorus and said sleeve is positioned extending through said pylorus and into said duodenum; using a working tool to unzip said zipped sheath to remove said sheath from said constricted intragastric device, allowing said intragastric device to automatically expand into said post-deployment configuration; and, sliding said distal end of said body of said delivery device coaxially away from said expanded intragastric device and removing said delivery device from said patient.

The present specification also discloses a method of delivering an intragastric device into the gastrointestinal tract of a patient using a delivery device, wherein said intragastric device comprises a wire mesh structure configurable between a compressed pre-deployment configuration and an expanded post-deployment configuration and an elongate sleeve coupled to a distal end of said wire mesh structure, and said delivery device comprises an elongate body having a proximal end, a distal end, and a standard sheath or a tear away sheath for coaxially sliding over said intragastric device for constricting said intragastric device in said pre-deployment configuration coaxially over said distal end of said body of said delivery device, said method comprising the steps of: coaxially placing said constricted intragastric device in said pre-deployment configuration over said distal end of said body of said delivery device; endoscopically inserting said delivery device with or without a guidewire into a patient and advancing said distal end of said body of said delivery device to a duodenum and/or jejunum of said patient; positioning said body of said delivery device in said gastrointestinal tract of said patient such that said wire mesh structure is positioned in a stomach of said patient proximate a pylorus and said sleeve is positioned extending through said pylorus and into said duodenum; using a working tool to tear said tear away sheath to remove said sheath from said constricted intragastric device, allowing said intragastric device to automatically expand into said post-deployment configuration; and, sliding said distal end of said body of said delivery device coaxially away from said expanded intragastric device and removing said delivery device from said patient such that the intragastric device freely moves in the gastric lumen and the sleeve freely moves inside the proximal gastrointestinal tract.

In various embodiments, the intragastric mesh occupies the gastric lumen and moves about freely in the gastric lumen, reducing the volume available for ingested food material. Partially digested food passes into the mesh, exits the mesh through one or more of its distal ports, enters into the sleeve, and bypasses a proximal portion of the small intestine. In one embodiment, the intragastric mesh structure can intermittently, with gastric peristalsis, block the passage of food from the stomach into the small intestine, thereby delaying gastric emptying. In another embodiment, the intragastric mesh slows the emptying of food that has entered the mesh into the small intestine, further delaying gastric emptying.

In one embodiment, the sleeve is made of more than one telescoping sleeves with the most proximal sleeve receiving food from the mesh and emptying into the distal sleeve, while the distal sleeve collects the food that has passed around the mesh into the small intestine and prevents such bypassed food from coming into contact with a part of the gastrointestinal tract.

In various embodiments, any of the delivery methods above further comprises the step of applying a cooling element to said compressed intragastric device to slow the expansion of said wire mesh structure during removal of said thread or sheath, facilitating the removal of said delivery device.

The present specification also discloses a method of retrieving an intragastric device from a gastrointestinal tract of a patient using a retrieval device, wherein said intragastric device comprises a wire mesh structure configurable between a compressed pre-deployment configuration and an expanded post-deployment configuration and includes at least one circumferential constricting mechanism positioned about said wire mesh structure and a retrieval mechanism at its proximal end and, an elongate sleeve coupled to a distal end of said wire mesh structure, and said retrieval device comprises an elongate body having a proximal end and a distal end and a lumen within, an elongate metal wire disposed within said lumen and having a proximal end and a distal end, an engaging or grasping mechanism formed from said distal end of said wire for engaging or grasping a free end of said at least one circumferential constricting mechanism and said retrieval mechanism of said wire mesh structure, and an actuator attached to said proximal end of said wire, said method comprising the steps of: endoscopically inserting said retrieval device into said patient and advancing said distal end of said body of said retrieval device to a proximal end of said intragastric device; manipulating said engaging or grasping mechanism of said retrieval device to engage a free end of said at least one circumferential constricting mechanism positioned about said wire mesh structure; pulling on said actuator of said retrieval device to constrict and automatically lock said at least one circumferential constricting mechanism, thereby compressing said wire mesh structure into said pre-deployment shape; manipulating said grasping mechanism of said retrieval device to disengage said free end of said at least one circumferential constricting mechanism; manipulating said grasping mechanism to engage said retrieval mechanism at said proximal end of said wire mesh structure; pulling said actuator to withdraw a proximal portion of said intragastric device into said lumen of said retrieval device; and, removing said retrieval device and said intragastric device from said patient.

The present specification also discloses a method of retrieving an intragastric device from a gastrointestinal tract of a patient using a retrieval device, wherein said intragastric device comprises a wire mesh structure configurable between a compressed pre-deployment configuration and an expanded post-deployment configuration and includes at least one circumferential constricting mechanism positioned about said wire mesh structure and, an elongate sleeve coupled to a distal end of said wire mesh structure, and said retrieval device comprises an elongate body having a proximal end and a distal end and a lumen within, an elongate metal wire disposed within said lumen and having a proximal end and a distal end, a grasping mechanism formed from said distal end of said wire for grasping a free end of said at least one circumferential constricting mechanism, an actuator attached to said proximal end of said wire, a grasper having two opposing jaws attached to said distal end of said elongate body and operatively connected to said actuator at said proximal end of said wire, and at least one clamp positioned between said jaws of said grasper, said method comprising the steps of: endoscopically inserting said retrieval device into said patient and advancing said distal end of said body of said retrieval device to a proximal end of said intragastric device; manipulating said grasping mechanism of said retrieval device to engage a free end of said at least one circumferential constricting mechanism positioned about said wire mesh structure; pulling on said actuator of said retrieval device to constrict said at least one circumferential constricting mechanism, thereby compressing said wire mesh structure into said pre-deployment shape; manipulating said grasper of said retrieval device to apply said at least one clamp to said free end of said at least one circumferential constricting mechanism proximate said compressed wire mesh structure; pulling said actuator to withdraw a proximal portion of said intragastric device into said lumen of said retrieval device; and, removing said retrieval device and said intragastric device from said patient.

In various embodiments, any of the retrieval methods above further comprises the step of applying a cooling element to said compressed intragastric device to prevent the re-expansion of said wire mesh structure during removal of said retrieval device and said intragastric device.

The aforementioned and other embodiments of the present invention shall be described in greater depth in the drawings and detailed description provided below.

BRIEF DESCRIPTION OF THE DRAWINGS

These and other features and advantages of the present invention will be appreciated as they become better understood by reference to the following detailed description when considered in connection with the accompanying drawings, wherein:

FIG. 2A is an illustration of a wire mesh structure of an intragastric device in a post-deployment configuration in accordance with one embodiment of the present specification, depicting a first weave pattern;

FIG. 2B is an illustration of a wire mesh structure of an intragastric device in a post-deployment configuration in accordance with another embodiment of the present specification, depicting a second weave pattern;

FIG. 2C is an illustration of a wire mesh structure of an intragastric device in a post-deployment configuration in accordance with another embodiment of the present specification, depicting a third weave pattern;

FIG. 2D is an illustration of a wire mesh structure of an intragastric device in a post-deployment configuration in accordance with another embodiment of the present specification, depicting a fourth weave pattern;

FIG. 2E is an illustration of a wire mesh structure of an intragastric device in a post-deployment configuration in accordance with yet another embodiment of the present specification, depicting a fifth weave pattern;

FIG. 2G is an illustration of yet another embodiment of an intragastric device in an exemplary post-deployment configuration;

FIG. 2H is a cross-sectional illustration of the embodiment of the intragastric device depicted in FIG. 2G;

FIG. 2O is an illustration of one embodiment depicting an exemplary post-deployment membrane covered intragastric device with varying sized holes along its surface;

FIG. 2Q is an illustration of a first exemplary wire mesh structure shape, in accordance with one embodiment of the present specification;

FIG. 2R is an illustration of a second exemplary wire mesh structure shape, in accordance with one embodiment of the present specification;

FIG. 2S is an illustration of a third exemplary wire mesh structure shape, in accordance with one embodiment of the present specification;

FIG. 2T is an illustration of a fourth exemplary wire mesh structure shape, in accordance with one embodiment of the present specification;

FIG. 2U is an illustration of a fifth exemplary wire mesh structure shape, in accordance with one embodiment of the present specification;

FIG. 3A is an illustration of a wire mesh structure and coupled sleeve of an intragastric device in a post-deployment configuration in accordance with one embodiment of the present specification, depicting the wire mesh structure with the weave pattern as shown in FIG. 2B;

FIG. 3B is an illustration of a wire mesh structure and coupled sleeve of an intragastric device in a post-deployment configuration in accordance with another embodiment of the present specification, depicting the wire mesh structure with the weave pattern as shown in FIG. 2C;

FIG. 4A is an illustration of a wire mesh structure with retrieval hook and coupled sleeve of an intragastric device in a post-deployment configuration in accordance with one embodiment of the present specification, depicting the wire mesh structure with the weave pattern as shown in FIG. 2B;

FIG. 4B is an illustration of a wire mesh structure with retrieval hook and coupled sleeve of an intragastric device in a post-deployment configuration in accordance with another embodiment of the present specification, depicting the wire mesh structure with the weave pattern as shown in FIG. 2C;

FIG. 4C is an illustration of a wire mesh structure with retrieval hook and coupled sleeve of an intragastric device in a post-deployment configuration in accordance with another embodiment of the present specification, depicting the wire mesh structure with the weave pattern as shown in FIG. 2D;

FIG. 4D is an illustration of a wire mesh structure with retrieval hook and coupled sleeve of an intragastric device in a post-deployment configuration in accordance with yet another embodiment of the present specification, depicting the wire mesh structure with the weave pattern as shown in FIG. 2E;

FIG. 5A is an illustration of a wire mesh structure with retrieval hook, coupled sleeve, and anti-migration component of an intragastric device in a post-deployment configuration in accordance with one embodiment of the present specification, depicting the wire mesh structure with the weave pattern as shown in FIG. 2B;

FIG. 5B is an illustration of a wire mesh structure with retrieval hook, coupled sleeve, and anti-migration component of an intragastric device in a post-deployment configuration in accordance with another embodiment of the present specification, depicting the wire mesh structure with the weave pattern as shown in FIG. 2C;

FIG. 5C is an illustration of a wire mesh structure with retrieval hook, coupled sleeve, and anti-migration component of an intragastric device in a post-deployment configuration in accordance with another embodiment of the present specification, depicting the wire mesh structure with the weave pattern as shown in FIG. 2D;

FIG. 5D is an illustration of a wire mesh structure with retrieval hook, coupled sleeve, and anti-migration component of an intragastric device in a post-deployment configuration in accordance with yet another embodiment of the present specification, depicting the wire mesh structure with the weave pattern as shown in FIG. 2E;

FIG. 6A is an illustration of one embodiment depicting a first exemplary configuration of the wire mesh structure;

FIG. 6B is an illustration of one embodiment depicting a second exemplary configuration of the wire mesh structure;

FIG. 6C is an illustration of one embodiment depicting a third exemplary configuration of the wire mesh structure;

FIG. 6D is an illustration of one embodiment depicting a fourth exemplary configuration of the wire mesh structure;

FIG. 6E is an illustration of one embodiment depicting a fifth exemplary configuration of the wire mesh structure;

FIG. 6F is an illustration of one embodiment depicting the expanded configuration of the wire mesh structure of FIG. 6E;

FIG. 6G is an illustration of one embodiment depicting a sixth exemplary configuration of the wire mesh structure;

FIG. 6H is an illustration of one embodiment depicting a seventh exemplary configuration of the wire mesh structure;

FIG. 6I is an illustration of one embodiment depicting an eighth exemplary configuration of the wire mesh structure;

FIG. 6J is an illustration of one embodiment depicting a ninth exemplary configuration of the wire mesh structure;

FIG. 17C is an illustration of a sleeve component of an intragastric device in a post-deployment configuration in accordance with one embodiment of the present specification, depicting a wire mesh support, a proximal first opening, and a side second opening proximate the distal end of the sleeve;

FIG. 17D is an illustration of a sleeve component of an intragastric device in a post-deployment configuration in accordance with one embodiment of the present specification, depicting a wire mesh support, a proximal first opening, and a second opening at the distal end of the sleeve;

FIG. 17E is an illustration of a sleeve component of an intragastric device in a post-deployment configuration in accordance with one embodiment of the present specification, depicting a spiral wire support, a proximal first opening, and a side second opening proximate the distal end of the sleeve;

FIG. 17F is an illustration of a sleeve component of an intragastric device in a post-deployment configuration in accordance with one embodiment of the present specification, depicting a spiral wire support, a proximal first opening, and a second opening at the distal end of the sleeve;

FIG. 18E is an illustration of another embodiment of the intragastric device with an attached sleeve in an exemplary pre-deployment configuration;

FIG. 18F is an illustration of the intragastric device with an attached sleeve of FIG. 18E in an exemplary post-deployment configuration;

FIG. 24D is an illustration of a fourth exemplary double-wire mesh structure intragastric device in a post-deployment configuration in accordance with one embodiment of the present specification;

FIG. 24E is an illustration of a fifth exemplary double-wire mesh structure intragastric device in a post-deployment configuration in accordance with one embodiment of the present specification;

FIG. 25 is an illustration of one embodiment of an intragastric device in a post-deployment configuration having a wire mesh structure, anti-migration disc, and sleeve, depicting a membrane covering the sleeve and a lower portion of the wire mesh structure;

FIG. 26A is an illustration of a portion of a patient's gastrointestinal tract following a sleeve gastrectomy procedure;

FIG. 26B is an illustration of a portion of a patient's gastrointestinal tract following a roux-en-y gastric bypass (RGB) procedure;

FIG. 36 is an illustration of one embodiment of an intragastric device in an exemplary pre-deployment configuration;

FIG. 38 is an illustration of one embodiment of an intragastric device in an exemplary post-deployment configuration;

FIG. 39 is an illustration of another embodiment of an intragastric device in an exemplary post-deployment configuration;

FIG. 40A is an illustration of a gastric device removal catheter attached to an intragastric device in an exemplary post-deployment configuration;

FIG. 40B is an illustration of a gastric device removal catheter attached to an intragastric device in an exemplary pre-deployment configuration;

FIG. 41 is an illustration of one embodiment of an intragastric device being deployed in a stomach;

FIG. 42 is an illustration of one embodiment of a fully deployed intragastric device in a stomach;

FIG. 43A is an illustration of an intragastric device having an oval shaped wire mesh structure deployed in the gastrointestinal tract of a patient, in accordance with one embodiment of the present specification;

FIG. 43B is an illustration of an intragastric device having a football shaped wire mesh structure deployed in the gastrointestinal tract of a patient, in accordance with one embodiment of the present specification;

FIG. 44 is an illustration of one embodiment of an intragastric device with an attached sleeve being deployed in an upper gastrointestinal tract;

FIG. 45 is an illustration of one embodiment of a fully deployed intragastric device with an attached sleeve in an upper gastrointestinal tract;

FIG. 46 is an illustration of one single exemplary intragastric device being attached to a previously deployed single intragastric device in a stomach;

FIG. 47 is an illustration of an exemplary fully deployed combined intragastric device in a stomach;

Figures 48, 49:
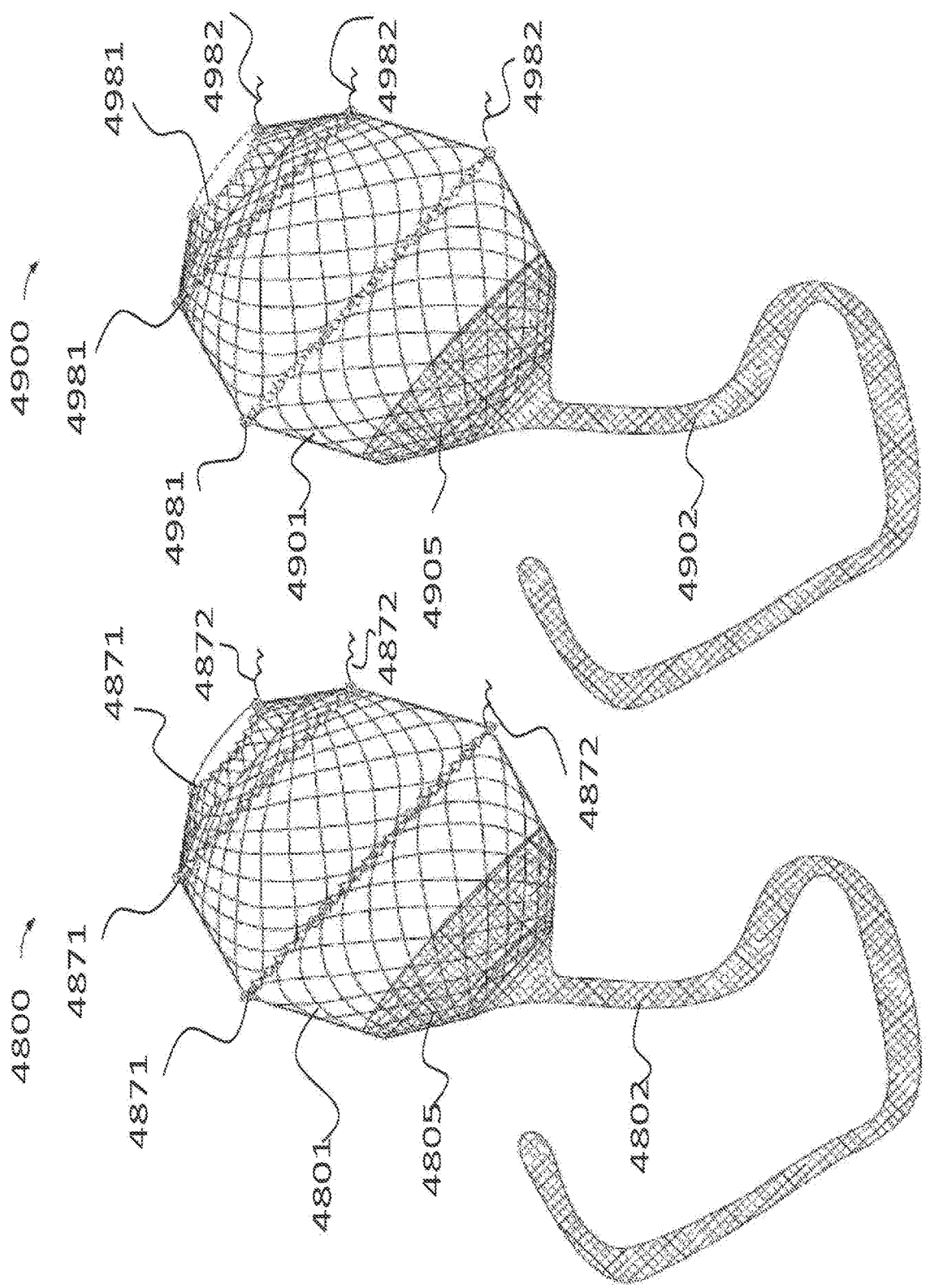
Figure 50:
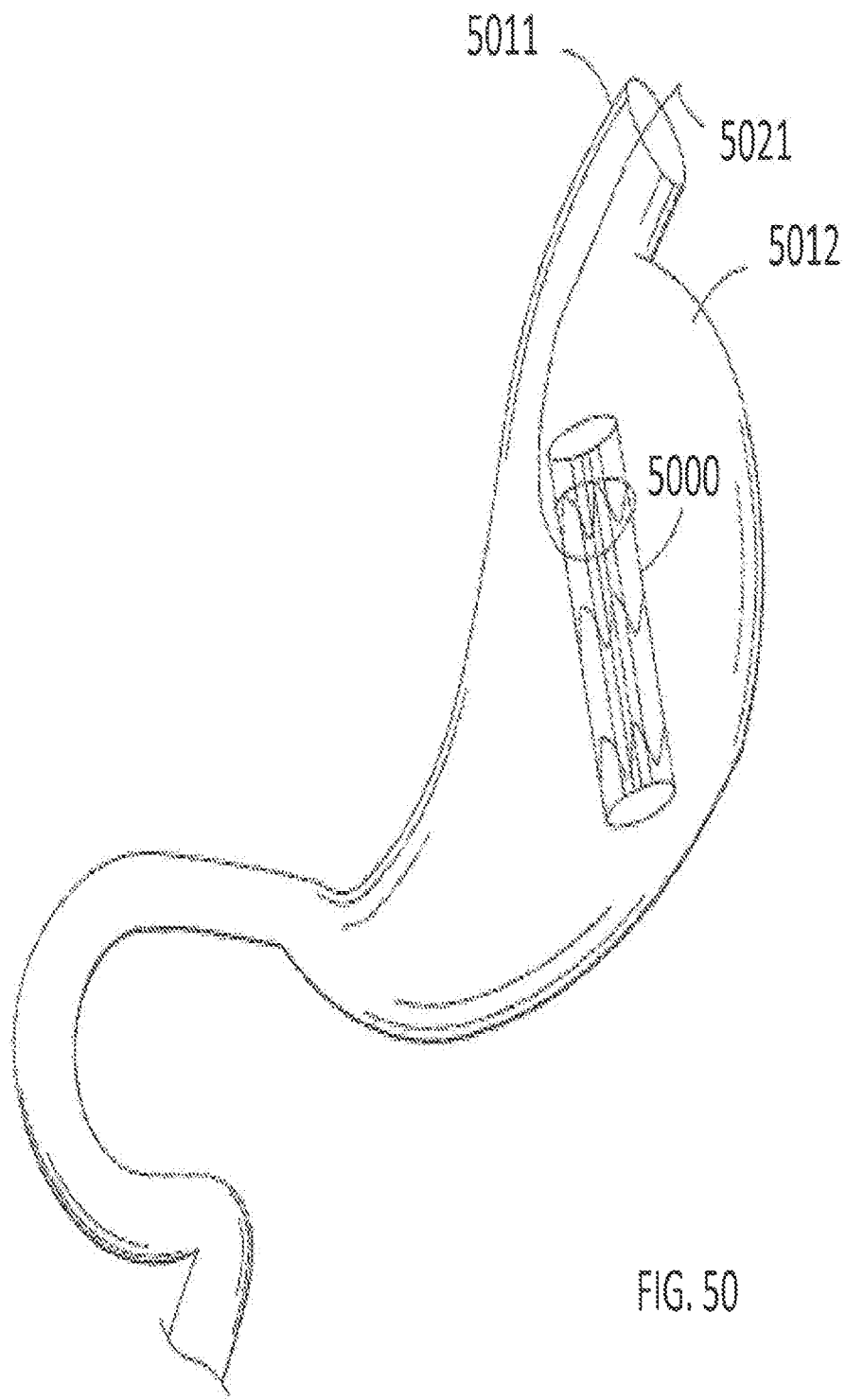
Figure 51:
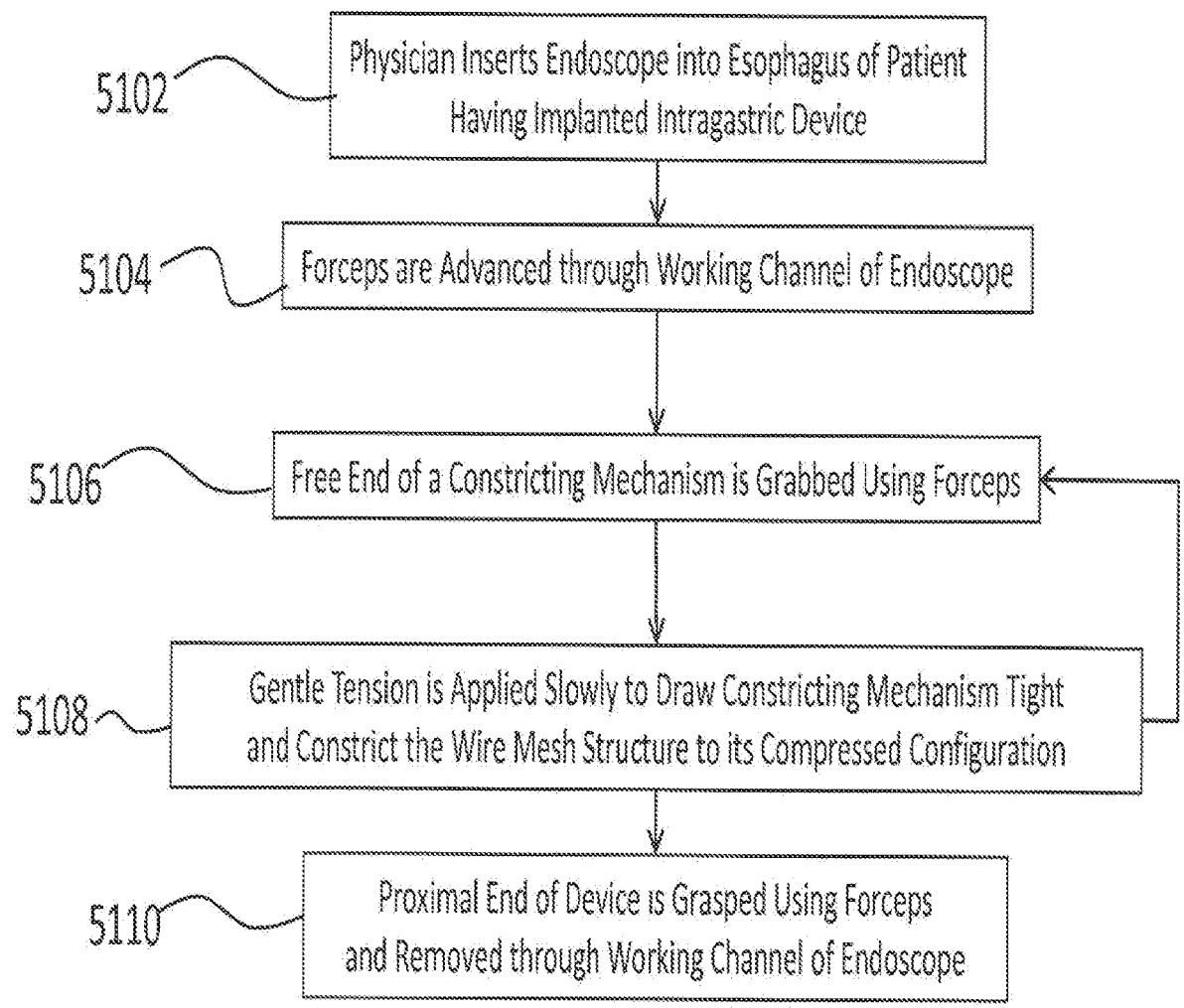
Figure 52:
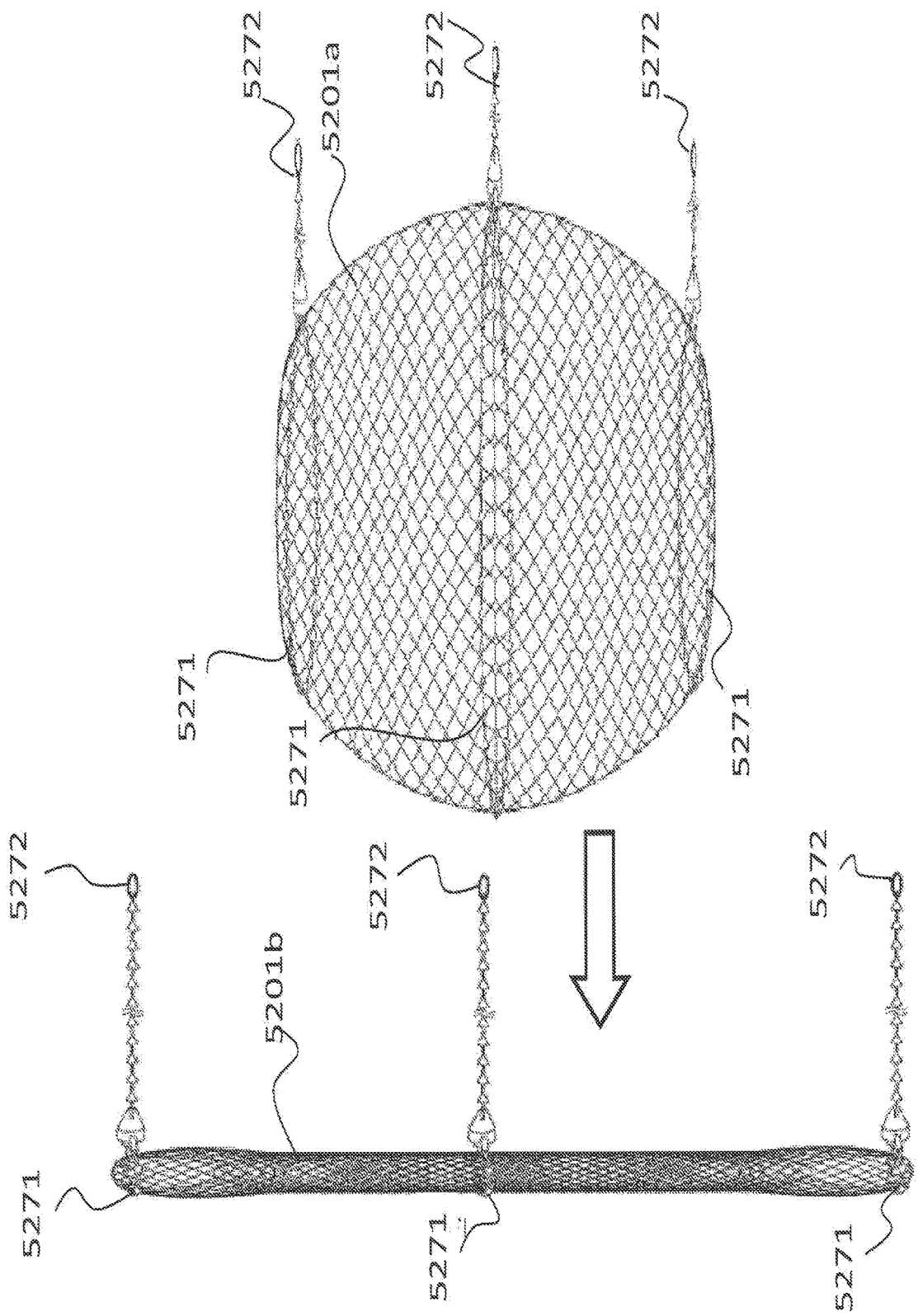
Figure 53:
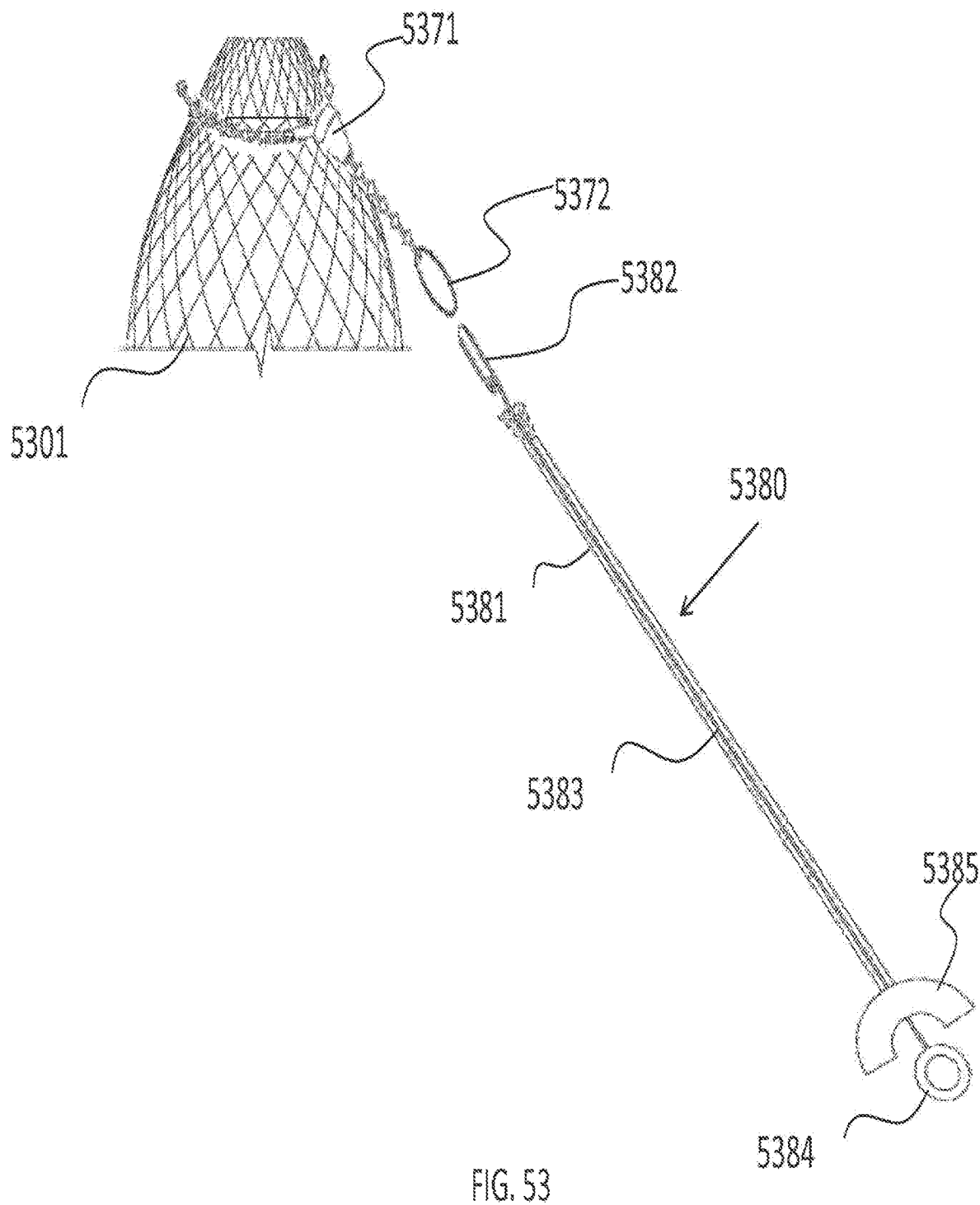
Figure 54:
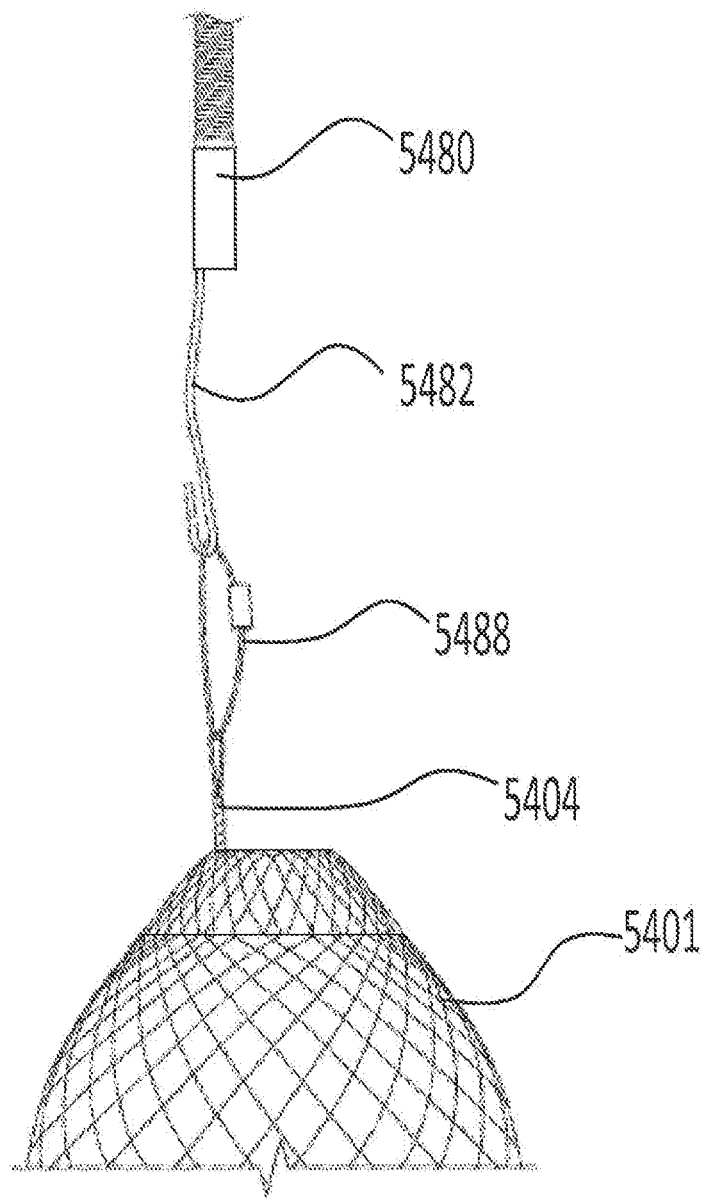
Figure 55A:
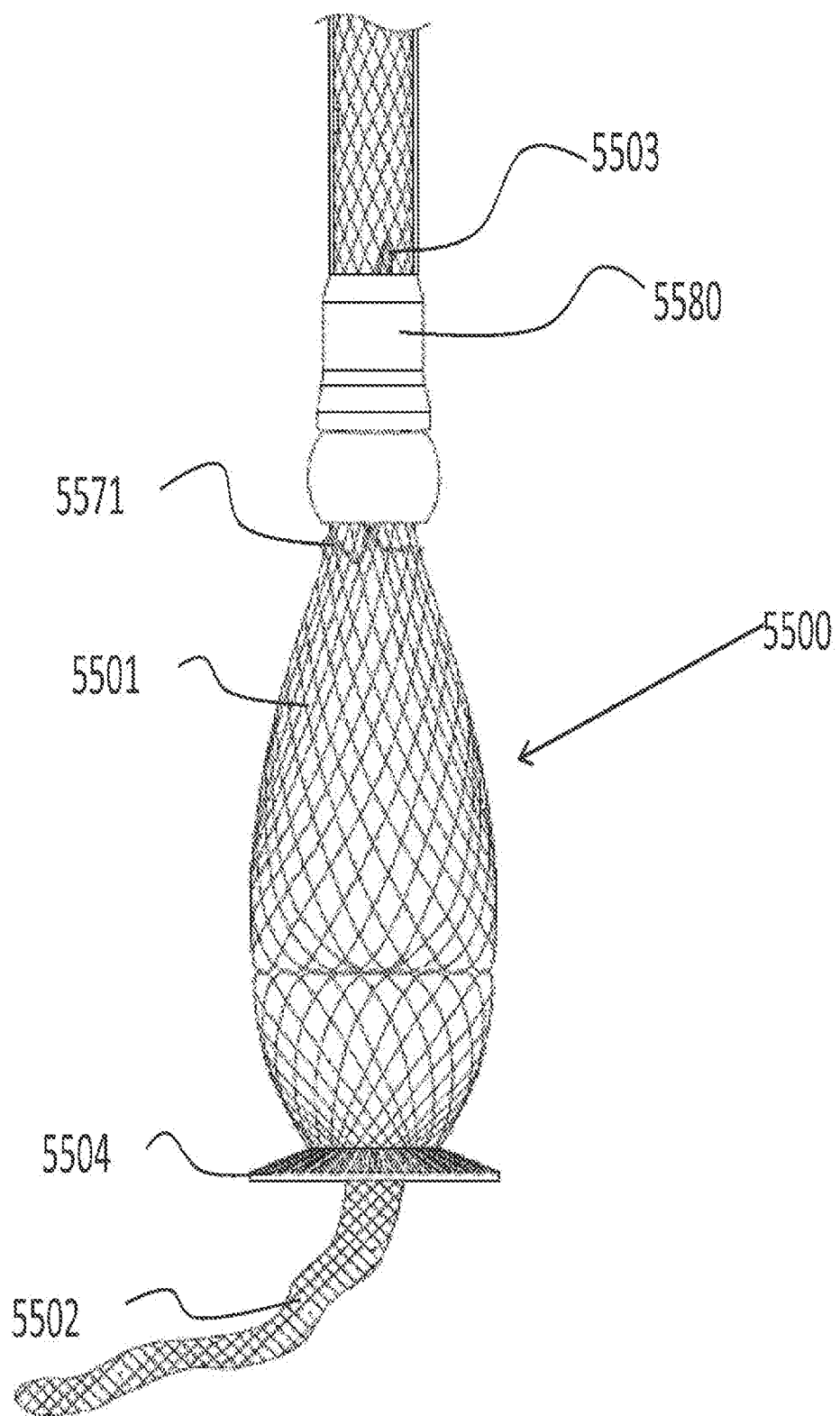
Figure 55B:
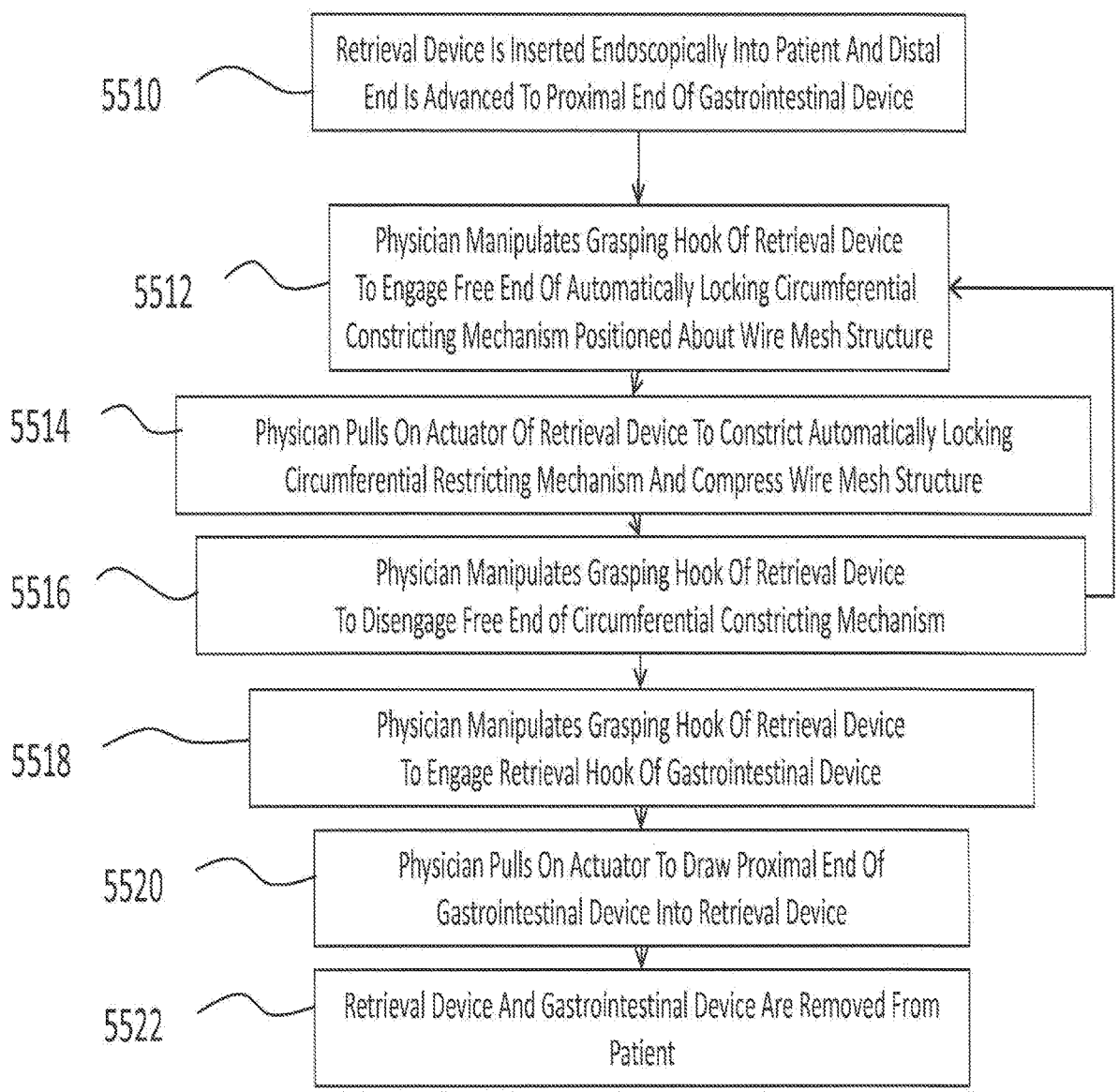
Figure 56A:
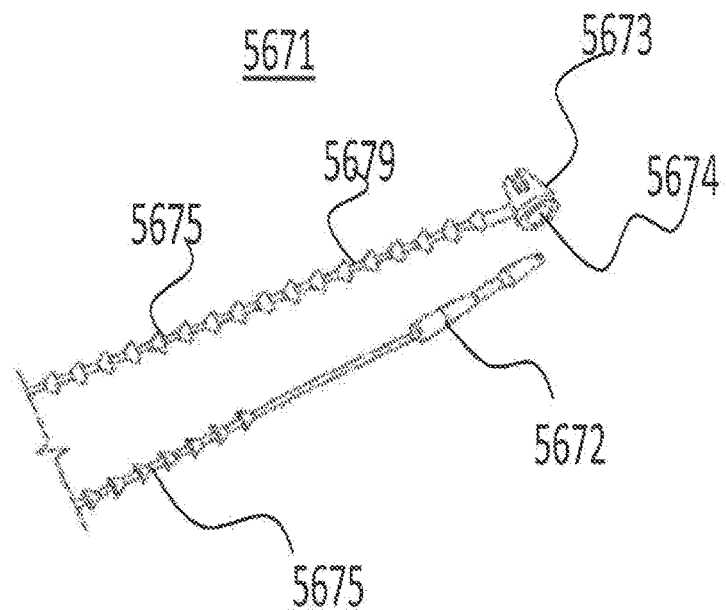
Figure 56B:
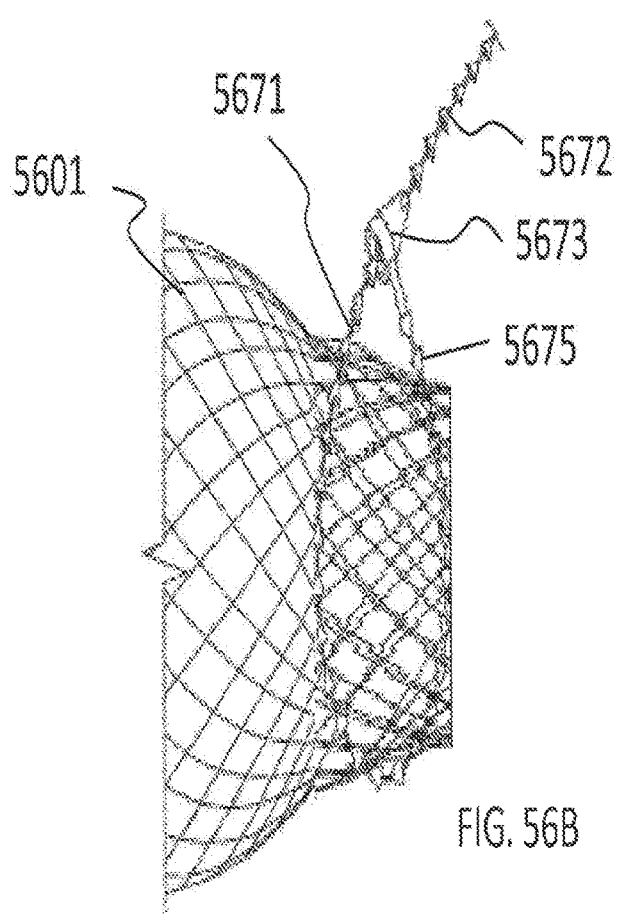
Figure 57:
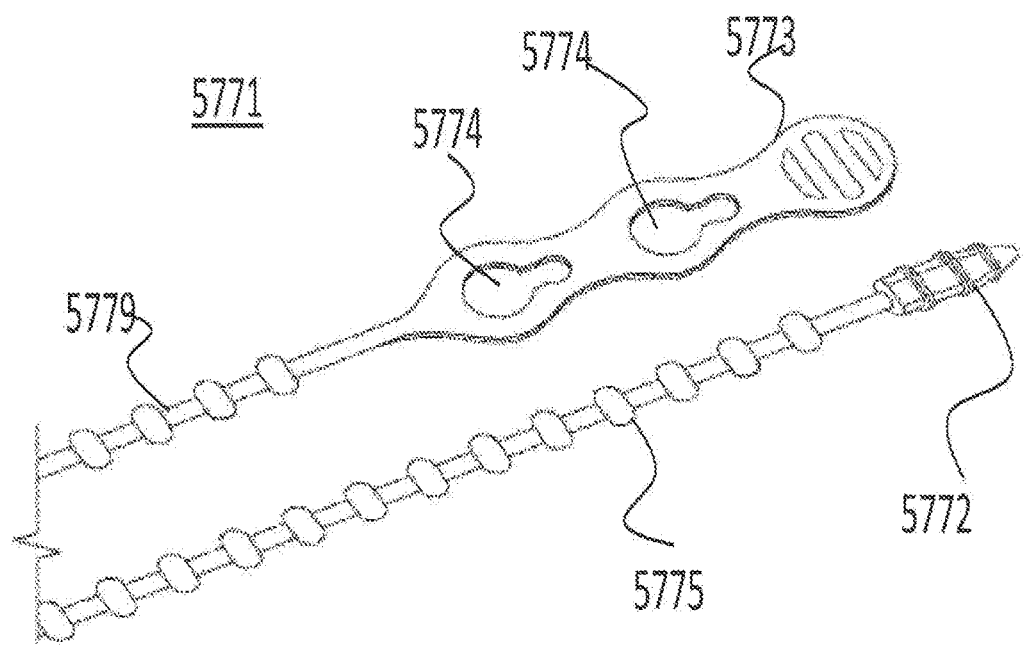
Figure 58:
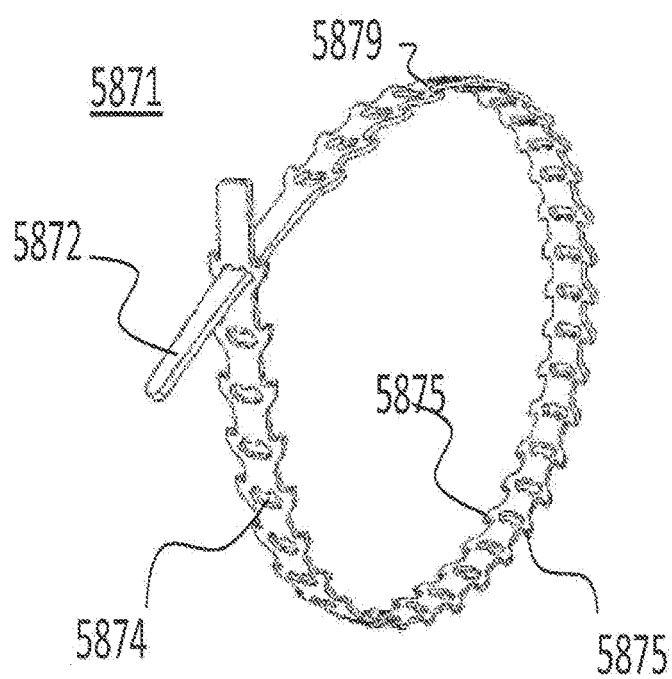
Figure 59A:
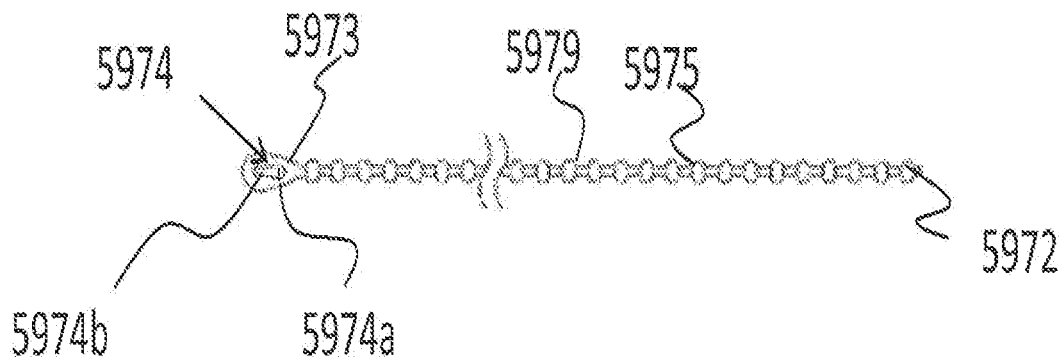
Figure 59B:
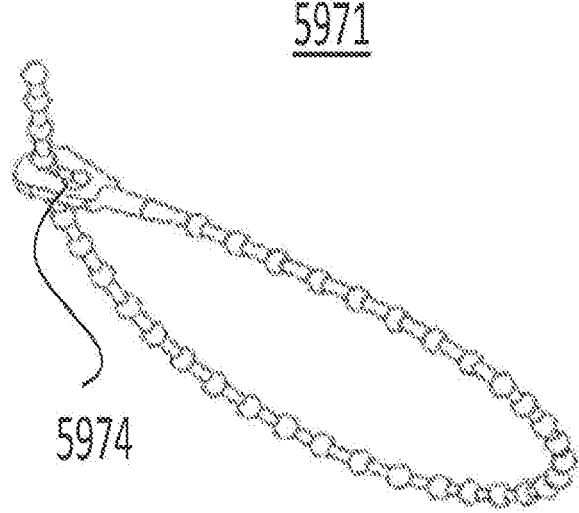
Figure 60:
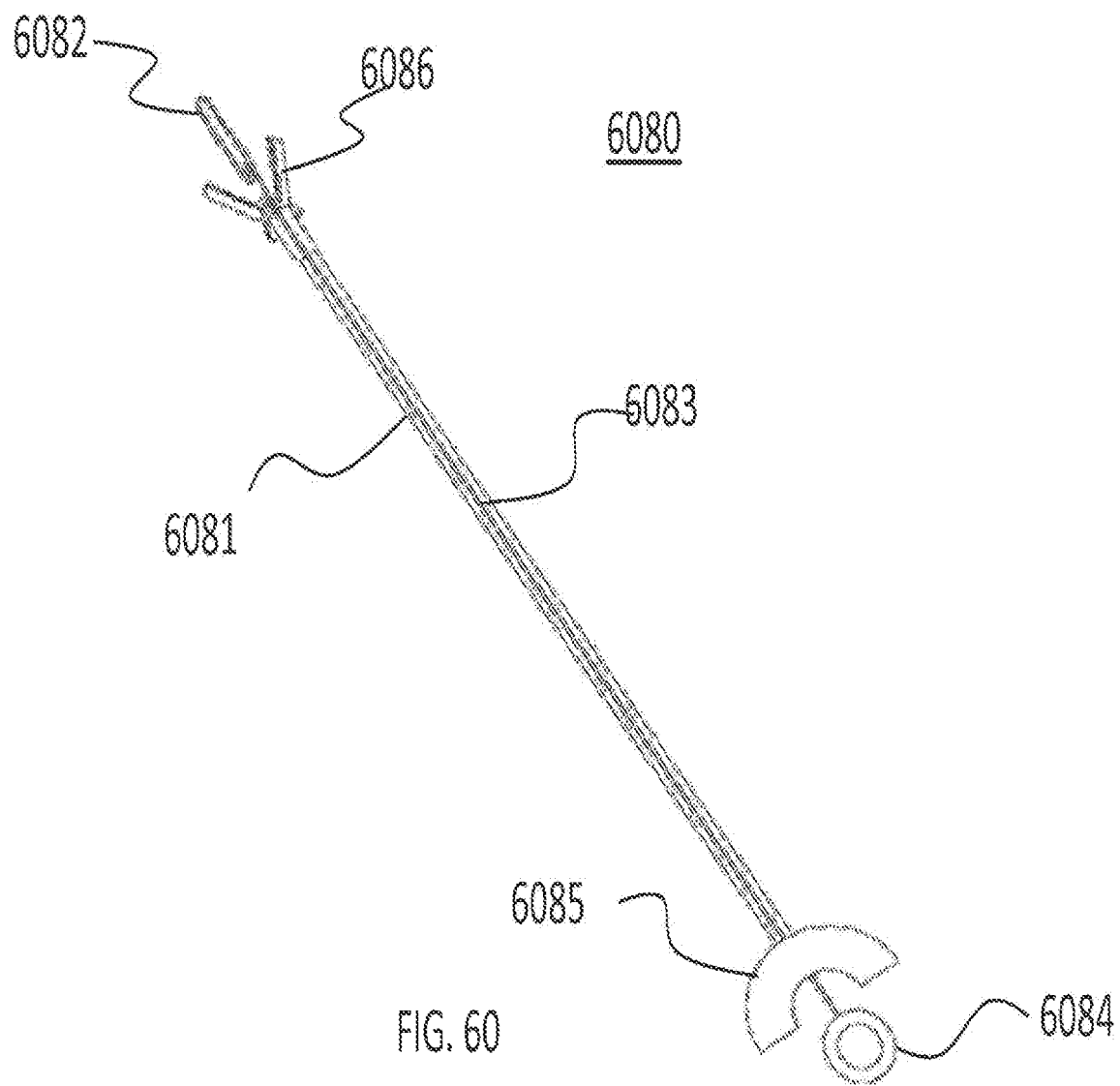
Figure 61:
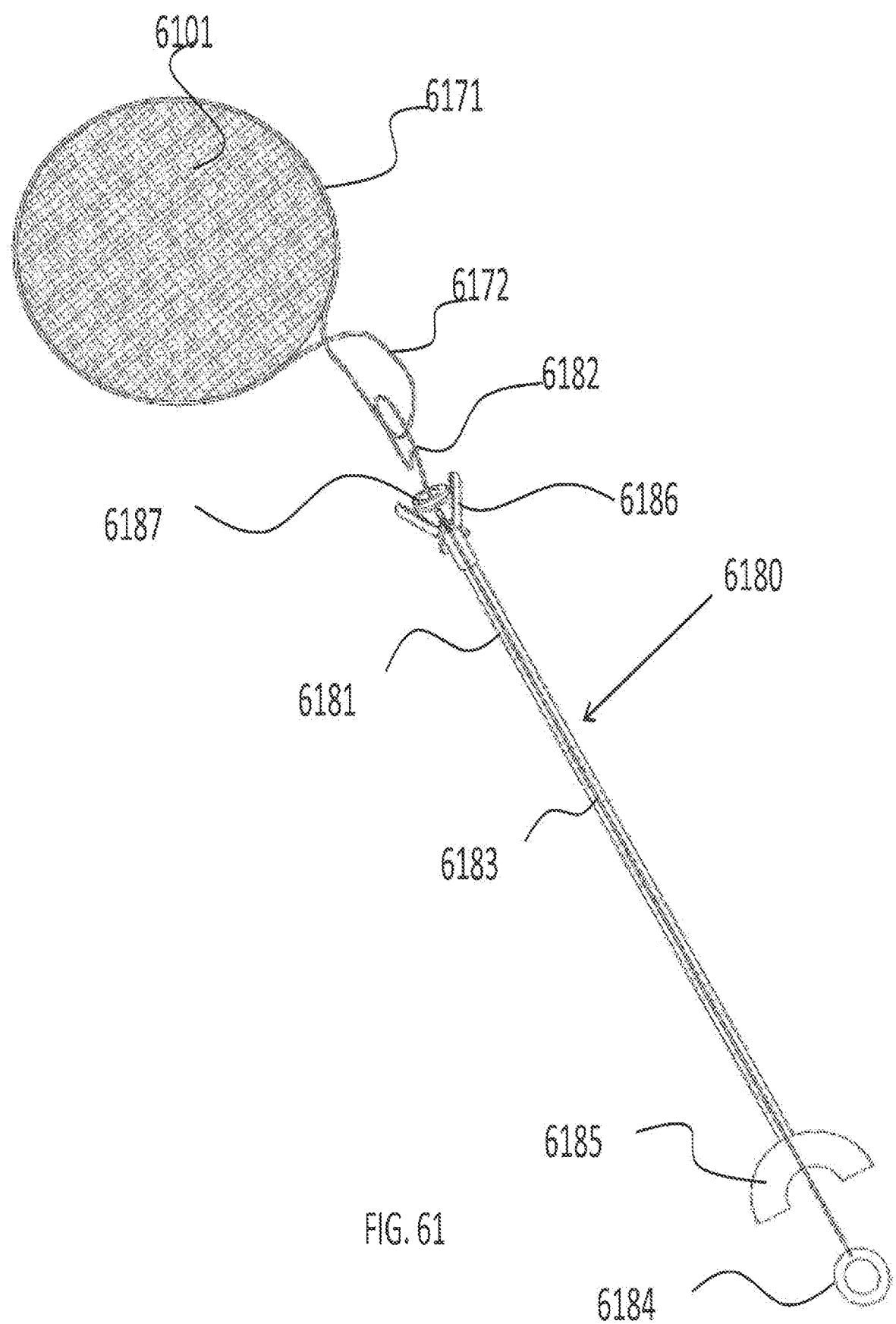
Figure 62:
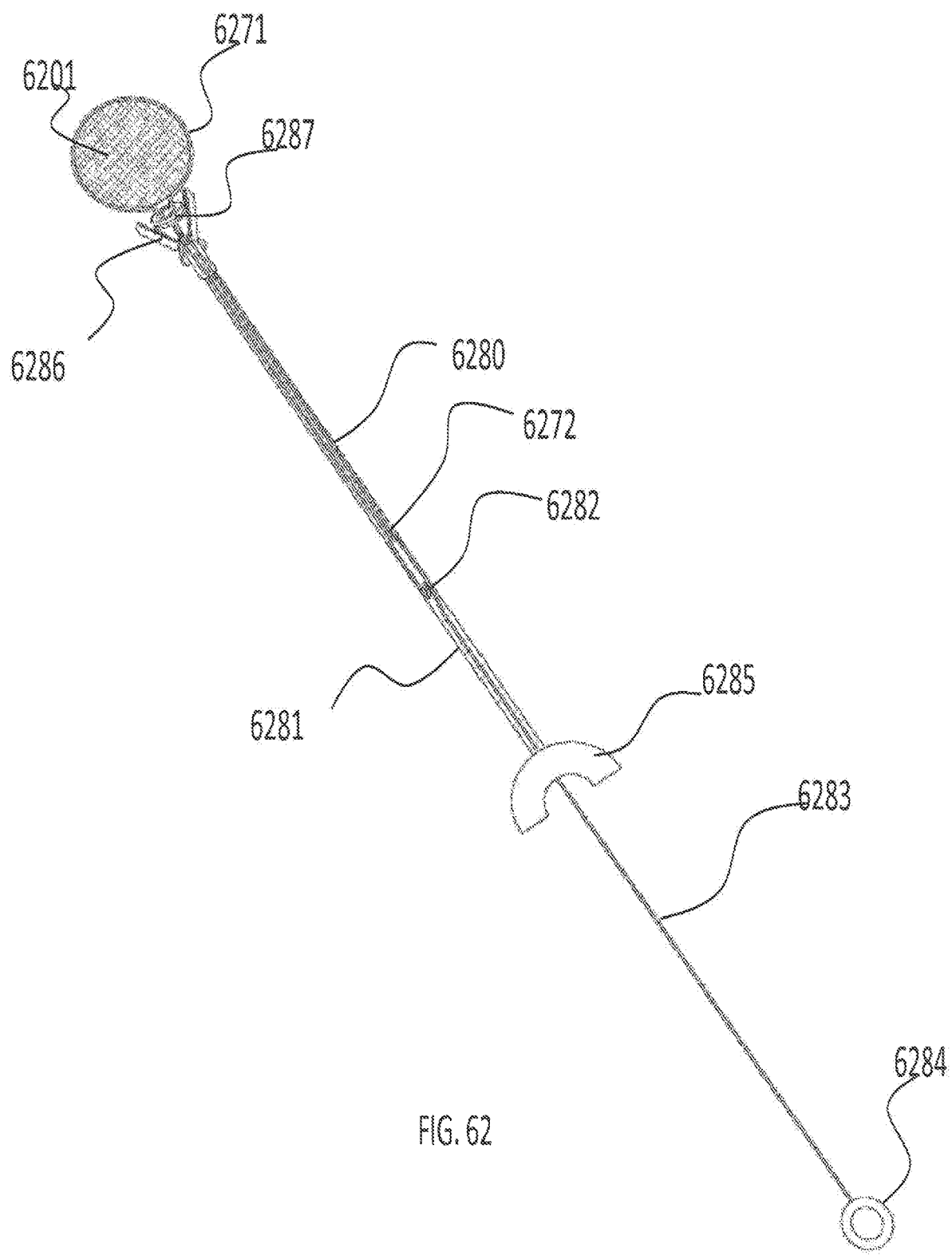
Figure 63:
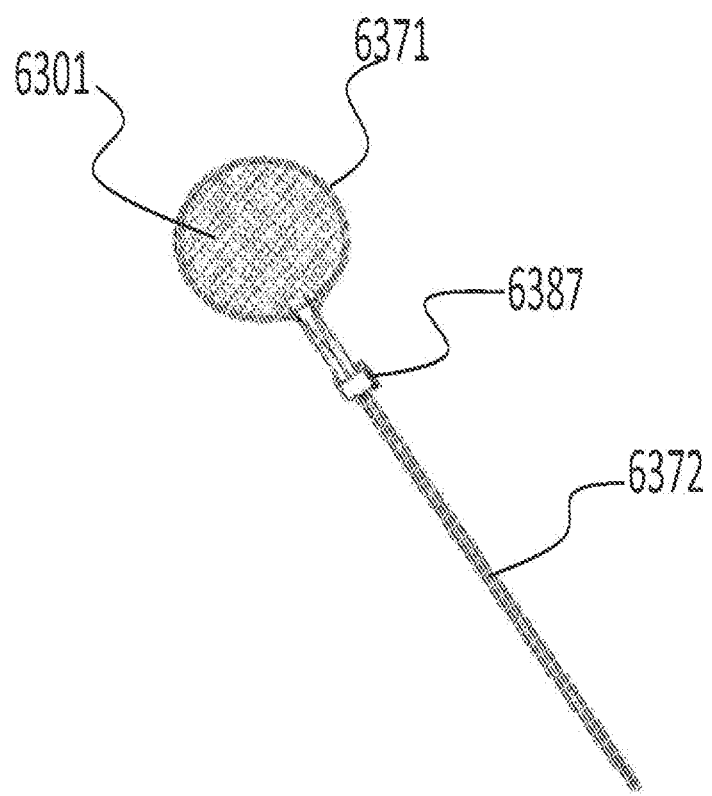
Figure 64:
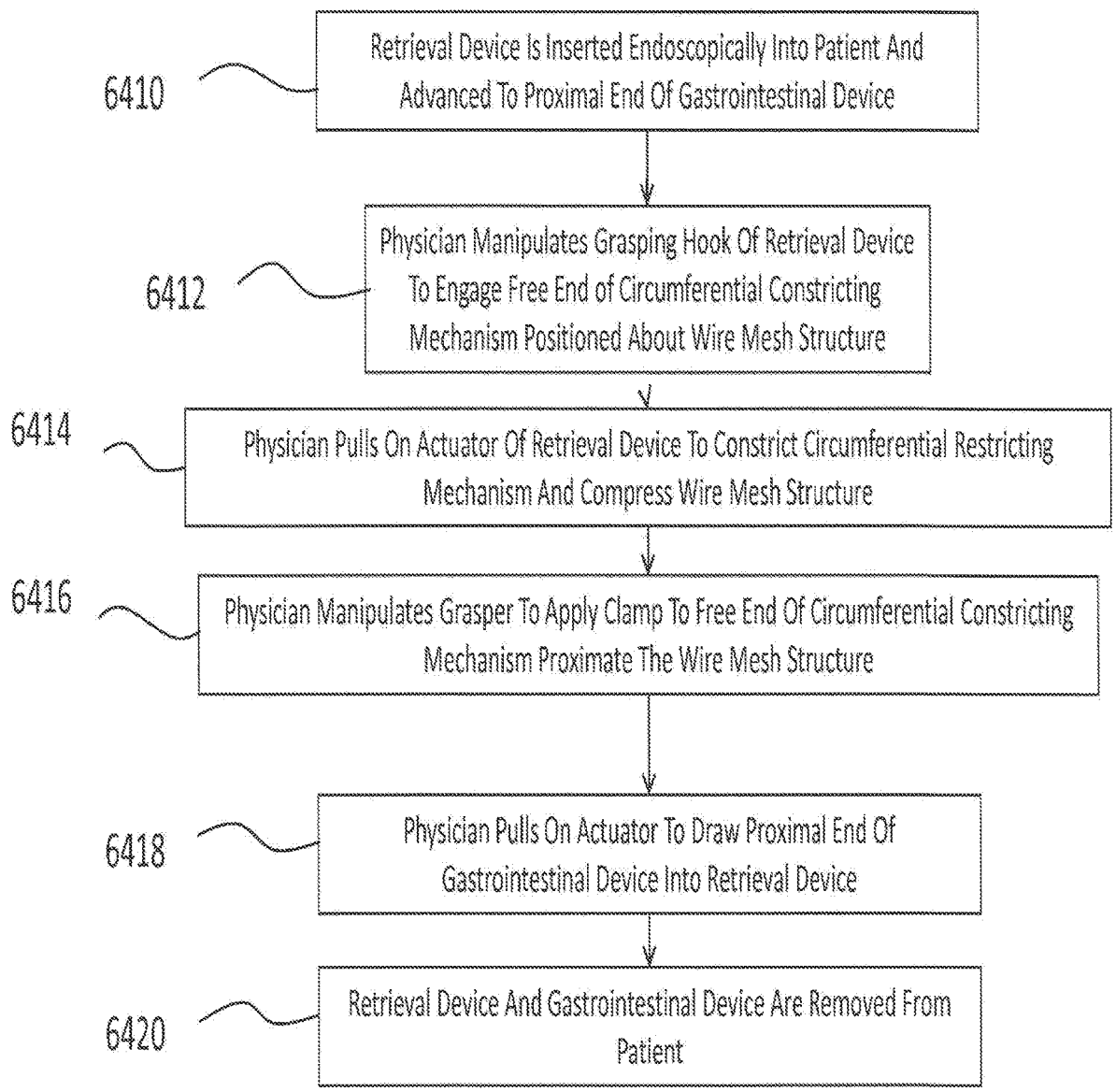
Figure 65A:
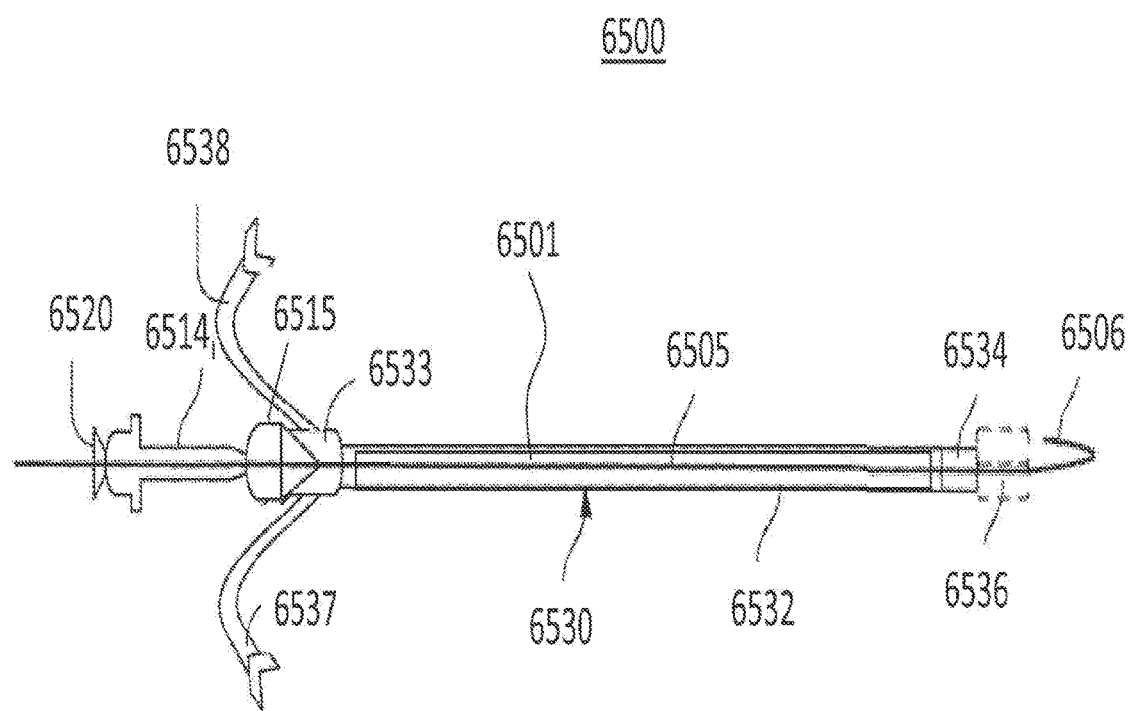
Figure 65B:
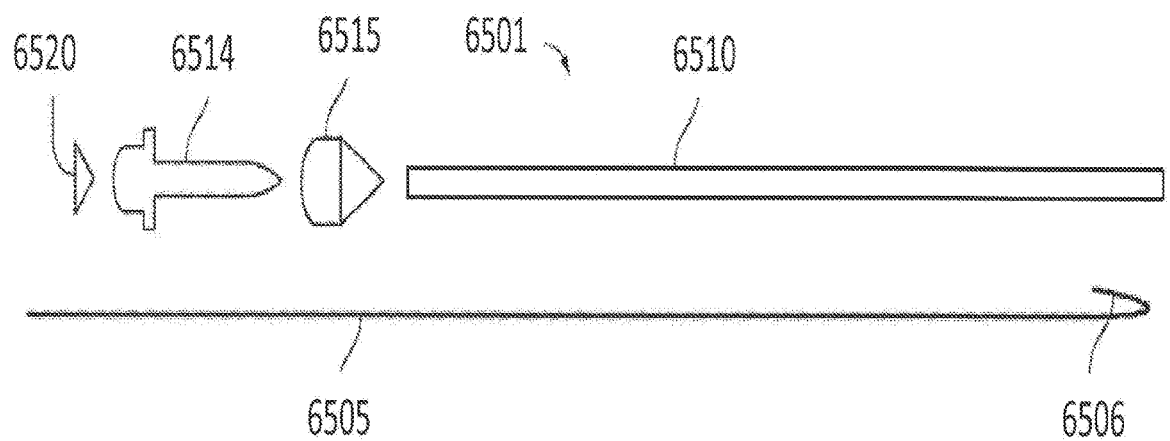
Figure 65C:
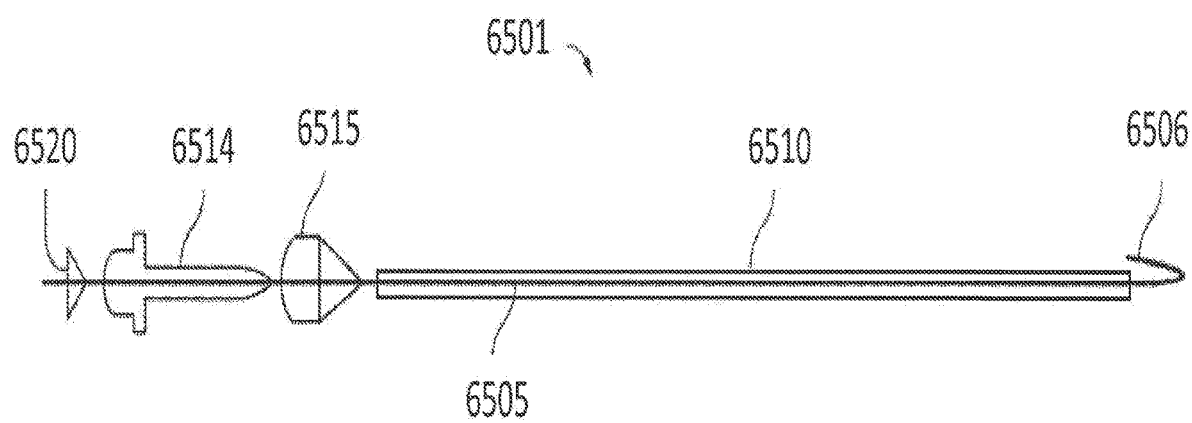
Figure 65D:
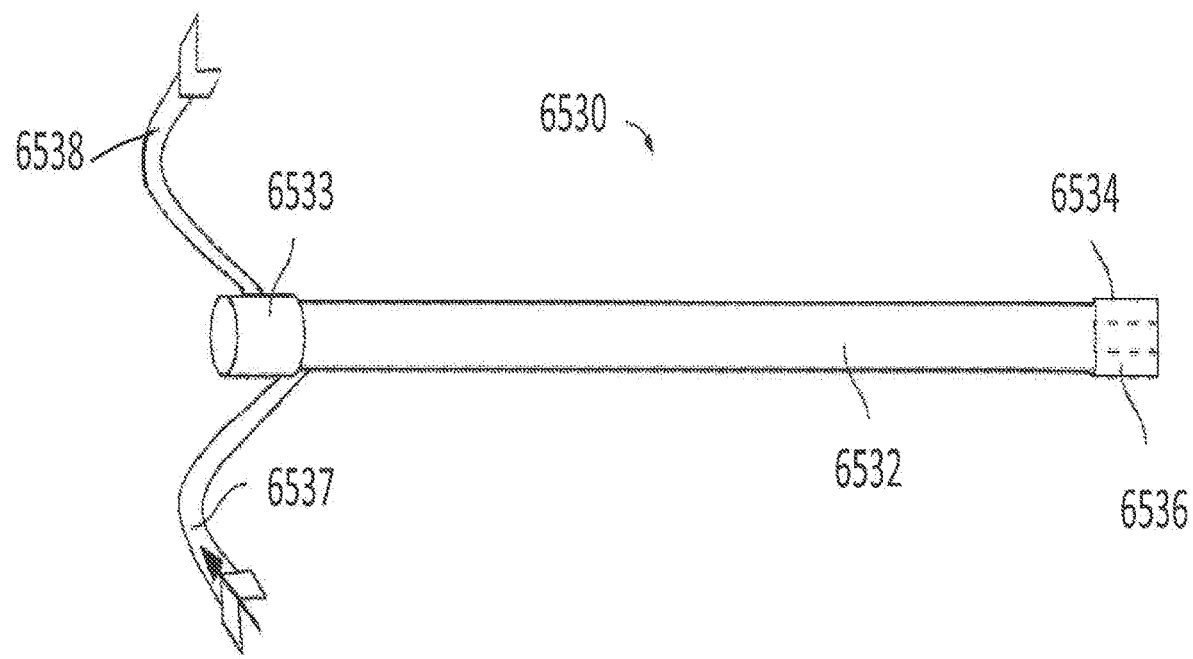
Figure 65E:
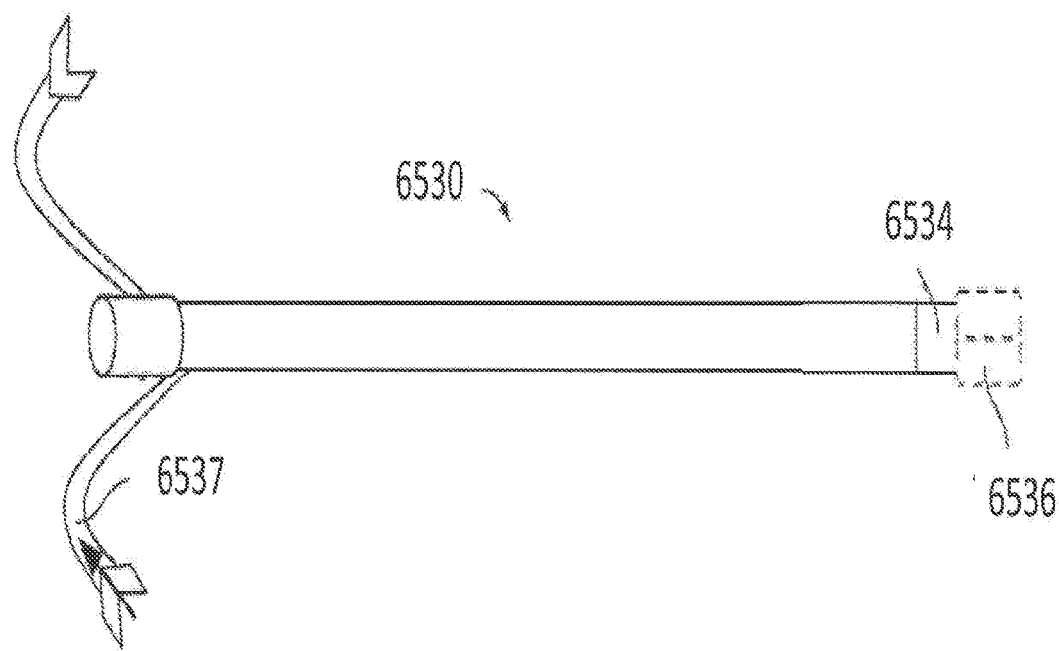
Figure 66:
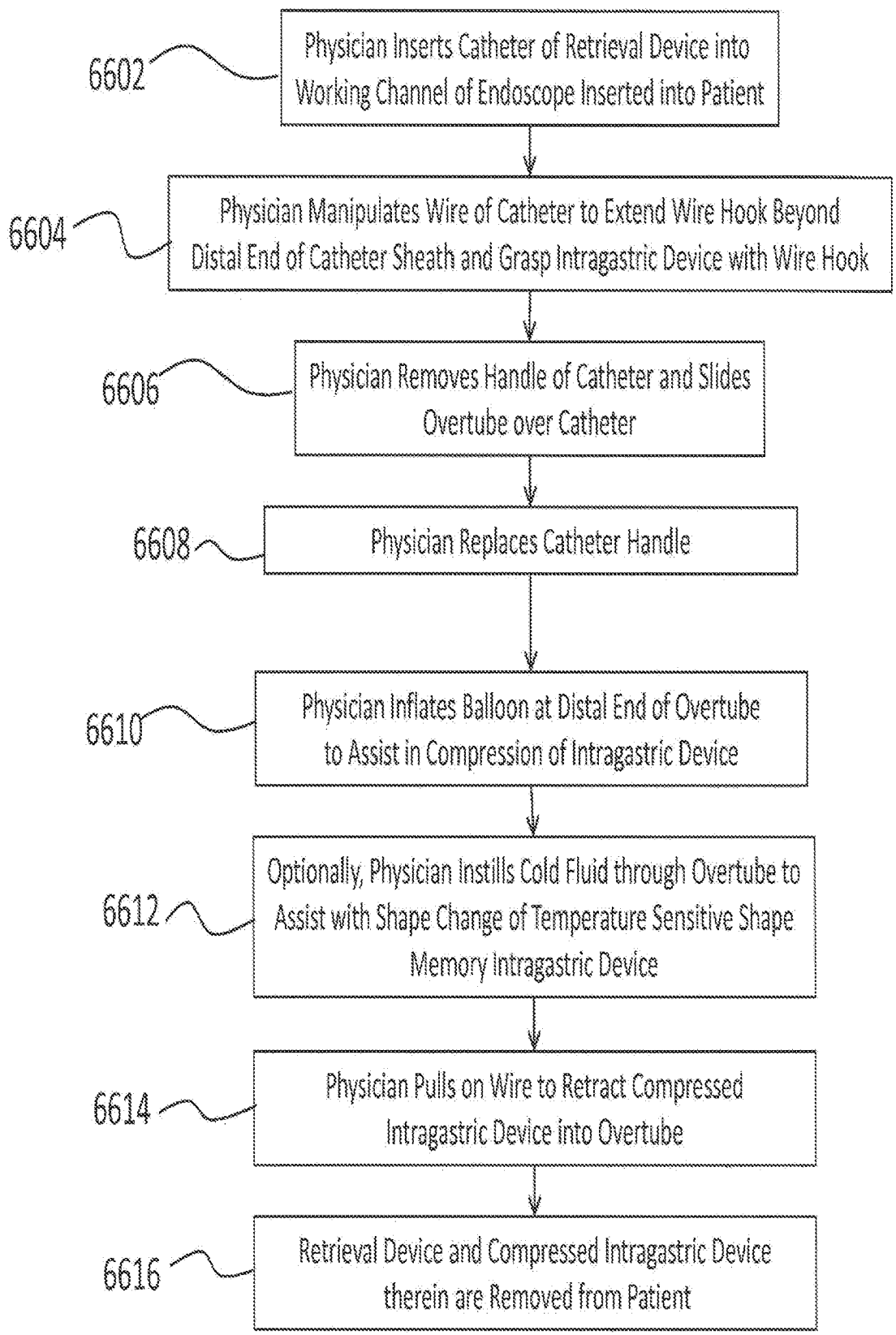

FIG. 48 is an illustration of one embodiment of an intragastric device in a post-deployment configuration having a first type of circumferential constraining mechanism positioned on a wire mesh structure;

FIG. 49 is an illustration of one embodiment of an intragastric device in a post-deployment configuration having a second type of circumferential constraining mechanism positioned on a wire mesh structure;

FIG. 50 is an illustration of an exemplary intragastric device being removed from a stomach;

FIG. 51 is a flow chart illustrating the steps involved during retrieval of an intragastric device in accordance with one embodiment of the present specification;

FIG. 52 is an illustration of one embodiment of a wire mesh structure of an intragastric device being restrained by circumferential constricting mechanisms prior to removal;

FIG. 53 is an illustration of one embodiment of a retrieval device and a portion of a wire mesh structure partially constrained by a circumferential constricting mechanism;

FIG. 54 is an illustration of one embodiment of a grasping hook of a retrieval device engaging a tie that has been secured to the retrieval hook of a wire mesh structure of an intragastric device;

FIG. 55A is an illustration of a wire mesh structure of an intragastric device partially drawn into the distal end of a retrieval device, in accordance with one embodiment of the present specification;

FIG. 55B is a flow chart illustrating the steps involved in retrieving a deployed intragastric device using the retrieval device of FIG. 54, in accordance with one embodiment of the present specification;

FIG. 56A is an illustration of a first exemplary circumferential constricting mechanism in accordance with one embodiment of the present specification;

FIG. 56B is an illustration of the first exemplary circumferential constricting mechanism of FIG. 56A, depicting the circumferential constricting mechanism tied about a portion of a wire mesh structure;

FIG. 57 is an illustration of a second exemplary circumferential constricting mechanism in accordance with one embodiment of the present specification;

FIG. 58 is an illustration of a third exemplary circumferential constricting mechanism in accordance with one embodiment of the present specification;

FIG. 59A is an illustration of a fourth exemplary circumferential constricting mechanism in accordance with one embodiment of the present specification;

FIG. 59B is an illustration of the exemplary circumferential constricting mechanism of FIG. 59A with a portion of the elongate body slid horizontally into the second section of the central opening, thereby locking the circumferential constricting mechanism;

FIG. 60 is an illustration of one embodiment of a retrieval device having a grasping hook and clampers at its distal end;

FIG. 61 is an illustration of one embodiment of a retrieval device with a grasping hook engaging the free end of a circumferential constricting mechanism positioned about a wire mesh structure;

FIG. 62 is an illustration of one embodiment of a retrieval device applying a clamp to a circumferential constricting mechanism positioned about a wire mesh structure of an intragastric device;

FIG. 63 is an illustration of one embodiment of a restrained wire mesh structure with a clamp applied to the free end of a circumferential constricting mechanism positioned about the wire mesh structure;

FIG. 64 is a flow chart illustrating the steps involved in retrieving a deployed intragastric device using the retrieval device of FIG. 60, in accordance with one embodiment of the present specification;

FIG. 65A is cross-section illustration of a retrieval device for removing an intragastric device in accordance with one embodiment of the present specification;

FIG. 65B is a cross-section illustration of an exploded view of the catheter component of the retrieval device of FIG. 65A;

FIG. 65C is a cross-section illustration of an assembled view of the catheter component of the retrieval device of FIG. 65A;

FIG. 65D is a cross-section illustration of the overtube of the retrieval device of FIG. 65A, depicting a deflated balloon at the distal end of the overtube;

FIG. 65E is a cross-section illustration of the overtube of the retrieval device of FIG. 65A, depicting an inflated balloon at the distal end of the overtube; and, FIG. 66 is a flow chart illustrating the steps involved in removing an intragastric device from a patient using the retrieval device of FIG. 65A, in accordance with one embodiment of the present specification.

DETAILED DESCRIPTION

In one embodiment, the present specification is directed toward an intragastric device of dynamic weight used in obese patients to induce weight loss. In various embodiments, the intragastric device comprises a porous three dimensional structure having a pre-deployment shape and a post-deployment shape. In one embodiment, the porous three dimensional structure is a non-inflatable wire mesh structure, or a spiral structure made of shape memory metal or shape memory polymer that changes from a pre-deployment compressed cylindrical shape to a post-deployment sphere, oval, kidney bean or any predefined shape of significant volume. In another embodiment, the intragastric device is made of a plastic material or a polymer such as polyether ether ketone (PEEK) or polyester or a bioresorbable material. The device changes back and forth from the pre-deployment to post-deployment shape by minimal mechanical force and/or temperature changes arising from the room temperature pre-deployment shape to the body temperature post-deployment shape. The device is delivered endoscopically to the stomach via a catheter. The device can be placed through the endoscope, over an endoscope or over a guidewire with endoscopic or fluoroscopic guidance/assistance.

The device has a pre-deployment compressed shape to facilitate insertion and a post-deployment expanded shape that resides in the gastric lumen. Post-deployment volume of the device is significantly larger than pre-deployment volume. In one embodiment, the post-deployment device has a volume of at least 100 mL. The post-deployment device occupies a significant volume in the stomach, thereby reducing available gastric volume available for storage of ingested food. This restricts the amount of food intake, inducing satiety and curbing one's appetite. In one embodiment, the device is also designed to intermittently, with gastric peristalsis, slow or block the passage of the food from the stomach into the small intestine, thereby slowing gastric emptying.

In one embodiment, the device comprises a shape memory metal and self-expands once deployed to change from the pre-deployment shape to the post-deployment shape. In another embodiment, the device comprises a temperature sensitive metal that is cooled in its pre-deployment shape and then self-expands when exposed to human body temperature to achieve its post-deployment shape. In another embodiment, an expansion tool is used to apply minimal mechanical force to change the device shape from its pre-deployment shape to its post-deployment shape. In another embodiment, a plastic, polymer, carbon fiber or a bioresorbable material is used to construct the intragastric device.

In one embodiment, the wire structure contains differently weighted material to assist in proper positioning within the stomach. In one embodiment, lighter weighted material is positioned at the top of the wire structure proximate to the top openings and heavier weighted material is positioned at the bottom of the structure, proximate to the bottom openings. This differential weighting insures that the device will be properly situated within the stomach to effectuate the intended effect of slower gastric emptying. In addition, the differential weighting provides for proper gastric positioning without the need of physically anchoring the wire mesh structure to the stomach wall. The differential weight property can also be provided by the ingested food material that enters the device and is selectively accumulated toward the bottom of the device facilitated by the gravitational pull. The differential weight can also be provided by using different amounts of material in the top and bottom halves. The wire mesh structure is free to move about within the stomach while still maintaining its correct top to bottom alignment facilitated by the gravitational pull.

In one embodiment, the device comprises a wire mesh structure which, when in the post-deployment shape, includes mesh openings between the wires of the mesh structure. In one embodiment, the mesh openings are greater than 1 mm in diameter. In one embodiment, the wires of the wire mesh structure are coated with a corrosion-resistant material. The corrosion resistant material prevents exposure and subsequent degradation of the wires of the wire mesh structure from acidic gastric contents once deployed. The corrosion-resistant material completely covers the wires of the wire mesh but does not cover the mesh openings. In various embodiments, the corrosion-resistant material comprises silicone, parylene, polyester, polyether ether ketone (PEEK), a medical grade epoxy, ceramic, an additional metal, or any other suitable, flexible corrosive resistant material. In one embodiment, the coating metal is tantalum.

Tantalum provides corrosive resistance and radiopacity. In one embodiment, wherein the coating is ceramic, the ceramic coating has a thickness of several angstroms. In various embodiments, any one or combination of the above corrosive resistant materials is used to coat the metal of the wire mesh structure.

In one embodiment, the mesh openings are differentially structured to regulate the flow of food in and out of the mesh. In one embodiment, at least one opening on the bottom half of the device is larger than any of the openings on the upper half of the device, allowing food entering the mesh to exit without the need for further reduction in size of food material.

The present specification discloses a method for manufacturing an intragastric device comprising a wire mesh structure having a corrosion-resistant material coated over the wires. In one embodiment, the corrosion-resistant material is silicone. The method comprises the steps of forming the wires into the post-deployment shape of the device and then coating the wires while taking care not to cover the mesh openings between the wires of the wire mesh. Covering and/or clogging the mesh openings is prevented by controlling the viscosity of the corrosion-resistant material and by controlling the size of the mesh openings between the wires. If the viscosity of the material is too high and/or the size of the mesh openings is too small, the corrosion-resistant material will become deposited over and will cover the mesh openings, interfering with the functioning of the device. If the viscosity is too low, the coating will be too thin to provide effective protection to the metal. In one embodiment, an intragastric device is formed by a method comprising heat setting a shape memory metal into a wire mesh structure having openings between the mesh wires which are in a range of 2-20 mm in diameter. The viscosity of the corrosion-resistant material, in one embodiment, silicone, is controlled by varying the concentration of silicone and methylbenzene. In various embodiments, the weight ratio of silicone to methylbenzene in the corrosion-resistant material is in a range of 1:100-25:100. In one embodiment, the weight ratio of silicone to methylbenzene in the corrosion-resistant material is 8:100. To achieve the desired coating thickness, the formed wire mesh structure is dipped multiple times into the corrosion-resistant material to apply multiple layers of coating. In various embodiments, the final thickness of the corrosion-resistant material coating is in a range of 0.001-0.010 inches.

In another embodiment, the corrosion-resistant material is applied by vapor deposition. In one embodiment, the corrosion-resistant material is parylene. Using vapor deposition lowers the likelihood that the mesh openings will be covered by the coating as the vapor passes through the openings and clings to the metal wires. The final thickness of the coating is determined by the amount of time spent depositing the coating and the amount of coating material used.

In another embodiment, the two methods described above are combined to apply the corrosion resistant materials. First, the fully formed wire mesh structure is dipped multiple times into silicone. Once the silicone coating has dried, parylene is vapor deposited onto the structure to provide additional protection. In another embodiment, parylene vapor is deposited first and then the wire mesh structure is dipped in silicone to apply the coating.

In one embodiment, the present specification is directed toward a wire mesh or spiral structure with an exterior housing structure that is defined by openings, holes, voids or spaces of varying sizes. In one embodiment, the wire mesh or spiral structure has larger spaces or openings within its upper portion and smaller spaces within its bottom portion. In another embodiment, the wire mesh or spiral structure has spaces or openings within its upper portion which are equal in size to spaces within its bottom portion. In yet another embodiment, the wire mesh or spiral structure has smaller spaces or openings within its upper portion and larger spaces within its bottom portion. In one embodiment, the hole or opening at the bottom of the wire mesh structure, designed for the exit of food from the device, is larger than any other hole in the device. By having a larger hole at the bottom of the device than at the top of the device, the device does not affect or control the exit of food out of the device based on the size of the food particle. Any particle of food adequately sized to freely enter the device through an opening proximate the top of the device will have no problem easily exiting from the larger hole at the bottom of the device. The spaces or openings within the upper portion of the device are preferably aligned with, and directed toward, the esophagus, the cardia, the fundus or the body of the stomach and the spaces or openings within the bottom portion of the device are preferably aligned with, and directed toward, the gastric antrum or the intestines.

These spaces or openings provide two additional benefits beyond the feeling of satiety provided by the expanded second configuration. First, differential sizes or numbers resulting in differential surface area of the upper and lower openings enable the device to act like a time release capsule. In the embodiment having larger openings in the upper portion than in the bottom portion, the larger surface area of the openings toward the top two-thirds of the structure permit a larger volume of food to enter into the device, as compared to the volume of food permitted to leave the device via the smaller surface area of the openings that define the bottom of the device, thereby making the device a temporary storage unit with a delayed release of the nutrients. As the stomach grinds solid food into liquid food, or chyme, the chyme passes into and is sequestered inside the intragastric device. The chyme is then slowly released back into the stomach, thereby delaying gastric emptying and inducing satiety. The gastric emptying can also be controlled by varying both the number and size of these openings, holes, spaces or voids to differentially control the inflow and outflow of the food from the device. In essence, the ratio of the surface area of the inflow and the outflow as calculated by the size and the number of inflow and outflow opening controls the rate of emptying from the device and hence the gastric emptying. Additionally, in one embodiment, at least one opening at the bottom of the device is larger than any of the openings on the top of the device, allowing any food particle entering the device to exit the device without the need for further reduction in size, thus preventing food trapping or prolonged stasis.

An additional embodiment of the device has large holes or openings in the middle and smaller openings in the top and bottom halves, thereby allowing the partially digested food to enter in the middle portion with the option to leave from either the top or the bottom half. In another embodiment the top two-thirds of the device has an opening but the lower one-third of the device has a membrane without any openings that stores the partially digested food in the upright position as a bowl and releases the food back through the same openings in the top two thirds of the device when the patient is supine. In addition, liquid foods, such as ice cream, will also be sequestered into the dependent portion of the device and released into the stomach more slowly at a later time.

Second, the varying shape, size and number of the openings or spaces in the wire mesh structure allow the device to store ingested food and undergo meal induced dynamic weight change. The device will have a greater weight during and post feeding resulting in an appropriately timed feeling of fullness or satiety. Heavier intra-gastric devices are associated with more satiety and weight loss however they have more side-effects such as nausea and abdominal pain. Slowly, as the food is released out of the device, the weight of the device will decrease over time and return to its baseline weight. Eventually, the device will have a lower weight during fasting, diminishing the side effects commonly associated with an intragastric device, improving patient tolerance. Conventional water filled intragastric balloons are heavier than air filled balloons resulting in a greater feeling of satiety and weight loss but patients suffer from increased side effects resulting in higher intolerance and the need for premature removal. Air filled balloons are lighter and therefore more tolerable, but are less effective in inducing satiety and hence weight loss. The intragastric devices of the present specification improve upon both devices by inducing a greater and more normalized feeling of satiety during feeding and post-feeding stages while reducing side effects during the fasting stage.

In another embodiment, the present specification is directed toward a wire mesh or spiral structure partially encompassed, housed, or otherwise enclosed by a membrane. When expanded into the post-deployment configuration, the membrane contains opening, holes, voids, or spaces proximate to the top of the device and holes proximate to the bottom of the device. The openings on the top of the device are preferably aligned with, and directed toward, the esophagus, cardia, fundus or the body of the stomach and the openings at the bottom of the device are preferably aligned with, and directed toward, the antrum or pylorus of the stomach or the small intestines. In one embodiment, the openings in the membrane proximate the top of the device have a larger surface area than the openings in the membrane proximate the bottom of the device. In another embodiment, the openings in the membrane proximate the top of the device are equal in surface area to the openings in the membrane proximate the bottom of the device. In yet another embodiment, the openings in the membrane proximate the top of the device have a smaller surface area than the openings in the membrane proximate the bottom of the device.

These openings provide two additional benefits beyond the feeling of satiety provided by the expanded post-deployment configuration. First, the device with differentially sized membrane opening, holes or voids acts as a time release capsule. In the embodiment having a larger surface area of openings in the membrane proximate the top of the device than proximate the bottom of the device, more food enters into the device from the large surface area of the openings at the top than exits from the smaller surface area of the openings at the bottom, resulting in a device that functions as a temporary storage unit with a delayed release of nutrients. As the stomach grinds solid food into liquid food, or chyme, the chyme is sequestered inside the wire mesh device. The chyme is then slowly released back into the stomach, thereby delaying gastric emptying and inducing satiety. In addition, liquid foods, such as ice cream, will also be sequestered into the dependent portion of the device and released back into the stomach more slowly.

Second, the two sets of openings in the wire mesh structure membrane allow the device to undergo dynamic weight change. The device will have a greater weight during and post feeding resulting in an appropriately timed feeling of fullness or satiety. Slowly, as the food exits the device, the weight of the device will decrease over time. Eventually, the device will have a lower weight during fasting, diminishing the side effects commonly associated with an intragastric device, such as nausea and pain. Conventional water filled intragastric balloons are heavier than air filled balloons resulting in a greater feeling of satiety but patients suffer from increased side effects. Air filled balloons are lighter and therefore more tolerable, but are less effective in inducing satiety. The intragastric devices of the present specification improve upon both devices by inducing a greater and more normalized feeling of satiety during the feeding and post-feeding stage while reducing the side effects.

In another embodiment, the wire mesh structure has portions that are completely covered by a membrane and some portions that are not, resulting in differential release of food. In one embodiment, the top and bottom of the wire mesh structure are completely covered by the membrane and the middle of the structure has openings in the membrane to allow the passage of food. In another embodiment, the wire mesh structure is 90-99% covered by the membrane, leaving only a small area for food passage, thereby increasing the time for gastric emptying.

In another embodiment, the membrane covering the wire mesh structure has a ring of large openings in the upper hemisphere of the structure and a ring of smaller openings in the bottom hemisphere of the structure. In another embodiment, the membrane covering the wire mesh structure has a ring of small openings in the upper hemisphere of the structure and a ring of larger openings in the bottom hemisphere of the structure. In another embodiment, the membrane covering the wire mesh structure has a ring of openings in the upper hemisphere of the structure and a ring of openings, equal in size to the upper openings, in the bottom hemisphere of the structure.

In another embodiment, the membrane covering the wire mesh structure has a greater number of openings in the upper hemisphere of the structure and fewer openings in the bottom hemisphere of the structure. In another embodiment, the membrane covering the wire mesh structure has fewer openings in the upper hemisphere of the structure and a greater number of openings in the bottom hemisphere of the structure. In another embodiment, the membrane covering the wire mesh structure has the same number of openings in the upper hemisphere of the structure as in the bottom hemisphere of the structure.

In another embodiment, the membrane covering the wire mesh structure has a larger surface area of openings in the upper hemisphere of the structure and a smaller surface area of openings in the bottom hemisphere of the structure. In another embodiment, the membrane covering the wire mesh structure has a smaller surface area of openings in the upper hemisphere of the structure and a larger surface area of openings in the bottom hemisphere of the structure. In another embodiment, the membrane covering the wire mesh structure has the same surface area of openings in the upper hemisphere of the structure as in the bottom hemisphere of the structure. These different configurations allow control of the rate of entry and/or exit of food into and out of the device, resulting in delayed gastric emptying and dynamic weight change of the wire mesh structure.

The gastric fundus is involved in the release of various gut hormones such as "hunger hormones", ghrelin, orexin and PYY 3-36, and "satiety hormones", e.g., leptin, obestatin, and nesfatin-1. The release of these hormones is mediated by contact of gastric mucosa with various nutrients in the ingested food. The top portion of the wire mesh structure will prevent sequestered food from coming into contact with the gastric cardia and fundus. This results in physiological exclusion of the gastric cardia and fundus, a mechanism thought to play a role in satiety and weight loss and one of the mechanisms in play in RGB gastric bypass surgery.

In another embodiment, layers of a membrane act as a flap valve controlling the directionality of the movement of the food in the various portions of an intragastric device. Just like the size of the openings, the size, shape, position and directionality of the valves can be varied to achieve desired gastric emptying effects.

In another embodiment, the intragastric device further includes an anti-migration component coupled to a portion of its distal end. The anti-migration component, similar to the wire mesh of the intragastric device, is configurable between a first, compressed configuration for delivery, and a second, expanded configuration once deployed. The anti-migration component functions as a physical stopper preventing passage of the intragastric device through the pylorus. In various embodiments, the anti-migration component has a diameter that is greater than the diameter of a relaxed pylorus. In one embodiment, the anti-migration component comprises an extension of the wire mesh structure of the intragastric device. In another embodiment, the anti-migration component is a separate piece of wire mesh which is attached to a portion of the distal end of the intragastric device. In various embodiments, the anti-migration component has a shape approximating a bumper, half-bumper, disc, saucer, or any other shape which will prevent migration of the device past the pylorus.

In another embodiment, a sleeve can be attached to the intragastric device, where the sleeve extends from the stomach through the duodenum and into the jejunum. In one embodiment, the sleeve functions to transit the sequestered chyme from the wire mesh structure directly to the mid-jejunum. In another embodiment, the sleeve is coupled to the intragastric device but does not directly receive food from the device. In this embodiment, the proximal end of the sleeve is distal to the device and receives food directly from either the stomach or the duodenum. The food entering the sleeve exits at the distal end, preferably into the jejunum, bypassing a portion of the small intestine.

The sleeve therefore acts to bypass portions of the gastrointestinal (GI) tract in order to limit the absorption of specific materials in the intestine. The benefits provided by a sleeve are similar to those provided by Roux-en-Y gastric bypass surgery, namely, weight loss and improvement of type II diabetes. These benefits are accomplished in at least two ways.

First, bypass of the duodenum and proximal jejunum improves type II diabetes by changing the hormone release from the proximal portion of the small intestine. This may also induce weight loss by inhibiting or decreasing the release of pacreatico-biliary secretions and inducing maldigestion and malabsorption. Second, the sleeve acts to release undigested nutrients into the mid-jejunum, improving type II diabetes by changing the hormone release from the mid portion of the small intestine. This may induce weight loss by maldigestion and malabsorption of these nutrients. While conventional sleeve devices may perform some of these functions, conventional sleeves must be anchored in the GI tract to avoid migration. Anchoring often results in complications, including infection, bleeding, perforation, and, if not anchored correctly, migration of the sleeve leading to possible obstruction and death. In various embodiments of the present specification, the sleeve is physically attached or coupled to the intragastric device, where the intragastric device serves as the anchor for the sleeve. This eliminates the need for the sleeve to be physically anchored to the GI tract, eliminating the associated complications. In addition, the intragastric devices with sleeves of the present specification offer functional advantages over conventional sleeves by concurrently controlling food and calorie intake, inducing satiety, and controlling gastric emptying, which is not accomplished by traditional sleeve devices. The anchorless device and/or sleeve system is not fixed to any portion of the gastrointestinal wall and is free to move relative to the gastrointestinal wall at all times.

Conventional sleeves are also typically very thin and formless. In essence, these conventional sleeves are formless, thin plastic covers that are physically anchored to the gastrointestinal (GI) tract, introducing the associated risks described above. Conventional sleeves must be very thin and formless so that they do not pull or tug on the anchoring points, causing failure of the anchor and/or trauma to the GI tissue at the anchor site. Additionally, these sleeves could twist, buckle or kink resulting in blockage of the sleeve and a functional failure. A thick or structured sleeve without food or filled with food would experience drag during peristalsis. The added weight of such a sleeve, if anchored to the GI tract, would result in increased trauma to the tissue at the anchoring site and anchor failure. As discussed, the sleeves disclosed in the present specification are physically coupled to the wire mesh structure of the intragastric device and therefore do not need to be anchored directly to the gastrointestinal wall, eliminating said risks. In fact, additional weight and/or structure included in the sleeve would pull on the intragastric device, positioning it at the desired location just proximal to the pylorus. Therefore, in various embodiments, the sleeves of the present specification include horizontal support elements, vertical support elements, wire mesh support, spiral mesh support, weighted distal end, and/or any other structural components that would provide the sleeves with structural integrity, preventing the sleeve from permanently kinking, buckling or twisting.

In another embodiment, the intragastric device has multiple opening, holes, voids or spaces in the top half and a membrane with at least one opening, hole, or void in the bottom half where the bottom opening directs the food preferentially into the sleeve device. In this embodiment, the bottom half of the intragastric device acts as a funnel, collecting all the food entering the device through the top half in the bottom half and preferentially releasing it into the sleeve which in turn will deliver the food/nutrients to the mid small intestine thus bypassing the proximal small intestine. In another embodiment with multiple sleeves, the proximal sleeve may release the food into a second, distal sleeve.

In one embodiment, the entire intragastric device is covered by a membrane with openings that have valves throughout the device directing the food into the intragastric device where it is sequestered and is preferentially emptied through the opening in the bottom half of the device into the sleeve, delivering it to the mid small bowel thus bypassing the proximal small intestine. In this embodiment, the intragastric device sequesters the nutrients/food and, through the sleeve attachment, empties them into the mid small intestine.

The above two embodiments mimic Roux-en-Y gastric bypass (RGB) surgery by creating gastric restriction and isolation of the gastric fundus and bypassing the proximal small intestine, thus resulting in maximum weight loss and control of Type-II diabetes. In addition, the device has the ability to regulate gastric emptying in a manner that cannot be traditionally achieved by RGB gastric bypass surgery. The controlled and prolonged release of nutrients into the mid and distal small bowel will result in prolonged satiety via modulation of the release of gut hormones such as "hunger hormones", ghrelin, orexin, and PYY 3-36, and "satiety hormones", e.g., leptin, obestatin, and nesfatin-1.

In one embodiment, a second intragastric device can be attached to an already deployed intragastric device, thereby increasing the volume occupied in the stomach. This serves to further limit the amount of food ingested by a patient and also further delays gastric emptying as food flows from one intragastric device into the other before releasing back into the stomach or into the attached sleeve device. This allows for tailoring the therapy to a specific patient's needs by increasing or decreasing the volume of the intragastric devices. In addition, this allows for the possibility of stepwise increases or decreases in the device based therapy based on therapeutic response and side-effect profile. This is usually performed in the inflatable intragastric devices by instilling or removing fluids. However, such devices do not have the ability to regulate gastric emptying.

The present specification also discloses a retrieval device used to remove an intragastric device. The retrieval device is a catheter inserted per-orally or via an endoscope and passed through a proximal, and optionally through a distal, opening of the intragastric device. The catheter then engages and secures the proximal and distal end of the expanded intragastric device and the intragastric device is then constrained back into its pre-deployed shape using mechanical force. The reversion to its pre-deployed state in a shape memory device can be further facilitated by instillation of cold fluid into the intragastric device, lowering the temperature of the intragastric device.

The present specification also discloses an intragastric device to be used following bariatric surgical procedures, such as, laparoscopic sleeve gastrectomy (LSG) and laparoscopic roux-en-y-gastric bypass (RGB) surgery. In one embodiment, the device includes a spherical or ovoid shaped wire mesh structure with a device sleeve attached to its distal end. In another embodiment, the device includes a tubular member having a distal diameter greater than its proximal diameter that is designed to be placed in a created gastric sleeve following LSG. In another embodiment, the device includes a proximal wire mesh structure designed to be positioned in a gastric pouch created following RGB surgery. The device could restrict the volume of the pouch, exert pressure on the pouch inducing satiety or has a valve deployed at the exit of the mesh to regulate the flow of the nutrients out of the pouch. The device could be anchored using barbs, t-tags, suture or other known anchoring mechanism into the gastric pouch.

In one embodiment, the intragastric device includes one or more constricting mechanisms that, when pulled upon, constrict the wire mesh structure of the device, thereby constricting the wire mesh structure into a compressed configuration to facilitate retrieval of the device.

The present specification also discloses a method of retrieving an intragastric device by first constricting the device to a compressed configuration using one or more constricting mechanisms on the wire mesh structure and then removing the compressed device from the patient through the working channel of an endoscope.

The present specification discloses a device for use in the treatment of obesity which functions by displacing volume in the stomach and providing a bypass for food past the pylorus and a portion of the small intestine. The device may have additional therapeutic effect by regulating the flow of the nutrients or food from the stomach into the small intestine. In one embodiment, the device displaces no less than 10% of the stomach volume. In one embodiment, the device provides a bypass for food such that ingested food enters the device at a first point proximal to the pylorus and exits the device at a second point distal to the pylorus. In another embodiment the ingested food enters a portion of the device in the duodenum and exits in the jejunum. In one embodiment, the device is partially mobile wherein said partial mobility is defined as movement proximally and distally within the stomach of no more than 15 inches. The mobility is along both the device's horizontal and vertical axes. Further, in one embodiment, at no point in time does the entirety of the functional device move into the duodenum. Optionally, in one embodiment, the device further acts to treat obesity by slowing the passage of food through the gastrointestinal (GI) tract. Optionally, in another embodiment, the device induces satiety by exerting intermittent pressure of stretch on a portion of the gastrointestinal wall. Optionally, in another embodiment, the functional device at no point applies a constant pressure or radial force to the same portion of the stomach or small intestine for a prolonged period of time. The prolonged period is defined as >30 day but ideally should be <1 day. Optionally, in another embodiment, the device induces satiety by intermittently obstructing or slowing the passage of food from the stomach into the small intestine but at no time does the device permanently obstruct the flow of food from the stomach to small intestine. In one embodiment, the device comprises a three dimensional structure defining an internal volume and having a proximal end and a distal end. The proximal end comprises at least one first opening and the distal end comprises at least one second opening. In various embodiments, said at least one first opening is smaller than said at least one second opening. Food enters the device through said at least one first opening, is sequestered within the device for a period of time, and then exits the device through said at least one second opening, thereby delaying gastric emptying and slowing the passage of food through the GI tract. In one embodiment, the device does not act to filter food as a portion of the digested food passes alongside or around the device. The larger food particles will flow around the device, rendering it an ineffective filter. As such, all food entering the device exits the device without the need for a size reduction. Having at least one opening at the distal end that is larger than all the other openings allows for food to pass, even if there is an increase in size due to aggregation of food particles. In one embodiment, the device is implanted endoscopically into the GI tract of a patient. To facilitate such an implantation, in various embodiments, the device is configurable between a first compressed configuration and a second expanded configuration once deployed. In addition, the device can be returned substantially to its first compressed configuration for removal. In various embodiments, the diameter of the device in the compressed configuration is 25 mm or less.

Wire Mesh Structure

In various embodiments, the intragastric device comprises a porous three dimensional structure having a pre-deployment shape and a post-deployment shape. In one embodiment, the device, in the post-deployment configuration, comprises a three dimensional wire mesh structure defining an internal volume and having a proximal end and a distal end. In another embodiment, the device, in the post-deployment configuration, comprises a three dimensional spiral structure having metal wires or metal strips. In one embodiment, the wire mesh structure is comprised of a metal. In one embodiment, the metal is a shape memory metal, such as Nitinol. In various embodiments, the metal wire comprises 50% or less of the surface area of the wire mesh structure. The remaining surface area of the wire mesh structure comprises the openings between the wires. The openings in the mesh structure could optionally be covered partially or completely with a membrane. The membrane along with wire-mesh structure could form a valve mechanism that controls the rate or directionality of flow. In various embodiments, the wire mesh structure has a post-deployment diameter that is greater than the diameter of an open pylorus. In various embodiments, the wire mesh structure is fabricated via automated braiding, non-automated braiding, laser cutting, tube cutting, or fixed or variable rigidity plate forming.

In one embodiment, in the post-deployment configuration, the wire mesh structure has a spherical shape. In various embodiments, the spherical wire mesh structure has a diameter in a range of 5 cm to 25 cm. In one embodiment, the spherical wire mesh structure has a diameter of 15 cm. In another embodiment, in the post-deployment configuration, the wire mesh structure has an oval shape. In various embodiments, the oval wire mesh structure has a diameter at its midpoint in a range of 1 cm to 20 cm and length from its proximal end to its distal end in a range of 5 cm to 25 cm. In one embodiment, the oval wire mesh structure has a diameter at its midpoint of 10 cm and a length from its proximal end to its distal end of 15 cm. In another embodiment, in the post-deployment configuration, the wire mesh structure has an ovoid shape. In another embodiment, in the post-deployment configuration, the wire mesh structure has a football shape. In various embodiments, the football shaped wire mesh structure has a diameter at its midpoint in a range of 5 cm to 25 cm and length from its proximal end to its distal end in a range of 10 cm to 25 cm. In one embodiment, the football shaped wire mesh structure has a diameter at its midpoint of 10 cm and a length from its proximal end to its distal end of 20 cm. In another embodiment, the mesh device has a dumbbell shape. The dumbbell shape could be primarily woven as such or can be created by coupling two spherical, oval or any other of the above shaped devices. In various other embodiments, in the post-deployment configuration, the wire mesh structure has a shape that approximates the shape of a normal or surgically altered stomach. In one embodiment, in the post-deployment configuration, the shape of the wire-mesh structure could be customized to the shape, size or volume of an individual stomach. In another embodiment, the size or volume of the wire-mesh structure depends upon the magnitude of the desired weight loss. Those skilled in the art would recognize the wire mesh structure can take on any number of post-deployment shapes that would enable the device to have a space occupying effect and prevent it from being passed completely through the pylorus. In one embodiment, the wire mesh structure has a width at its midpoint that is less than its length from its proximal end to its distal end. In another embodiment, the wire mesh structure has a width at its midpoint that is equal to its length from its proximal end to its distal end. In another embodiment, the wire mesh structure has a width at its midpoint that is greater than its length from its proximal end to its distal end.

In various embodiments, the wire mesh structure includes at least one first opening proximate its proximal end and at least one second opening proximate its distal end. In various embodiments, the first opening at the proximal end is 50 mm or less in diameter and the second opening at the distal end is 100 mm or less in diameter. The first opening at the proximal end of the wire mesh structure is in fluid communication with the internal volume of the wire mesh structure which, in turn, is in fluid communication with the second opening at the distal end of the wire mesh structure. The first opening proximate the proximal end is for the entrance of food into the wire mesh structure and the second opening proximate the distal end is for the exit of food from the wire mesh structure. In some embodiments, the first opening or total area of multiple first openings proximate the proximal end of the wire mesh structure is smaller than the second opening or total area of multiple second openings proximate the distal end of the wire mesh structure. In other embodiments, the first opening or total area of multiple first openings proximate the proximal end of the wire mesh structure is equal in size to the second opening or total area of multiple second openings proximate the distal end of the wire mesh structure. In other embodiments, the first opening or total area of multiple first openings proximate the proximal end of the wire mesh structure is larger than the second opening or total area of multiple second openings proximate the distal end of the wire mesh structure. The wire mesh also includes openings between the wires of its mesh weave. These openings, while also allowing the passage of food into and out of the device, are substantially smaller than those positioned at either the proximal or the distal ends of the wire mesh structure or both.

In various embodiments, the wire mesh structure comprises different wire mesh weave patterns that impart particular performance characteristics to the device. For example, in one embodiment, the wire mesh structure comprises a weave pattern that provides the wire mesh with a consistent radial strength throughout, wherein said radial strength resists the compressive force of the stomach. The radial strength of the wire mesh structure prevents it from being compressed completely or permanently by the contractions of the stomach and passed through the pylorus. In another embodiment, the wire mesh structure comprises a weave pattern designed to make the wire mesh more easily compressible along its horizontal axis than along its vertical axis. In another embodiment, the wire mesh structure comprises a weave pattern designed to make the wire mesh more easily compressible along its vertical axis than along its horizontal axis. The wire mesh structure includes a midpoint defining an upper portion and a lower portion (for example, in an embodiment wherein the wire mesh structure has a spherical shape, it includes an equator with an upper hemisphere and a lower hemisphere). In one embodiment, the upper and lower portions comprise different wire mesh weave patterns such that the upper portion has a greater radial strength as provided by its wire mesh weave pattern than the radial strength provided to the lower portion by its wire mesh weave pattern. In this embodiment, forces from the contractions of the stomach antrum are transmitted through the weaker lower portion of the wire mesh structure to help move the food through the device. In another embodiment, the upper portion of the device comprises a wire mesh weave and the lower portion comprises only a flexible membrane. This membrane is pliable enough to allow forces from stomach contractions to pass through and help move food through the device.

In another embodiment, the wire mesh structure includes a mechanism for fixing the wire mesh structure in its expanded configuration so it cannot be completely or permanently compressed by gastric contractions. In various embodiments, the mechanism comprises a rod, radial spokes, or disc within the wire mesh structure. In one embodiment, the mechanism comprises a separate device or structure having a radial strength greater than that of the wire mesh structure. The mechanism is not engaged while the device is in the compressed configuration. After delivery, a physician uses a working tool of an endoscope to fix the mechanism in place. When the device is ready to be removed, the physician disengages the mechanism so the device can be returned to its compressed configuration for retrieval.

Most wire mesh structures elongate when they are compressed. Preventing the elongation of the device will prevent accidental or unplanned compression of the device and hence prevent inadvertent passage or migration from its desired location. In one embodiment, a structure can be engaged post-deployment that prevents elongation of the device. The structure can be disengaged at the time of removal allowing for the device to be compressed. The structure could be a wire structure, a plastic structure, or a polymer or silk structure which connects the proximal and distal ends of the device and prevents the device from elongating while the structure is engaged.

In another embodiment, the metal wire of the wire mesh structure is temperature sensitive. While in the gastric environment and exposed to body temperature, the metal wire has a greater strength and the wire mesh structure in noncompressible. In one embodiment, for delivery, a cooling element is applied to the wire mesh structure. As the wire is cooled, the wire mesh structure remains in a more compressed shape as a coaxial covering sheath or constricting thread is removed, facilitating withdrawal of a delivery device. In one embodiment, for removal, a cooling element is applied to the wire mesh structure. As the wire is cooled, the wire mesh structure becomes more malleable and can be easily constricted to its compressed configuration for retrieval.

In various embodiments, the wire mesh structure further includes a membrane covering at least a portion of the wire mesh. The membrane is designed to be flexible and move with the wire mesh as it transfigures between its various configurations. In one embodiment, the membrane does not cover the first or second openings of the wire mesh structure. In one embodiment, the membrane is substantially nonporous and prevents the passage of food through any openings in the wire mesh structure over which the membrane is positioned. In another embodiment, the membrane has some level of porosity and allows small amounts of chyme to pass through. In one embodiment, the membrane includes at least one opening positioned to align directly with at least one opening between the wires of the wire mesh structure. In one embodiment, the membrane with the wire mesh structure forms at least one valve or flap corresponding to said at least one opening. In one embodiment, the valve or flap is unidirectional and allows food to enter the device but not exit the device. In another embodiment, the valve controls the rate of flow.

The gastric fundus is involved in the release of various gut hormones such as "hunger hormones" ghrelin, orexin and pancreatic peptide 3-36 (PYY 3-36), and "satiety hormones", e.g., leptin, obestatin, and nesfatin-1. The release of these hormones is mediated by contact of the gastric mucosa with various nutrients in the ingested food. The wire mesh structure will prevent sequestered food from coming into contact with the gastric cardia and fundus or reduce its contact time. This will result in physiological exclusion of the gastric cardia and fundus, a mechanism thought to play a role in satiety and weight loss and is one of the mechanisms in play in RGB gastric bypass surgery. In one embodiment, the wire mesh structure sequesters food within its internal volume for no more than 24 hours.

The wire mesh structure freely floats in the gastric cavity without exerting constant force at a singular point for a prolonged period. One or more portions of the wire-mesh structure can temporarily put pressure or create stretch or distension of one or more portions of the stomach to create a desirable therapeutic effect. The top of the mesh structure could press on the gastric cardia or fundus, thus generating a feeling of fullness or satiety, decreasing caloric intake or inducing weight loss or glycemic control. The lower portion of the device is designed to temporarily and intermittently engage the distal body or the antrum of the stomach to create stretch or distension to create a desirable therapeutic effect. Additionally this may create intermittent obstruction and/or delay the passage of food from the stomach into the intestine.

Sleeve

In various embodiments, the intragastric device of the present specification further comprises a flexible sleeve component coupled to the wire mesh structure. In multiple embodiments, any of the wire mesh structures discussed above is coupled with any of the sleeve components discussed below. The sleeve component comprises an elongate tubular body having a proximal end and a distal end a lumen within. In various embodiments, the sleeve has a length within a range of 6 inches to 120 inches. In one embodiment, the sleeve has a length of 24 inches. In another embodiment, the sleeve has a length of 30 inches. In one embodiment, the sleeve could be functionally made out of multiple sleeves wherein the cumulative length of the sleeves in combination is greater than 6 inches. In various embodiments, the sleeve has a diameter within a range of 1 cm to 10 cm. In one embodiment, the sleeve has a diameter of 5 cm. In another embodiment the sleeve has a diameter of 3 cm. The proximal end of the sleeve body includes a first opening for passage of food from the wire mesh structure into the sleeve. In one embodiment, the sleeve component comprises a second opening at the distal end of the sleeve body for the exit of food into the small intestine. In another embodiment, the sleeve component comprises a second opening along the length of the sleeve body proximate its distal end for the exit of food into the small intestine. The first opening at the proximal end of the sleeve body is in fluid communication with the lumen of the sleeve body which, in turn, is in fluid communication with the second opening at the distal end of the sleeve body. In various embodiments, the first and second openings of the sleeve each have a diameter that is less than, equal to or greater than the diameter of the duodenum. In one embodiment, a portion of the wire-mesh structure can intermittently engage the pylorus or pass through the pylorus. The sleeve component is designed to extend distally from the distal end of the wire mesh structure. The wire mesh structure resides in the stomach of the patient, just proximal to the pylorus. In various embodiments, the sleeve component passes through the pylorus and into the duodenum or proximal portion of the jejunum, where it remains during deployment. Food enters the proximal end of the wire mesh structure, passes through the wire mesh structure, into the sleeve component, through the sleeve component, and out into the small intestine through the distal end of the sleeve. As such, food bypasses the very distal end of the stomach, the pylorus, the duodenum (and therefore ampulla of vater), and optionally the proximal portion of the jejunum. The sleeve therefore acts to bypass portions of the GI tract in order to limit the absorption of specific materials in the intestine. The benefits provided by a sleeve are similar to those provided by Roux-en-Y gastric bypass surgery, namely, weight loss and improvement of type II diabetes.

In one embodiment, the proximal end of the sleeve body is coupled directly to the wire mesh structure at any position on the lower portion of said wire mesh structure such that the sleeve component covers the second opening at the distal end of the wire mesh structure and the second opening of the wire mesh structure is in fluid communication with the first opening of the proximal end of the sleeve body. In another embodiment, the device includes an additional wire mesh junction connecting the wire mesh structure to the sleeve component. In another embodiment, the sleeve component is tethered to the wire mesh structure by two or more connecting elements such that the first opening at the proximal end of the sleeve body is spaced apart from the second opening at the distal end of the wire mesh structure. This embodiment is designed to capture food in the sleeve that does not enter and exit through the wire mesh structure. In yet another embodiment, a first sleeve component is coupled directly to the lower portion of the wire mesh structure and a second sleeve component is tethered to the wire mesh structure at a distance spaced apart from said wire mesh structure as discussed above. In another embodiment the second sleeve is coupled to the first sleeve. This embodiment is designed to allow for the capture of both food passing through the wire mesh structure and food passing around the wire mesh structure.

In various embodiments, multiple sleeves can be added to the end of the most distal existing sleeve, continually elongating the device and resulting in multiple telescoping sleeves.

In various embodiments, the sleeve is glued, sutured, or thermally fused to the wire mesh structure. In one embodiment, the sleeve comprises a mesh having a radial force that pushes the sleeve onto the wire mesh structure and thereby secures said sleeve to said wire mesh structure.

The distal end of the sleeve can be designed to be weighted so that the sleeve remains in an elongated shape extending through a portion of the duodenum. In one embodiment, the sleeve includes a small weight attached to its distal end. In another embodiment, wherein the second opening at the distal end of the sleeve body is positioned along the sleeve body at its distal end, the distal end of the sleeve body further includes a blind pouch. The blind pouch functions to intermittently trap a small portion of food or fluid there within. The trapped food or fluid acts to weigh down the distal end of the sleeve body, thereby keeping the sleeve component elongated.

In one embodiment, the sleeve component comprises a mesh that is flexible and compressible by the contractions of the small intestine. The mesh weave pattern of the sleeve component is different than that of the three dimensional wire mesh structure in that it has a lower radial strength, allowing the sleeve component to be compressed by the duodenum wherein the compression helps food progress along the sleeve length. Although the mesh weave pattern of the sleeve component allows the sleeve to be compressed by intestinal contractions, it is strong enough to provide structural support to the sleeve body and maintain the sleeve in an elongated shape, preventing permanent bending, twisting or kinking of the sleeve which may lead to sleeve obstruction.

In one embodiment, the sleeve comprises a differential mesh structure wherein the sleeve has a greater radial strength proximally and less radial force distally to provide less buckling proximally and allow for more flexibility distally.

In one embodiment, the sleeve includes at least one component comprised of a bio-absorbable material and at least one component comprised of a non-bio-absorbable material. The components comprising a non-bio-absorbable material comprise the proximal portion of the sleeve and the components comprising a bio-absorbable material comprise the distal portion of the sleeve. As the distal components are absorbed by the human body, the sleeve shortens in length. In another embodiment the sleeve is made of multiple non-bio-absorbable components connected by bio-absorbable components. The bio-absorbable components dissolve over time resulting in planned disassembly of the sleeve and spontaneous passage of the components through the gastrointestinal tract.

In one embodiment, the sleeve is made of a biocompatible fabric such as a Dacron mesh. The fabric mesh could serve as a scaffolding for growth and colonization by microbiota that promote weight loss. Such microbiota could be applied before insertion of such a device or administered as probiotics to the patient. Other therapeutic agents could be combined with the device to enhance the therapeutic effect of the device.

In another embodiment, the sleeve component comprises a membrane that is flexible and compressible by the contractions of the small intestine. In one embodiment, the membranous sleeve component comprises a plurality of horizontal and/or vertical support elements along the length of the sleeve body. In one embodiment, the horizontal elements include wire rings spaced apart along the length of the sleeve body. In various embodiments, the rings are spaced between 2 and 24 inches apart. In one embodiment, the rings are spaced 6 inches apart. In one embodiment, the vertical support elements include elongate metal wires. In various embodiments, the wires are between 2 and 60 inches in length. In one embodiment, the metal wires are 6 inches in length. In another embodiment, the membranous sleeve component comprises a spiral metal wire extending along its length. The spiral metal wire provides support to the sleeve component and maintains its elongated shape. In various embodiments, the membrane of the sleeve component extends proximally onto the lower portion of the wire mesh structure and covers all or a portion of said lower portion.

The sleeve is flexible and compressible such that during delivery it is restrained in a compressed configuration on the distal end of a delivery device. In one embodiment, the sleeve telescopes into itself to shorten its length and facilitate delivery.

In one embodiment, the wire mesh structure and sleeve are delivered separately and assembled within a patient's gastrointestinal tract. The wire mesh structure is delivered into the stomach of a patient by a first catheter and then the sleeve is delivered into the wire mesh structure by a second catheter. The distal end of the sleeve is extended through the distal opening in the wire mesh structure and then the proximal end of the sleeve is coupled to said distal end of the wire mesh structure.

In one embodiment, a first small wire mesh structure with coupled sleeve is implanted into a patient. Later, if desired, a second, larger wire mesh structure can be deployed around the first small wire mesh structure to increase device efficacy.

In various embodiments, the sleeve includes one or more radiopaque markers to ensure proper positioning of the sleeve using radiographic imaging.

In various embodiments, 1-99% of ingested food passes through the sleeve. In one embodiment, more than 25% of the ingested food passes through the sleeve. In another embodiment, more than 10% of the ingested food passes through the sleeve.

Retrieval Mechanism

In various embodiments, the wire mesh structure or wire mesh structure with coupled sleeve component includes one or more retrieval mechanisms with at least one retrieval mechanism positioned proximate the at least one opening at the proximal end of the wire mesh structure. In one embodiment, the retrieval mechanism is formed from an extension of the wire mesh comprising the wire mesh structure. In another embodiment, the retrieval mechanism is a separate piece of wire or thread or tie that is fixedly attached to the wire mesh structure. The retrieval mechanism comprises an engaging mechanism such as a loop that, in various embodiments, can be engaged by a hook or grasper from a retrieval instrument. A physician can use a retrieval instrument to engage the retrieval mechanism of the deployed intragastric device to compress the intragastric device to withdraw the device from a patient's body. The retrieval mechanism can be included on any of the wire mesh structure, wire mesh structure with sleeve, or wire mesh structure with sleeve and anti-migration component embodiments (as discussed below) of the present specification.

Anti-Migration Component

In various embodiments, the wire mesh structure or wire mesh structure with coupled sleeve component includes one or more anti-migration components. In one embodiment, the anti-migration component is comprised of a metal. In one embodiment, the metal is a shape memory metal, such as Nitinol. The anti-migration component is preferably positioned at the distal end of the wire mesh structure (at the junction of the wire mesh structure with the sleeve component in the embodiment of the device including a sleeve) and, once the device is deployed, comes to rest proximal to the pylorus. The anti-migration component functions to prevent passage of the wire mesh structure or entire device through the pylorus. In one embodiment, the anti-migration component is compressed along with the wire mesh structure when the device is in its first configuration. Once deployed, in one embodiment, the anti-migration component has a width that is greater than that of the wire mesh structure, preventing passage through the pylorus. In another embodiment, the anti-migration component comprises a wire weave pattern having a radial strength sufficient to resist the compressive force of the stomach, preventing complete or permanent constriction of the anti-migration component by stomach contractions and subsequent migration of the device through the pylorus.

In one embodiment, in the post-deployment configuration, the anti-migration component has a distally sloping disc shape. In another embodiment, in the post-deployment configuration, the anti-migration component has a proximally sloping disc shape. In another embodiment, in the post-deployment configuration, the anti-migration component has a flat disc shape. In another embodiment, the disc can assume any of these three disc shapes depending on the position of the device in the stomach. In another embodiment, in the post-deployment configuration, the anti-migration component has a half-bumper shape. In another embodiment, in the post-deployment configuration, the anti-migration component has a full bumper shape. Those skilled in the art would recognize, in the post-deployment configuration, the anti-migration component can take on any number of shapes that would prevent the device from being passed completely through the pylorus.

In various embodiments, various components of the device, including the wire mesh structure, retrieval mechanism, and/or anti-migration component are made of or coated with a corrosion-resistant material to prevent damage to the device upon exposure to gastrointestinal contents. In one embodiment, the material is silicone. In another embodiment, the material is polyester. In another embodiment the material is a medical grade epoxy or Parylene. In another embodiment, the material is PEEK. In another embodiment, the material is carbon fiber. In another embodiment, the material is ceramic. In another embodiment, the material is an additional metal. In one embodiment, the coating metal is tantalum. Tantalum provides corrosive resistance and radiopacity. In one embodiment, wherein the coating is ceramic, the ceramic coating has a thickness of several angstrom. In various embodiments, any one or combination of the above corrosive resistant materials is used to coat the device components.

In various embodiments, the wire mesh structure of the intragastric device includes one or more circumferential constricting mechanisms used to constrict the wire mesh structure, returning it to its compressed configuration for retrieval. In one embodiment the constricting mechanism is a zip-tie. In another embodiment, the constricting mechanism is a twist-tie. In various embodiments the circumferential constricting mechanism has additional mechanisms to keep the wire mesh structure in the constricted position without the need for application of constant force by the operator. In one embodiment, the additional mechanism is a crimp or a clamp.

In various embodiments, the wire mesh structure, hook, and/or anti-migration component include a radiopaque marker for radiographic visualization to facilitate delivery and retrieval.

In various embodiments, the intragastric device of the present specification further includes at least one sensor. In one embodiment, the sensor is a flow or impedance sensor and measures the amount of food passing through and/or around the device. In one embodiment, the sensor is a glucose sensor and measures the quality and/or quantity of food passing through and/or around the device. In another embodiment, the sensor is a temperature sensor. In another embodiment, the sensor is an accelerometer. In another embodiment, the sensor is a pH sensor.

It should be appreciated that any combination of one or more of any the embodiments of the wire mesh structure, sleeve, retrieval mechanism, and anti-migration component disclosed in the present specification can be used to create an intragastric device.

Delivery Device

The present specification also discloses various embodiments of a delivery device used to deploy an intragastric device in the gastrointestinal tract of a patient. In various embodiments, the proximal portion of the delivery device is less flexible than the distal portion to allow for deployment of the wire mesh structure in the stomach and deployment of the sleeve in the more tortuous small intestine. The variable flexibility is achieved by the delivery catheter alone or the combination of the delivery catheter and the intragastric device loaded onto that catheter. In various embodiments, the most distal portion of the delivery device comprises a material that is more flexible than the more proximal distal portion of the device. In other embodiments, the most distal portion of the delivery device has a smaller diameter than the more proximal distal portion of the device, imparting greater flexibility to the most distal portion relative to said more proximal distal portion. In various embodiments, the variable flexibility is achieved by the combination of the delivery catheter and the device. In various embodiments, the delivery device comprises an elongate body having a proximal end and a distal end and includes a suture or thread to constrict the intragastric device, ports to access said suture or thread, and/or a locking mechanism to lock the delivery device. In one embodiment the delivery device has a lumen for passage over a guidewire. In one embodiment, the most distal portion has a spherical shape to end to help track the catheter over a guidewire. In various embodiments, the delivery device includes a shrink wrapped coaxial sheath that slides over the compressed intragastric device and unzips or tears away to allow for delivery. In one embodiment, the delivery device includes a first sheath covering the wire mesh structure and a second sheath covering the sleeve. The second sheath has a smaller diameter and is removed from the sleeve by pulling the second sheath through the openings in the wire mesh structure. In one embodiment, the delivery device includes two handles for deploying the wire mesh structure and sleeve separately. In one embodiment, the delivery device includes distinct segments of suture material constraining various segments of the device. In another embodiment, there are two or more mechanisms employed and operated separately to deploy various components of the device.

Retrieval Device

The present specification also discloses various embodiments of a retrieval device used to remove an intragastric device from the gastrointestinal tract of a patient. In various embodiments, the retrieval device comprises an elongate body having a proximal end, a distal end and includes a wire, a grasping hook, a grasper, an actuator, a handle, and/or at least one clamp.

Assembly of Device Components Inside the Human Body

In one embodiment, various components of the device come pre-assembled from the manufacturer. In another embodiment, the various components of the device are assembled pre-procedure or intra-procedure by the operator. In one embodiment, the wire-mesh structure and the sleeve are supplied as two separate device components. The operators deploy the two components separately and intra-procedure couple the sleeve with the wire-mesh structure. The optional anti-migration structure could be a portion of the mesh, sleeve or could be supplied separately as a third structure. Additionally, one or more mesh structures or one or more sleeve structures could be coupled for enhanced therapeutic benefit.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
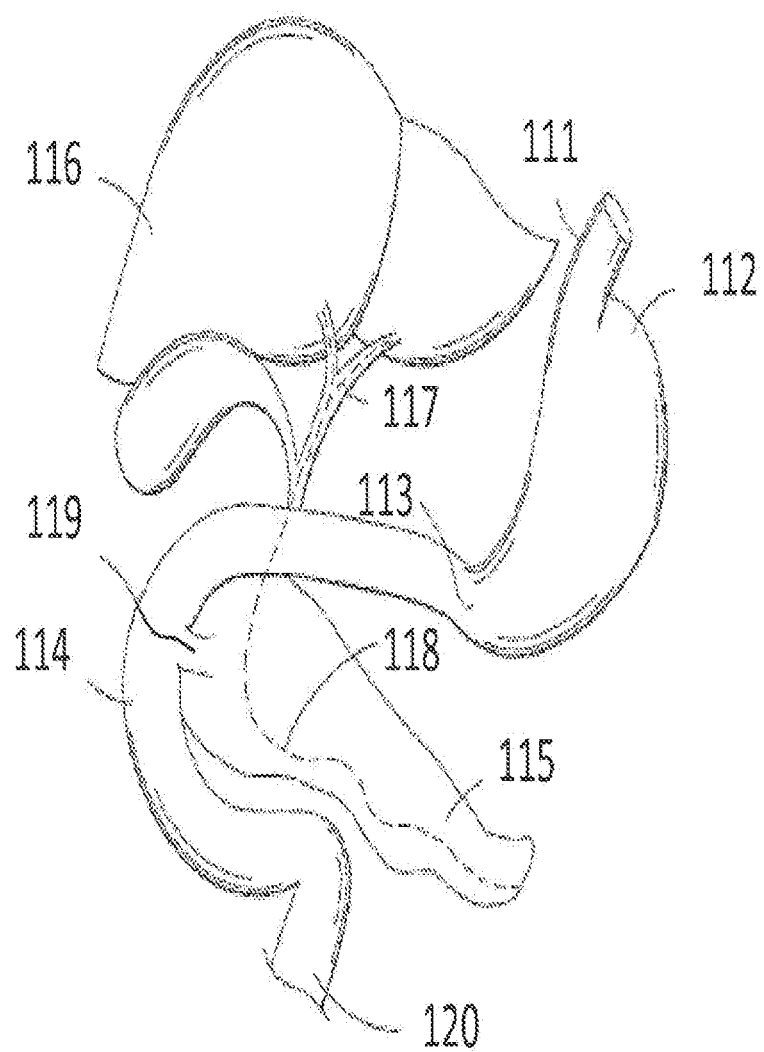
FIG. 1 is an illustration of an upper gastrointestinal system.

FIG. 1 is an illustration of an upper gastrointestinal system. After swallowing, food passes rapidly through the esophagus 111 into the stomach 112. There, it is digested for a period of time and undergoes the process of dilution to an iso-osmotic concentration by grinding and mixing with gastric juices. The stomach 112 relaxes to accommodate the volume of ingested food. As the stomach 112 gets filled with food the sensation of fullness or satiety is generated by stretch receptors in the gastric wall and the person stops eating. The iso-osmotic food, known as chyme, then passes through the pylorus 113 into the duodenum 114. Passage of chyme into the duodenum 114 results in the release of enzyme rich pancreatic secretions from the pancreas 115 and bile salt rich biliary secretions from the liver 116. The biliary secretions travel through the common bile duct 117 where they combine with the pancreatic secretions arriving through the pancreatic duct 118 and the two ducts combine to form the ampulla of vater 119. The ampulla of vater 119 serves as the entry point for the secretions to be deposited into the duodenum 114. In the jejunum 120, the mixing of pancreatic and biliary secretions with the chyme results in the digestion of proteins, fats, and carbohydrates, which are then absorbed into the blood stream.

FIG. 2A is an illustration of a wire mesh structure 201 of an intragastric device 200a in a post-deployment configuration in accordance with one embodiment of the present specification, depicting a first weave pattern. The weave pattern is substantially uniform throughout the entire structure 201. The wire mesh structure 201 includes a proximal end and a distal end and defines an internal volume. The wire mesh structure 201 has a length l extending from its proximal end to its distal end and a width w extending horizontally across its midpoint. In the pictured embodiment, the length l is greater than the width w. The proximal end of the wire mesh structure 201 includes a first opening 210 and the distal end of the wire mesh structure 201 includes a second opening 215 that is larger than the first opening 210. The wire mesh structure 201 helps to treat obesity by occupying and displacing a volume of space in a patient's stomach, thereby decreasing the amount of food the patient can eat before experiencing a feeling of satiety. In one embodiment, the wire mesh structure displaces no less than 10% of the volume of a patient's stomach. Optionally, the wire mesh structure 201 also helps to treat obesity by slowing the passage of food in the gastrointestinal (GI) tract. Food enters the device 200a at the first opening 210, passes through the internal volume of the wire mesh structure 201, and then passes out of the device 200a through the second opening 215. Food captured by the device 200a is sequestered within the wire mesh structure 201 for a period of time, thereby delaying gastric emptying and prolonging a patient's feeling of satiety.

FIG. 2B is an illustration of a wire mesh structure 202 of an intragastric device 200b in a post-deployment configuration in accordance with another embodiment of the present specification, depicting a second weave pattern. The wire mesh structure 202 includes a proximal end and a distal end and defines an internal volume. The wire mesh structure 202 has a length l extending from its proximal end to its distal end and a width w extending horizontally across its midpoint. In the pictured embodiment, the length l is greater than the width w. The wire mesh structure 202 comprises an upper portion 221 and a lower portion 222. The weave patterns of the two portions 221, 222 are substantially identical. In addition, the wire mesh structure 202 comprises a proximal wire mesh header 223 at the top of the upper portion 221. In one embodiment, the proximal wire mesh header 223 has a weave pattern that is different than the weave pattern of the upper portion 221 and lower portion 222. In one embodiment, the proximal wire mesh header 223 comprises a wire that is an extension of the wire comprising the upper portion 221. In another embodiment, the proximal wire mesh header 223 comprises a separate wire that is fixedly attached to the upper portion 221. The proximal wire mesh header 223 has a first opening 220 at its proximal end. The wire mesh structure 202 has a second opening 225 at its distal end that is smaller than the first opening 220. Food enters the device 200b at the first opening 220, passes through the internal volume of the wire mesh structure 202, and then passes out of the device 200b through the second opening 225.

FIG. 2C is an illustration of a wire mesh structure 203 of an intragastric device in a post-deployment configuration in accordance with another embodiment of the present specification, depicting a third weave pattern. The wire mesh structure 203 includes a proximal end and a distal end and defines an internal volume. The wire mesh structure 203 has a length l extending from its proximal end to its distal end and a width w extending horizontally across its midpoint. In the pictured embodiment, the length l is greater than the width w. The wire mesh structure 203 comprises an upper portion 231 and a lower portion 232. The weave patterns of the two portions 231, 232 are substantially identical. In addition, the wire mesh structure 203 comprises a proximal wire mesh header 233 at the top of the upper portion 231 and a distal wire mesh footer 234 at the bottom of the lower portion 232. In one embodiment, the proximal wire mesh header 233 has a weave pattern that is different than the weave pattern of the upper portion 231 and lower portion 232. In one embodiment, the proximal wire mesh header 233 comprises a wire that is an extension of the wire comprising the upper portion 231. In another embodiment, the proximal wire mesh header 233 comprises a separate wire that is fixedly attached to the upper portion 231. In one embodiment, the distal wire mesh footer 234 has a weave pattern that is different than the weave pattern of the upper portion 231 and lower portion 232. In one embodiment, the distal wire mesh footer 234 comprises a wire that is an extension of the wire comprising the lower portion 232. In another embodiment, the distal wire mesh footer 234 comprises a separate wire that is fixedly attached to the lower portion 232. The proximal wire mesh header 233 has a first opening 230 at its proximal end and the distal wire mesh footer 234 has a second opening 235 at its distal end. The second opening 235 is smaller than the first opening 230. Food enters the device 200c at the first opening 230, passes through the internal volume of the wire mesh structure 203, and then passes out of the device 200c through the second opening 235.

The wire mesh structures of FIGS. 2A through 2C are all configurable between a first, compressed configuration (as seen in FIG. 52) to facilitate delivery and removal and a second expanded configuration (as seen in FIGS. 2A through 2C) once deployed. The wire mesh structures depicted in FIGS. 2A through 2C are all more easily compressible along the vertical axis.

FIG. 2D is an illustration of a wire mesh structure 204 of an intragastric device 200d in a post-deployment configuration in accordance with another embodiment of the present specification, depicting a fourth weave pattern. The wire mesh structure 204 includes a proximal end and a distal end and defines an internal volume. The wire mesh structure 204 has a length l extending from its proximal end to its distal end and a width w extending horizontally across its midpoint. The weave pattern of the wire mesh structure 204 depicted in FIG. 2D is substantially similar to the weave pattern of the wire mesh structure 202 depicted in FIG. 2B. However, referring to FIG. 2D, the length l of the wire mesh structure 204 is less than the width w. The wire mesh structure 204 comprises an upper portion 241 and a lower portion 242. The weave patterns of the two portions 241, 242 are substantially identical. In addition, the wire mesh structure 204 comprises a proximal wire mesh header 243 at the top of the upper portion 241. The proximal wire mesh header 243 has a first opening 240 at its proximal end. The wire mesh structure 204 has a second opening 245 at its distal end. Food enters the device 200d at the first opening 240, passes through the internal volume of the wire mesh structure 204, and then passes out of the device 200d through the second opening 245.

FIG. 2E is an illustration of a wire mesh structure 205 of an intragastric device 200e in a post-deployment configuration in accordance with yet another embodiment of the present specification, depicting a fifth weave pattern. The wire mesh structure 205 includes a proximal end and a distal end and defines an internal volume. The wire mesh structure 205 has a length l extending from its proximal end to its distal end and a width w extending horizontally across its midpoint. The weave pattern of the wire mesh structure 205 depicted in FIG. 2E is substantially similar to a 90 degree rotation of the weave pattern of the wire mesh structure 202 depicted in FIG. 2B. Referring to FIG. 2E, the length l of the wire mesh structure 205 is less than the width w. The wire mesh structure 205 comprises an upper portion 251 and a lower portion 252. The weave patterns of the two portions 251, 252 are substantially identical. In addition, the wire mesh structure 205 comprises a proximal wire mesh header 253 at the top of the upper portion 251. The proximal wire mesh header 253 has a first opening 250 at its proximal end. The wire mesh structure 205 has a second opening 255 at its distal end. Food enters the device 200e at the first opening 250, passes through the internal volume of the wire mesh structure 205, and then passes out of the device 200e through the second opening 255.

The wire mesh structures of FIGS. 2D and 2E are both configurable between a first, compressed configuration to facilitate delivery and removal and a second expanded configuration (as seen in FIGS. 2D and 2E) once deployed. The wire mesh structures depicted in FIGS. 2D and 2E are all more easily compressible along the horizontal axis. As such, it will be more difficult for gastric contractions to compress the wire mesh structures vertically. Vertical compression would make the device thinner along its length, allowing it to be more easily passed through the pylorus. Therefore, the shape of the wire mesh structures depicted in FIGS. 2D and 2E provides an additional benefit of immovability relative to a patient's pylorus.

Figure 2F:
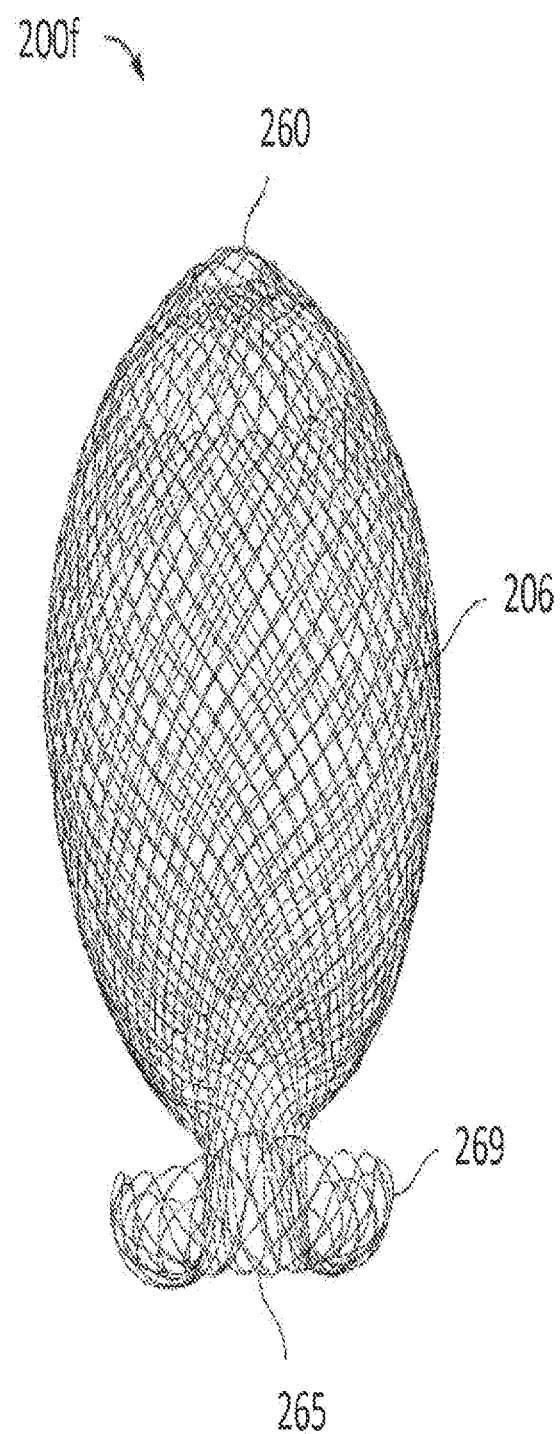
FIG. 2F is an illustration of another embodiment of an intragastric device in an exemplary post-deployment configuration.

FIG. 2F is an illustration of another embodiment of a wire mesh structure 206 of an intragastric device 200f in an exemplary post-deployment configuration. The device 200f comprises an oval shaped wire mesh structure 206 and includes a first opening 260 at its proximal end and a second, larger opening 265 at its distal end. In various embodiments, the wire mesh of the device 200f is coated with a corrosion resistant material to prevent damage to the wire mesh of the device 200f by gastric contents. The device 200f further includes, at its distal end, an anti-migration component 269 to prevent migration of the device 200f past the pylorus. In various embodiments, the diameter of the anti-migration component 269 is greater than the diameter of the pylorus when fully relaxed. As such, the anti-migration component 269 functions as a physical barrier to prevent passage of the device through the pylorus. In the pictured embodiment, the anti-migration component 269 comprises a distal extension of the wire mesh from the distal end of the device 200f. The wire mesh extension curls outwardly and then extends back a short distance proximally, forming a rounded bumper shaped anti-migration component 269. In various embodiments (not shown), the anti-migration component can have a disc shape, saucer shape, or any other shape which will help prevent passage of the device through the pylorus. In various embodiments, the anti-migration component can be an extension of the wire mesh (as pictured) or can be a separate piece of wire mesh (not shown) that is attached to the distal end of the wire mesh structure of the device. In one embodiment, the wires of the device 200f, including the wires of the anti-migration component 269, are covered in a corrosion-resistant material. In one embodiment, the material is silicone. In another embodiment, the material is parylene.

FIG. 2G is an illustration of yet another embodiment of a wire mesh structure 207 of an intragastric device 200g in an exemplary post-deployment configuration and FIG. 2H is a cross-sectional illustration of the embodiment of the intragastric device depicted in FIG. 2G. Referring to FIGS. 2G and 2H simultaneously, the device 200g, 200h comprises a wire mesh structure covered 207, 208 by a membrane 277, 287 about its entire outer surface with the exception of a first opening 270, 280 at its proximal end and a second, larger opening 275, 285 at its distal end. The device 200g, 200h also includes an anti-migration component 279, 289 at its distal end. Similar to the device shown in FIG. 2F, the anti-migration component 279, 289 approximates a bumper shape and is formed from an extension of the wire mesh structure extending distally and then curling outward and extending back a short distance proximally. The curved shape of the anti-migration component 279, 289 is well visualized in the cross-sectional illustration of FIG. 2H.

Figures 2I, 2J:
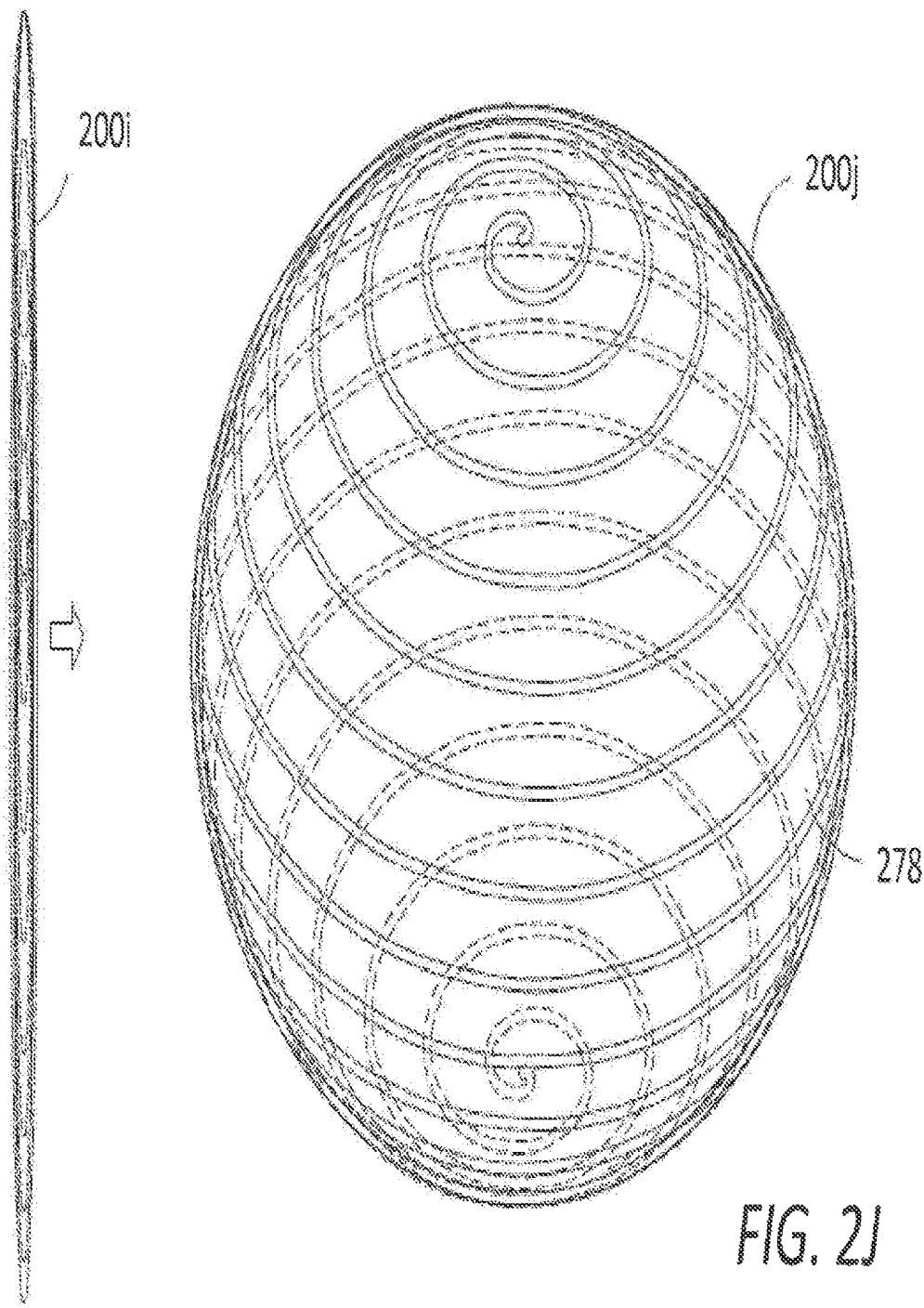
FIG. 2I is an illustration of another embodiment of an intragastric device in an exemplary pre-deployment configuration.
FIG. 2J is an illustration of the intragastric device of FIG. 2I in an exemplary post-deployment configuration, depicting a spherical structure comprised of spiral wires.

FIG. 2I is an illustration of another embodiment of a wire mesh structure of an intragastric device 200i in an exemplary pre-deployment configuration. The pre-deployment configuration takes a compressed, cylindrical shape to facilitate insertion.

FIG. 2J is an illustration of the intragastric device 200j of FIG. 2I in an exemplary post-deployment configuration. The post-deployment configuration takes an expanded, spiral wire shape to occupy gastric volume and permit the sequestering of food within the device. In one embodiment, the spiral structure is covered with a membrane 278 containing openings of the same or different sizes. In one embodiment, the openings have valves to direct the flow of food preferentially in an inward or an outward direction.

Figures 2K, 2L:
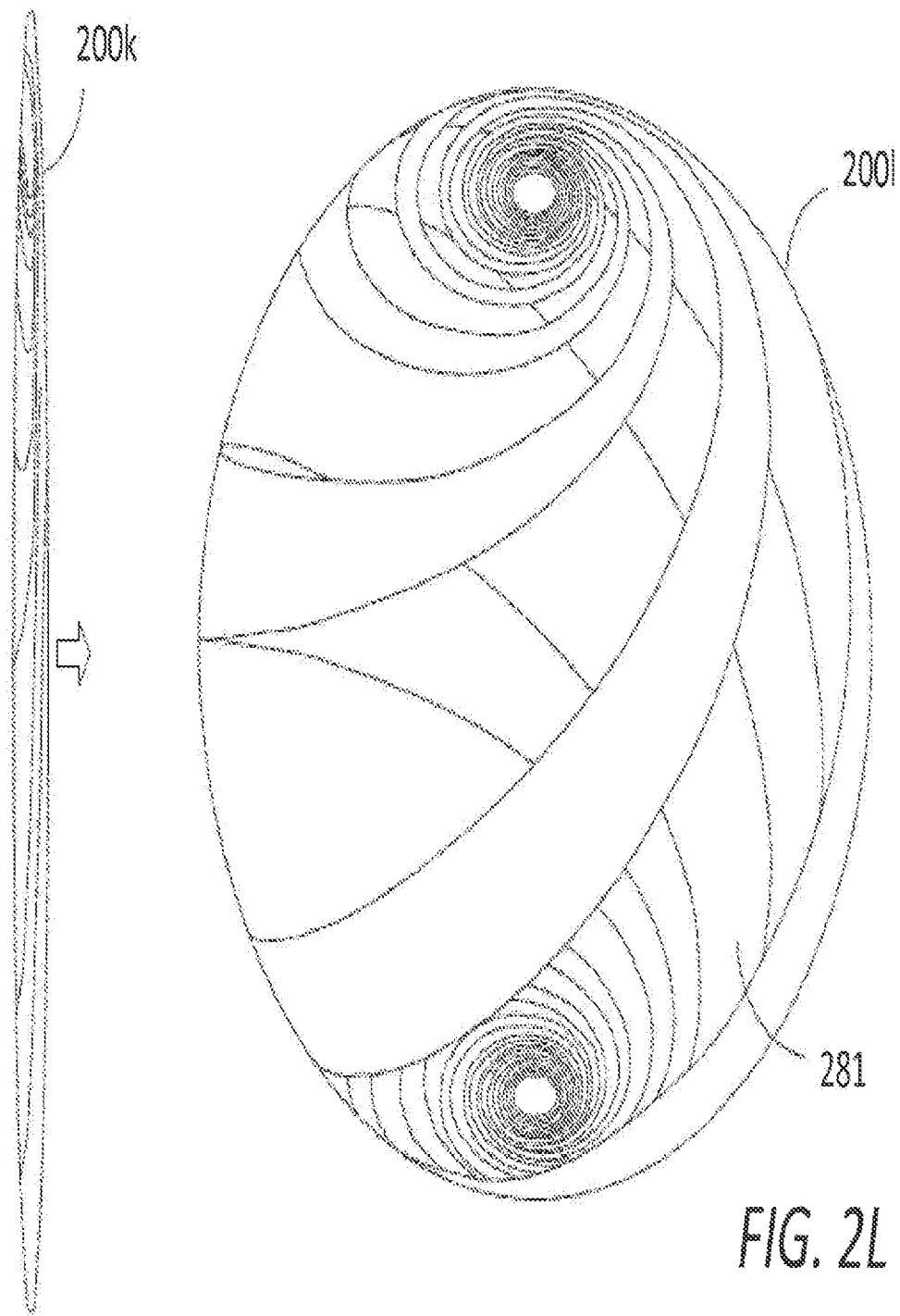
FIG. 2K is an illustration of another embodiment of an intragastric device in an exemplary pre-deployment configuration.
FIG. 2L is an illustration of the intragastric device of FIG. 2K in an exemplary post-deployment configuration, depicting a spherical structure comprised of spiral strips.

FIG. 2K is an illustration of yet another embodiment of a wire mesh structure of an intragastric device 200k in an exemplary pre-deployment configuration. The pre-deployment configuration takes a compressed, cylindrical shape to facilitate insertion.

FIG. 2L is an illustration of the intragastric device 200l of FIG. 2K in an exemplary post-deployment configuration. The post-deployment configuration takes an expanded, spiral strip shape, similar to an orange peel, to occupy gastric volume and permit the sequestering of food within the device. In one embodiment, the spiral structure is covered with a membrane 281 containing openings of the same or different sizes. In one embodiment, the openings have valves to direct the flow of food preferentially in an inward or an outward direction.

Figures 2M, 2N:
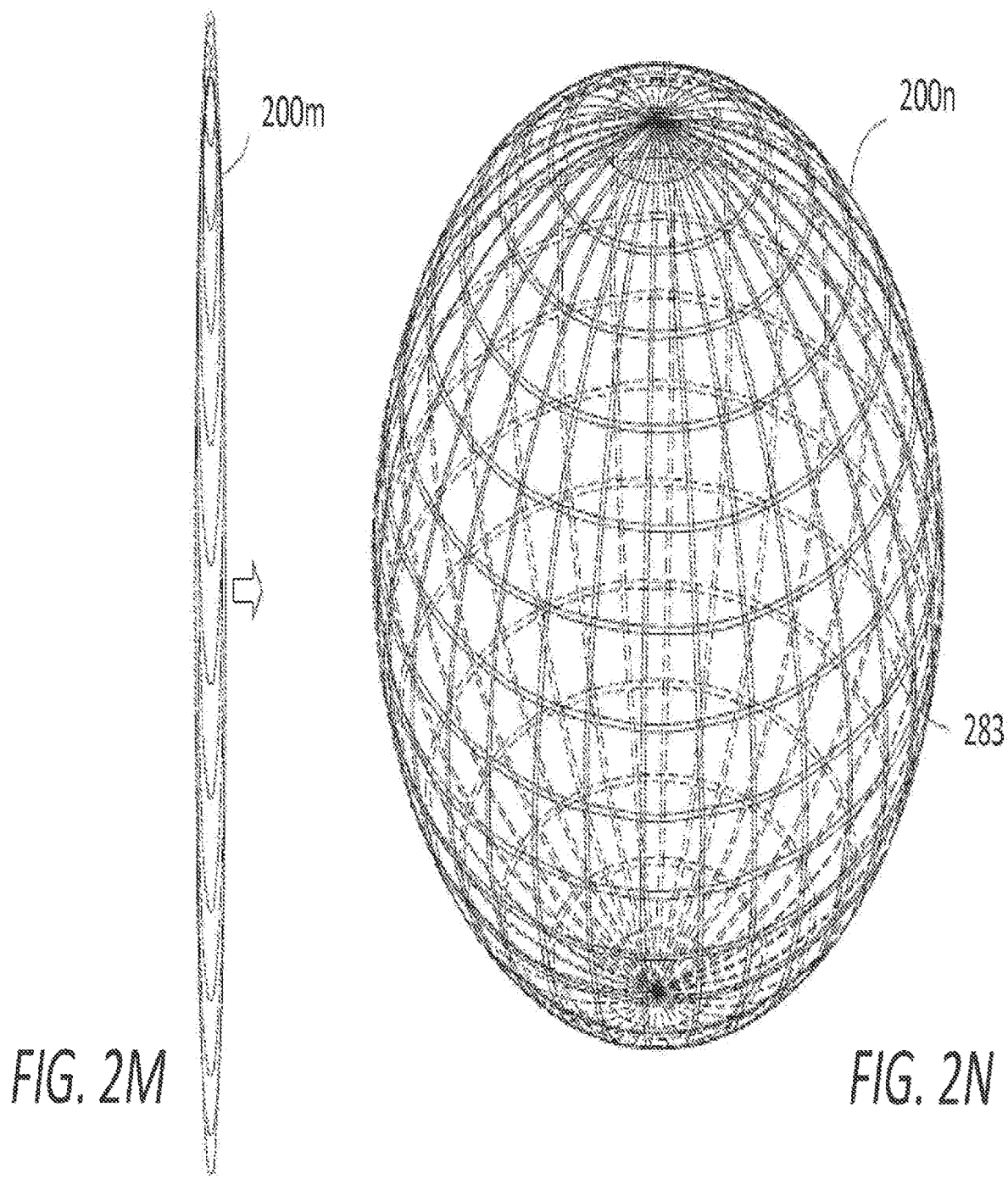
FIG. 2M is an illustration of yet another embodiment of an intragastric device in an exemplary pre-deployment configuration.
FIG. 2N is an illustration of the intragastric device of FIG. 2M in an exemplary post-deployment configuration.

FIG. 2M is an illustration of yet another embodiment of a wire mesh structure of an intragastric device 200m in an exemplary pre-deployment configuration. The pre-deployment configuration takes a compressed, cylindrical shape to facilitate insertion.

FIG. 2N is an illustration of the intragastric device 200n of FIG. 2M in an exemplary post-deployment configuration. The post-deployment configuration takes an expanded, wire mesh shape to occupy gastric volume and permit the sequestering of food within the device. In one embodiment, the wire mesh structure is covered with a membrane 283 containing openings of the same or different sizes. In one embodiment, the openings have valves to direct the flow of food preferentially in an inward or an outward direction.

FIG. 2O is an illustration of one embodiment depicting an exemplary post-deployment, membrane 284 covered intragastric device 200o with varying sized openings along its surface. The middle two-thirds of the device 200o contain larger holes 286 and the top and bottom one-third contain smaller holes 288. In one embodiment, the larger holes 286 have valves composed of the same membranous material to direct the flow of food preferentially into the device 200o. Thereafter, food slowly exits the device 200o through the smaller holes 288 positioned at the top and bottom of the device 200o, thereby delaying gastric emptying.

Figure 2P:
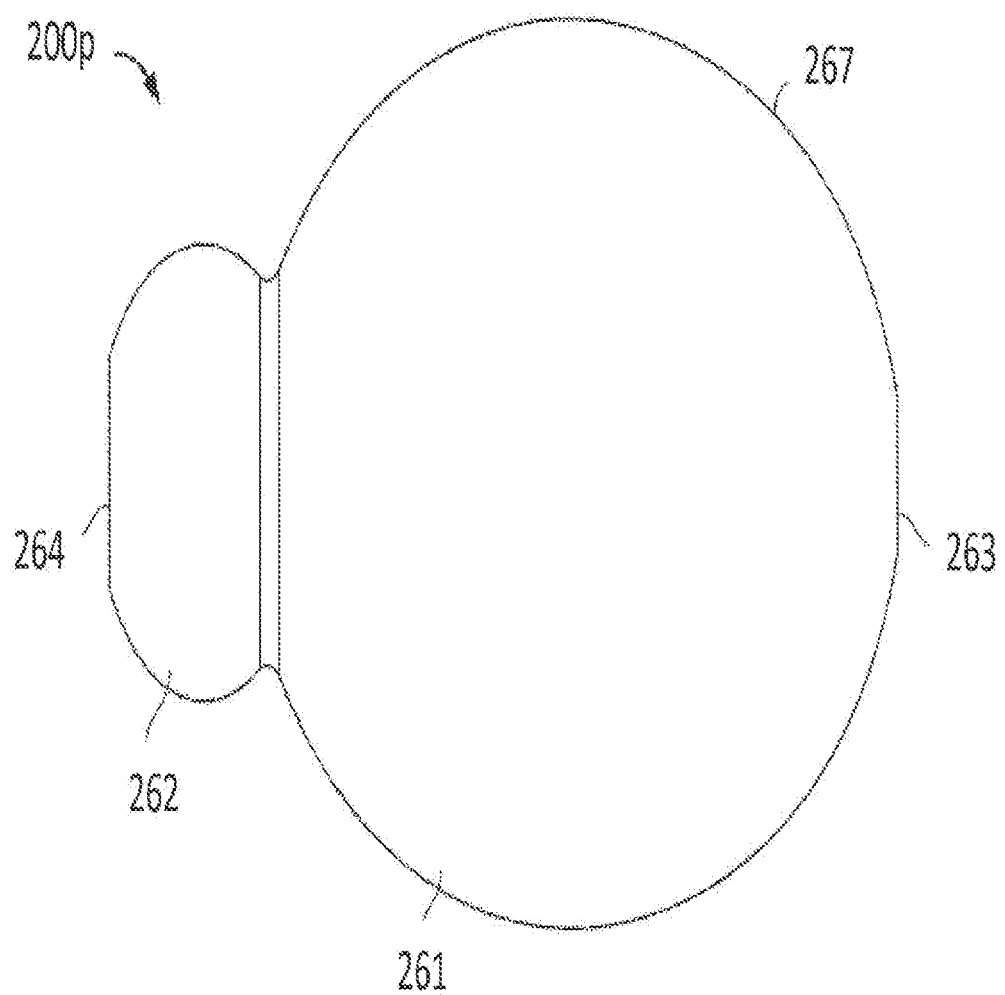
FIG. 2P is an illustration of another embodiment of an intragastric device in an exemplary post-deployment configuration having a dumbbell shape.

FIG. 2P is an illustration of another embodiment of an intragastric device 200p in an exemplary post-deployment configuration having a dumbbell shape. The device 200p includes a first, upper wire mesh 261 at its proximal end and a second, lower wire mesh 262 at its distal end. The internal volumes of the two wire meshes 261, 262 are in fluid communication with one another. In various embodiments, the size of the second wire mesh 262 is equal to or smaller than the size of the upper wire mesh 261. The device 200p further includes a first opening 263 at the proximal end of the upper wire mesh 261 and a second, larger opening 264 at the distal end of the lower wire mesh 262. Food enters the device 200p at the first opening 263, travels through the internal volume of the upper wire mesh 261, into and through the internal volume of the lower wire mesh 262, and exits through the second opening 264. In one embodiment, the wire mesh of the lower wire mesh portion 262 is an extension of the wire mesh of the upper wire mesh portion 261. In another embodiment, the two wire mesh portions 261, 262 are comprised of separate wire mesh structures which are then attached prior to deployment. In the pictured embodiment, the device 200p includes a membrane 267 covering the entire outer surface of the device 200p with the exception of the two openings 263, 264.

In various embodiments, the device 200p has a total length ranging between 50 and 500 mm. In a preferred embodiment, the device 200p has a total length of 180 mm. In various embodiments, the upper wire mesh 261 has a length ranging between 70 and 250 mm. In a preferred embodiment, the upper wire mesh 261 has a length of 140 mm. In various embodiments, the lower wire mesh 262 has a length ranging between 30 and 250 mm. In a preferred embodiment, the lower wire mesh 262 has a length of 40 mm. In various embodiments, the upper wire mesh 261 has a width ranging between 70 and 170 mm. In a preferred embodiment, the upper wire mesh 261 has a width of 120 mm. In various embodiments, the lower wire mesh 262 has a width ranging between 20 and 170 mm. In a preferred embodiment, the lower wire mesh 262 has a width of 60 mm. In various embodiments, the first opening 263 has a diameter ranging between 5 and 30 mm. In a preferred embodiment, the first opening 263 has a diameter of 20 mm. In various embodiments, the second opening 264 has a diameter ranging from 10 to 45 mm. In a preferred embodiment, the second opening 264 has a diameter of 30 mm.

FIG. 2Q is an illustration of a first exemplary wire mesh structure 291 shape in a post-deployment configuration, in accordance with one embodiment of the present specification. In the pictured embodiment, the wire mesh structure 291 has a spherical shape.

FIG. 2R is an illustration of a second exemplary wire mesh structure 292 shape in a post-deployment configuration, in accordance with one embodiment of the present specification. In the pictured embodiment, the wire mesh structure 292 has a kidney bean shape.

FIG. 2S is an illustration of a third exemplary wire mesh structure 292 shape in a post-deployment configuration, in accordance with one embodiment of the present specification. In the pictured embodiment, the wire mesh structure 293 has an oval shape.

FIG. 2T is an illustration of a fourth exemplary wire mesh structure 294 shape in a post-deployment configuration, in accordance with one embodiment of the present specification. In the pictured embodiment, the wire mesh structure 294 has a shape that approximates that of a stomach and of a boot, with the lower, toe shaped portion positioned proximate to the pylorus.

FIG. 2U is an illustration of a fifth exemplary wire mesh structure 295 shape in a post-deployment configuration, in accordance with one embodiment of the present specification. In the pictured embodiment, the wire mesh structure 295 has an ovoid or inverted egg shape.

FIG. 3A is an illustration of a wire mesh structure 301 and coupled sleeve 360 of an intragastric device 300a in a post-deployment configuration in accordance with one embodiment of the present specification, depicting the wire mesh structure 301 with the weave pattern as shown in FIG. 2B. The wire mesh structure 301 has a length l which is greater than its width w. The wire mesh structure 301 comprises an upper portion 321, a lower portion 322, a proximal wire mesh header 323, and a first opening 320 at its proximal end. The wire mesh structure 301 also includes a second opening at its distal end which is covered entirely by the coupled sleeve 360 and therefore not visible in FIG. 3A. In the pictured embodiment, the first opening 320 at the proximal end of the wire mesh structure 301 is smaller than the second opening at its distal end leading into the sleeve 360. In one embodiment, the sleeve 360 is coupled to the wire mesh structure 301 via sutures.

The sleeve 360 includes a sleeve body 361 having a proximal end, a distal end and a lumen within. The sleeve body 361 is comprised of a flexible and compressible mesh material. The sleeve body 361 includes a first opening (not shown) at its proximal end and a second opening 375 at its distal end. The first opening 320 of the wire mesh structure 301 is in fluid communication with the internal volume of the wire mesh structure 301, which is in fluid communication with the second opening of the wire mesh structure. The second opening of the wire mesh structure 301 is in fluid communication with the first opening of the sleeve body 361, which is in fluid communication with the lumen of the sleeve body 361. Finally, the lumen of the sleeve body 361 is in fluid communication with the second opening 375 at the distal end of the sleeve body 361.

Once deployed, the device 300a is positioned within the gastrointestinal tract of a patient such that the wire mesh structure 301 is positioned in the mid/distal stomach with the lower portion 322 resting just proximal to the antrum or the pylorus. The sleeve 360 passes through the pylorus and extends into the duodenum. Food enters the first opening 320 of the wire mesh structure 301, passes through the internal volume of the wire mesh structure 301, through the second opening of the wire mesh structure and the first opening of the sleeve body 361, through the lumen of the sleeve body 361, and exits the through the second opening 375 of the sleeve body 361. Food that travels through the device 300*a* effectively bypasses the pylorus and proximal portion of the small intestine.

FIG. 3B is an illustration of a wire mesh structure 303 and coupled sleeve 362 of an intragastric device 300*b* in a post-deployment configuration in accordance with another embodiment of the present specification, depicting the wire mesh structure 302 with the weave pattern as shown in FIG. 2C. The wire mesh structure 302 has a length l which is greater than its width w. The wire mesh structure 302 comprises an upper portion 331, a lower portion 332, a proximal wire mesh header 333, a distal wire mesh footer 334, and a first opening 330 at its proximal end. The wire mesh structure 302 also includes a second opening at its distal end which is covered entirely by the coupled sleeve 362 and therefore not visible in FIG. 3B. In the pictured embodiment, the first opening 330 at the proximal end of the wire mesh structure 302 is larger than the second opening at its distal end leading into the sleeve 362. In one embodiment, the sleeve 362 is coupled to the wire mesh structure 302 via sutures.

The sleeve 362 includes a sleeve body 363 having a proximal end, a distal end and a lumen within. The sleeve body 363 is comprised of a flexible and compressible mesh material. The sleeve body 363 includes a first opening (not shown) at its proximal end and a second opening 376 at its distal end. Food travels through the device 300*b* in a similar manner as discussed with reference to FIG. 3A.

Figure 3C:
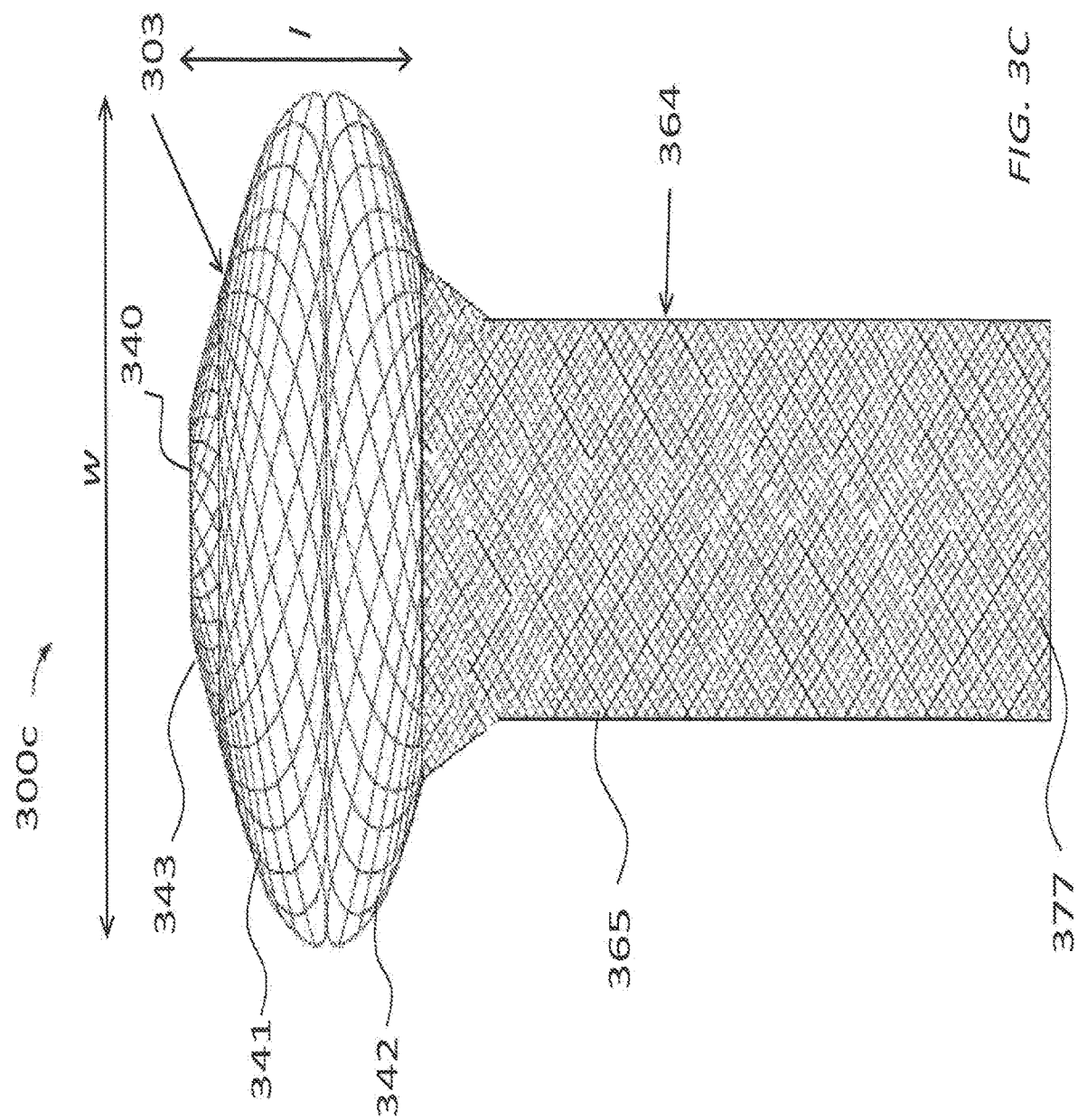
FIG. 3C is an illustration of a wire mesh structure and coupled sleeve of an intragastric device in a post-deployment configuration in accordance with another embodiment of the present specification, depicting the wire mesh structure with the weave pattern as shown in FIG. 2D.

FIG. 3C is an illustration of a wire mesh structure 303 and coupled sleeve 364 of an intragastric device 300*c* in a post-deployment configuration in accordance with another embodiment of the present specification, depicting the wire mesh structure 303 with the weave pattern as shown in FIG. 2D. The wire mesh structure 303 has a length l which is less than its width w. The wire mesh structure 303 comprises an upper portion 341, a lower portion 342, a proximal wire mesh header 343, and a first opening 340 at its proximal end. The wire mesh structure 303 also includes a second opening at its distal end which is covered entirely by the coupled sleeve 364 and therefore not visible in FIG. 3C. In the pictured embodiment, the first opening 340 at the proximal end of the wire mesh structure 303 is smaller than the second opening at its distal end leading into the sleeve 364. In one embodiment, the sleeve 364 is coupled to the wire mesh structure 303 via sutures or glued or bonded to the mesh structure.

The sleeve 364 includes a sleeve body 365 having a proximal end, a distal end and a lumen within. The sleeve body 365 is comprised of a flexible and compressible mesh material. The sleeve body 365 includes a first opening (not shown) at its proximal end and a second opening 377 at its distal end. Food travels through the device 300*c* in a similar manner as discussed with reference to FIG. 3A.

Figure 3D:
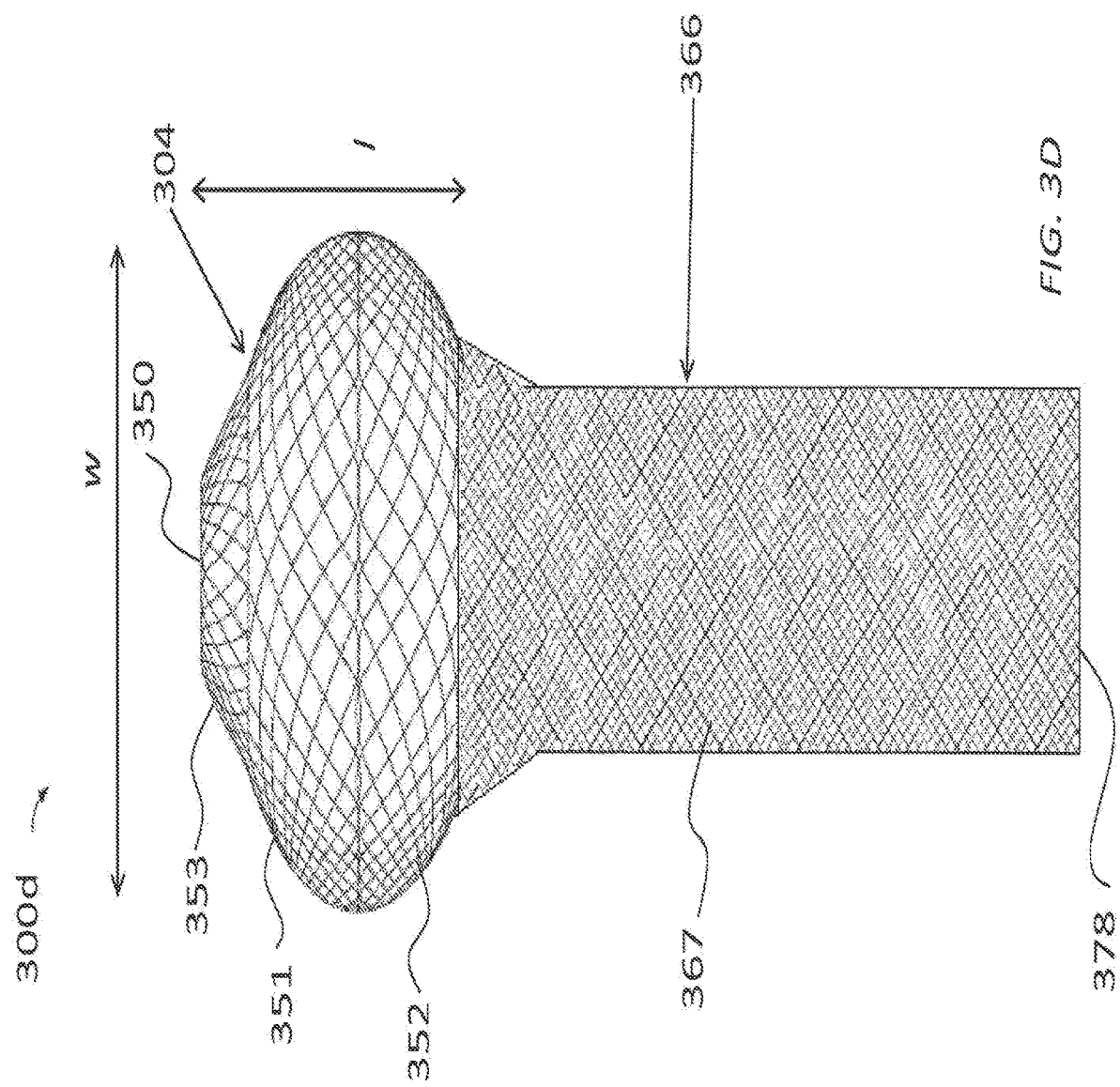
FIG. 3D is an illustration of a wire mesh structure and coupled sleeve of an intragastric device in a post-deployment configuration in accordance with yet another embodiment of the present specification, depicting the wire mesh structure with the weave pattern as shown in FIG. 2E.

FIG. 3D is an illustration of a wire mesh structure 304 and coupled sleeve 366 of an intragastric device 300*d* in a post-deployment configuration in accordance with yet another embodiment of the present specification, depicting the wire mesh structure 304 with the weave pattern as shown in FIG. 2E. The wire mesh structure 304 has a length l which is less than its width w. The wire mesh structure 304 comprises an upper portion 351, a lower portion 352, a proximal wire mesh header 353, and a first opening 350 at its proximal end. The wire mesh structure 304 also includes a second opening at its distal end which is covered entirely by the coupled sleeve 366 and therefore not visible in FIG. 3D. In the pictured embodiment, the first opening 350 at the proximal end of the wire mesh structure 304 is smaller than the second opening at its distal end leading into the sleeve 366. In one embodiment, the sleeve 366 is coupled to the wire mesh structure 304 via sutures.

The sleeve 366 includes a sleeve body 367 having a proximal end, a distal end and a lumen within. The sleeve body 367 is comprised of a flexible and compressible mesh material. The sleeve body 367 includes a first opening (not shown) at its proximal end and a second opening 378 at its distal end. Food travels through the device 300*d* in a similar manner as discussed with reference to FIG. 3A.

FIG. 4A is an illustration of a wire mesh structure 401 with retrieval mechanism 481 and coupled sleeve 460 of an intragastric device 400*a* in a post-deployment configuration in accordance with one embodiment of the present specification, depicting the wire mesh structure 401 with the weave pattern as shown in FIG. 2B. The wire mesh structure 401 has a length l which is greater than its width w. The wire mesh structure 401 comprises an upper portion 421, a lower portion 422, a proximal wire mesh header 423, and a first opening 420 at its proximal end. A retrieval mechanism 481 extends proximally from the proximal wire mesh header 423. In one embodiment, the retrieval mechanism 481 includes a retrieval loop 482. In one embodiment, the retrieval mechanism 481 is an extension of the wire comprising the proximal wire mesh header 423. In another embodiment, the retrieval mechanism 481 is a separate piece of wire that is fixedly attached to the proximal wire mesh header 423. The wire mesh structure 401 also includes a second opening at its distal end which is covered entirely by the coupled sleeve 460 and therefore not visible in FIG. 4A. In the pictured embodiment, the first opening 420 at the proximal end of the wire mesh structure 401 is smaller than the second opening at its distal end leading into the sleeve 460. In one embodiment, the sleeve 460 is coupled to the wire mesh structure 401 via sutures.

The sleeve 460 includes a sleeve body 461 having a proximal end, a distal end and a lumen within. The sleeve body 461 is comprised of a flexible and compressible mesh material. The sleeve body 461 includes a first opening (not shown) at its proximal end and a second opening 475 at its distal end. The first opening 420 of the wire mesh structure 401 is in fluid communication with the internal volume of the wire mesh structure 401, which is in fluid communication with the second opening of the wire mesh structure. The second opening of the wire mesh structure 401 is in fluid communication with the first opening of the sleeve body 461, which is in fluid communication with the lumen of the sleeve body 461. Finally, the lumen of the sleeve body 461 is in fluid communication with the second opening 475 at the distal end of the sleeve body 461.

Once deployed, the device 400*a* is positioned within the gastrointestinal tract of a patient such that the wire mesh structure 401 is positioned in the distal stomach with the lower portion 422 resting just proximal to the antrum or the pylorus. The sleeve 460 passes through the pylorus and extends into the duodenum. Food enters the first opening 420 of the wire mesh structure 401, passes through the internal volume of the wire mesh structure 401, through the second opening of the wire mesh structure and the first opening of the sleeve body 461, through the lumen of the sleeve body 461, and exits the through the second opening 475 of the sleeve body 461. Food that travels through the device 400a effectively bypasses the pylorus and proximal portion of the small intestine.

FIG. 4B is an illustration of a wire mesh structure 402 with retrieval hook 483 and coupled sleeve 462 of an intragastric device 400b in a post-deployment configuration in accordance with another embodiment of the present specification, depicting the wire mesh structure 402 with the weave pattern as shown in FIG. 2C. The wire mesh structure 402 has a length l which is greater than its width w. The wire mesh structure 402 comprises an upper portion 431, a lower portion 432, a proximal wire mesh header 433, a distal wire mesh footer 434, and a first opening 430 at its proximal end. A retrieval mechanism 483 extends proximally from the proximal wire mesh header 433. In one embodiment, the retrieval mechanism 483 includes a retrieval loop 484. In one embodiment, the retrieval mechanism 483 is an extension of the wire comprising the proximal wire mesh header 433. In another embodiment, the retrieval mechanism 483 is a separate piece of wire that is fixedly attached to the proximal wire mesh header 433. The wire mesh structure 402 also includes a second opening at its distal end which is covered entirely by the coupled sleeve 462 and therefore not visible in FIG. 4B. In the pictured embodiment, the first opening 430 at the proximal end of the wire mesh structure 402 is larger than the second opening at its distal end leading into the sleeve 462. In one embodiment, the sleeve 462 is coupled to the wire mesh structure 402 via sutures.

The sleeve 462 includes a sleeve body 463 having a proximal end, a distal end and a lumen within. The sleeve body 463 is comprised of a flexible and compressible mesh material. The sleeve body 463 includes a first opening (not shown) at its proximal end and a second opening 476 at its distal end. Food travels through the device 400b in a similar manner as discussed with reference to FIG. 4A.

FIG. 4C is an illustration of a wire mesh structure 403 with retrieval mechanism 485 and coupled sleeve 464 of an intragastric device 400c in a post-deployment configuration in accordance with another embodiment of the present specification, depicting the wire mesh structure 403 with the weave pattern as shown in FIG. 2D. The wire mesh structure 403 has a length l which is less than its width w. The wire mesh structure 403 comprises an upper portion 441, a lower portion 442, a proximal wire mesh header 443, and a first opening 440 at its proximal end. A retrieval mechanism 485 extends proximally from the proximal wire mesh header 443. In one embodiment, the retrieval mechanism 485 includes a retrieval loop 486. In one embodiment, the retrieval hook 485 is an extension of the wire comprising the proximal wire mesh header 443. In another embodiment, the retrieval mechanism 485 is a separate piece of wire that is fixedly attached to the proximal wire mesh header 443. The wire mesh structure 403 also includes a second opening at its distal end which is covered entirely by the coupled sleeve 464 and therefore not visible in FIG. 4C. In the pictured embodiment, the first opening 440 at the proximal end of the wire mesh structure 403 is smaller than the second opening at its distal end leading into the sleeve 464. In one embodiment, the sleeve 464 is coupled to the wire mesh structure 403 via sutures.

The sleeve 464 includes a sleeve body 465 having a proximal end, a distal end and a lumen within. The sleeve body 465 is comprised of a flexible and compressible mesh or a wire material. The sleeve body 465 includes a first opening (not shown) at its proximal end and a second opening 477 at its distal end. Food travels through the device 400c in a similar manner as discussed with reference to FIG. 4A.

FIG. 4D is an illustration of a wire mesh structure 404 with retrieval mechanism 487 and coupled sleeve 466 of an intragastric device 400d in a post-deployment configuration in accordance with yet another embodiment of the present specification, depicting the wire mesh structure 404 with the weave pattern as shown in FIG. 2E. The wire mesh structure 404 has a length l which is less than its width w. The wire mesh structure 404 comprises an upper portion 451, a lower portion 452, a proximal wire mesh header 453, and a first opening 450 at its proximal end. A retrieval mechanism 487 extends proximally from the proximal wire mesh header 453. In one embodiment, the retrieval mechanism 487 includes a retrieval loop 488. In one embodiment, the retrieval mechanism 487 is an extension of the wire comprising the proximal wire mesh header 453. In another embodiment, the retrieval mechanism 487 is a separate piece of wire that is fixedly attached to the proximal wire mesh header 453. The wire mesh structure 404 also includes a second opening at its distal end which is covered entirely by the coupled sleeve 466 and therefore not visible in FIG. 4D. In the pictured embodiment, the first opening 450 at the proximal end of the wire mesh structure 404 is smaller than the second opening at its distal end leading into the sleeve 466. In one embodiment, the sleeve 466 is coupled to the wire mesh structure 404 via sutures.

The sleeve 466 includes a sleeve body 467 having a proximal end, a distal end and a lumen within. The sleeve body 467 is comprised of a flexible and compressible mesh material. The sleeve body 467 includes a first opening (not shown) at its proximal end and a second opening 478 at its distal end. Food travels through the device 400d in a similar manner as discussed with reference to FIG. 4A.

FIG. 5A is an illustration of a wire mesh structure 501 with retrieval hook 581, coupled sleeve 560, and anti-migration component 591 of an intragastric device 500a in a post-deployment configuration in accordance with one embodiment of the present specification, depicting the wire mesh structure 501 with the weave pattern as shown in FIG. 2B. The wire mesh structure 501 has a length l which is greater than its width w. The wire mesh structure 501 comprises an upper portion 521, a lower portion 522, a proximal wire mesh header 523, and a first opening 520 at its proximal end. A retrieval mechanism 581 extends proximally from the proximal wire mesh header 523. In one embodiment, the retrieval mechanism 581 includes a retrieval loop 582. In one embodiment, the retrieval mechanism 581 is an extension of the wire comprising the proximal wire mesh header 523. In another embodiment, the retrieval mechanism 581 is a separate piece of wire that is fixedly attached to the proximal wire mesh header 523. The wire mesh structure 501 also includes a second opening at its distal end which is covered entirely by the coupled sleeve 560 and therefore not visible in FIG. 5A. In the pictured embodiment, the first opening 520 at the proximal end of the wire mesh structure 501 is smaller than the second opening at its distal end leading into the sleeve 560. In one embodiment, the sleeve 560 is coupled to the wire mesh structure 501 via sutures.

The sleeve 560 includes a sleeve body 561 having a proximal end, a distal end and a lumen within. The sleeve body 561 is comprised of a flexible and compressible mesh material. The sleeve body 561 includes a first opening (not shown) at its proximal end and a second opening 575 at its distal end. The first opening 520 of the wire mesh structure 501 is in fluid communication with the internal volume of the wire mesh structure 501, which is in fluid communication with the second opening of the wire mesh structure. The second opening of the wire mesh structure 501 is in fluid communication with the first opening of the sleeve body 561, which is in fluid communication with the lumen of the sleeve body 561. Finally, the lumen of the sleeve body 561 is in fluid communication with the second opening 575 at the distal end of the sleeve body 561.

An anti-migration component 591 is positioned at the junction of the wire mesh structure 501 with the sleeve 560. In the pictured embodiment, the anti-migration component 591 has the shape of a distally sloping disc and is comprised of a wire mesh with a silicone covering. In one embodiment, the anti-migration component 591 is fixedly attached to the lower portion 522 of the wire mesh structure 501 via sutures.

Once deployed, the device 500a is positioned within the gastrointestinal tract of a patient such that the wire mesh structure 501 is positioned in the distal stomach with the lower portion 522 resting proximal to the pylorus. The anti-migration component 591 sits just proximal to the pylorus and acts as a physical stopper, preventing distal migration of the entirety of the device 500a through the pylorus and into the duodenum. The sleeve 560 passes through the pylorus and extends into the duodenum. Food enters the first opening 520 of the wire mesh structure 501, passes through the internal volume of the wire mesh structure 501, through the second opening of the wire mesh structure and the first opening of the sleeve body 561, through the lumen of the sleeve body 561, and exits the through the second opening 575 of the sleeve body 561. Food that travels through the device 500a effectively bypasses the pylorus and proximal portion of the small intestine.

FIG. 5B is an illustration of a wire mesh structure 502 with retrieval hook 583, coupled sleeve 562, and anti-migration component 592 of an intragastric device 500b in a post-deployment configuration in accordance with another embodiment of the present specification, depicting the wire mesh structure 502 with the weave pattern as shown in FIG. 2C. The wire mesh structure 502 has a length l which is greater than its width w. The wire mesh structure 502 comprises an upper portion 531, a lower portion 532, a proximal wire mesh header 533, a distal wire mesh footer 534, and a first opening 530 at its proximal end. A retrieval mechanism 583 extends proximally from the proximal wire mesh header 533. In one embodiment, the retrieval mechanism 583 includes a retrieval loop 584. In one embodiment, the retrieval mechanism 583 is an extension of the wire comprising the proximal wire mesh header 533. In another embodiment, the retrieval mechanism 583 is a separate piece of wire that is fixedly attached to the proximal wire mesh header 533. The wire mesh structure 502 also includes a second opening at its distal end which is covered entirely by the coupled sleeve 562 and therefore not visible in FIG. 5B. In the pictured embodiment, the first opening 530 at the proximal end of the wire mesh structure 502 is larger than the second opening at its distal end leading into the sleeve 562. In one embodiment, the sleeve 562 is coupled to the wire mesh structure 502 via sutures.

The sleeve 562 includes a sleeve body 563 having a proximal end, a distal end and a lumen within. The sleeve body 563 is comprised of a flexible and compressible mesh material. The sleeve body 563 includes a first opening (not shown) at its proximal end and a second opening 576 at its distal end. An anti-migration component 592 is positioned at the junction of the wire mesh structure 502 with the sleeve 562. In the pictured embodiment, the anti-migration component 592 has the shape of a distally sloping disc and is comprised of a wire mesh with a silicone covering. In one embodiment, the anti-migration component 592 is fixedly attached to the lower portion 532 of the wire mesh structure 502 via sutures. The anti-migration component 592 prevents distal migration of the entirety of the device 500b through the pylorus and into the duodenum. Food travels through the device 500b in a similar manner as discussed with reference to FIG. 5A.

FIG. 5C is an illustration of a wire mesh structure 503 with retrieval hook 585, coupled sleeve 564, and anti-migration component 593 of an intragastric device 500c in a post-deployment configuration in accordance with another embodiment of the present specification, depicting the wire mesh structure 503 with the weave pattern as shown in FIG. 2D. The wire mesh structure 503 has a length l which is less than its width w. The wire mesh structure 503 comprises an upper portion 541, a lower portion 542, a proximal wire mesh header 543, and a first opening 540 at its proximal end. A retrieval hook 585 extends proximally from the proximal wire mesh header 543. In one embodiment, the retrieval hook 585 includes a retrieval loop 586. In one embodiment, the retrieval hook 585 is an extension of the wire comprising the proximal wire mesh header 543. In another embodiment, the retrieval hook 585 is a separate piece of wire that is fixedly attached to the proximal wire mesh header 543. The wire mesh structure 503 also includes a second opening at its distal end which is covered entirely by the coupled sleeve 564 and therefore not visible in FIG. 5C. In the pictured embodiment, the first opening 540 at the proximal end of the wire mesh structure 503 is smaller than the second opening at its distal end leading into the sleeve 564. In one embodiment, the sleeve 564 is coupled to the wire mesh structure 503 via sutures.

The sleeve 564 includes a sleeve body 365 having a proximal end, a distal end and a lumen within. The sleeve body 565 is comprised of a flexible and compressible mesh material. The sleeve body 565 includes a first opening (not shown) at its proximal end and a second opening 577 at its distal end. An anti-migration component 593 is positioned at the junction of the wire mesh structure 503 with the sleeve 564. In the pictured embodiment, the anti-migration component 593 has the shape of a distally sloping disc and is comprised of a wire mesh with a silicone covering. In one embodiment, the anti-migration component 593 is fixedly attached to the lower portion 542 of the wire mesh structure 503 via sutures. The anti-migration component 593 prevents distal migration of the entirety of the device 500c through the pylorus and into the duodenum. Food travels through the device 500c in a similar manner as discussed with reference to FIG. 5A.

FIG. 5D is an illustration of a wire mesh structure 504 with retrieval hook 587, coupled sleeve 566, and anti-migration component 594 of an intragastric device 500d in a post-deployment configuration in accordance with yet another embodiment of the present specification, depicting the wire mesh structure 504 with the weave pattern as shown in FIG. 2E. The wire mesh structure 504 has a length l which is less than its width w. The wire mesh structure 504 comprises an upper portion 551, a lower portion 552, a proximal wire mesh header 553, and a first opening 550 at its proximal end. A retrieval hook 587 extends proximally from the proximal wire mesh header 553. In one embodiment, the retrieval hook 587 includes a retrieval loop 588. In one embodiment, the retrieval hook 587 is an extension of the wire comprising the proximal wire mesh header 553. In another embodiment, the retrieval hook 587 is a separate piece of wire that is fixedly attached to the proximal wire mesh header 553. The wire mesh structure 504 also includes a second opening at its distal end which is covered entirely by the coupled sleeve 566 and therefore not visible in FIG. 5D. In the pictured embodiment, the first opening 550 at the proximal end of the wire mesh structure 504 is smaller than the second opening at its distal end leading into the sleeve 566. In one embodiment, the sleeve 566 is coupled to the wire mesh structure 504 via sutures.

The sleeve 566 includes a sleeve body 567 having a proximal end, a distal end and a lumen within. The sleeve body 567 is comprised of a flexible and compressible mesh material. The sleeve body 567 includes a first opening (not shown) at its proximal end and a second opening 578 at its distal end. An anti-migration component 594 is positioned at the junction of the wire mesh structure 504 with the sleeve 566. In the pictured embodiment, the anti-migration component 594 has the shape of a distally sloping disc and is comprised of a wire mesh with a silicone covering. In one embodiment, the anti-migration component 594 is fixedly attached to the lower portion 552 of the wire mesh structure 504 via sutures. The anti-migration component 594 prevents distal migration of the entirety of the device 500d through the pylorus and into the duodenum. Food travels through the device 500d in a similar manner as discussed with reference to FIG. 5A.

Figure 6K:
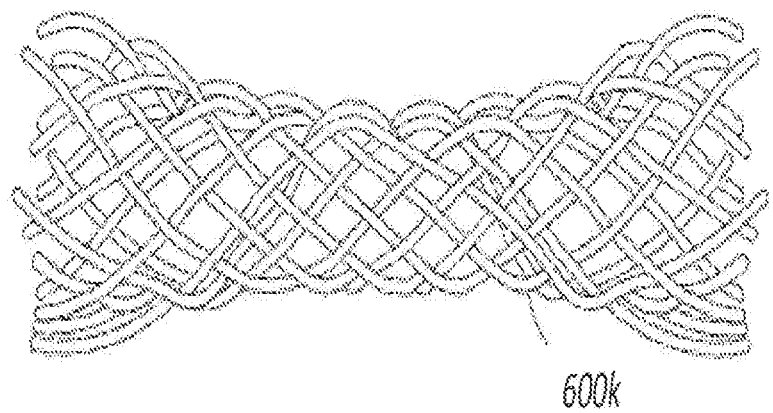
FIG. 6K is an illustration of one embodiment depicting a tenth exemplary configuration of the wire mesh structure.
Figure 6L:
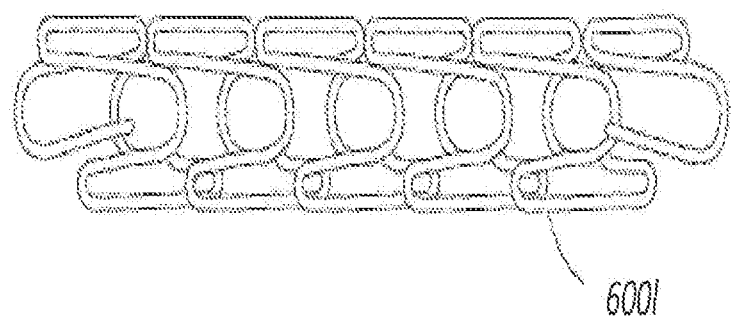
FIG. 6L is an illustration of one embodiment depicting an eleventh exemplary configuration of the wire mesh structure.
Figure 6M:
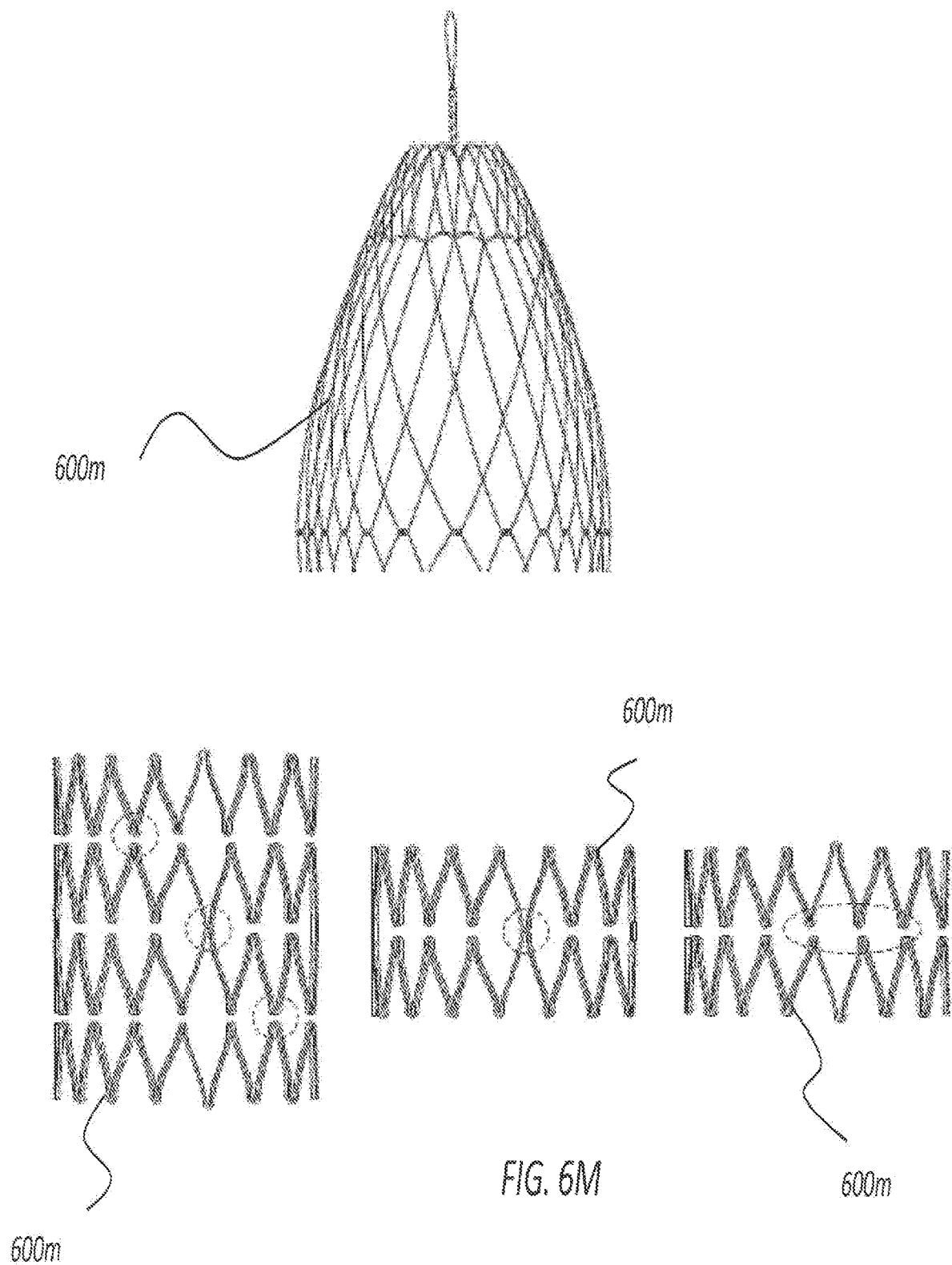
FIG. 6M is an illustration of a twelfth exemplary wire mesh weave pattern in accordance with one embodiment of the present specification.
Figure 6N:
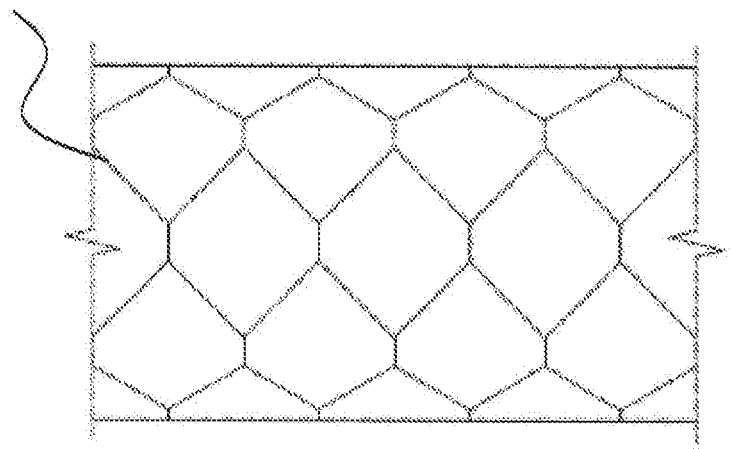
FIG. 6N is an illustration of a thirteenth exemplary wire mesh weave pattern in accordance with one embodiment of the present specification.
Figure 6O:
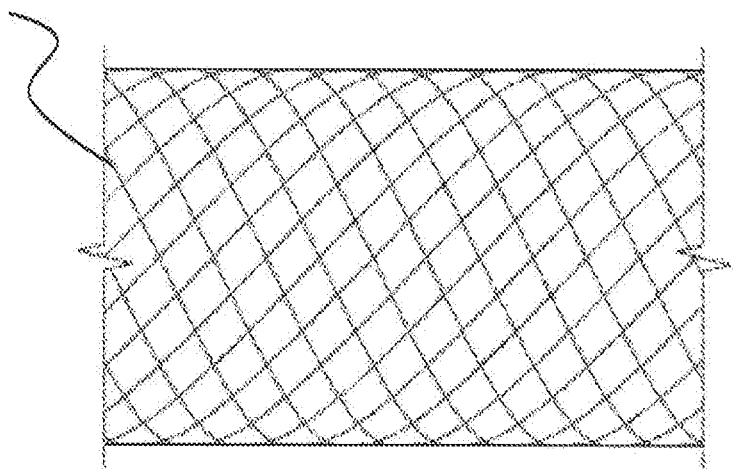
FIG. 6O is an illustration of a fourteenth exemplary wire mesh weave pattern in accordance with one embodiment of the present specification.
Figure 6P:
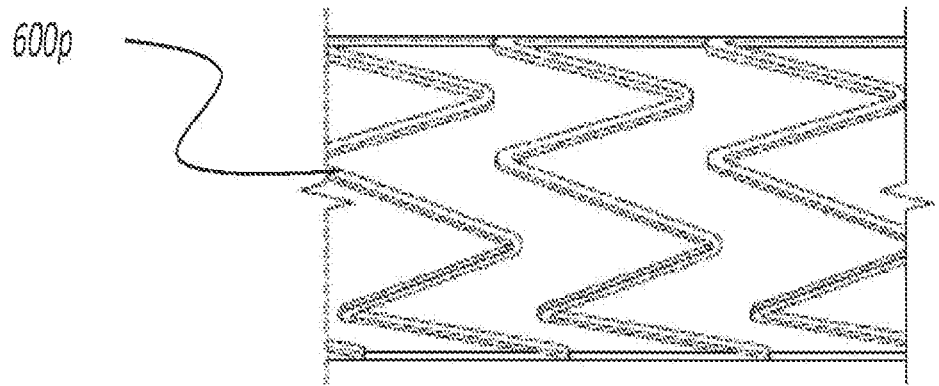
FIG. 6P is an illustration of a fifteenth exemplary wire mesh weave pattern in accordance with one embodiment of the present specification.
Figure 6Q:
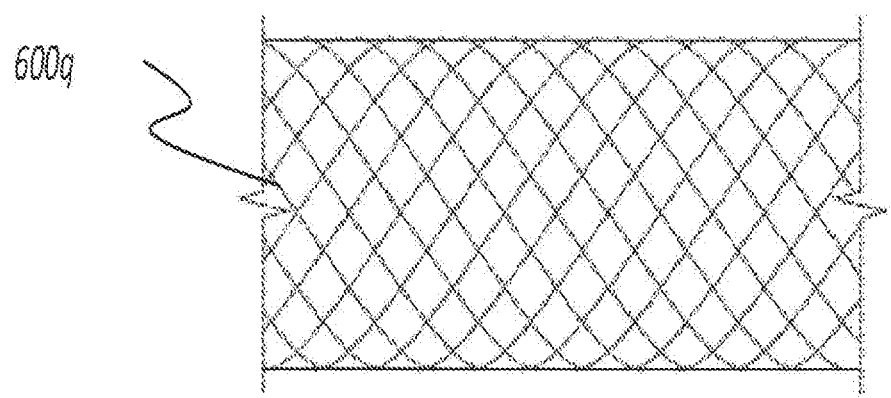
FIG. 6Q is an illustration of a sixteenth exemplary wire mesh weave pattern in accordance with one embodiment of the present specification.
Figure 6R:
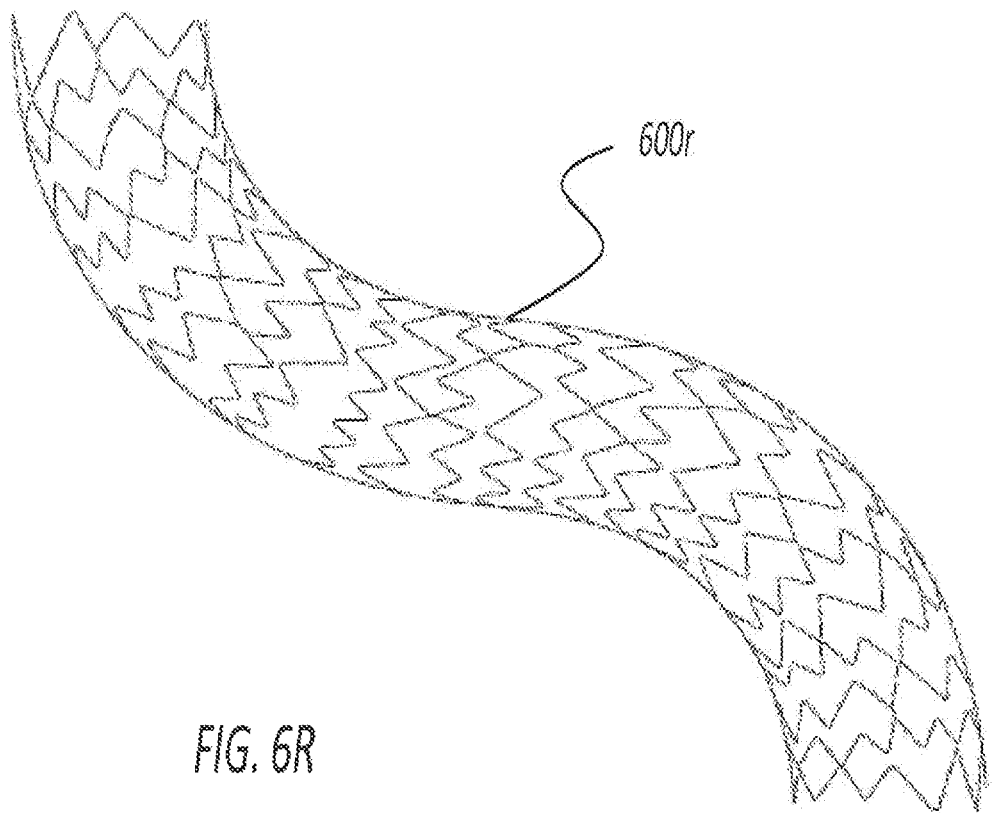
FIG. 6R is an illustration of a seventeenth exemplary wire mesh weave pattern in accordance with one embodiment of the present specification.
Figure 6S:
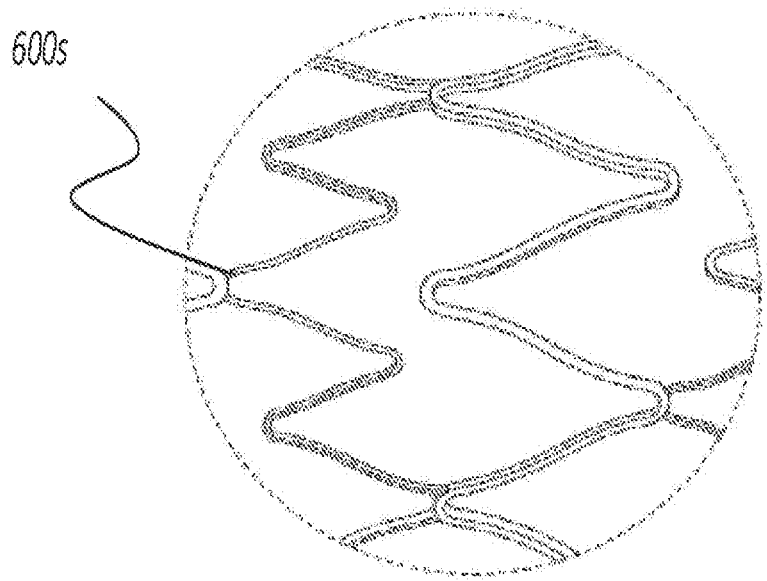
FIG. 6S is an illustration of an eighteenth exemplary wire mesh weave pattern in accordance with one embodiment of the present specification.

FIGS. 6A through 6S depict various exemplary configurations of wire mesh weave patterns, 600a, 600b, 600c, 600d, 600e, 600f, 600g, 600h, 600i, 600j, 600k, 600l, 600m, 600n, 600o, 600p, 600q, 600r, and 600s comprised within the intragastric device. As shown in the Figures, the mesh weave can have a plurality of different configurations, with varying degrees of density between the wires components and varying sizes of holes defining the mesh structure. The spatial density may be defined in a plurality of dimensions, including along lengths and spaces a, b, c, d, e, f, g, h, i, j, and k as seen in FIGS. 6A through 6C. Any of the depicted weave patterns can be used for the wire mesh structure of an intragastric device of the present specification. Those skilled in the art would recognize that the wire mesh structure can have any number of different weave patterns that enable it to be compressed for delivery and retrieval and provide it with adequate radial strength once deployed such that it will not be passed through the pylorus as a result of gastric contractions.

Figure 7A:
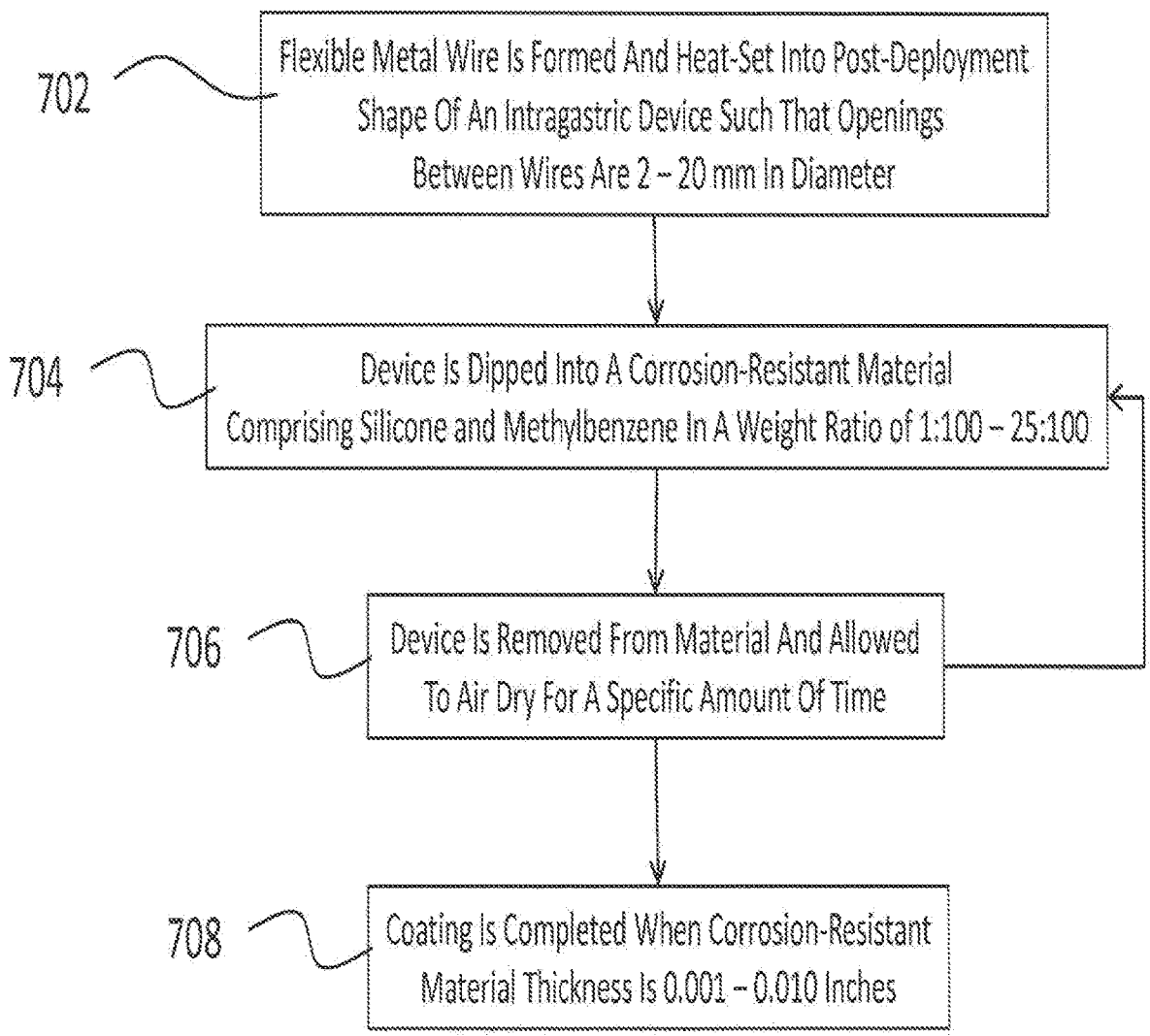
FIG. 7A is a flow chart illustrating the steps involved during the manufacture of an intragastric device having a corrosion-resistant coating, in accordance with one embodiment of the present specification.

FIG. 7 is a flow chart illustrating the steps involved during the manufacture of an intragastric device having a corrosion-resistant coating, in accordance with one embodiment of the present specification. At step 702, a flexible metal wire, such as a shape memory metal wire, is manipulated, formed, and heat-set into a desired post-deployment shape for an intragastric device in accordance with the devices disclosed in the present specification. Then, at step 704, the device is dipped in its entirety into a corrosion-resistant material, silicone, comprising silicone and methylbenzene in a weight ratio range of 1:100-25:100. The material has been heated that it is in a liquid state. The device is then removed from the liquid material at step 706. Some of the material sticks to the wires and is allowed to air dry for a specific amount of time, becoming a solid coating over the wires of the device. Steps 704 and 706 are repeated as the device is dipped into the material multiple times, followed by air drying after each dip, until the coating reaches a desired thickness. At step 708, coating is completed once the thickness of the corrosion-resistant material is in a range of 0.001-0.010 inches.

Figure 7B:
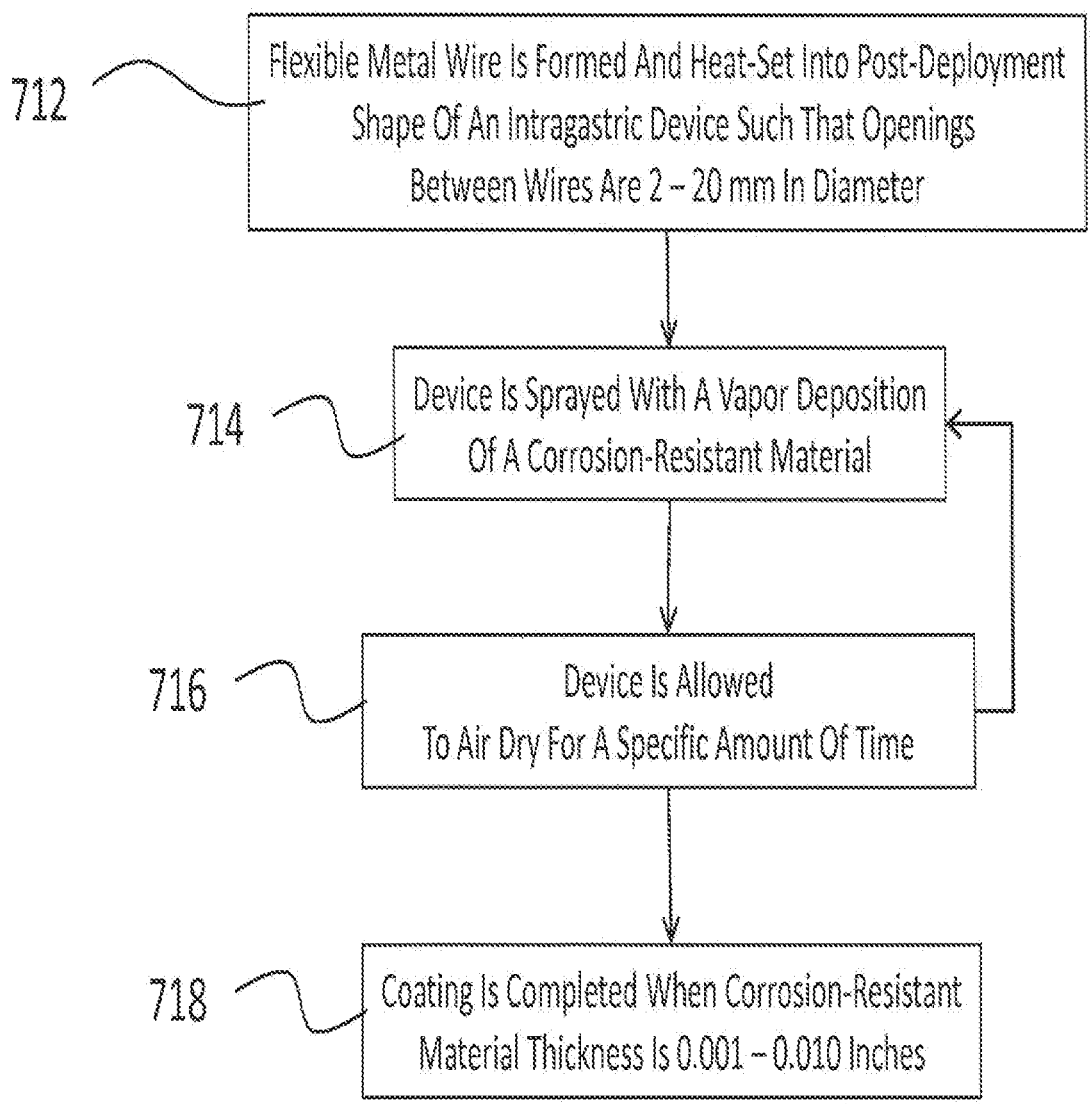
FIG. 7B is a flow chart illustrating the steps involved during the manufacture of an intragastric device having a corrosion-resistant coating, in accordance with another embodiment of the present specification.

FIG. 7B is a flow chart illustrating the steps involved during the manufacture of an intragastric device having a corrosion-resistant coating, in accordance with another embodiment of the present specification. At step 712, a flexible metal wire, such as a shape memory metal wire, is manipulated, formed, and heat-set into a desired post-deployment shape for an intragastric device in accordance with the devices disclosed in the present specification. Then, at step 714, the device is sprayed with a vapor deposition of a corrosion-resistant material. In one embodiment, the corrosion-resistant material is parylene. The device is allowed to air dry for a specific amount of time such that the vapor deposition hardens into a solid form at step 716. Steps 714 and 716 are repeated multiple times until the desired coating thickness is achieved. Coating is completed at step 718 once the corrosion-material thickness is in a range of 0.001-0.010 inches.

Figure 7C:
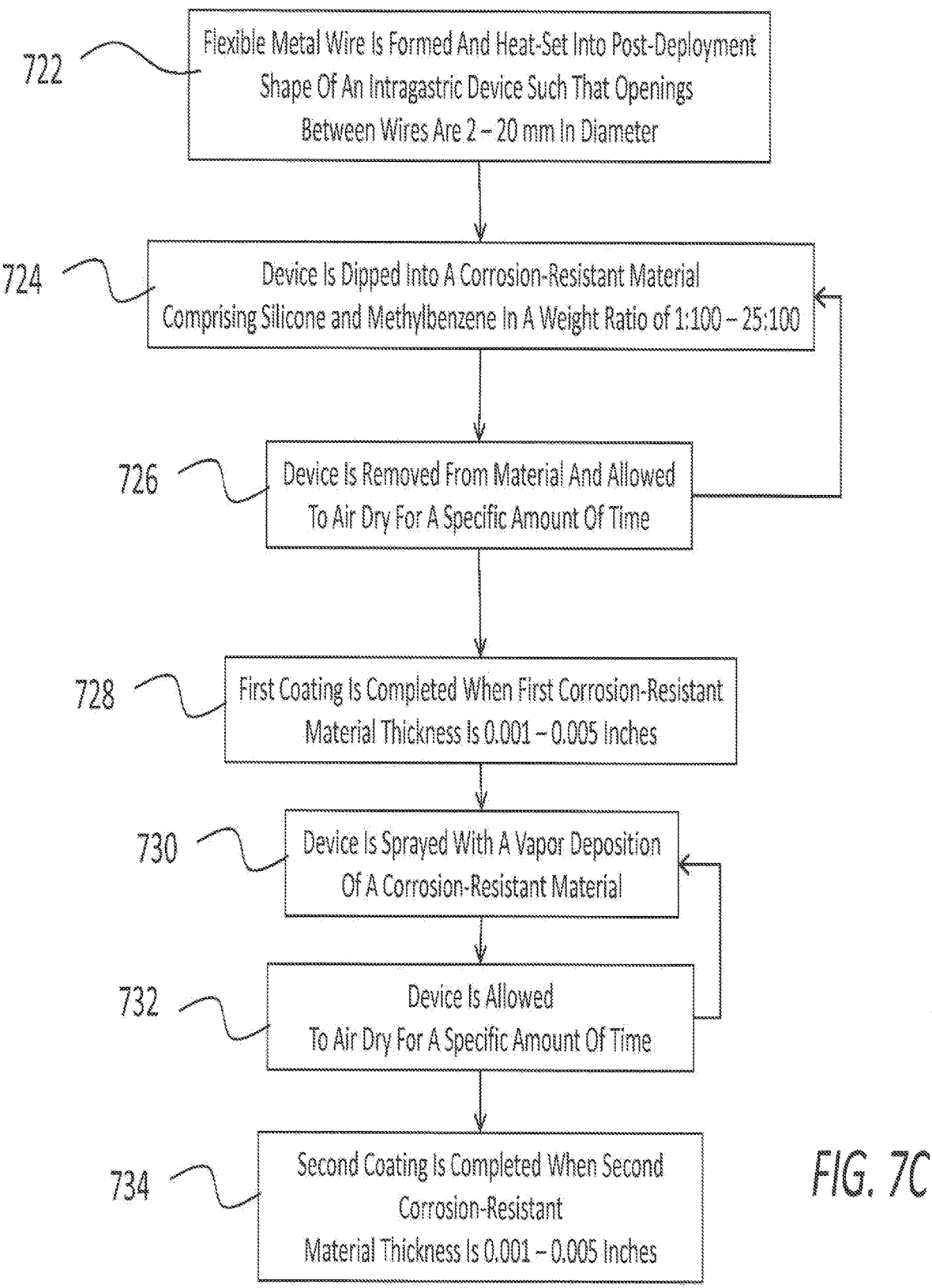
FIG. 7C is a flow chart illustrating the steps involved during the manufacture of an intragastric device having a corrosion-resistant coating, in accordance with yet another embodiment of the present specification.

FIG. 7C is a flow chart illustrating the steps involved during the manufacture of an intragastric device having a corrosion-resistant coating, in accordance with yet another embodiment of the present specification. The method comprises applying a first coating of a first corrosion-resistant material and then applying a second coating of a second corrosion-resistant material to provide additional protection. At step 722, a flexible metal wire, such as a shape memory metal wire, is manipulated, formed, and heat-set into a desired post-deployment shape for an intragastric device in accordance with the devices disclosed in the present specification. Then, at step 724, the device is dipped in its entirety into a first corrosion-resistant material, silicone, comprising silicone and methylbenzene in a weight ratio range of 1:100-25:100. The material has been heated that it is in a liquid state. The device is then removed from the liquid material at step 726. Some of the material sticks to the wires and is allowed to air dry for a specific amount of time, becoming a solid coating over the wires of the device. Steps 724 and 726 are repeated as the device is dipped into the material multiple times, followed by air drying after each dip, until the coating reaches a desired thickness. At step 728, the first coating is completed once the thickness of the first corrosion-resistant material is in a range of 0.001-0.005 inches. At step 730, the device is then sprayed with a vapor deposition of a second corrosion-resistant material. In one embodiment, the second corrosion-resistant material is parylene. The device is allowed to air dry for a specific amount of time such that the vapor deposition hardens into a solid form at step 732. Steps 730 and 732 are repeated multiple times until the desired coating thickness is achieved. The second coating is completed at step 734 once the second corrosion-material thickness is in a range of 0.001-0.005 inches.

Figure 8:
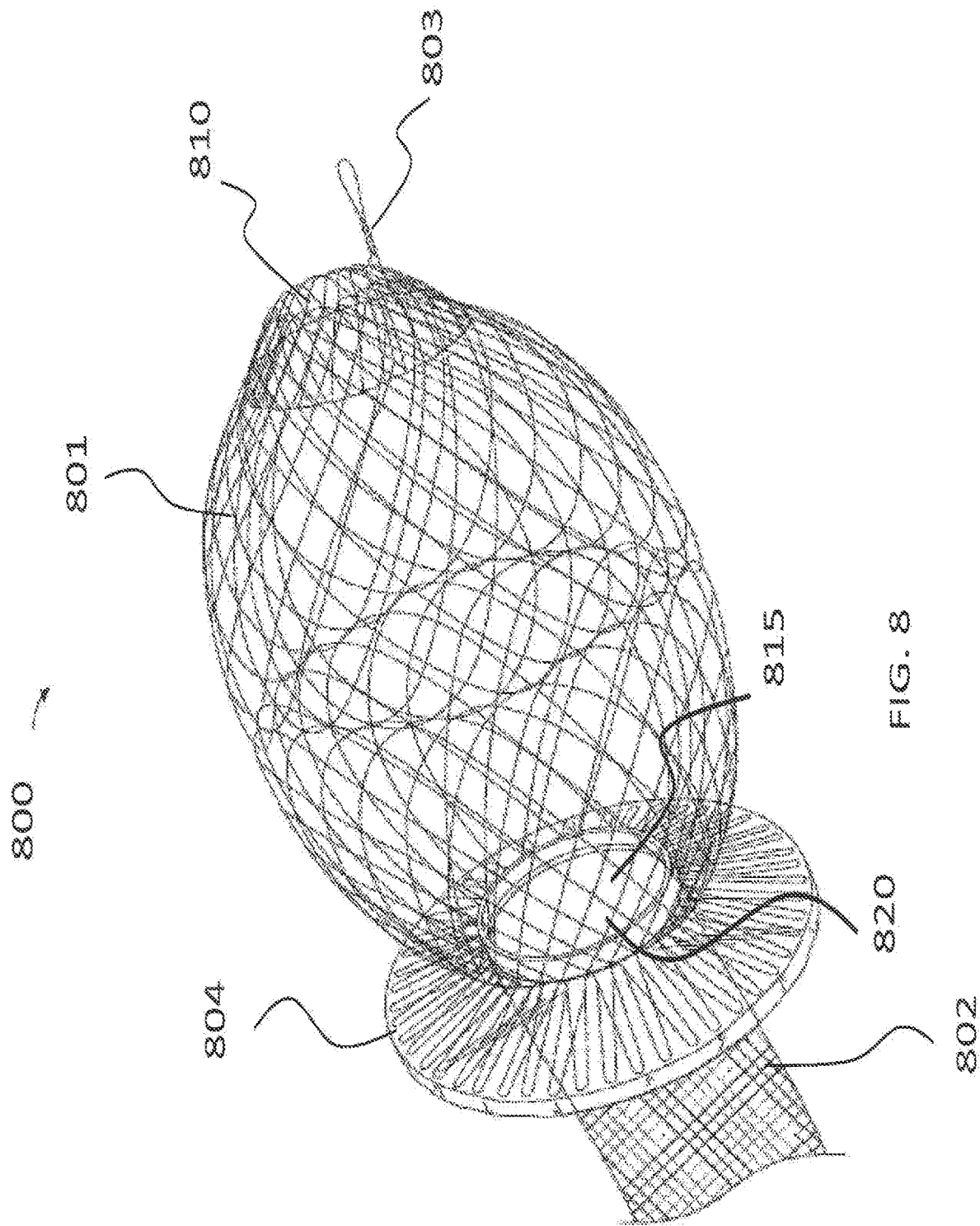
FIG. 8 is an oblique side view illustration of the proximal end of an intragastric device in a post-deployment configuration in accordance with one embodiment of the present specification, depicting first and second openings in the proximal and distal ends, respectively of a wire mesh structure of the device.
Figure 9:
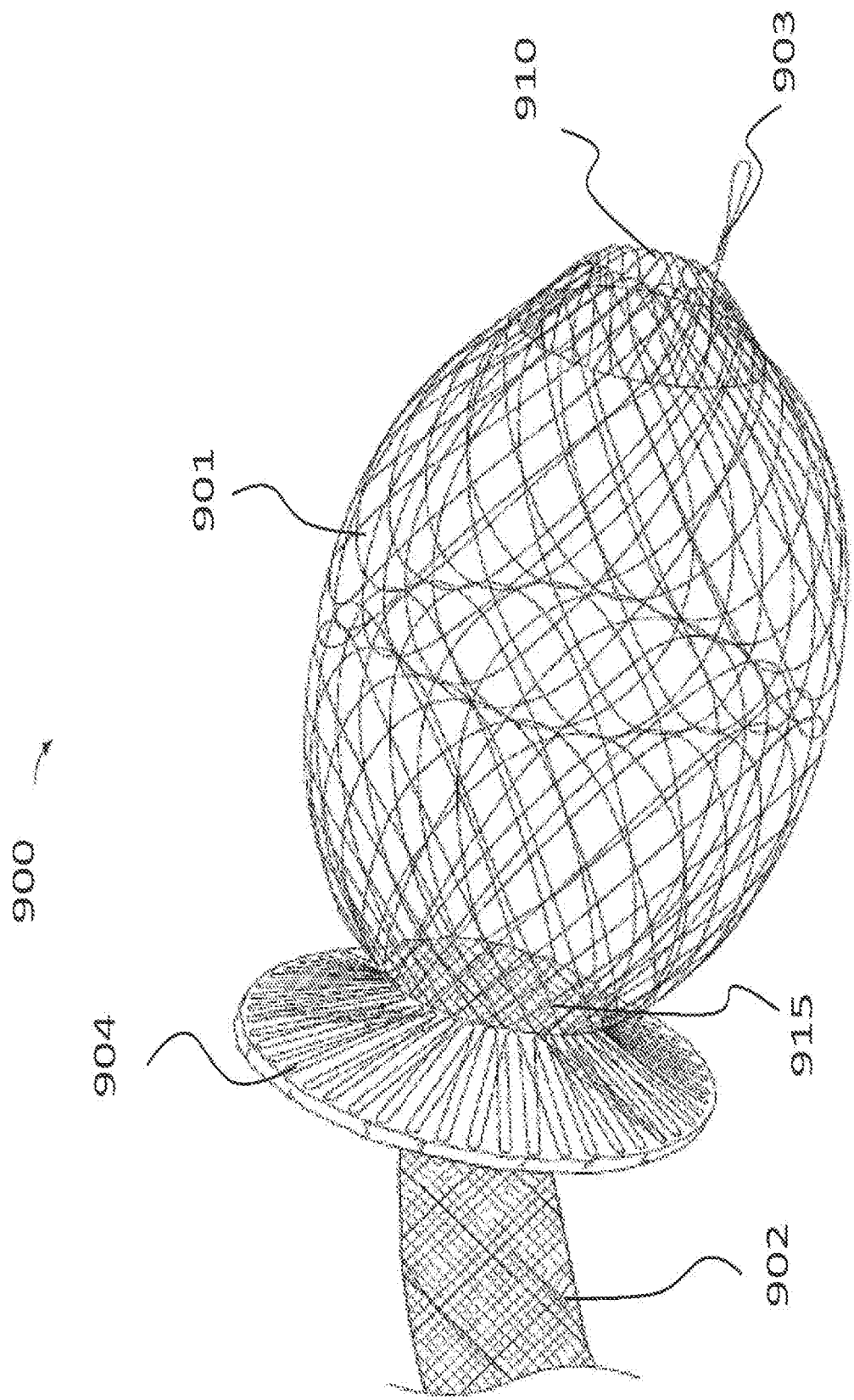
FIG. 9 is another oblique side view illustration of the proximal end of an intragastric device in a post-deployment configuration in accordance with one embodiment of the present specification.

FIGS. 8 and 9 are oblique side view illustrations of the proximal end of an intragastric device 800, 900 in a post-deployment configuration in accordance with one embodiment of the present specification, depicting first 810, 910 and second 815, 915 openings in the proximal and distal ends, respectively of a wire mesh structure 801, 901 of the device 800, 900. Devices 800, 900 each further include a retrieval hook 803, 903, coupled sleeve 802, 902, and anti-migration disc 804, 904. As can be seen in FIGS. 8 and 9, the first openings 810, 910 of both devices 800, 900 are smaller than the second openings 815, 915 of the devices 800, 900. Referring to FIG. 8, a first sleeve opening 820 is depicted at the proximal end of the sleeve 802 in fluid communication with the second opening 815 of the wire mesh structure 801. The sleeve 802 also includes a second opening (not shown) at or proximate its distal end.

Figure 10:
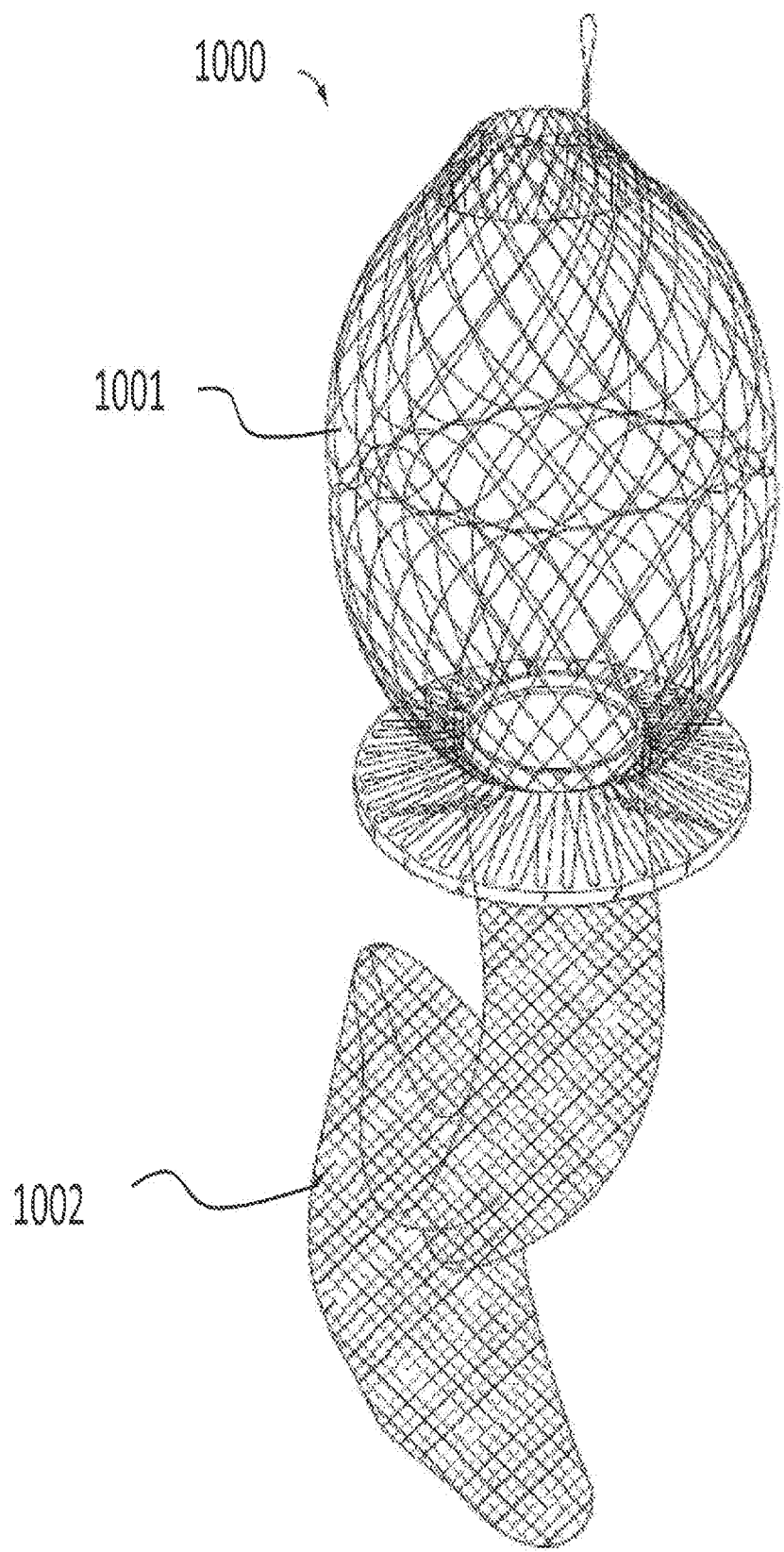
FIG. 10 is an illustration of one embodiment of an intragastric device of the present specification in a post-deployment configuration, depicting a sleeve component as it would conform to the shape of the proximal small intestine.

FIG. 10 is an illustration of one embodiment of an intragastric device 1000 of the present specification in a post-deployment configuration, depicting a sleeve component 1002 as it would conform to the shape of the proximal small intestine. In the pictured embodiment, the sleeve 1002 is comprised of a flexible mesh material that allows it to bend as it traverses the small intestine. The mesh material also allows the sleeve 1002 to be compressed by the contractions of the small intestine and re-expand as it fills with food that enters the sleeve 1002 from the coupled wire mesh structure 1001. The sleeve 1002 includes an elongate tube having a proximal end, a distal end, and a lumen within. The proximal end of the sleeve 1002 is attached to the distal end of the wire mesh structure 1001 such that an opening in the distal end of the wire mesh structure 1001 is in fluid communication with the lumen of the sleeve 1002. Food is sequestered within the wire mesh structure 1001, enters the sleeve 1002 via the opening in the distal end of the wire mesh structure 1001, and passes through the sleeve 1002 and into the proximal jejunum, thus bypassing the stomach and duodenum.

Figure 11:
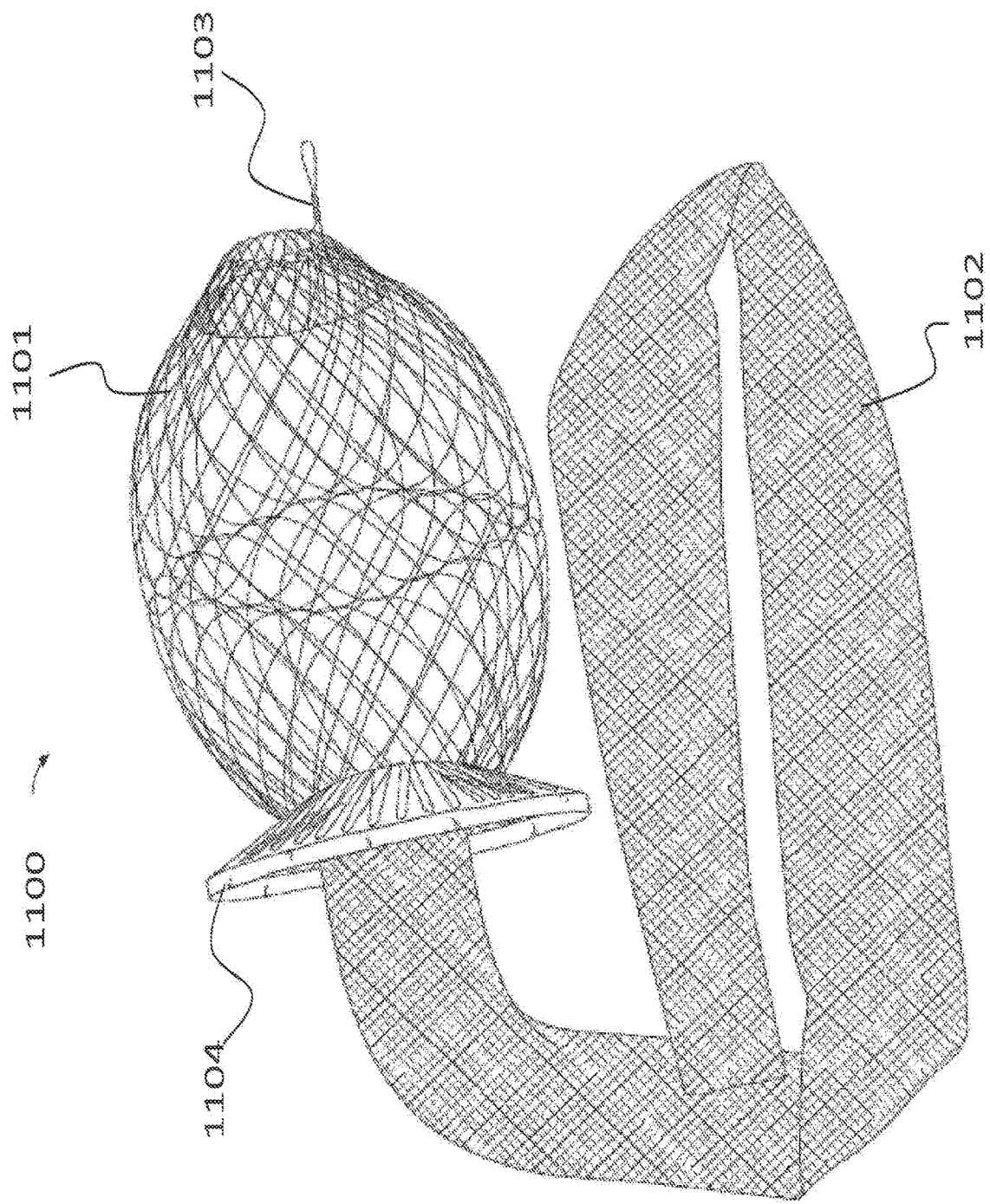
FIG. 11 is a side view illustration of one embodiment of an intragastric device of the present specification in a post-deployment configuration, depicting a wire mesh structure, retrieval hook, coupled sleeve, and distally sloping anti-migration disc.

FIG. 11 is a side view illustration of one embodiment of an intragastric device 1100 of the present specification in a post-deployment configuration, depicting a wire mesh structure 1101, retrieval hook 1103, coupled sleeve 1102, and distally sloping anti-migration disc 1104. The wire mesh structure 1101 is substantially oval shaped and functions to occupy volume in a patient's stomach. The anti-migration disc 1104 prevents slippage of the wire mesh portion 1101 of the device 1100 through the pylorus. Making the disc 1104 have a distally sloping shape allows it to function as an upside-down funnel, helping to keep the wire mesh structure 1101 out of the pylorus. The sleeve 1102 transmits food from the wire mesh structure 1101 past the pylorus and duodenum.

Figure 12:
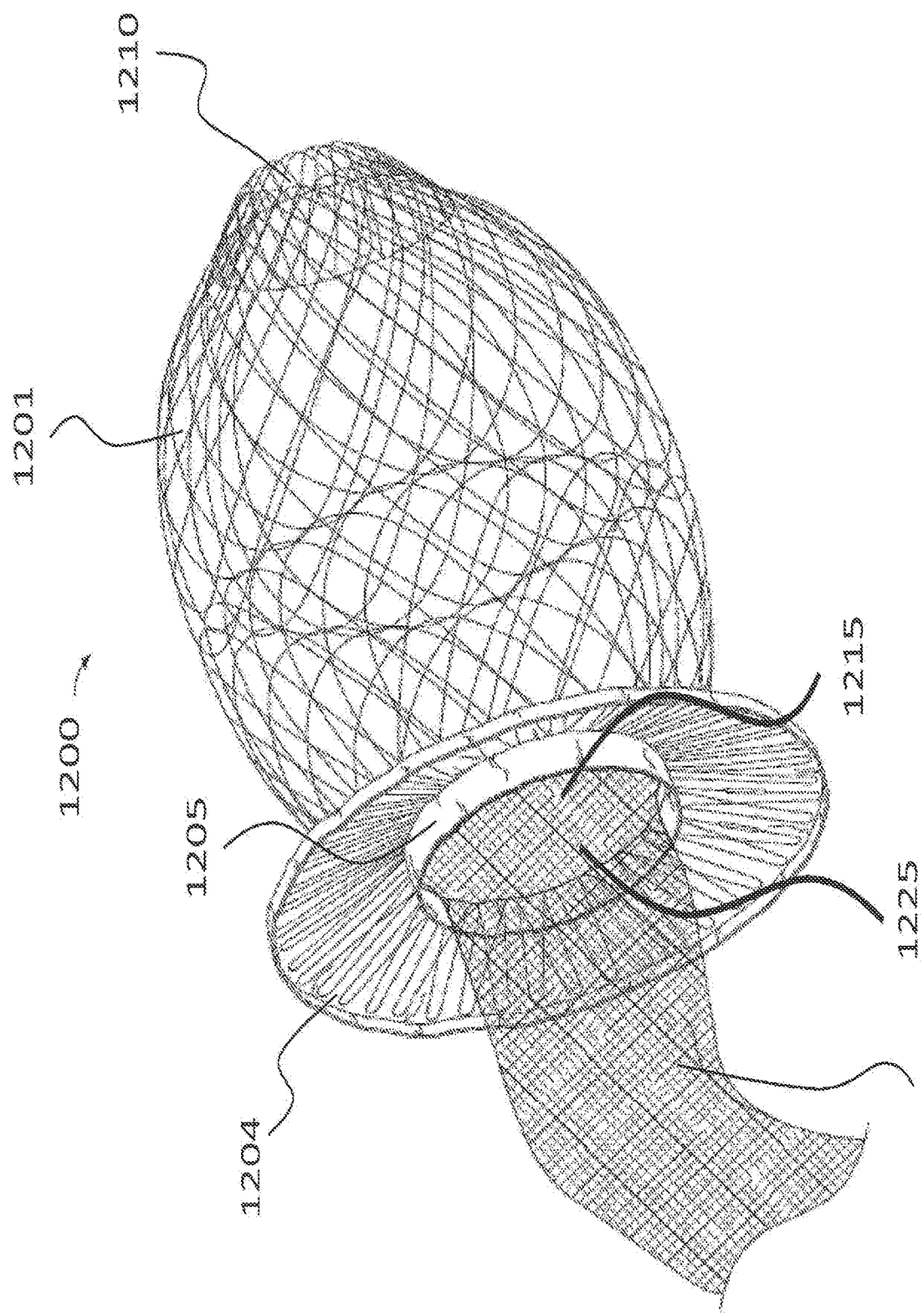
FIG. 12 is an oblique side view illustration of one embodiment of an intragastric device of the present specification in a post-deployment configuration, depicting a second opening at the distal end of a wire mesh structure and the underside of a distally sloping anti-migration disc.

FIG. 12 is an oblique side view illustration of one embodiment of an intragastric device 1200 of the present specification in a post-deployment configuration, depicting a second opening 1215 at the distal end of a wire mesh structure 1201 and the underside of a distally sloping anti-migration disc 1204. The wire mesh structure also includes a first opening 1210 at its proximal end. The second opening 1215 at the distal end of the wire mesh structure 1201 is in fluid communication with a first opening 1220 of a coupled sleeve 1202. In the pictured embodiment, the disc 1204 includes a collar 1205 that fits about the junction of the wire mesh structure 1201 with the sleeve 1202.

Figure 13A:
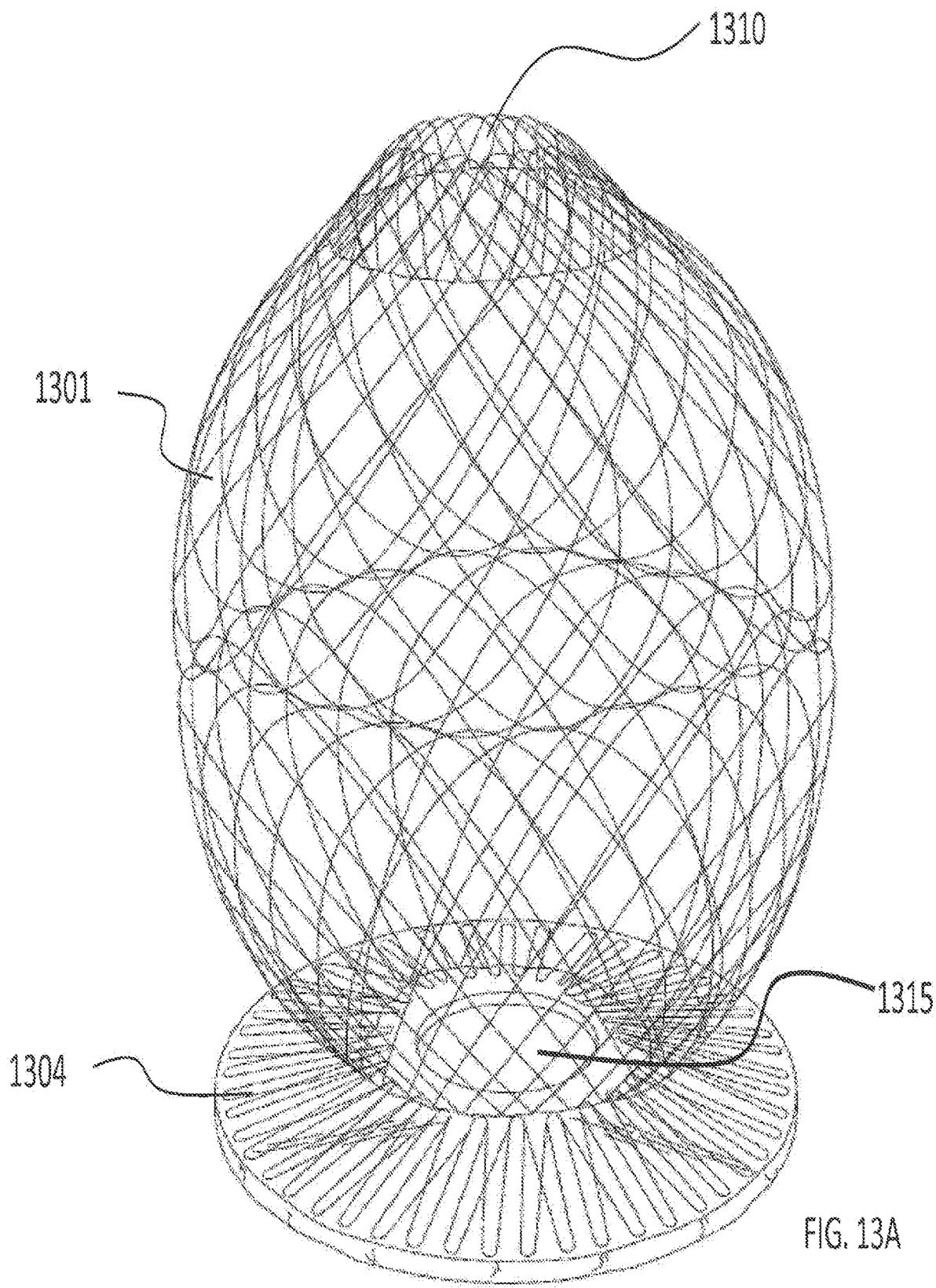
FIG. 13A is an illustration of a wire mesh structure in a post-deployment configuration with a distally sloping anti-migration disc attached to its distal end, in accordance with one embodiment of the present specification.
Figure 13B:
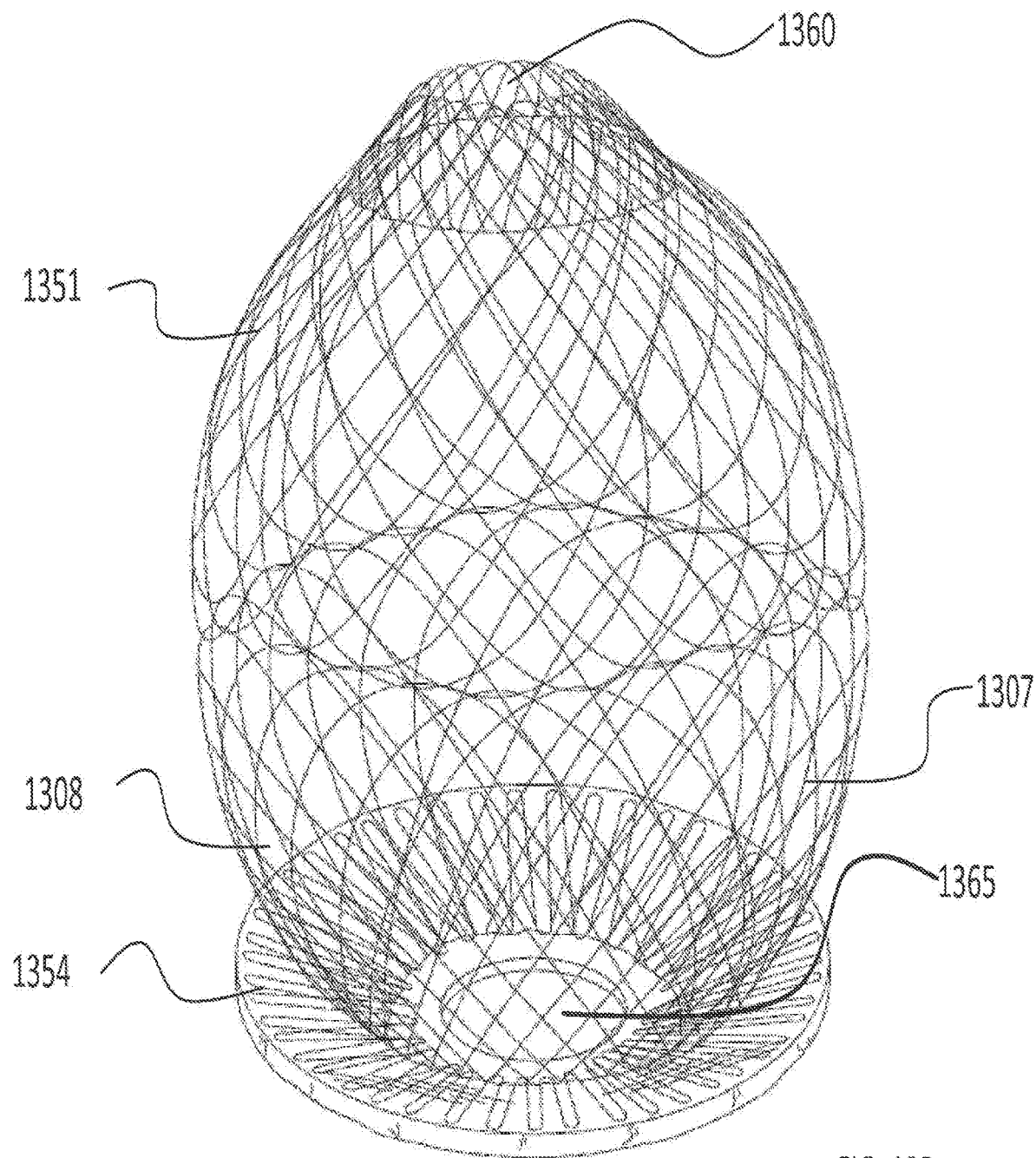
FIG. 13B is an illustration of a wire mesh structure in a post-deployment configuration with a proximally sloping anti-migration disc attached to its distal end, in accordance with one embodiment of the present specification.

FIG. 13A is an illustration of a wire mesh structure 1301 in a post-deployment configuration with a distally sloping anti-migration disc 1304 attached to its distal end, in accordance with one embodiment of the present specification. A first opening 1310 at the proximal end of the wire mesh structure 1301 and a second opening 1315 at the distal end of the wire mesh structure 1301 are also visible. FIG. 13B is an illustration of a wire mesh structure 1351 in a post-deployment configuration with a proximally sloping anti-migration disc 1354 attached to its distal end, in accordance with one embodiment of the present specification. A first opening 1360 at the proximal end of the wire mesh structure 1351 and a second opening 1365 at the distal end of the wire mesh structure 1351 are also visible. In one embodiment, the proximally sloping anti-migration disc 1354 helps direct food that has passed the first opening 1360 through the openings 1355 between the wires 1357 and into the wire mesh structure 1351. In various embodiments, the attachment of the disc to the mesh could allow for the same disc to assume different sloping configurations.

Figure 14:
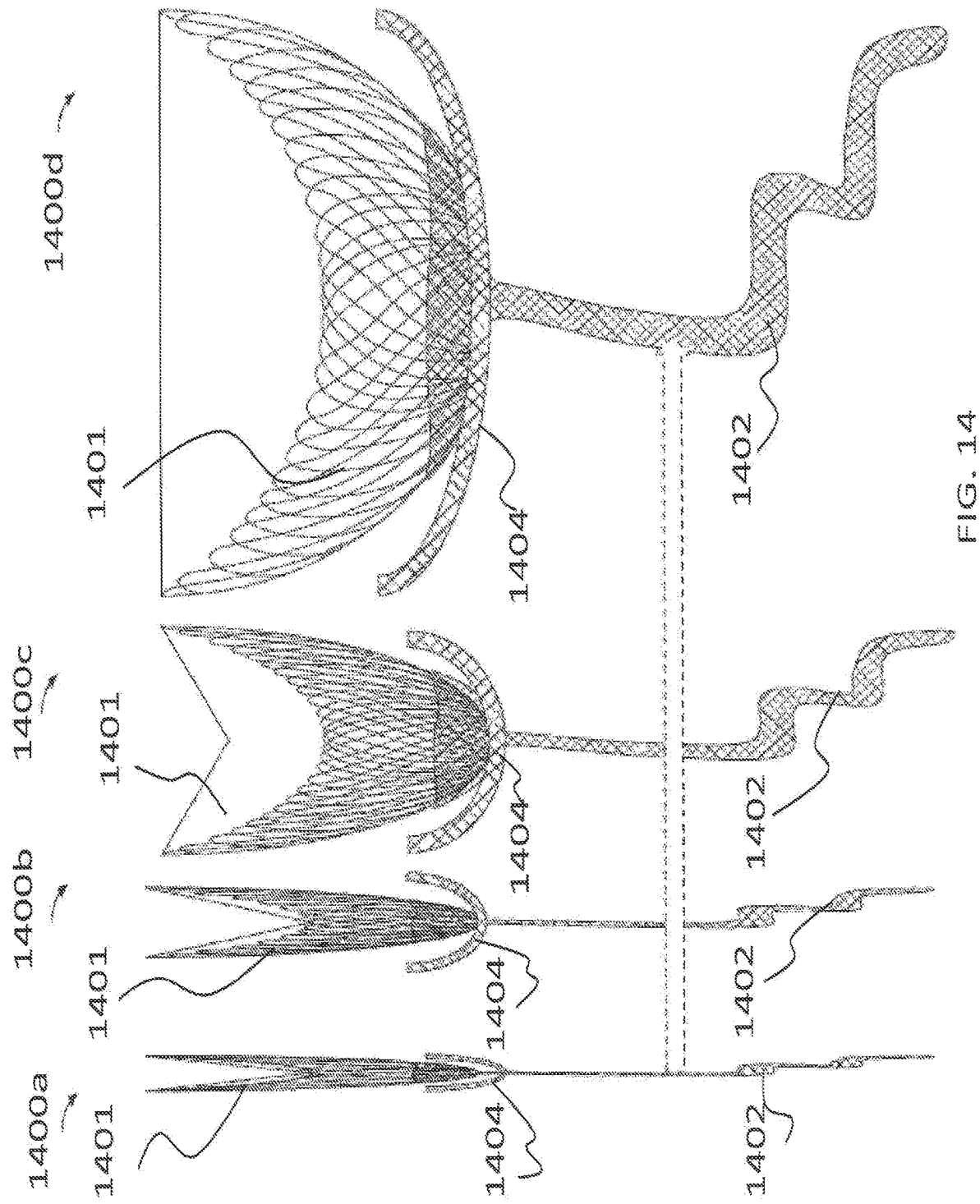
FIG. 14 is an illustration depicting the expansion of an intragastric device having a half sphere wire mesh structure, anti-migration component, and sleeve during deployment, in accordance with one embodiment of the present specification.

FIG. 14 is an illustration depicting the expansion of an intragastric device having a half sphere wire mesh structure 1401, anti-migration component 1404, and sleeve 1402 during deployment, in accordance with one embodiment of the present specification. For implantation, the device is compressible into an elongate, narrow compressed configuration 1400a. The narrow shape of the device in this configuration allows for delivery of the device through the working channel of an endoscope or through the esophagus over a guidewire or an endoscope or through an overtube. Once the device is passed beyond the distal end of the endoscope channel, it begins to passively expand 1400b, getting larger 1400c until it reaches its fully deployed configuration 1400d.

Figure 15A:
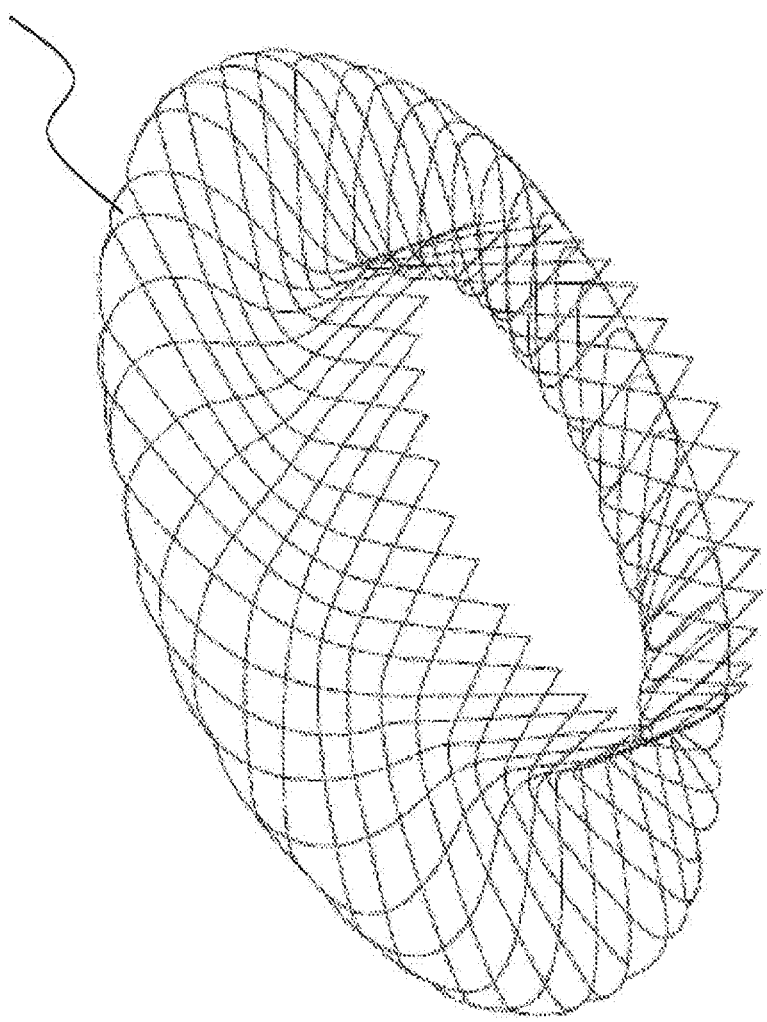
FIG. 15A is an illustration of a first exemplary anti-migration component shape in a post-deployment configuration, in accordance with one embodiment of the present specification.

FIG. 15A is an illustration of a first exemplary anti-migration component 1501 shape in a post-deployment configuration, in accordance with one embodiment of the present specification. In the pictured embodiment, the anti-migration component 1501 has a half-bumper shape.

Figure 15B:
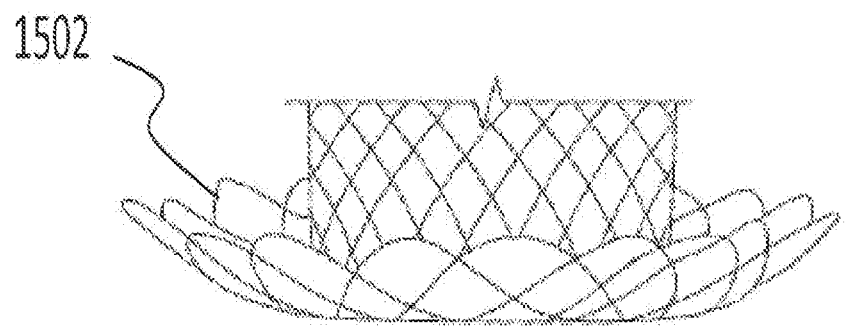
FIG. 15B is an illustration of a second exemplary anti-migration component shape in a post-deployment configuration, in accordance with one embodiment of the present specification.

FIG. 15B is an illustration of a second exemplary anti-migration component 1502 shape in a post-deployment configuration, in accordance with one embodiment of the present specification. In the pictured embodiment, the anti-migration component 1502 has a proximally extending flower shape.

Figure 15C:
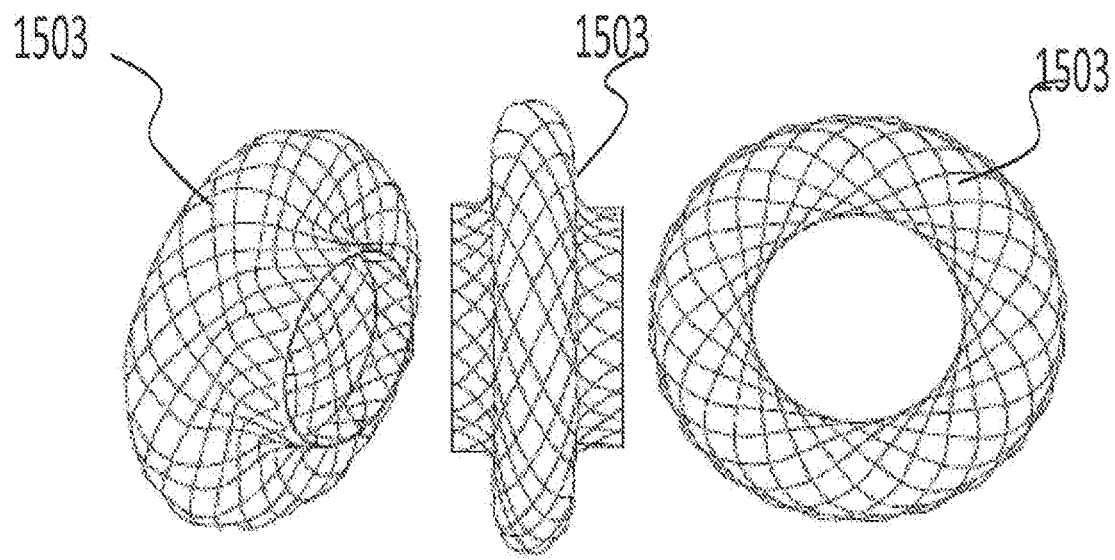
FIG. 15C is an illustration of a third exemplary anti-migration component shape in a post-deployment configuration, in accordance with one embodiment of the present specification.

FIG. 15C is an illustration of a third exemplary anti-migration component 1503 shape in a post-deployment configuration, in accordance with one embodiment of the present specification. In the pictured embodiment, the anti-migration component 1503 has a full-bumper shape.

Figure 15D:
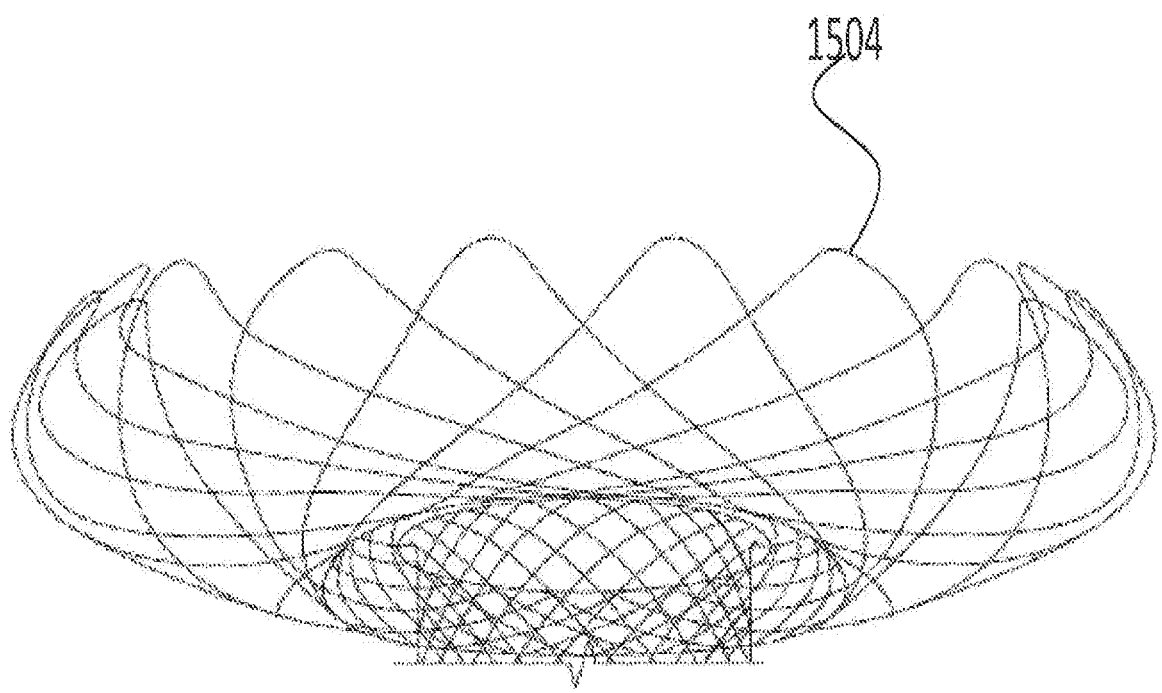
FIG. 15D is an illustration of a fourth exemplary anti-migration component shape in a post-deployment configuration, in accordance with one embodiment of the present specification.

FIG. 15D is an illustration of a fourth exemplary anti-migration component 1504 shape in a post-deployment configuration, in accordance with one embodiment of the present specification. In the pictured embodiment, the anti-migration component 1504 has a saucer shape.

Figure 15E:
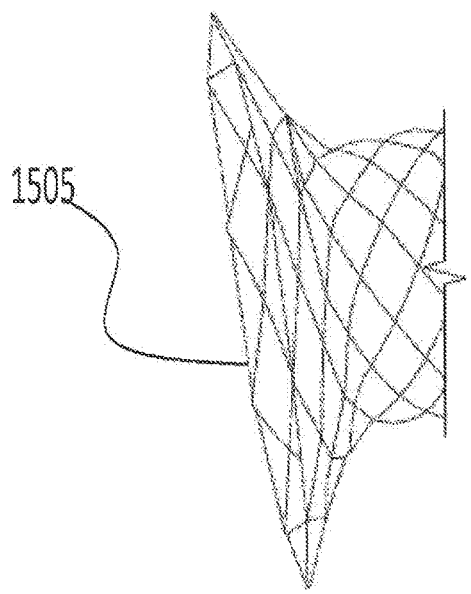
FIG. 15E is an illustration of a fifth exemplary anti-migration component shape in a post-deployment configuration, in accordance with one embodiment of the present specification.

FIG. 15E is an illustration of a fifth exemplary anti-migration component 1505 shape in a post-deployment configuration, in accordance with one embodiment of the present specification. In the pictured embodiment, the anti-migration component 1505 has a funnel shape.

Figure 15F:
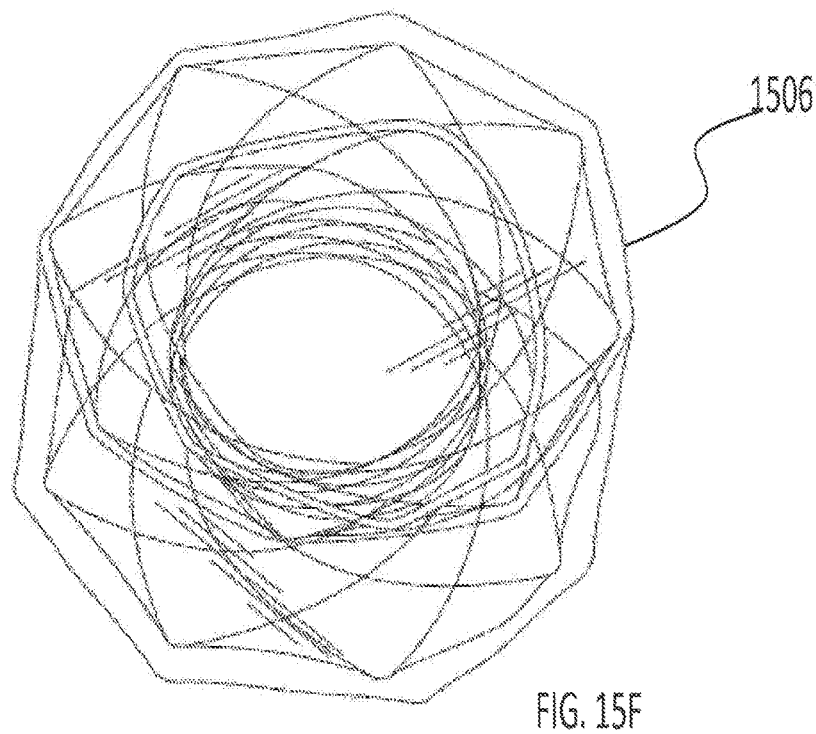
FIG. 15F is an illustration of a sixth exemplary anti-migration component shape in a post-deployment configuration, in accordance with one embodiment of the present specification.

FIG. 15F is an illustration of a sixth exemplary anti-migration component 1506 shape in a post-deployment configuration, in accordance with one embodiment of the present specification. In the pictured embodiment, the anti-migration component 1506 has a funnel shape.

Figure 15G:
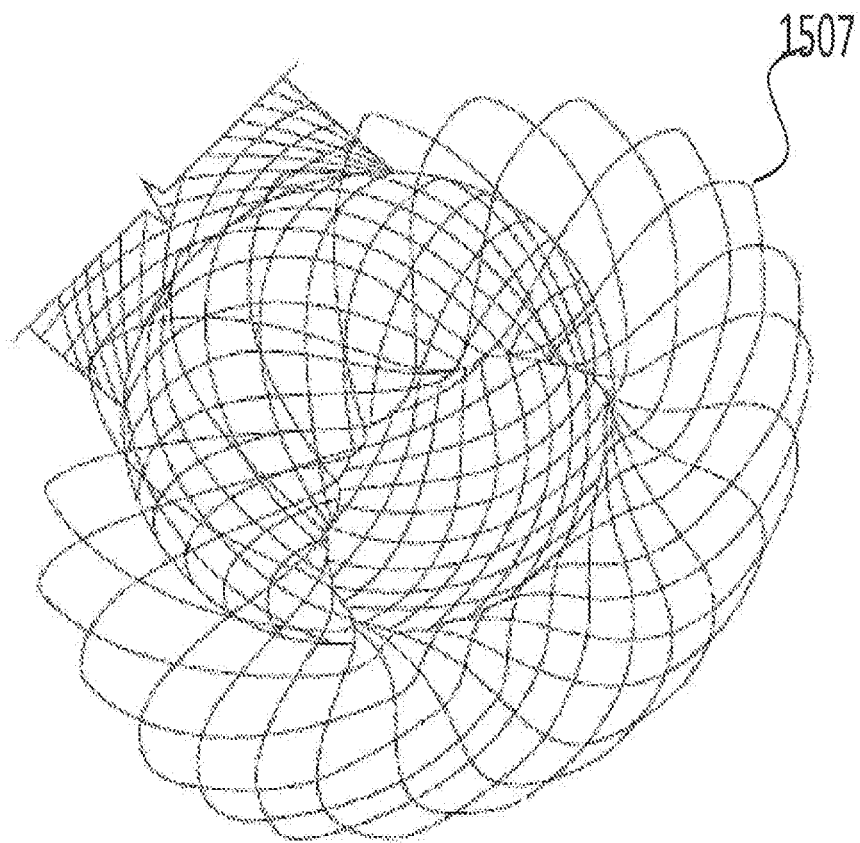
FIG. 15G is an illustration of a seventh exemplary anti-migration component shape in a post-deployment configuration, in accordance with one embodiment of the present specification.

FIG. 15G is an illustration of a seventh exemplary anti-migration component 1507 shape in a post-deployment configuration, in accordance with one embodiment of the present specification. In the pictured embodiment, the anti-migration component 1507 has a flower shape.

Figure 15H:
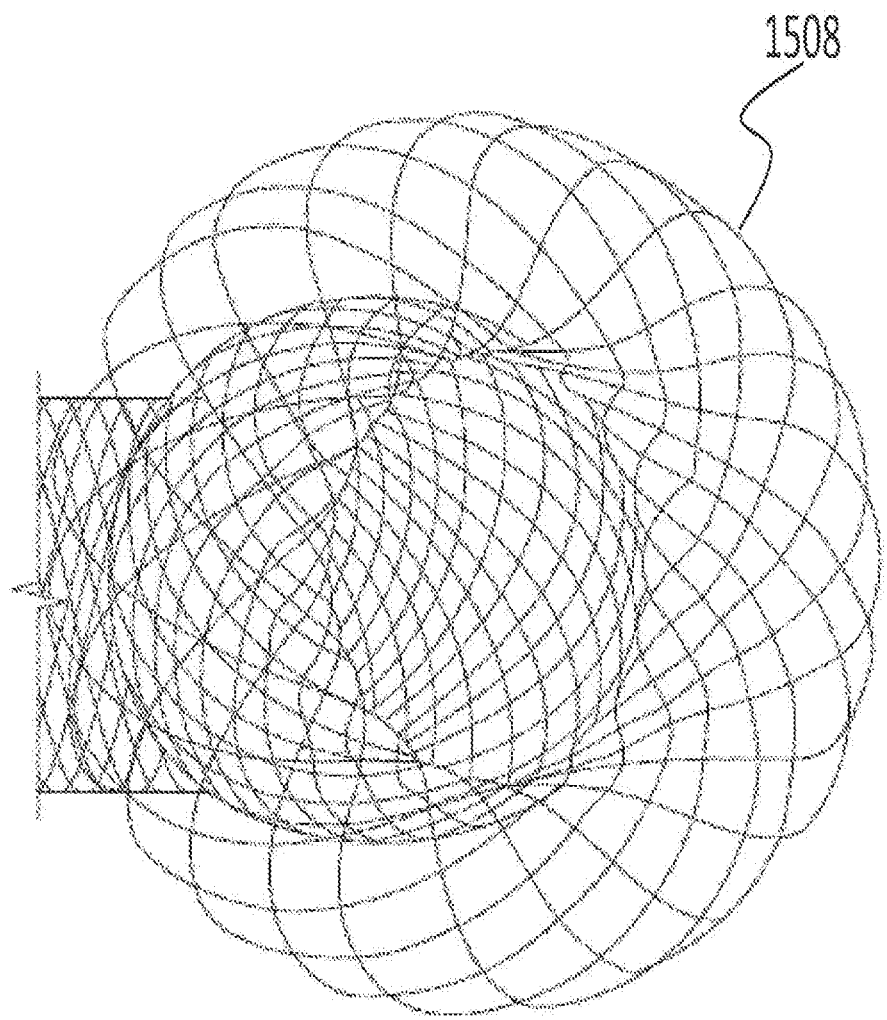
FIG. 15H is an illustration of an eighth exemplary anti-migration component shape in a post-deployment configuration, in accordance with one embodiment of the present specification.

FIG. 15H is an illustration of an eighth exemplary anti-migration component 1508 shape in a post-deployment configuration, in accordance with one embodiment of the present specification. In the pictured embodiment, the anti-migration component 1508 has a circular shape.

Figure 16:
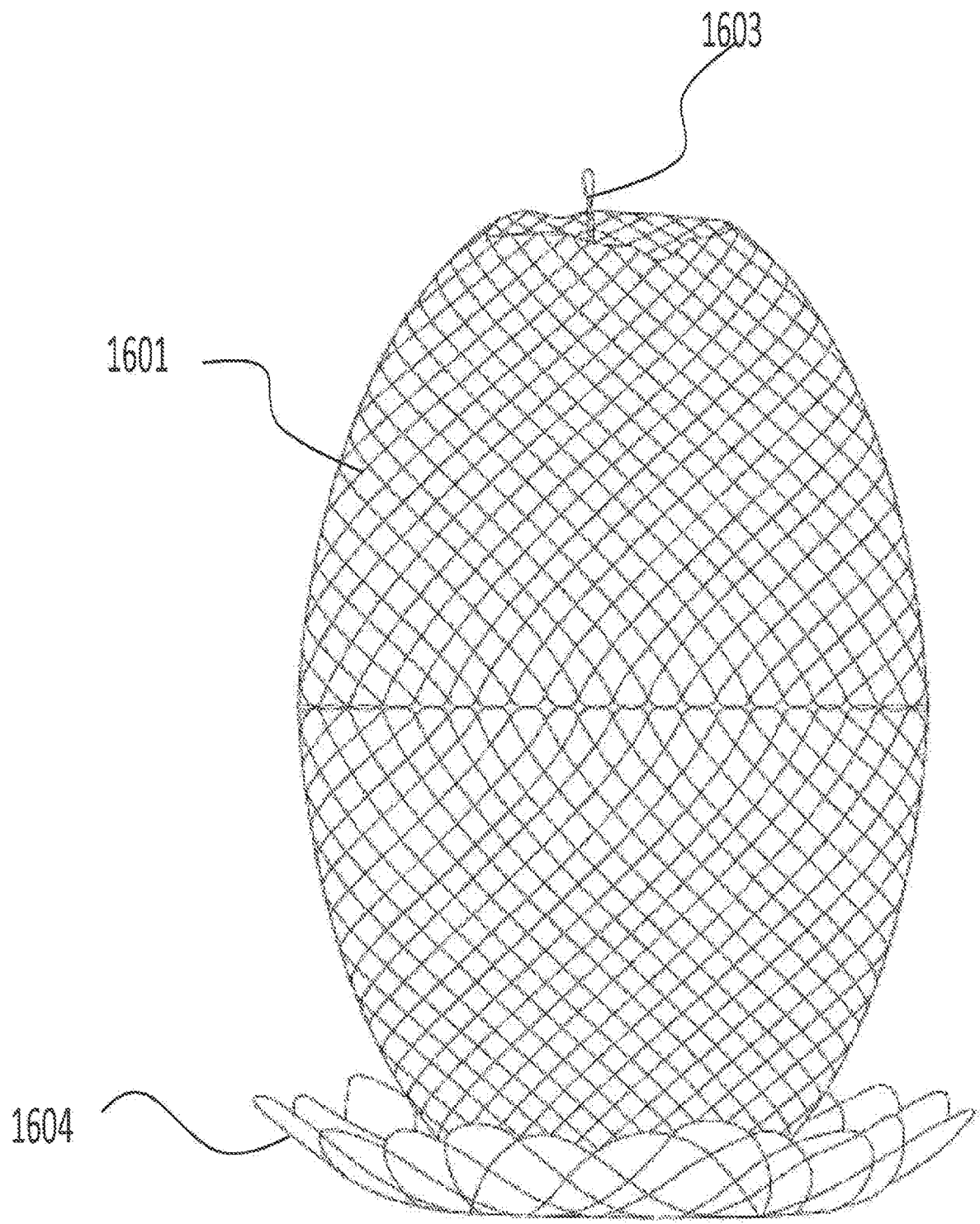
FIG. 16 is an illustration of a wire mesh structure in a post-deployment configuration with a flower-shaped, proximally sloping anti-migration disc attached to its distal end, in accordance with one embodiment of the present specification.

FIG. 16 is an illustration of a wire mesh structure 1601 in a post-deployment configuration with a flower-shaped, proximally sloping anti-migration disc 1604 attached to its distal end, in accordance with one embodiment of the present specification. The wire mesh structure 1601 has an oval shape and includes a retrieval mechanism 1603. In one embodiment, the retrieval mechanism is a silk suture loop. The disc 1604 helps prevent the wire mesh structure 1601 from entering and passing through the pylorus or gastrojejunostomy following an RGB procedure. In one embodiment, the wire mesh structure 1601 includes a bulbous, predominantly spherical or ovoid proximal end and an expanded distal end. In one embodiment, the distal half of the structure is covered with a membrane to impede the passage of food out of the structure 1601, directing the food through a distal opening. In one embodiment, the structure 1601 has an optional anti-reflux valve at the proximal end and another optional valve at the distal end. The valve at the distal end acts to control the flow of chyme or partially digested food from the inside of the structure 1601 to the outside of the structure 1601. In various other embodiments, the structure 1601 includes differently shaped wire meshes including, but not limited to, those discussed with reference to FIGS. 6A through 6S.

Figures 17A, 17B:
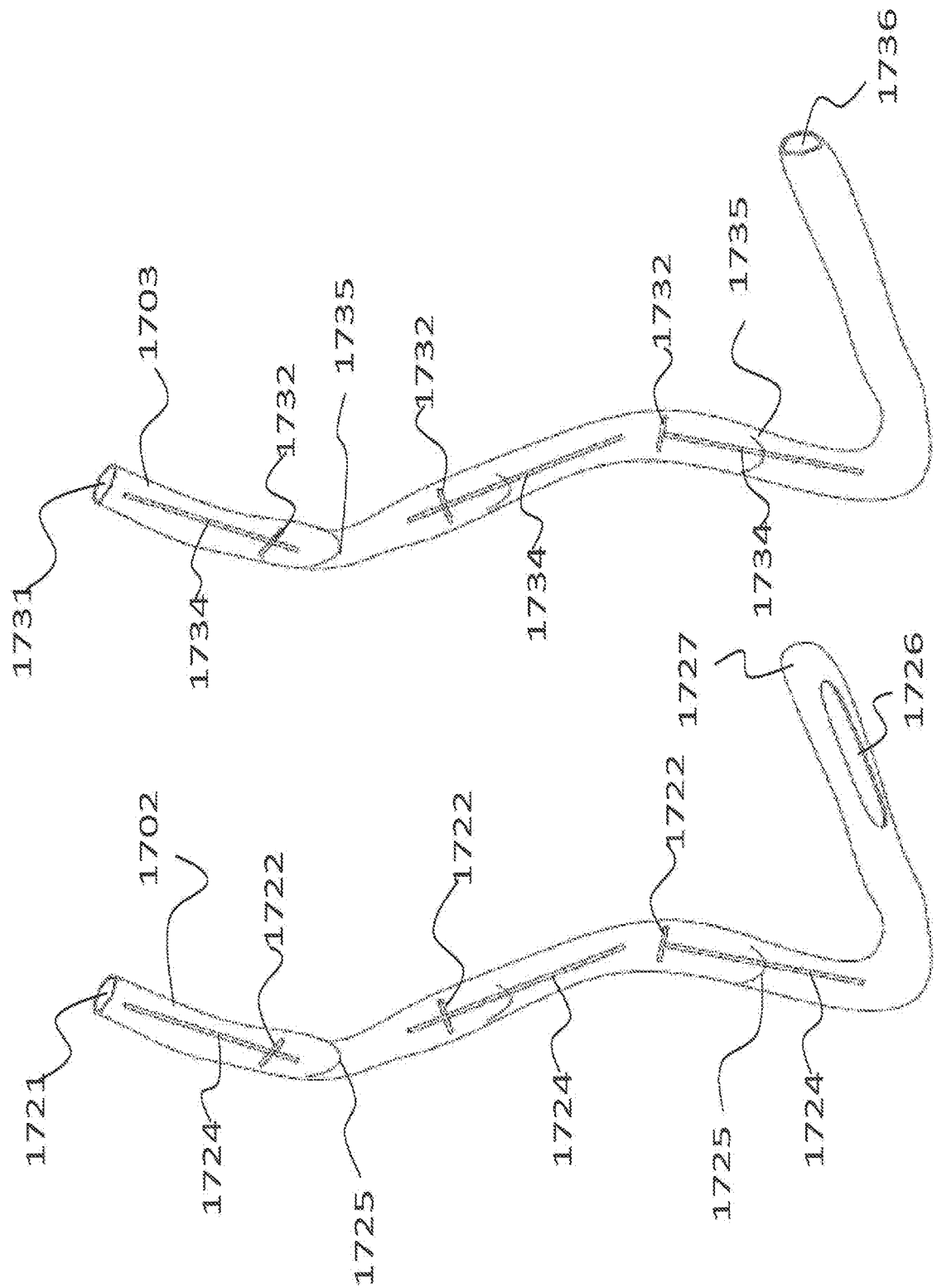
FIG. 17A is an illustration of a sleeve component of an intragastric device in a post-deployment configuration in accordance with one embodiment of the present specification, depicting horizontal and vertical support elements, a proximal first opening, and a side second opening proximate the distal end of the sleeve.
FIG. 17B is an illustration of a sleeve component of an intragastric device in a post-deployment configuration in accordance with one embodiment of the present specification, depicting horizontal and vertical support elements, a proximal first opening, and a second opening at the distal end of the sleeve.

FIG. 17A is an illustration of a sleeve component 1702 of an intragastric device in accordance with one embodiment of the present specification, depicting horizontal 1722 and vertical support elements 1724, a proximal first opening 1721, and a side second opening 1726 proximate the distal end of the sleeve 1702. The horizontal support elements 1722 serve to maintain the sleeve 1702 in an elongate shape in the duodenum and to keep the sleeve lumen open. The vertical support elements 1724 help keep the lumen of the sleeve 1702 open after contractions have compressed the sleeve 1702, thereby allowing more ingested food to enter the sleeve 1702 from a coupled wire mesh structure (not shown). The vertical support elements 1724 also keep the segments of the sleeve 1702 straight and prevent segments from folding or buckling. The horizontal 1722 and vertical 1724 support elements also impart anti-torsional properties to the sleeve 1702 so that it will not become twisted as a result of exposure to intestinal contractions. In addition, in one embodiment, the horizontal support elements 1722 and vertical support elements 1724 additionally act as weighted structures keeping the sleeve 1702 in place in the gastrointestinal tract. The sleeve 1702 further includes a blind pouch 1727 at its distal end, distal to the second opening 1726. Food and fluid intermittently collect and are trapped in this pouch 1727, thereby weighting down the distal end of the sleeve 1702 and helping to maintain the sleeve 1702 in an elongated shape. This weighted distal end is designed to pull the tube distally into the small bowel maintaining it in a predominantly straightened position. In various embodiments, the length of the blind pouch 1727 is in a range from one half inch to 12 inches beyond the distal opening 1726. In another embodiment, the distal end is weighted down by incorporating a weighted structure into the length of the sleeve component 1702. Food traveling down the sleeve 1702 after entering from a wire mesh device into the proximal first opening 1721 exits the sleeve 1702 at the second opening 1726. In addition, food that has been caught in the pouch 1727 is intermittently pushed out of the pouch 1727 and out the second opening 1702 by intestinal contractions. In one embodiment, the sleeve component 1702 includes one or more valves 1725 to prevent retrograde flow of food within the sleeve component 1703.

In various embodiments, the horizontal support elements 1722 are spaced between 1 inches and 24 inches apart from one another and the vertical support elements 1724 are between 1 inches and 60 inches in length. In one embodiment, the horizontal support elements are spaced 6 inches apart from one another and the vertical support elements are 6 inches in length. It is desirable that the sleeve be flexible, while also being torsion, buckling or kink resistant, and could be made of any material that allows it to have these properties.

In various embodiments, the sleeve component is made of polytetrafluoroethylene (PTFE) or polyethylene or cast PTFE (e.g., Teflon), PTFE with fluorinated ethylene propylene (FEP) or perfluoroalkoxy (PFA) coating, extruded FEP and extruded PFA or extruded PTFE or a fluoropolymer or silicone. In various embodiments, the sleeve component has a length in a range of 6 inches to 6 feet or longer. In one embodiment, the sleeve component has a length of 24 inches. In another embodiment, the sleeve component has a length of 30 inches. In various embodiments, the sleeve component has a diameter in a range of 1 cm to 10 cm. In one embodiment, the sleeve component has a diameter of 3 cm.

FIG. 17B is an illustration of a sleeve component 1703 of an intragastric device in accordance with one embodiment of the present specification, depicting horizontal 1732 and vertical support elements 1734, a proximal first opening 1731, and a second opening 1736 at the distal end of the sleeve 1703. The horizontal support elements 1732 serve to maintain the sleeve 1703 in an elongate shape in the duodenum. The vertical support elements 1734 help keep the lumen of the sleeve 1703 open after contractions have compressed the sleeve 1703, thereby allowing more ingested food to enter the sleeve 1703 from a coupled wire mesh structure (not shown). The horizontal 1732 and vertical 1734 support elements also impart anti-torsional properties to the sleeve 1703 so that it will not become twisted as a result of exposure to intestinal contractions. Food traveling down the sleeve 1703 after entering from the proximal first opening 1731 exits the sleeve 1703 at the second opening 1736. In one embodiment, the sleeve component 1703 includes one or more valves 1735 to prevent retrograde flow of food within the sleeve component 1703.

FIG. 17C is an illustration of a sleeve component 1704 of an intragastric device in accordance with one embodiment of the present specification, depicting a coil or wire mesh support 1743, a proximal first opening 1741, and a side second opening 1746 proximate the distal end of the sleeve 1704. The wire mesh support 1743 serves to maintain the sleeve 1704 in an elongate shape in the duodenum and keep the lumen of the sleeve 1704 open after contractions have compressed the sleeve 1704, thereby allowing more ingested food to enter the sleeve 1704 from a coupled wire mesh structure (not shown). The wire mesh support 1743 also imparts anti-torsional properties to the sleeve 1704 so that it will not become twisted as a result of exposure to intestinal contractions. The sleeve 1704 further includes a blind pouch 1747 at its distal end, distal to the second opening 1746. Food intermittently collects in this pouch 1747, thereby weighting down the distal end of the sleeve 1704 and helping to maintain the sleeve 1704 in an elongated shape. Food traveling down the sleeve 1704 after entering from the proximal first opening 1741 exits the sleeve at the second opening 1746. In addition, food that has been caught in the pouch 1747 is intermittently pushed out of the pouch 1747 and out the second opening 1704 by intestinal contractions.

FIG. 17D is an illustration of a sleeve component 1705 of an intragastric device in accordance with one embodiment of the present specification, depicting a wire mesh support 1753, a proximal first opening 1751, and a second opening 1756 at the distal end of the sleeve 1705. The wire mesh support 1753 serves to maintain the sleeve 1705 in an elongate shape in the duodenum and keep the lumen of the sleeve 1705 open after contractions have compressed the sleeve 1705, thereby allowing more ingested food to enter the sleeve 1705 from a coupled wire mesh structure (not shown). The wire mesh support 1753 also imparts anti-torsional properties to the sleeve 1705 so that it will not become twisted as a result of exposure to intestinal contractions. Food traveling down the sleeve 1705 after entering from the proximal first opening 1751 exits the sleeve at the second opening 1756.

FIG. 17E is an illustration of a sleeve component 1706 of an intragastric device in accordance with one embodiment of the present specification, depicting a spiral wire support 1768, a proximal first opening 1761, and a side second opening 1766 proximate the distal end of the sleeve 1706. The spiral wire support 1768 serves to maintain the sleeve 1706 in an elongate shape in the duodenum and keep the lumen of the sleeve 1706 open after contractions have compressed the sleeve 1706, thereby allowing more ingested food to enter the sleeve 1706 from a coupled wire mesh structure (not shown). The spiral wire support 1768 also imparts anti-torsional properties to the sleeve 1706 so that it will not become twisted as a result of exposure to intestinal contractions. The sleeve 1706 further includes a blind pouch 1767 at its distal end, distal to the second opening 1766. Food intermittently collects in this pouch 1767, thereby weighting down the distal end of the sleeve 1706 and helping to maintain the sleeve 1706 in an elongated shape. Food traveling down the sleeve 1706 after entering from the proximal first opening 1761 exits the sleeve at the second opening 1766. In addition, food that has been caught in the pouch 1767 is intermittently pushed out of the pouch 1767 and out the second opening 1706 by intestinal contractions.

FIG. 17F is an illustration of a sleeve component 1707 of an intragastric device in accordance with one embodiment of the present specification, depicting a spiral wire support 1778, a proximal first opening 1771, and a second opening 1776 at the distal end of the sleeve 1707. The spiral wire support 1778 serves to maintain the sleeve 1707 in an elongate shape in the duodenum and keep the lumen of the sleeve 1707 open after contractions have compressed the sleeve 1707, thereby allowing more ingested food to enter the sleeve 1707 from a coupled wire mesh structure (not shown). The spiral wire support 1778 also imparts anti-torsional properties to the sleeve 1707 so that it will not become twisted as a result of exposure to intestinal contractions. Food traveling down the sleeve 1707 after entering from the proximal first opening 1771 exits the sleeve at the second opening 1776. One or more spiral wires can be used based on desired rigidity, kink, torsion or buckle resistance. Wires of different material or wire diameter can be used.

Figure 18A:
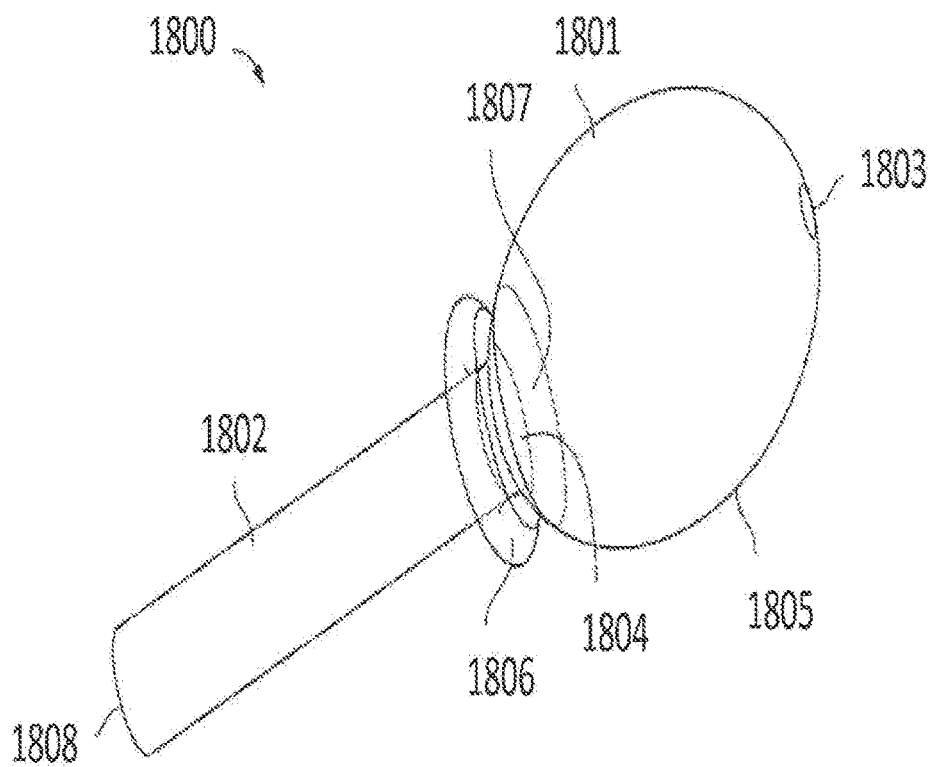
FIG. 18A is an illustration of another embodiment of an intragastric device with an attached sleeve in an exemplary post-deployment configuration.
Figure 18B:
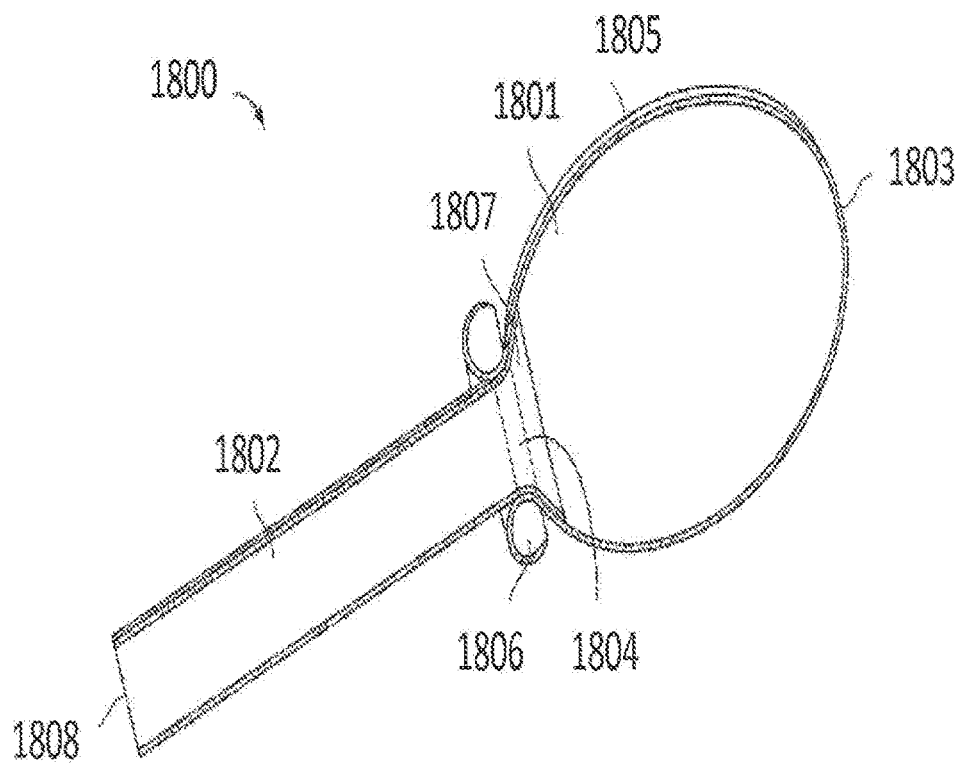
FIG. 18B is a cross-sectional illustration of the embodiment of an intragastric device with an attached sleeve in an exemplary post-deployment configuration of FIG. 18A.

FIG. 18A is an illustration of another embodiment of an intragastric device 1800 with a coupled sleeve 1802 in an exemplary post-deployment configuration and FIG. 18B is a cross-sectional illustration of the embodiment of an intragastric device 1800 with a coupled sleeve 1802 in an exemplary post-deployment configuration of FIG. 18A. The device 1800 includes a wire mesh structure 1801 having a first opening 1803 at its proximal end and a second, larger opening 1804 at its distal end. The device 1800 is covered by a membrane 1805 about its entire outer surface with the exception of at the first 1803 and second 1804 openings. The device 1800 further includes an anti-migration component 1806 in the shape of a bumper at its distal end. The anti-migration component 1806 is formed from an extension of the wire mesh of the device 1800 and is also covered by the membrane 1805. A sleeve 1802 is coupled to the distal end of the wire mesh structure 1801 of the device 1800 and includes a first sleeve opening 1807 and a second sleeve opening 1808. The proximal end of the sleeve 1802 entirely covers the second, larger opening 1804 of the wire mesh structure 1801 such that the first sleeve opening 1807 is in fluid communication with the second, larger opening 1804 of the wire mesh structure 1801 and food is allowed to pass from the wire mesh structure 1801 into the sleeve 1802. In one embodiment, the sleeve 1802 is deployed in the gastrointestinal tract of the patient such that the second sleeve opening 1808 is positioned within the jejunum of the patient, allowing food to bypass the pylorus and duodenum and empty into said jejunum.

Figure 18C:
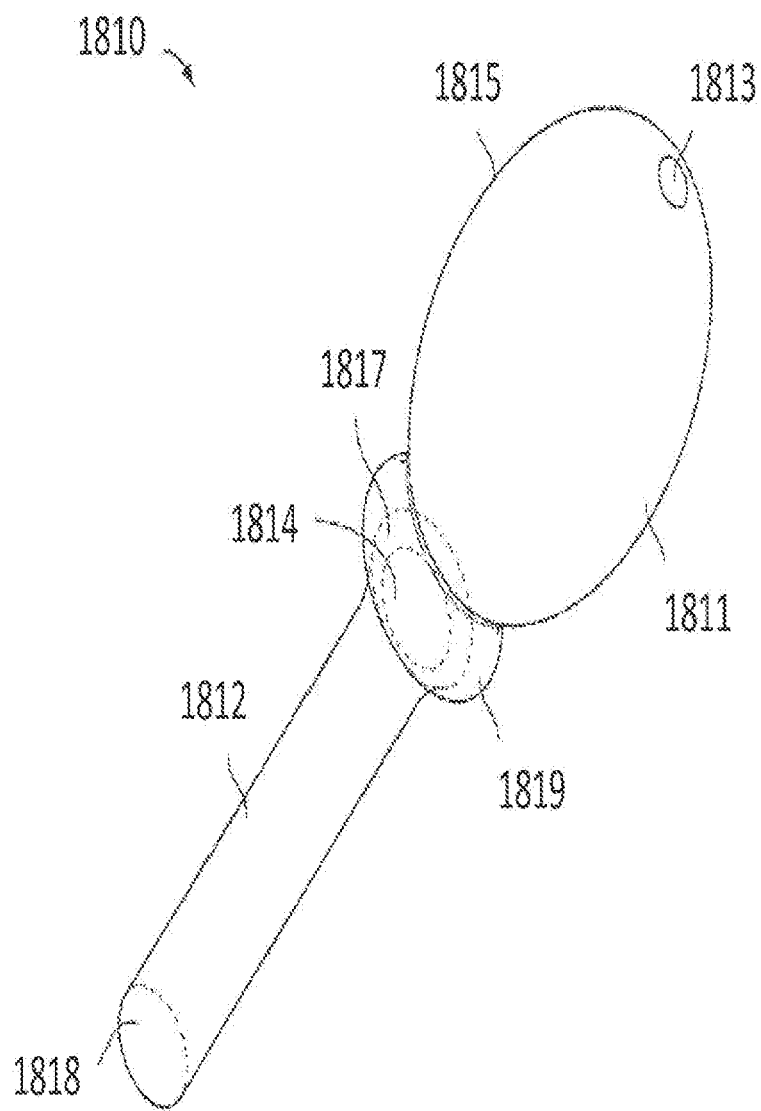
FIG. 18C is an illustration of an embodiment of an intragastric device having a dumbbell shape with an attached sleeve in an exemplary post-deployment configuration.

FIG. 18C is an illustration of an embodiment of an intragastric device 1810 having a dumbbell shape with a coupled sleeve 1812 in an exemplary post-deployment configuration. The device 1810 includes an upper wire mesh portion 1811 and a lower wire mesh portion 1819. A first opening 1813 is positioned at the proximal end of the upper wire mesh portion 1811 and a second, larger opening 1814 is positioned at the distal end of the lower wire mesh portion 1819. In the pictured embodiment, a membrane 1815 covers the entire outer surfaces of both wire mesh portions 1811, 1819 with the exception of the two openings 1813, 1814. A sleeve 1812 is coupled to a portion of the lower wire mesh portion 1819. The sleeve 1812 includes a first sleeve opening 1817 covering, and in fluid communication with, the second opening 1814 at the distal end of the lower wire mesh portion 1819. The sleeve 1812 further includes a second sleeve opening 1818 at its distal end. Food enters the device 1810 through the first opening 1813 at the proximal end of the upper wire mesh 1811 and then travels through the upper wire mesh 1811 and lower wire mesh 1819. The food then passes through the second opening 1814 at the distal end of the lower wire mesh 1819, through first sleeve opening 1817, and into the sleeve 1812. Finally, food exits the device 1810 through the second sleeve opening 1818. In one embodiment, the device 1810 is deployed with the distal end of the sleeve 1812 positioned in the jejunum so the food exiting the device 1810 through the second sleeve opening 1818 empties into said jejunum. In various embodiments, the proximal end of the sleeve is coupled to any portion of the lower wire mesh 1819 or to a distal portion of the upper wire mesh 1811.

Figure 18D:
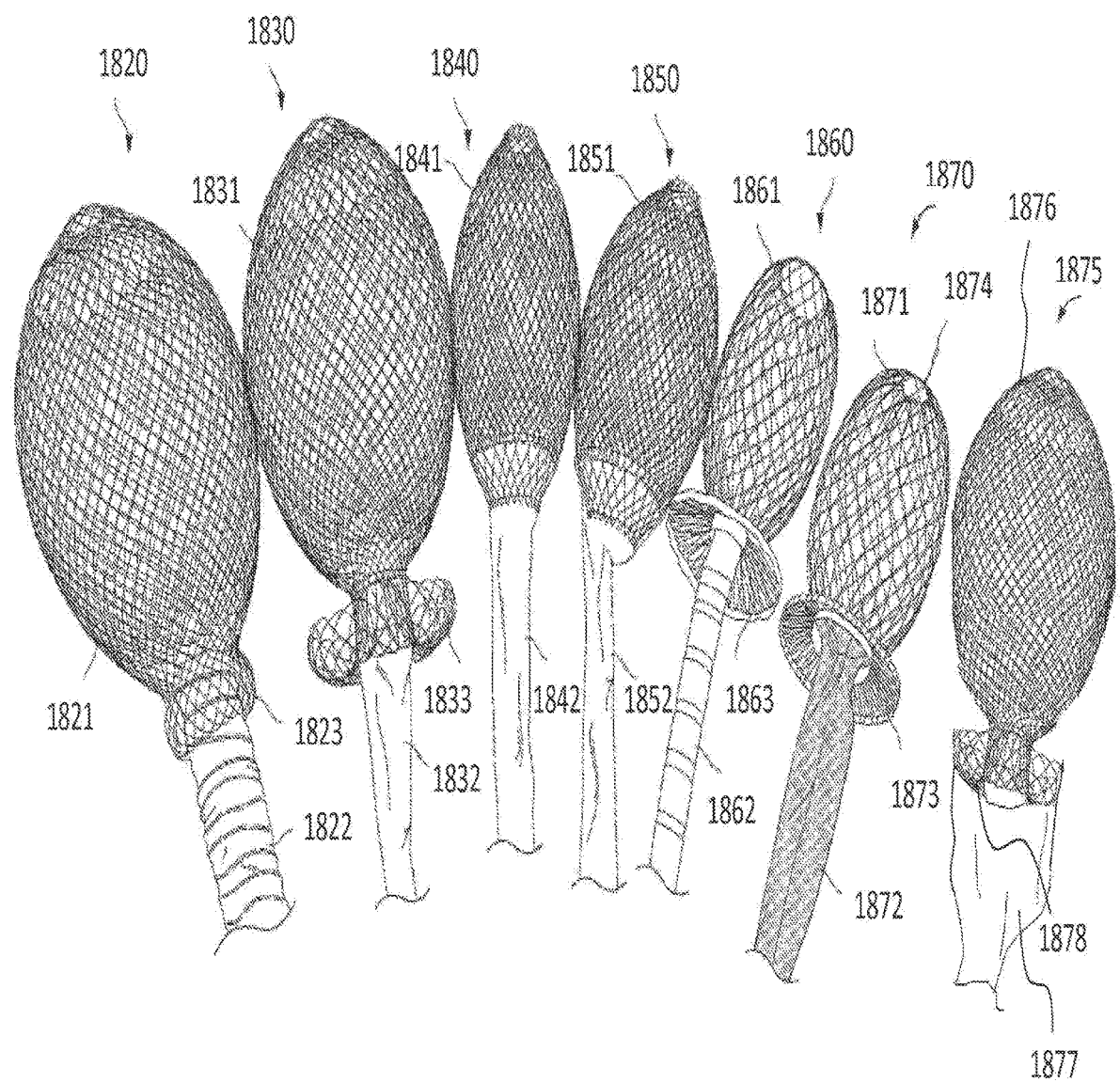
FIG. 18D is an illustration depicting various exemplary post-deployment configuration intragastric devices in accordance with multiple embodiments of the present specification.

FIG. 18D is an illustration depicting various exemplary post-deployment configuration intragastric devices 1820, 1830, 1840, 1850, 1860, 1870 in accordance with multiple embodiments of the present specification. Intragastric device 1820 comprises a wire mesh structure 1821 with a sleeve 1822 coupled to its distal end. The sleeve 1822 includes circumferential support elements to maintain sleeve shape and the wire mesh structure 1821 includes a narrow bumper shaped anti-migration component 1823. Intragastric device 1830 comprises a wire mesh structure 1831 with a coupled sleeve 1832. The wire mesh structure 1830 includes a bumper shaped anti-migration component 1833 that is wider than the anti-migration component 1823 depicted on device 1820. Intragastric device 1840 and intragastric device 1850 each include a wire mesh structure 1841, 1851 and a coupled sleeve 1842, 1852. The sleeve 1842 of device 1840 is coupled to the wire mesh structure 1841 such that the proximal portion of the sleeve 1842 is positioned within the distal portion of the wire mesh structure 1841. Conversely, with respect to device 1850, the sleeve 1852 is coupled to the wire mesh structure 1851 such that the proximal portion of the sleeve 1852 covers the outer surface of the distal portion of the wire mesh structure 1851. Intragastric device 1860 comprises a wire mesh structure 1861 with a thin coupled sleeve 1862. The device 1860 includes a distally extending, disc shaped anti-migration component 1863 positioned at the junction of the wire mesh structure 1861 and the sleeve 1862. Intragastric device 1870 also comprises a wire mesh structure 1871 with a coupled sleeve 1872 and includes a distally extending, disc shaped anti-migration component 1873 positioned at the junction of the wire mesh structure 1871 and the sleeve 1872. Device 1870 further includes a retrieval hook 1874 attached to the proximal end of the wire mesh structure 1871 to facilitate removal of the device 1870 from a human body. Intragastric device 1875 also comprises a wire mesh structure 1876 with a coupled sleeve 1877 and includes a bumper shaped anti-migration component 1878 similar to that seen in device 1830. However, the sleeve 1877 of device 1875 extends over anti-migration component 1878 and is coupled to the outer edge of the anti-migration component 1878 such that food entering through the holes in the anti-migration component 1878 enters into the sleeve 1877.

FIG. 18E is an illustration of another embodiment of an intragastric device 1880 with a wire mesh structure 1881 and an attached sleeve 1882 in an exemplary pre-deployment configuration. The pre-deployment configuration takes a compressed, cylindrical shape to facilitate insertion.

FIG. 18F is an illustration of the intragastric device 1890 with a wire mesh structure 1891 and an attached sleeve 1892 of FIG. 18E in an exemplary post-deployment configuration. The post-deployment configuration takes an expanded, honeycomb shape to occupy gastric volume and permit the sequestering of food within the device 1890. In one embodiment, the honeycomb shaped device is covered with a membrane (not shown) containing openings of the same or different sizes. In one embodiment, the openings have valves composed of the same membranous material to direct the flow of food preferentially into the device. In one embodiment, the device 1890 contains one large opening 1894 at the bottom that is wholly covered by the attached sleeve 1892. The opening 1894 at the bottom of the device 1890 allows for the preferential passage of food into the sleeve 1892 which in turn delivers the food into the jejunum.

Figure 19A:
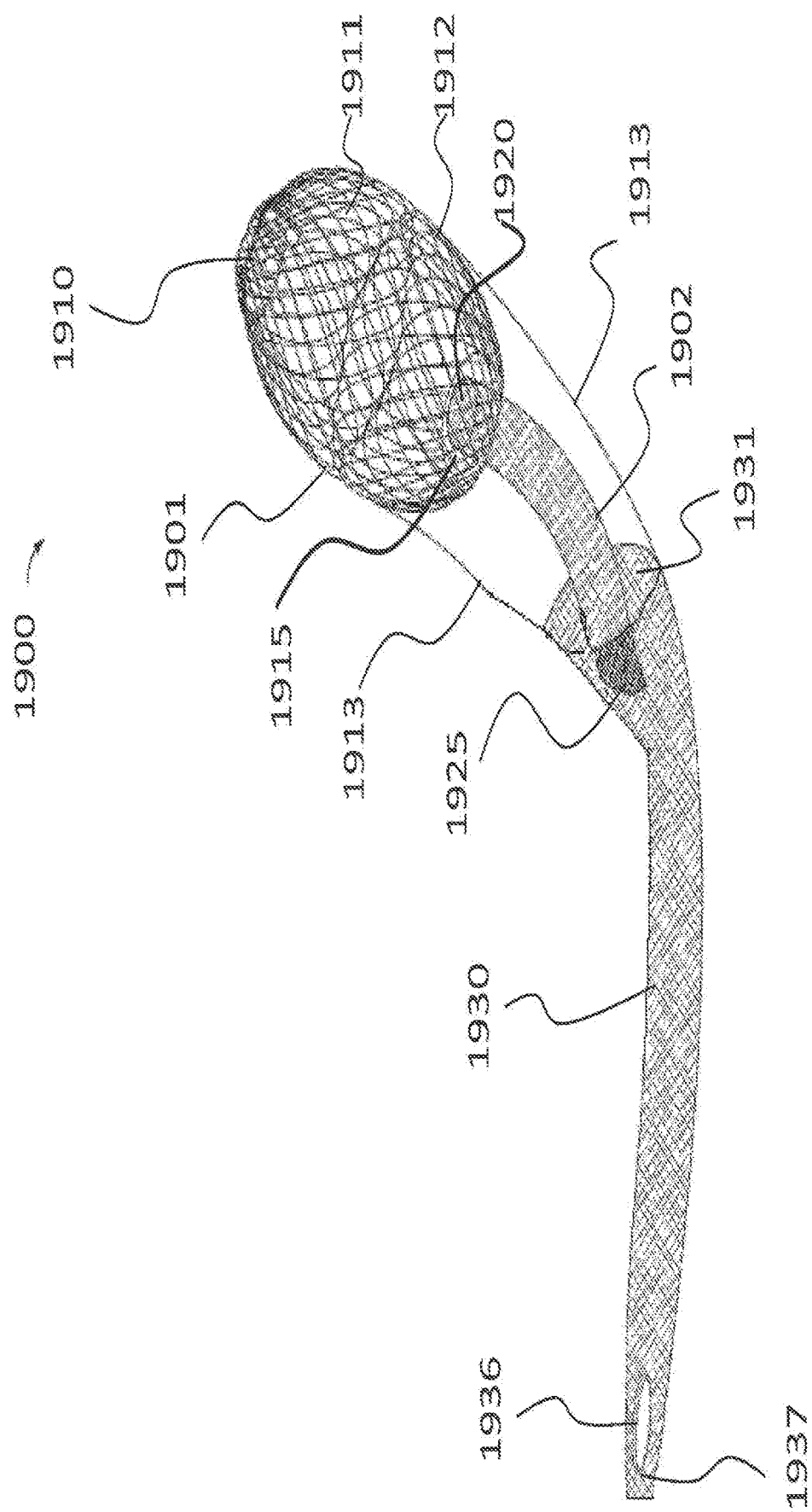
FIG. 19A is an illustration of one embodiment of an intragastric device in a post-deployment configuration having first and second sleeves coupled to a wire mesh structure.

FIG. 19A is an illustration of one embodiment of an intragastric device 1900 in a post-deployment configuration having first sleeve 1902 and second sleeves 1930 coupled to a wire mesh structure 1901. The wire mesh structure includes an upper portion 1911 and a lower portion 1912. The first sleeve 1902 is coupled directly to the distal end of the lower portion 1912 such that the sleeve 1902 covers a second opening 1915 at the distal end of the wire mesh structure 1901. In one embodiment, the first sleeve 1902 is coupled to the lower portion 1912 of the wire mesh structure via sutures. The second sleeve 1930 is coupled to the any part of the lower portion 1912 of the wire mesh structure 1901, at a distance away from the wire mesh structure 1901, in a manner that the distal end of the first sleeve 1902 passes through a proximal first opening 1931 in the second sleeve 1930 and comes to rest within said second sleeve 1930. The second sleeve 1930 is coupled to the lower portion 1912 of the wire mesh structure 1901 via one or more connecting elements 1913. In one embodiment, the connecting elements 1913 comprise sutures or thread or wire.

Once deployed, the device 1900 is positioned such that the wire mesh structure 1900 sits in the stomach just proximal to the pylorus, the first sleeve 1902 extends from the wire mesh structure 1901 through the pylorus and into the duodenum, and the second sleeve 1930 sits in the duodenum and/or jejunum. A distal portion of the first sleeve 1902 is positioned within a proximal portion of the second sleeve 1930 and the connecting elements 1913 extend from the wire mesh structure 1901, through the pylorus and a portion of the duodenum and/or jejunum, and to the proximal end of the second sleeve 1930.

Food entering the stomach and intestines can follow one of two paths. Following a first path, food can enter the wire mesh structure 1901 via the first opening 1910 at its proximal end, pass through the wire mesh structure 1901, through the second opening 1915 at the distal end of the wire mesh structure 1901, and into the first sleeve 1902 through a first opening 1920 at its proximal end. The food then passes through the first sleeve 1902, exits the first sleeve 1902 through a second opening 1925 at its distal end, and enters the second sleeve 1930. Finally, food travels through the second sleeve 1930, exits the second sleeve 1930 through a second opening 1936 at its distal end, and passes into the duodenum or jejunum.

Following a second pathway, food that does not enter but bypasses the wire mesh structure 1901 flows past the first sleeve 1902 and enters the second sleeve 1930 via the first opening 1931 at its proximal end. Food then travels through the second sleeve 1930, exits the second sleeve 1930 through a second opening 1936 at its distal end, and passes into the duodenum or jejunum. The pictured embodiment is useful for capturing food that flows around the wire mesh structure 1901 as it bobs up and down in the stomach, allowing for that food to still bypass portions of the duodenum and/or jejunum. In the pictured embodiment, the second sleeve 1930 includes an optional blind pouch 1937 distal to the second opening 1936 that captures food intermittently, weighting down the second sleeve 1930 and keeping it in an elongated shape. Intestinal contractions intermittently compress the pouch 1937, pushing the food back out of the pouch 1937 and through the second opening 1936. In various embodiments, the first and second sleeves are comprised of different support elements and have varying second openings with or without pouches as described with reference to FIGS. 17A through 17F.

In another embodiment, the first opening 1920 of the first sleeve 1902 completely covers, encases, or otherwise envelopes any and all of second opening or openings 1915 at the distal end of the wire mesh structure 1901 so that all chyme released from the wire mesh structure 1901 will enter only into the first sleeve 1902. The second sleeve 1930 is attached to the wire mesh structure 1901 using connecting elements 1913, such as, wires, sutures or strings, and the first opening 1931 of the second sleeve 1930 resides in the proximal duodenum to capture any food that does not enter the wire mesh structure 1901 but passes alongside the wire mesh structure 1901 through the pylorus into the duodenum.

Figure 19B:
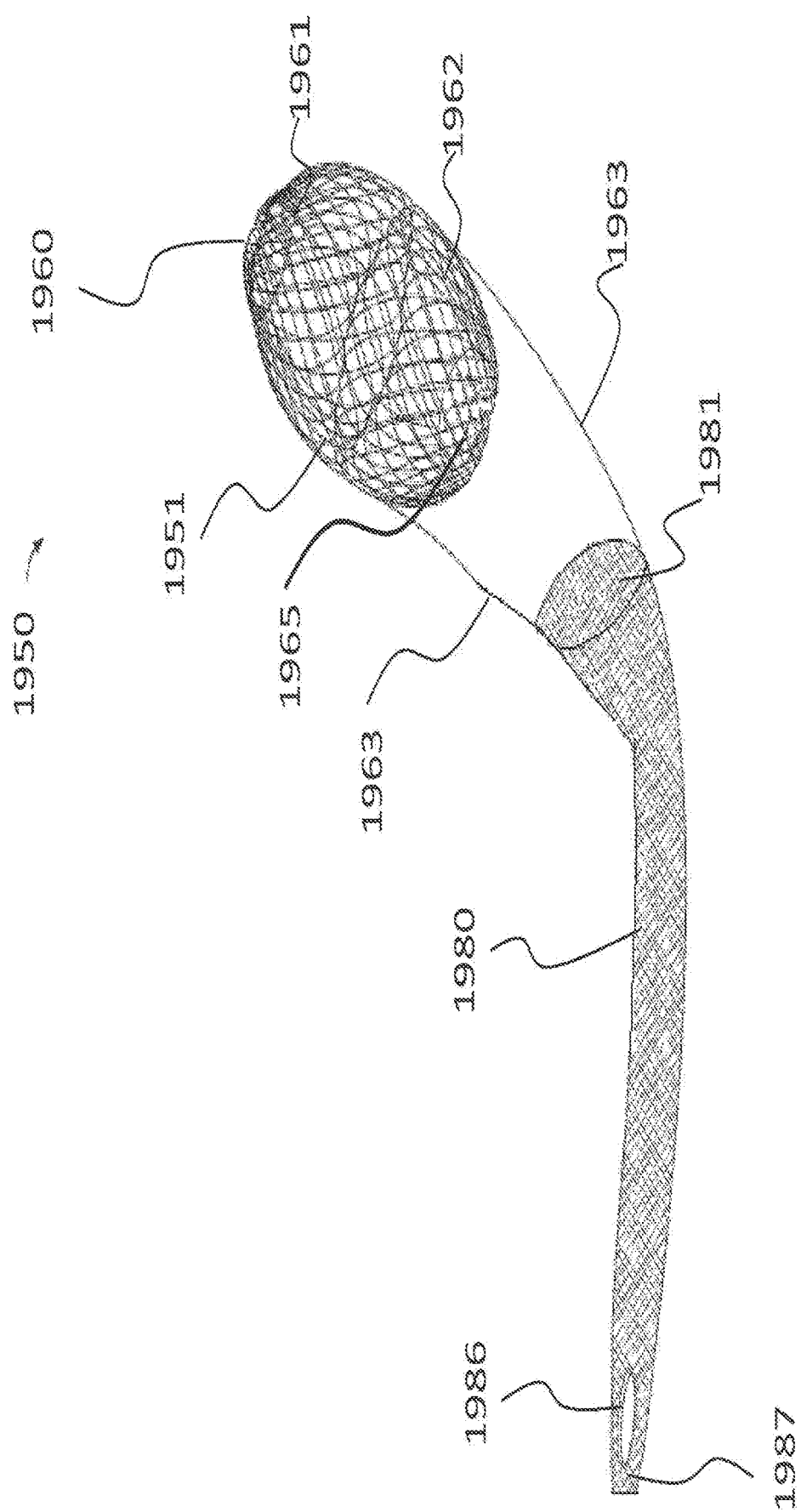
FIG. 19B is an illustration of one embodiment of an intragastric device in a post-deployment configuration having one sleeve coupled to a wire mesh structure at a distance distally away from said wire mesh structure.

FIG. 19B is an illustration of one embodiment of an intragastric device 1950 in a post-deployment configuration having one sleeve 1980 coupled to a wire mesh structure 1951 at a distance distally away from said wire mesh structure 1951. The wire mesh structure 1951 includes an upper portion 1961 and a lower portion 1962. The sleeve 1980 is coupled to the wire mesh structure 1951 using connecting elements 1963, such as, wires, sutures or strings that are attached to the lower portion 1962 of the wire mesh structure 1951.

Once deployed, the device 1950 is positioned such that the wire mesh structure 1951 sits in the stomach proximal to the antrum or the pylorus and the sleeve 1980 sits in the duodenum and/or jejunum with the opening 1981 preferably in the patient's duodenum. Food entering the stomach and intestines can follow multiple paths. Food can enter the wire mesh structure 1951 via the first opening 1960 at its proximal end, pass through the wire mesh structure 1951, and exit through the second opening 1965 at the distal end of the wire mesh structure 1951 back into the stomach. In this situation the wire mesh structure acts to reduce food intake and slow the passage of food from the stomach into the duodenum by delaying gastric emptying. Food can then pass through the pylorus and into the small intestine and then pass through the sleeve 1980, as described below.

Food that either passes through the wire mesh structure 1951 or that does not enter but bypasses the wire mesh structure 1951 can enter the sleeve 1980 via the first opening 1981 at its proximal end. Food then travels through the sleeve 1980, exits the sleeve 1980 through a second opening 1986 at its distal end, and passes into the duodenum or jejunum. The pictured embodiment is useful for capturing food that flows around the wire mesh structure 1951 as it bobs up and down in the stomach, allowing for that food to still bypass portions of the duodenum and/or jejunum. In the pictured embodiment, the sleeve 1980 includes a blind pouch 1987 distal to the second opening 1986 that captures food intermittently, weighting down the sleeve 1980 and keeping it in an elongated shape. Intestinal contractions intermittently compress the pouch 1987, pushing the food back out of the pouch 1987 and through the second opening 1986. In various embodiments, the second sleeve is comprised of different support elements and has varying second openings with or without pouches as described with reference to FIGS. 17A through 17F.

Figure 19C:
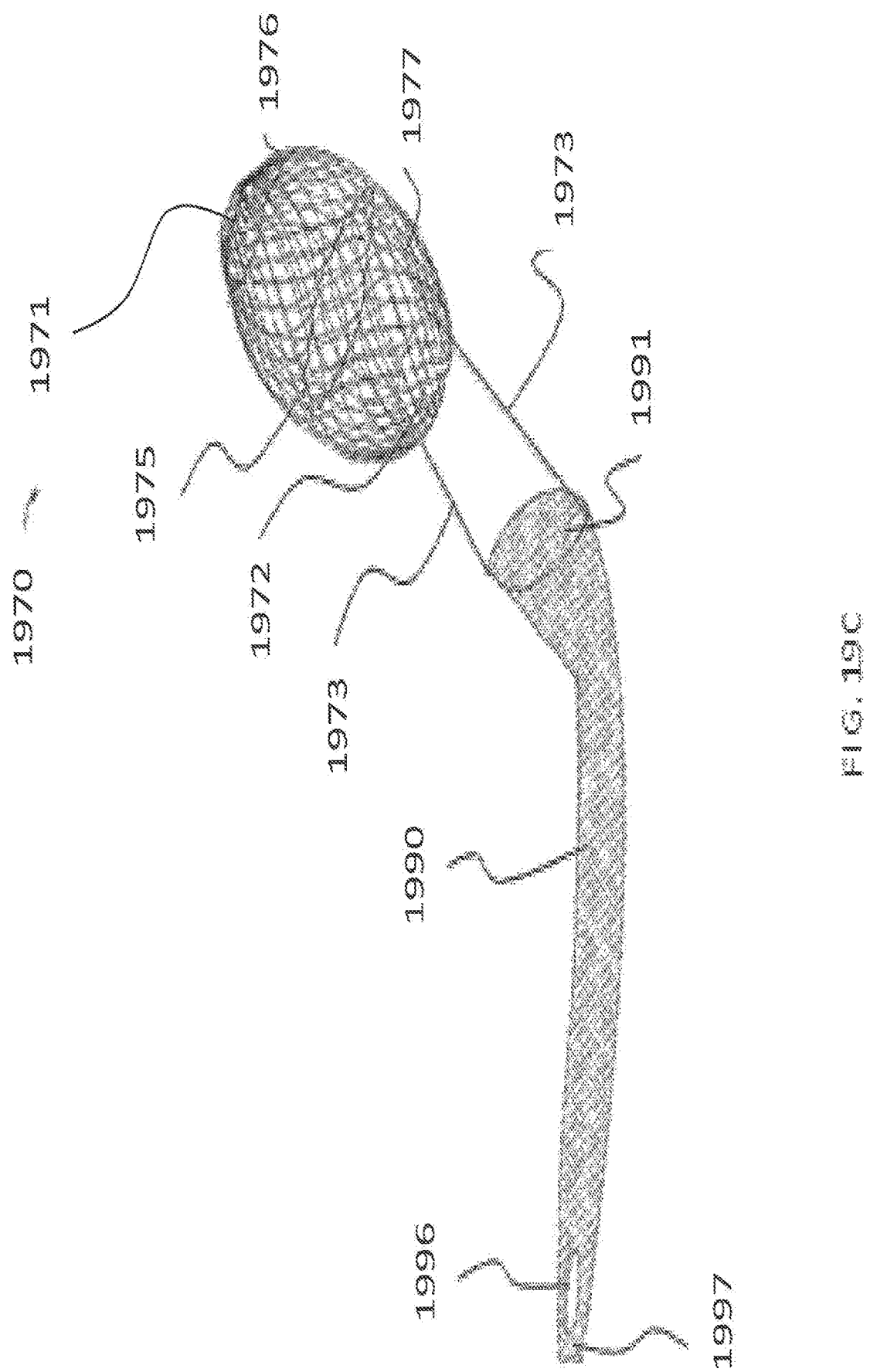
FIG. 19C is an illustration of another embodiment of an intragastric device in a post-deployment configuration having one sleeve coupled to a wire mesh structure at a distance distally away from said wire mesh structure.
Figure 20:
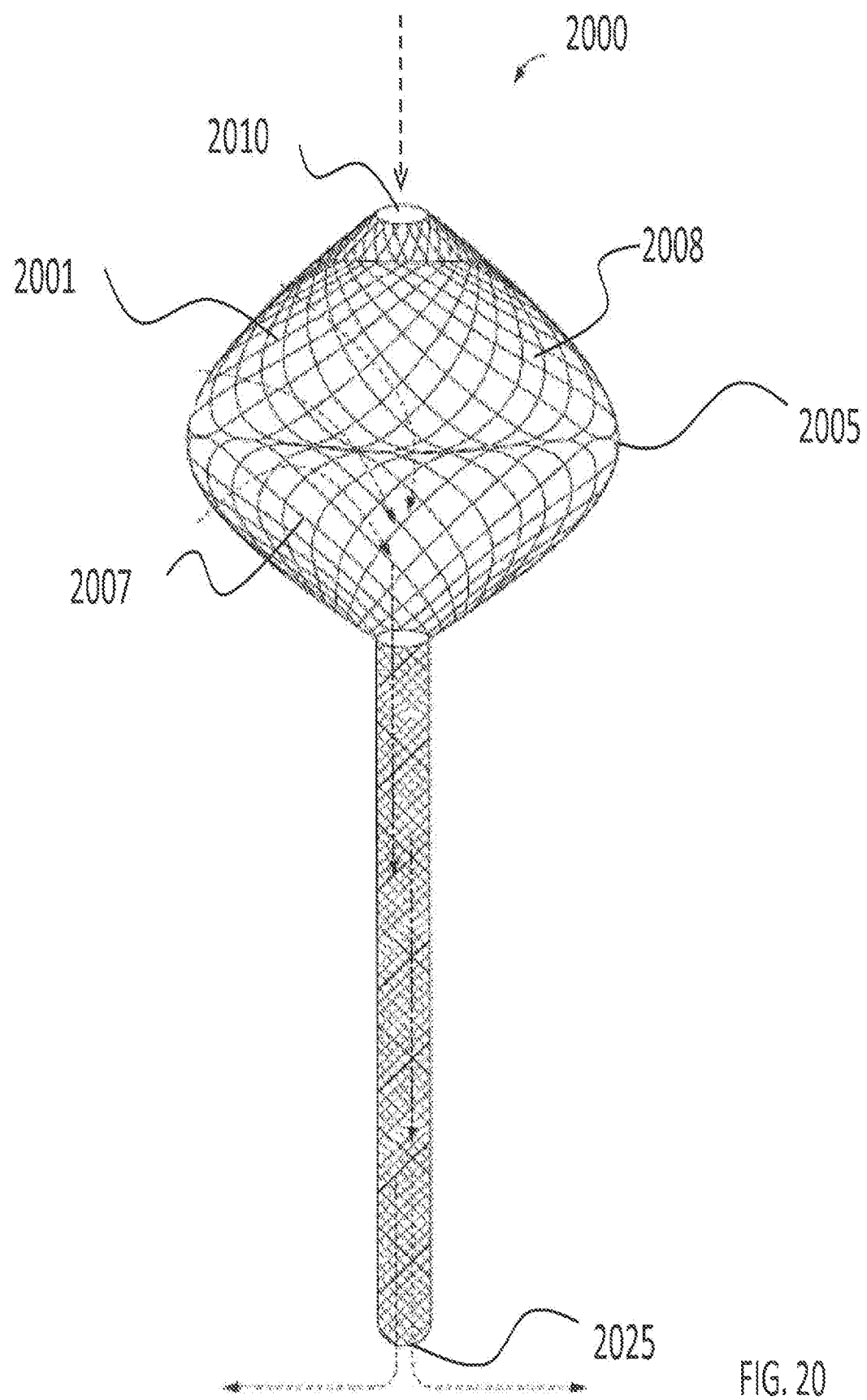
Figure 21:
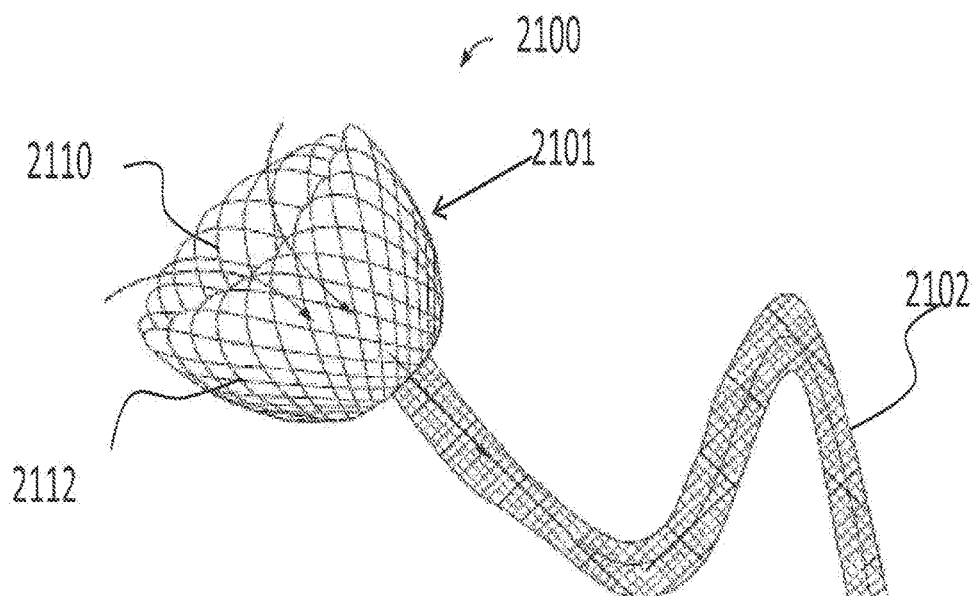
FIG. 21 is an illustration of one embodiment of an intragastric device in a post-deployment configuration having a half sphere wire mesh structure and a sleeve coupled to the wire mesh.

FIG. 19C is an illustration of another embodiment of an intragastric device 1970 in a post-deployment configuration having one sleeve 1990 coupled to a wire mesh structure 1975 at a distance distally away from said wire mesh structure 1975. The wire mesh structure 1975 includes an upper portion 1976 with a first opening 1971 and a lower portion 1977 with a second opening 1972. The sleeve 1990 includes a first opening 1991 and a second opening 1996 with a blind pouch 1997 at its distal end. The device 1970 functions similarly to the device 1950 described with reference to FIG. 19B, the only difference being the location of attachment of the connecting elements 1973 to the wire mesh structure 1975. Referring to FIG. 19C, the connecting elements 1973 attach to the wire mesh structure 1975 at the location of the second opening 1972.

Figure 20:
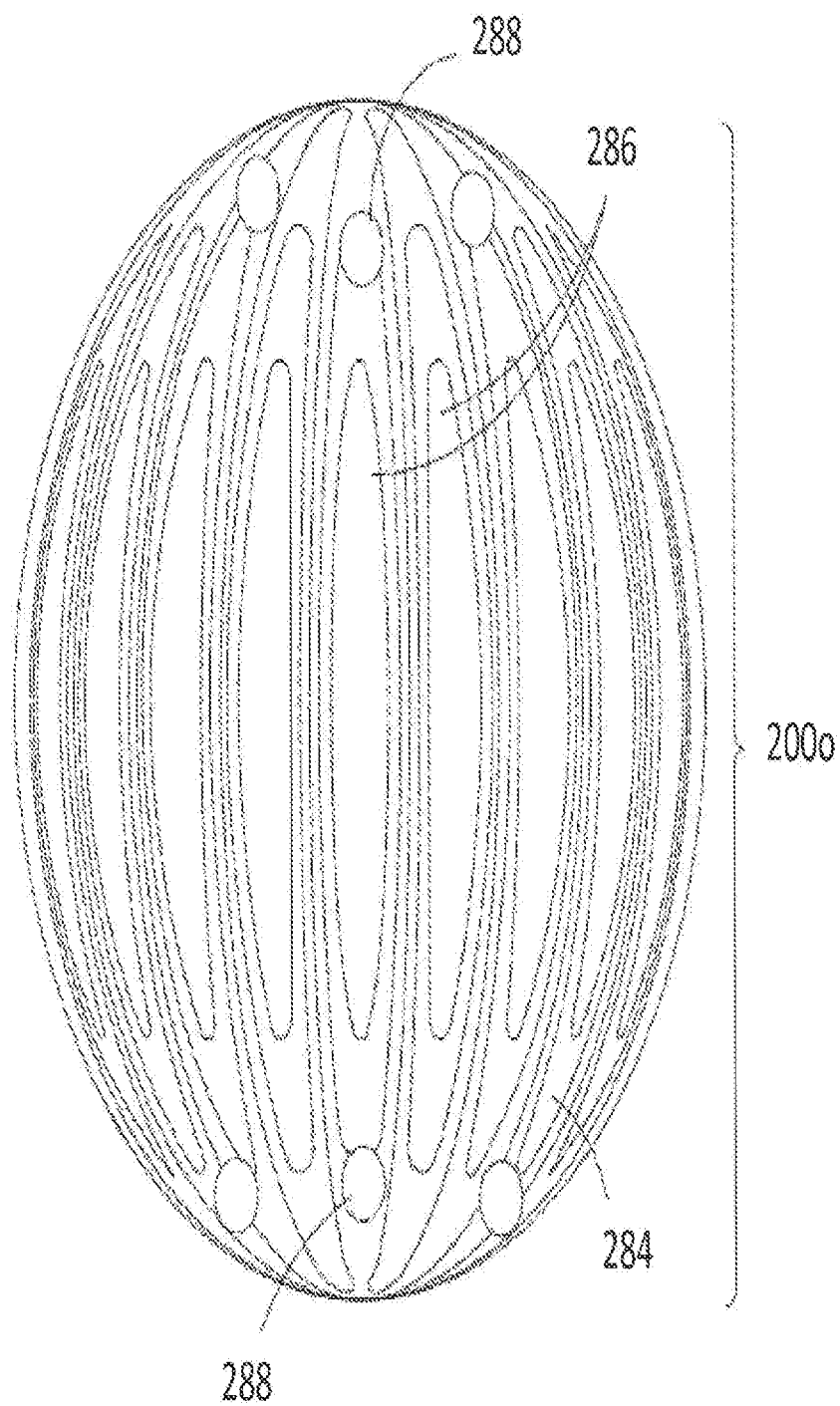
FIG. 20 is an illustration of one embodiment of an intragastric device in a post-deployment configuration having a wire mesh structure and a sleeve coupled to the wire mesh structure and a membrane covering both the sleeve and wire mesh structure.

FIG. 20 is an illustration of one embodiment of an intragastric device 2000 in a post-deployment configuration having a wire mesh structure 2001 and a sleeve 2002 coupled to the wire mesh structure 2001 and a membrane 2005 covering both the sleeve 2002 and wire mesh structure 2001. The device 2000 is depicted in the post-deployment configuration. In one embodiment, the membrane 2005 is flexible and non-porous. In one embodiment, the membrane 2005 covers the entire outer surface of the wire mesh structure 2001 with the exception of the first opening 2010 at its proximal end. The membrane 2005 covers the entire outer surface of the sleeve 2002 with the exception of the second opening 2025 at its distal end. The membrane 2005 prevents any food from entering or exiting the wire mesh structure 2001 in the spaces 2008 between the wires 2007 of the wire mesh structure 2001. Food passing through the device 2000 can only do so by entering at the first opening 2010 of the wire mesh structure 2001, traveling through the wire mesh structure 2001 and the sleeve 2002, and then exiting the sleeve 2002 at its second opening 2025. Alternatively, the food could enter the wire mesh through the other openings in the wire mesh.

Occasionally, food that enters the wire mesh structure can encounter difficulty in exiting the structure due to stasis or bezoar formation. This will interfere in proper functioning of the device. Therefore, in various embodiments, it is desirable to include mechanisms to assist with emptying of the wire mesh structure.

FIG. 2I is an illustration of one embodiment of an intragastric device 2100 in a post-deployment configuration having a half sphere wire mesh structure 2101 and a sleeve 2102 coupled to the wire mesh structure 2101. Since the device 2100 has no 'upper portion' as described with reference to spherical wire mesh structures above, the opening 2110 at the top of the 'lower portion' 2112 acts as the proximal first opening 2110. The 'lower portion' 2112 further includes a second opening (not shown) at its distal end. The sleeve 2102 includes a first opening (not shown) at its proximal end in fluid communication with the second opening of the 'lower portion' 2112 of the wire mesh structure 2101. Food enters the wire mesh structure 2101 through the first opening 2110 of the 'lower portion' 2112, passes through the 'lower portion' 2112, through the second opening at the distal end of the lower portion, through the first opening at the proximal end of the sleeve, into and through the sleeve 2102 and then out of the device 2100 at the second opening at the distal end of the sleeve 2102. Food that does not exit through the second opening due to particle size will exit the wire mesh lower structure 2101 via the large proximal first opening 2110 when the patient is in the supine position. This food will then exit the stomach normally through the pylorus. Allowing for emptying of the device whenever the patient is in the supine position prevents stasis and bezoar formation.

Figure 22:
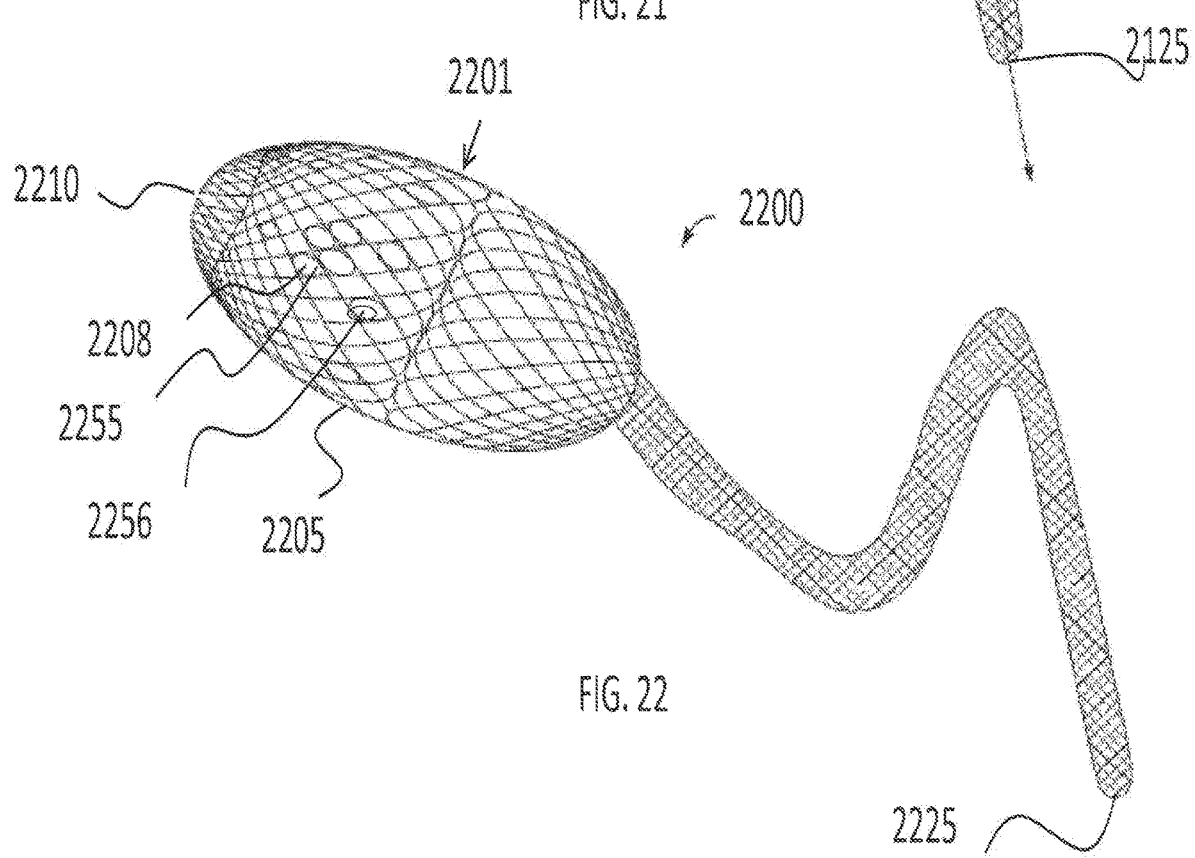
FIG. 22 is an illustration of one embodiment of an intragastric device in a post-deployment configuration having a wire mesh structure and a sleeve coupled to the wire mesh structure and a membrane covering the sleeve and wire mesh structure, depicting a plurality of openings in the membrane.

FIG. 22 is an illustration of one embodiment of an intragastric device 2200 in a post-deployment configuration having a wire mesh structure 2201 and a sleeve 2202 coupled to the wire mesh structure 2201 and a membrane 2205 covering the sleeve 2202 and wire mesh structure 2201, depicting a plurality of openings 2255 in the membrane 2205. The membrane 2205 covers the entire outer surface of both the wire mesh structure and the sleeve with the exception of the first opening at the proximal end of the wire mesh structure 2210, the second opening at the distal end of the sleeve 2225, and the plurality of openings 2255 in the membrane 2205. In one embodiment, the plurality of openings 2255 in the membrane 2205 aligns with the spaces 2208 between the wires 2207 in the wire mesh structure 2201. Besides the proximal to distal pathway of food through the device as discussed with reference to multiple embodiments above, food can pass into the wire mesh structure 2201 through the openings 2255 in the membrane 2205. In one embodiment, the membrane 2205 further includes unidirectional valves or flaps 2256 that allow food to pass into the wire mesh structure 2201 at the plurality of openings 2255 and prevent food from flowing back out through the same openings 2255.

Figure 23A:
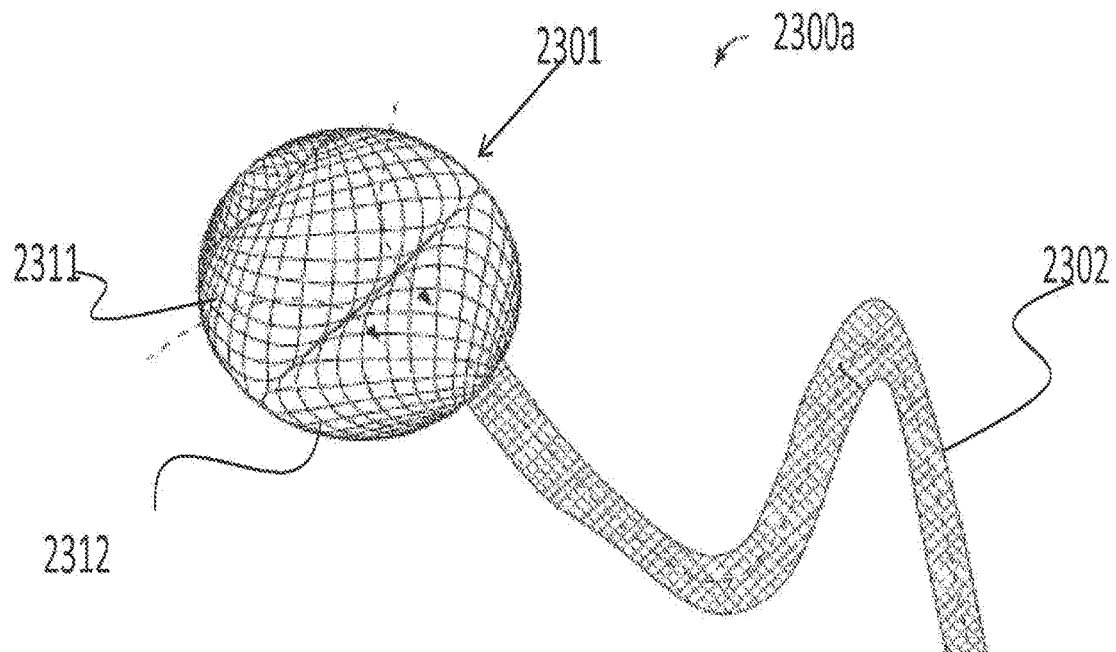
FIG. 23A is an illustration of one embodiment of an intragastric device in a post-deployment configuration having a wire mesh structure and a sleeve coupled to the wire mesh.

FIG. 23A is an illustration of one embodiment of an intragastric device 2300a in a post-deployment configuration having a wire mesh structure 2301 and a sleeve 2302 coupled to the wire mesh structure 2301. The wire mesh structure 2301 includes an upper portion 2311 and a lower portion 2312. Referring to FIG. 23A, the upper portion 2311 and the lower portion 2312 of the wire mesh structure 2301 have the same weave pattern and radial strength to resist compression by gastric contractions.

Figure 23B:
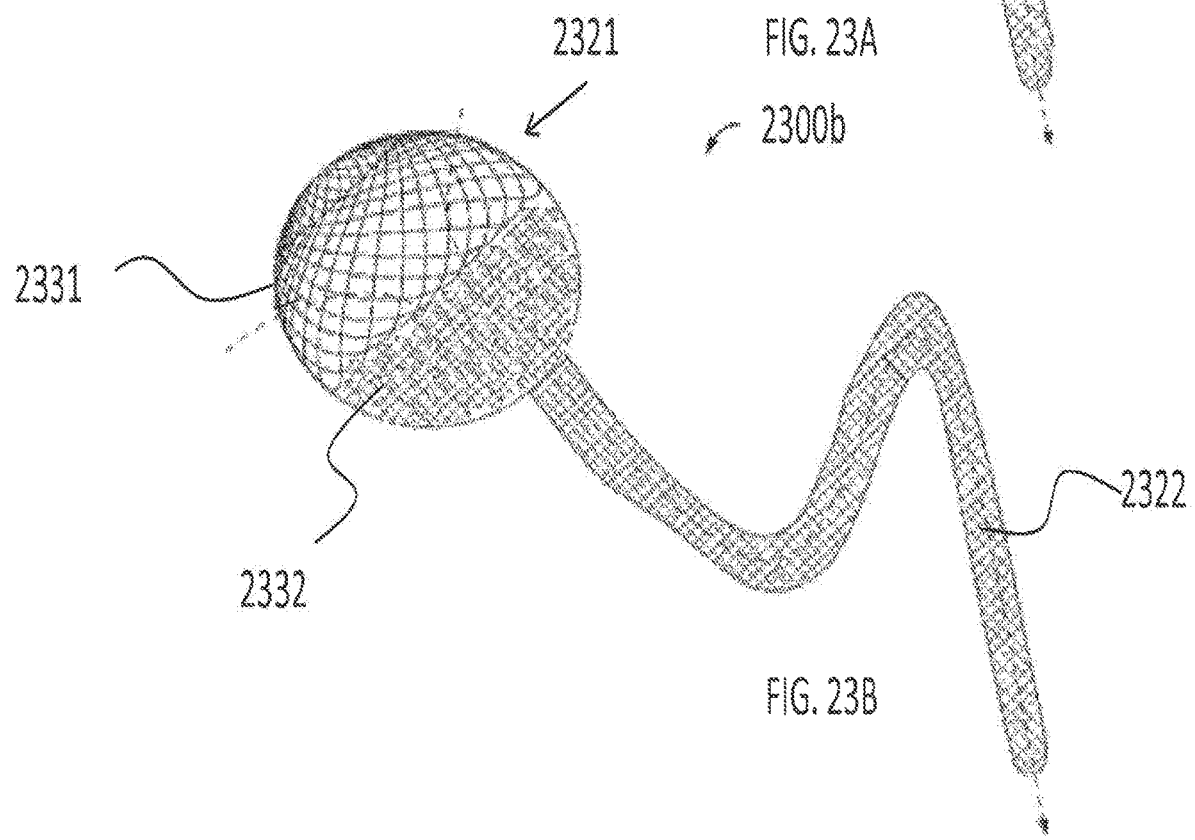
FIG. 23B is an illustration of one embodiment of an intragastric device in a post-deployment configuration having a wire mesh structure and a sleeve coupled to the wire mesh structure, wherein the upper portion of the wire mesh structure comprises a wire mesh and the lower portion comprises only a membrane.

FIG. 23B is an illustration of one embodiment of an intragastric device 2300b in a post-deployment configuration having a wire mesh structure 2321 and a sleeve 2322 coupled to the wire mesh structure 2321, wherein the upper portion 2331 of the wire mesh structure 2321 comprises a wire mesh and the lower portion 2332 comprises only a membrane. The upper portion 2331 of the wire mesh structure 2321 comprises a weave pattern that provides the upper portion 2331 with a radial strength great enough to prevent it from being substantially compressed by gastric contractions. In one embodiment, the upper portion 2331 includes a plurality of openings for passage of food into the device. The membranous composition of the lower portion 2332 allows the force of gastric contractions to pass through the lower portion 2332 and reach the food inside, helping to push the food down through the wire mesh structure 2321 and into the sleeve 2322. Antral contractions are fully transmitted to the partially digested food in the lower portion 2332, agitating the food and squeezing it through the opening at the distal end of the lower portion 2332 and into the sleeve 2322.

Figure 23C:
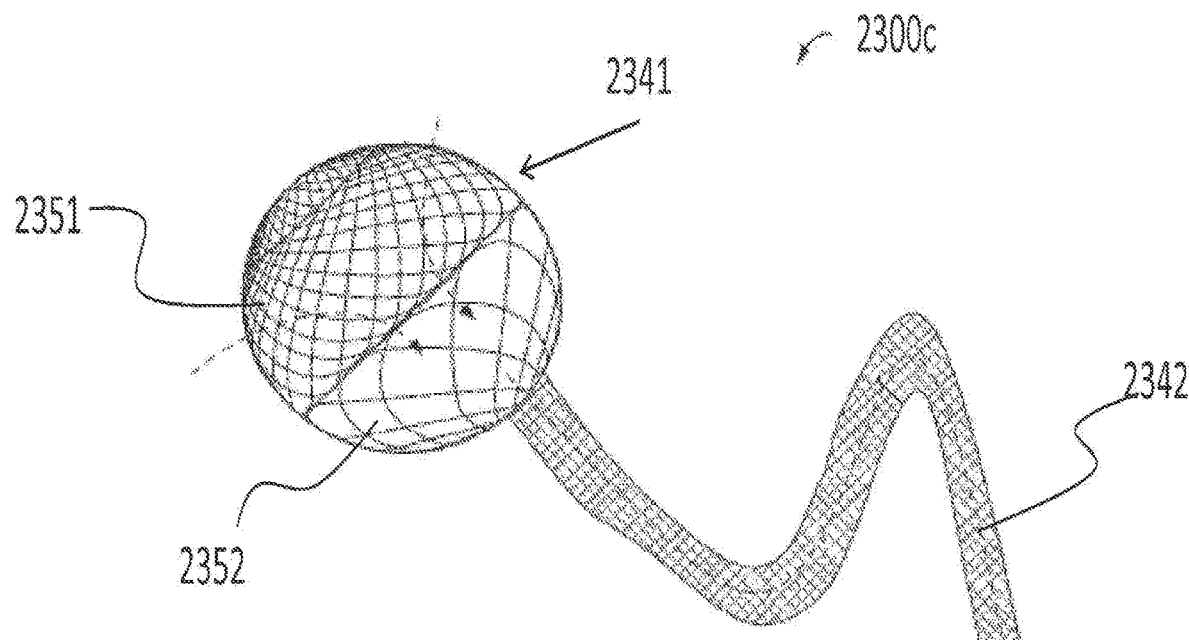
FIG. 23C is an illustration of one embodiment of an intragastric device in a post-deployment configuration having a wire mesh structure and a sleeve coupled to the wire mesh structure, wherein the upper portion of the wire mesh structure has a greater radial strength than the lower portion.

FIG. 23C is an illustration of one embodiment of an intragastric device 2300c in a post-deployment configuration having a wire mesh structure 2341 and a sleeve 2342 coupled to the wire mesh structure 2341, wherein the upper portion 2351 of the wire mesh structure 2341 has a greater radial strength than the lower portion 2352. The upper portion 2351 has a greater radial force that is provided by its denser weave pattern when compared with the weave pattern of the lower portion 2352. The upper portion 2351 of the wire mesh structure 2341 comprises a weave pattern that provides the upper portion 2351 with a radial strength great enough to prevent it from being substantially compressed by gastric contractions, thereby resisting significant distortion and maintaining its shape. In one embodiment, the upper portion 2351 includes a plurality of openings to allow food to enter the device. The less dense weave pattern of the lower portion 2352 allows the force of gastric contractions to pass through the lower portion 2352 and reach the food inside, helping to push the food down through the wire mesh structure 2341 and into the sleeve 2342. The wire mesh lower portion 2352 has enough radial force to maintain its shape in the absence of gastric contractions, but it does not resist distortion caused by the contractions when they occur. The gastric contractions are transmitted to the lumen of the wire mesh lower portion 2352 to cause agitation and active propulsion of the food within the lower portion 2352 through an opening at its distal end and into the sleeve 2342. Antral contractions squeeze the food out of the lower portion 2352 and into the sleeve 2342. In various embodiments, the differential radial strength can be constructed by using different size wires or by using different mesh weave patterns.

Figure 24A:
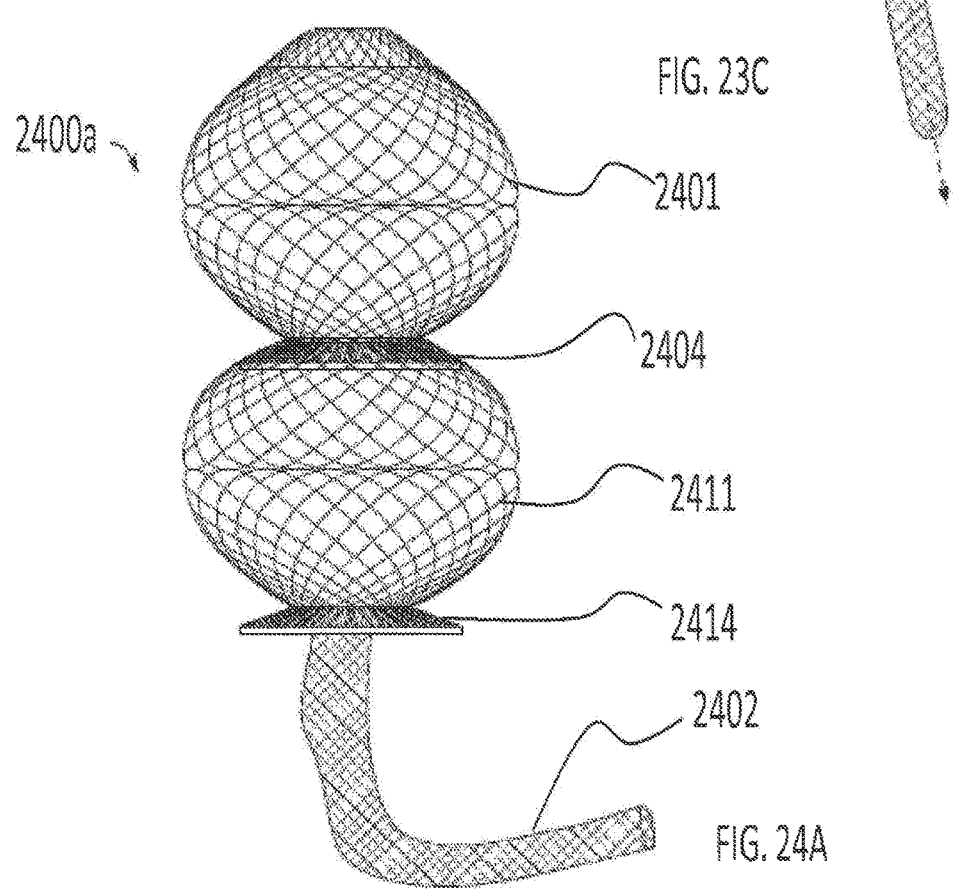
FIG. 24A is an illustration of a first exemplary double-wire mesh structure intragastric device in a post-deployment configuration in accordance with one embodiment of the present specification.

FIG. 24A is an illustration of a first exemplary double-wire mesh intragastric device 2400a in a post-deployment configuration in accordance with one embodiment of the present specification. The pictured embodiment includes a first wire mesh structure 2401 positioned on top of a second wire mesh structure 2411 and a sleeve 2402 coupled to the distal end of the second wire mesh structure 2411. A first anti-migration component 2404 at the base of the first wire mesh structure 2401 rests inside the second wire mesh structure 2411 and functions to couple the two wire mesh structures 2401, 2411 together. The first anti-migration component 2404 also helps to prevent the second wire mesh structure 2411 from being compressed by gastric contractions and keeps the device 2400a out of the pylorus. A second anti-migration component 2414, at the base of the second wire mesh structure 2411, acts to prevent the entirety of the device 2400a from being passed through the pylorus. Food first passes through openings in the top of the combined intragastric device 2400a and is sequestered in the first wire mesh structure 2401. The food then slowly passes into, and is sequestered in, the second wire mesh structure 2411. Finally, the food slowly releases through the openings in the bottom of the combined intragastric device 2400a and back into the stomach. The combined wire mesh structures 2401, 2411 work together to occupy an increased volume in a patient's stomach and further delay the passage of food through the gastrointestinal tract. The combined two wire mesh structures 2401, 2411 also act to induce satiety even more quickly and induce a longer lasting satiety than a single mesh structure device.

Figure 24B:
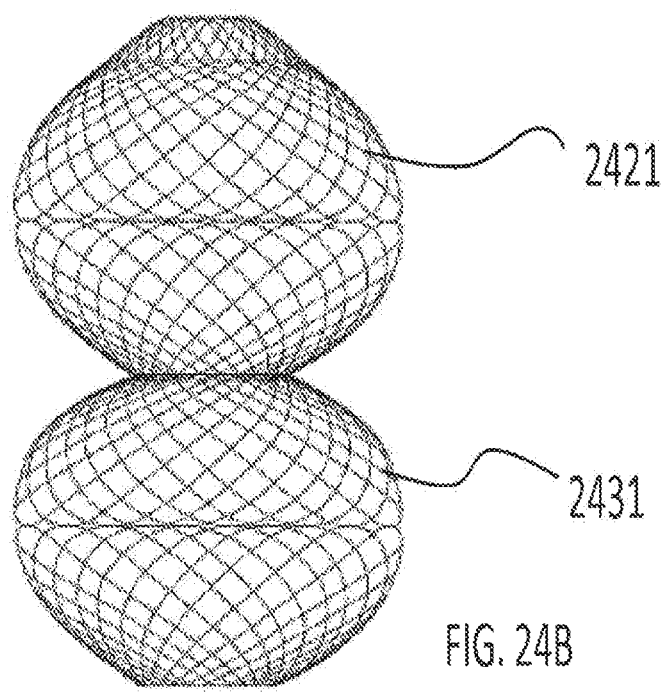
FIG. 24B is an illustration of a second exemplary double-wire mesh structure intragastric device in a post-deployment configuration in accordance with one embodiment of the present specification.

FIG. 24B is an illustration of a second exemplary double-wire mesh intragastric device 2400b in a post-deployment configuration in accordance with one embodiment of the present specification. The pictured embodiment includes a first wire mesh structure 2421 positioned on top of a second wire mesh structure 2431. The two wire mesh structures 2421, 2431 work together to occupy an increased volume in a patient's stomach and further delay the passage of food through the gastrointestinal tract.

Figure 24C:
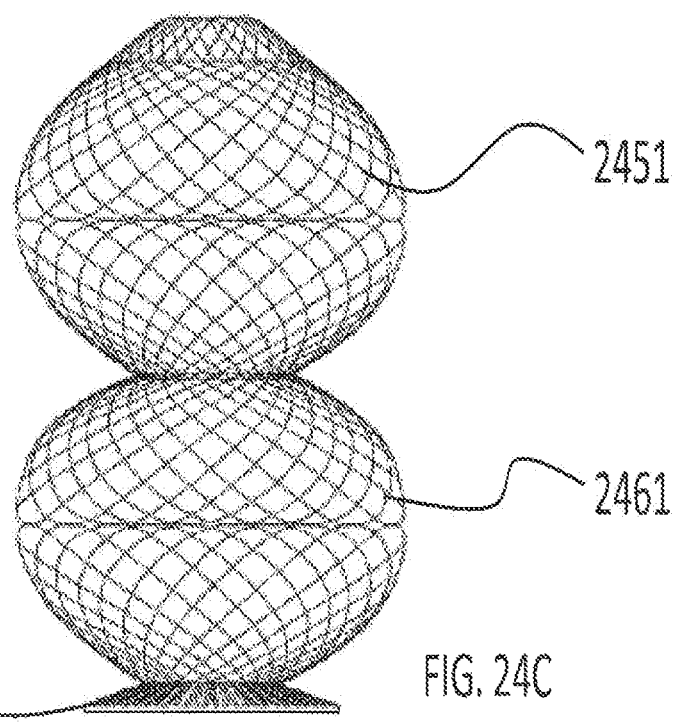
FIG. 24C is an illustration of a third exemplary double-wire mesh structure intragastric device in a post-deployment configuration in accordance with one embodiment of the present specification.

FIG. 24C is an illustration of a third exemplary double-wire mesh intragastric device 2400c in a post-deployment configuration in accordance with one embodiment of the present specification. The pictured embodiment includes a first wire mesh structure 2451 positioned on top of a second wire mesh structure 2461. An anti-migration component 2464 at the base of the second wire mesh structure 2461 acts to prevent the entirety of the device 2400c from being passed through the pylorus. The two wire mesh structures 2451, 2461 work together to occupy an increased volume in a patient's stomach and further delay the passage of food through the gastrointestinal tract.

FIG. 24D is an illustration of a fourth exemplary double-wire mesh intragastric device 2400d in a post-deployment configuration in accordance with one embodiment of the present specification. The pictured embodiment includes a first wire mesh structure 2471 positioned on top of a second wire mesh structure 2481. A first anti-migration component 2474 at the base of the first wire mesh structure 2471 rests inside the second wire mesh structure 2481 and functions to couple the two wire mesh structures 2471, 2481 together. The first anti-migration component 2474 also helps to prevent the second wire mesh structure 2481 from being compressed by gastric contractions and keeps the device 2400d out of the pylorus. A second anti-migration component 2484 at the base of the second wire mesh structure 2481 acts to prevent the entirety of the device 2400d from being passed through the pylorus. The two wire mesh structures 2471, 2481 work together to occupy an increased volume in a patient's stomach and further delay the passage of food through the gastrointestinal tract.

FIG. 24E is an illustration of a fifth exemplary double-wire mesh intragastric device 2400e in a post-deployment configuration in accordance with one embodiment of the present specification. The pictured embodiment includes a first wire mesh structure 2491 positioned on top of a second wire mesh structure 2499 and a sleeve 2492 coupled to the distal end of the second wire mesh structure 2499. An anti-migration component 2494 at the base of the second wire mesh structure 2499 acts to prevent the entirety of the device 2400e from being passed through the pylorus. The two wire mesh structures 2491, 2499 work together to occupy an increased volume in a patient's stomach and further delay the passage of food through the gastrointestinal tract.

FIG. 25 is an illustration of one embodiment of an intragastric device 2500 in a post-deployment configuration having a wire mesh structure 2501, anti-migration disc 2504, and sleeve 2502, depicting a membrane 2505 covering the sleeve 2502 and a lower portion of the wire mesh structure 2501. In the pictured embodiment, the membrane 2505 covers the entire outer surface of the sleeve 2502 with the exception of a second opening 2525 along its length and proximate its distal end. The membrane 2505 covering the sleeve 2502 extends onto a portion of the wire mesh structure 2501. In various embodiments, the membrane 2505 covers 0 to 100% of the outer surface of the wire mesh structure 2501, with the exception of a first opening 2510 at the proximal end of the wire mesh structure 2501.

In one embodiment, the wire mesh structure 2501 includes a first valve 2530 at the first opening 2510 to prevent reflux of food into the esophagus. In one embodiment, the wire mesh structure 2501 further includes a second valve 2533 at the junction between the wire mesh structure 2501 and the sleeve 2502 to direct food into the sleeve 2502 and prevent the flow of food back into the wire mesh structure 2501. In one embodiment, the sleeve 2502 includes one or more valves 2527 to prevent retrograde flow of food proximally within the sleeve 2502.

FIG. 26A is an illustration of a portion of a patient's gastrointestinal tract following a sleeve gastrectomy procedure. A large portion of the stomach 2605 along the greater curvature has been removed, effectively creating a "sleeve" 2610 along the lesser curvature. The sleeve 2610 connects the esophagus 2615 with the duodenum 2620. The procedure eliminates the reservoir function of the stomach, thereby limiting caloric intake and resulting in weight loss and control of diabetes.

FIG. 26B is an illustration of a portion of a patient's gastrointestinal tract following a roux-en-y gastric bypass (RGB) procedure. Most of the stomach 2607 and a proximal portion of the duodenum 2620 are resected and bypassed. A small gastric pouch 2608 is created and connected to the jejunum 2625, allowing food to pass from the esophagus 2615 via the pouch 2608 into the jejunum 2625. Pancreaticobiliary juices pass from the duodenum 2620 into the jejunum 2625 at an anastomosis point 2623. As with sleeve gastrectomy, the RGB procedure eliminates the reservoir function of the stomach, thereby limiting caloric intake and resulting in weight loss and control of diabetes.

Figure 27:
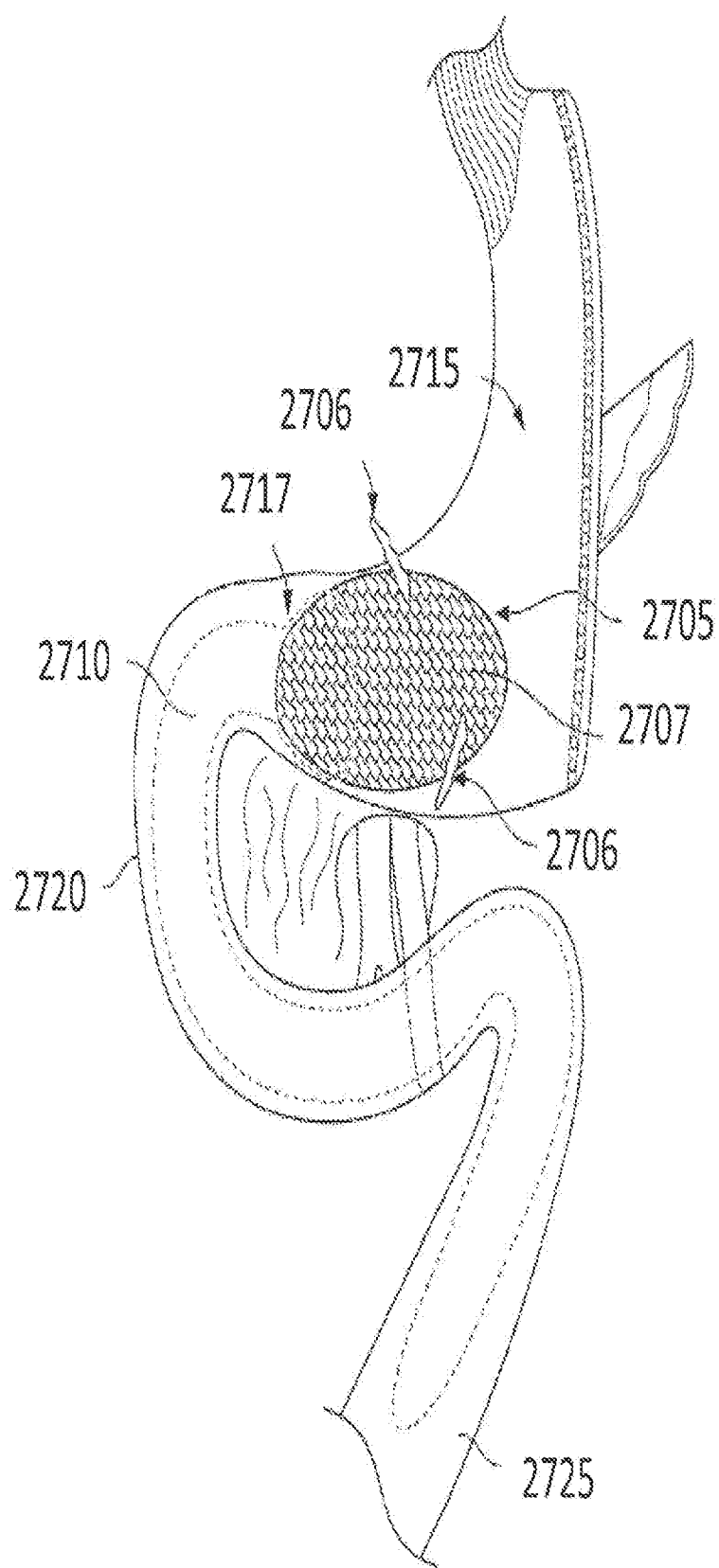
FIG. 27 is an illustration of an intragastric device with an attached device sleeve deployed in the stomach and duodenum following a sleeve gastrectomy procedure.

FIG. 27 is an illustration of one embodiment of an intragastric device 2705 with an attached device sleeve 2710 deployed in a stomach 2715 and duodenum 2720 following a sleeve gastrectomy procedure. In one embodiment, the device 2705 comprises a spherical or ovoid shaped wire mesh structure 2707 having a proximal end and a distal end and a membrane covering a portion of the wire mesh. A device sleeve 2710 is attached to the distal end of the wire mesh structure 2707 and passes through the pylorus 2717 and duodenum 2720 and into the jejunum 2725. In one embodiment, the wire mesh structure 2707 includes a plurality of small openings to allow for the passage of partially digested food into the device 2705, through the device sleeve 2710, and into the jejunum 2725. In one embodiment, the device 2705 includes one or more anchoring elements 2706 that anchor the device 2705 into the created gastric sleeve, preventing migration of the device 2705. In one of the embodiment, an anti-migration structure is attached at the junction of the mesh and sleeve and prevents the device from migrating out of the stomach.

The device acts to further restrict the capacity of the gastric sleeve following the sleeve gastrectomy procedure. The device sequesters the partially digested food and passes it through the device sleeve, thereby bypassing the duodenum. This routing of food effectively creates a duodenal bypass and biliopancreatic dissociation, increasing the weight loss benefits provided by the sleeve gastrectomy procedure.

Figure 28A:
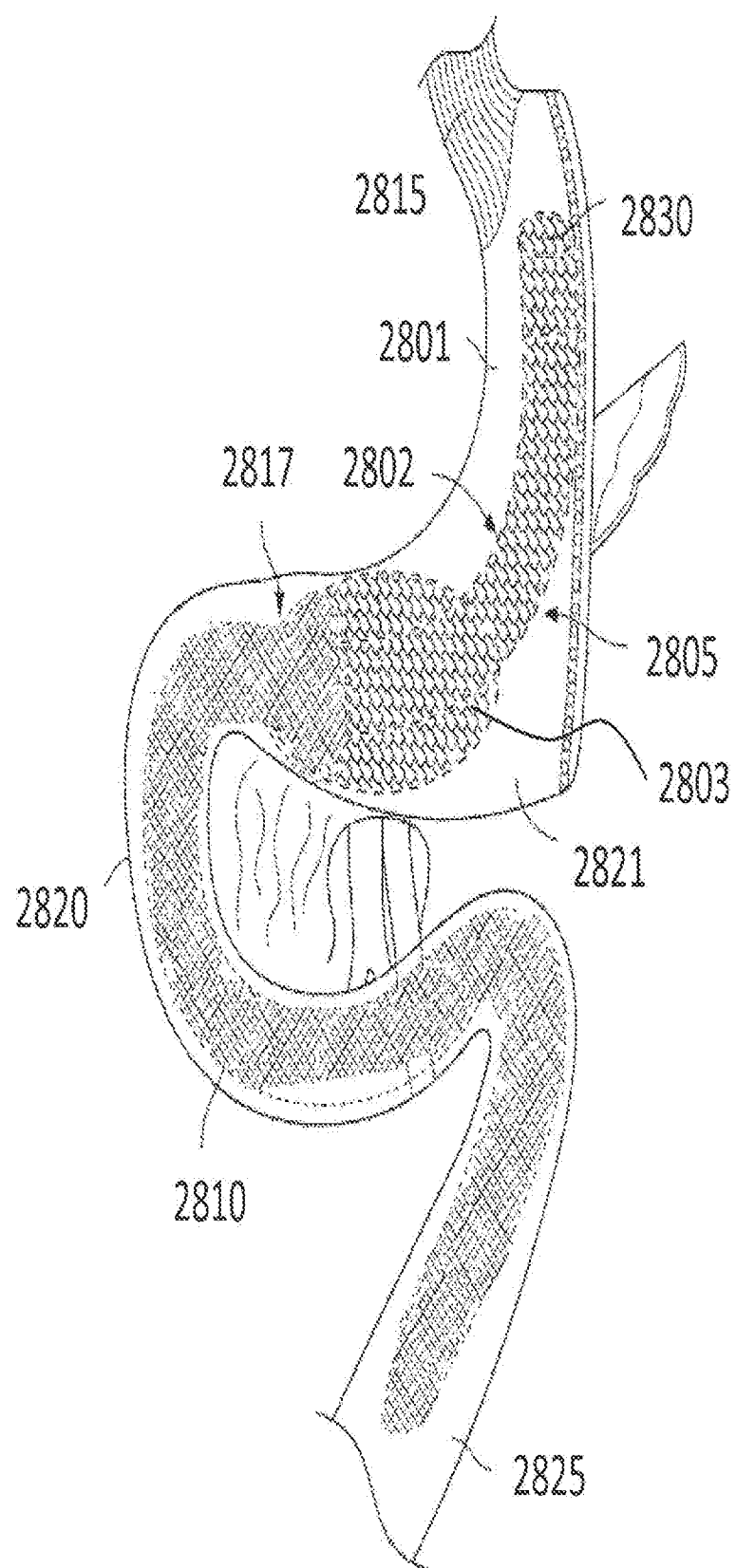
FIG. 28A is an illustration of another embodiment of an intragastric device with a proximal tubular end and an attached device sleeve deployed in the stomach and duodenum following a sleeve gastrectomy procedure.

FIG. 28A is an illustration of another embodiment of an intragastric device 2805 with a proximal tubular end 2802 and an attached device sleeve 2810 deployed in a stomach 2801 and duodenum 2820 following a sleeve gastrectomy procedure. In one embodiment, the device 2805 comprises an elongate, club shaped tube 2802 having a proximal end and a spherical distal end 2803. In one embodiment, the distal end has a diameter greater than that of the proximal end and rests in the distal antrum 2821. The tube 2802 is designed to conform to the shape of the created gastric sleeve 2801 and is placed with its proximal end just distal to the esophagus 2815. The tube 2802 includes a first opening at its proximal end to receive food from the esophagus 2815 and a second opening at its distal end to release food into the duodenum 2820 or into an attached device sleeve 2810. In one embodiment, the proximal end includes a valve 2830 to allow food to enter the tube 2802 and to prevent the reflux of gastric contents into the esophagus 2815. In one embodiment, an optional device sleeve 2810 is attached to the distal end of the tube 2802 and passes through the pylorus 2817 and duodenum 2820 and into the jejunum 2825. The device 2805 acts to further restrict the capacity of the gastric sleeve 2801 following the sleeve gastrectomy procedure. The device 2805 sequesters the partially digested food and passes it through the device tube 2802 and optional sleeve 2810, thereby completely bypassing the stomach 2801 and duodenum 2820. FIG. 28A depicts a cross-section of the device 2805 showing the tubular proximal portion 2802 which curves outward to form the spherical distal end 2803, with the sleeve 2010 attached to the spherical distal end 2803.

Figure 28B:
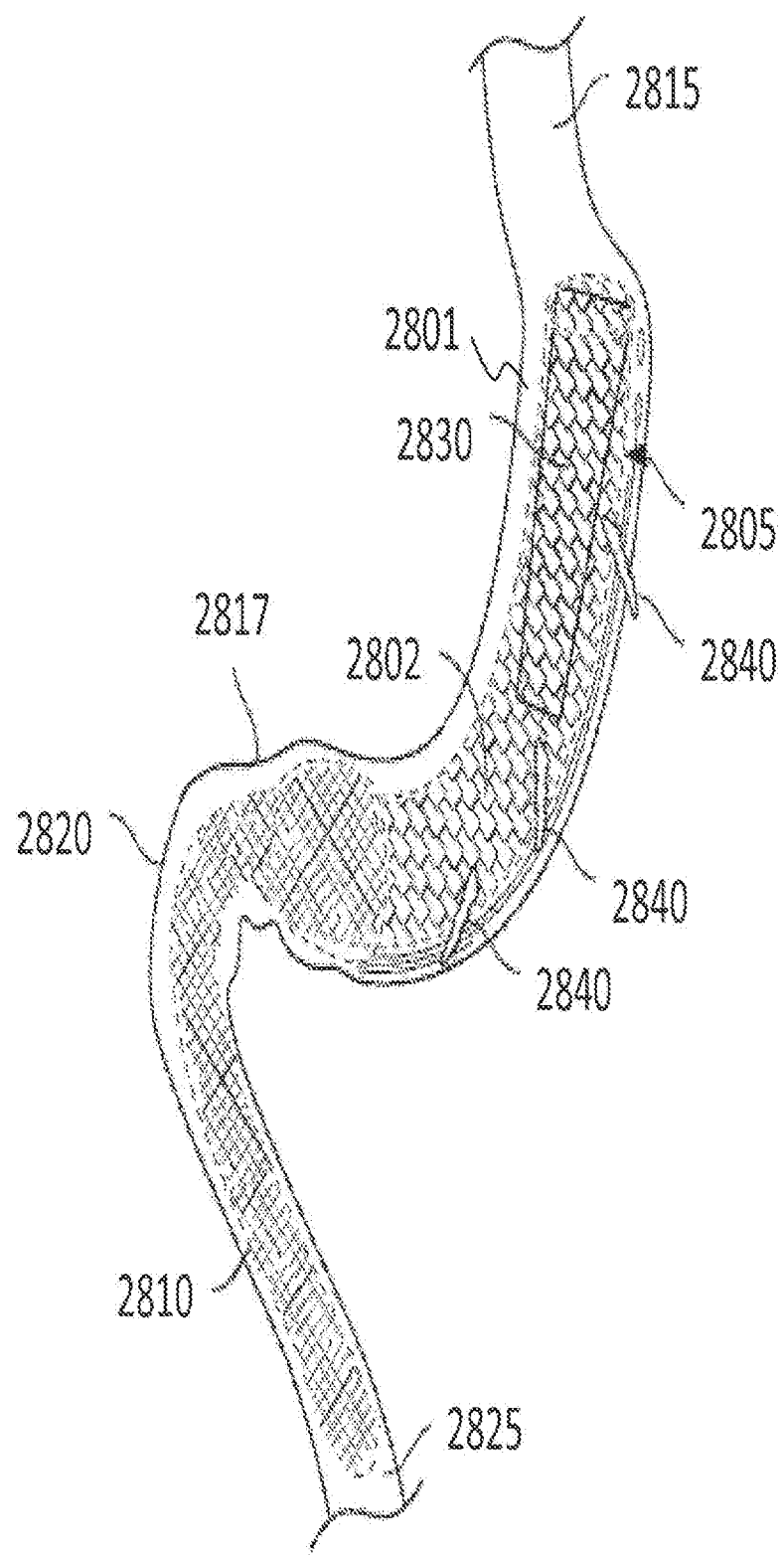
FIG. 28B is an illustration of an embodiment of an intragastric device with a proximal tubular end and an attached device sleeve similar to the device of the embodiment of FIG. 28A, depicting the device deployed in the stomach and duodenum following a sleeve gastrectomy procedure.

FIG. 28B is an illustration of an embodiment of an intragastric device 2805 with a proximal tubular end 2802 and an attached device sleeve 2810 similar to the device of the embodiment of FIG. 28A, depicting the device 2805 deployed in a stomach 2801 and duodenum 2820 following a sleeve gastrectomy procedure. In one embodiment, the device 2805 comprises an elongate, club shaped tube 2802 having a proximal end and a distal end. In one embodiment, the distal end has a diameter greater than that of the proximal end. The tube 2802 is designed to conform to the shape of the created gastric sleeve and is placed with its proximal end just distal to the esophagus 2815. The tube 2802 includes a first opening at its proximal end to receive food from the esophagus 2815 and a second opening at its distal end to release food into the duodenum 2820 or into an attached device sleeve 2810. In one embodiment, the proximal end includes a valve 2830 to allow food to enter the tube 2802 and to prevent the reflux of gastric contents into the esophagus 2815. In one embodiment, the device 2805 includes one or more anchors 2840 along the length of the tube 2802 to anchor the device 2805 in the created gastric sleeve and prevent migration. In one embodiment, an optional device sleeve 2810 is attached to the distal end of the tube 2802 and passes through the pylorus 2817 and duodenum 2820 and into the jejunum 2825. The device 2805 acts to further restrict the capacity of the gastric sleeve 2801 following the sleeve gastrectomy procedure. The device 2805 sequesters the partially digested food and passes it through the device tube 2802 and optional sleeve 2810, thereby completely bypassing the stomach 2801 and duodenum 2820.

Figure 29:
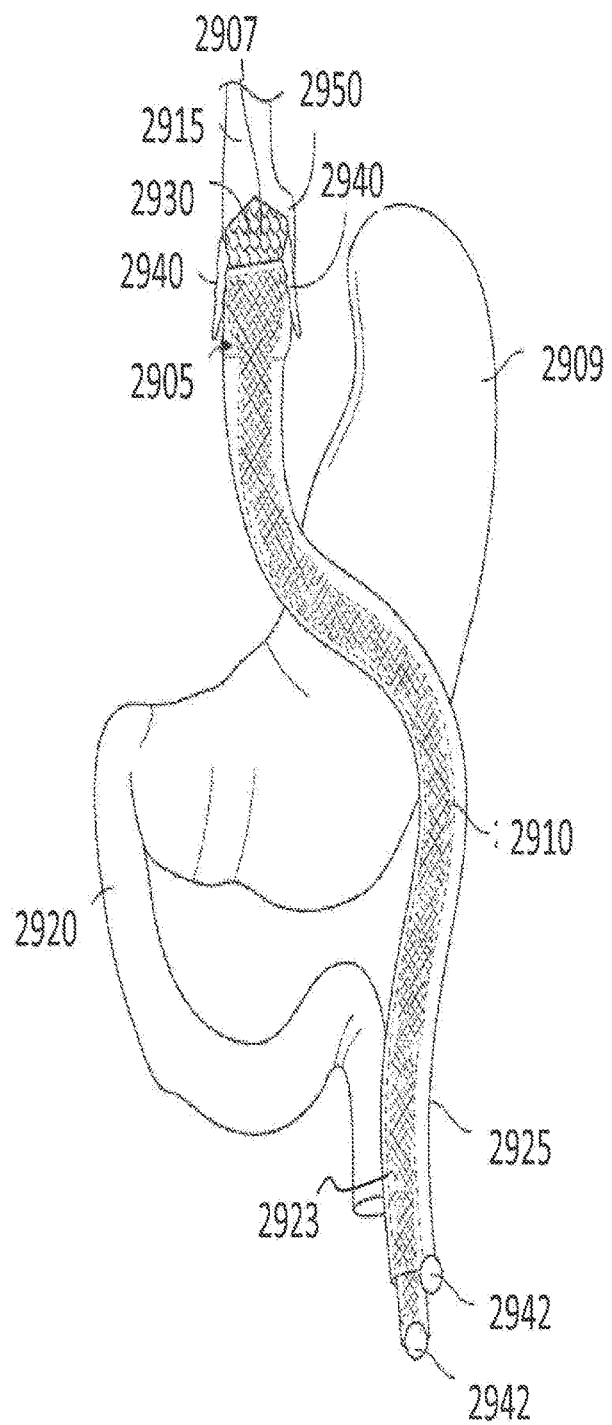
FIG. 29 is an illustration of another embodiment of an intragastric device with an attached device sleeve deployed in the gastric pouch following a roux-en-y gastric bypass (RGB) procedure.

FIG. 29 is an illustration of another embodiment of an intragastric device 2905 with an attached device sleeve 2910 deployed in the gastric pouch 2950 following a roux-en-y gastric bypass (RGB) procedure. In one embodiment, the device 2905 comprises a spherical wire mesh structure 2907 having a proximal end and a distal end. The proximal end of the wire mesh structure 2907 has one or more openings to allow food to enter from the esophagus 2915. In one embodiment, the wire mesh structure 2907 has one opening at its proximal end for food to enter and includes an anti-reflux valve 2930 at the opening to prevent food from refluxing into the esophagus 2915. The distal end of the structure 2907 is covered by a membrane that prevents food from exiting through the wire mesh. An opening is positioned at the bottom of the distal end of the wire mesh structure 2907. In one embodiment, a device sleeve 2910 is attached to the distal end of the wire mesh structure 2907. The device sleeve 2910 extends through the jejunum 2925 to a point beyond the anastomosis 2923 of the jejunum 2925 with the duodenum 2920. Food passes from the esophagus 2915 into the wire mesh structure 2907 and through the device sleeve 2910, bypassing the stomach 2909, duodenum 2920, and proximal portion of the jejunum 2925. The device assists with weight loss by further slowing the emptying of food from the gastric pouch 2950.

In one embodiment, the device 2905 further includes one or more anchoring mechanisms 2940 to anchor the device 2905 in the gastric pouch 2950 and prevent migration. In one embodiment, the anchoring mechanisms 2940 are attached to the wire mesh structure 2907. In one embodiment, the anchoring mechanisms 2940 are barbs. In one embodiment, the device 2905 further includes one or more weighting mechanisms 2942 attached to the device sleeve 2910 to position the device sleeve 2910 in the small bowel. In various embodiments, the weighting mechanisms 2942 include any one or combination of metal beads, metal rings and fluid filled pockets. Other mechanisms known in the art can be used to add weight to the device sleeve 2910.

Figure 30:
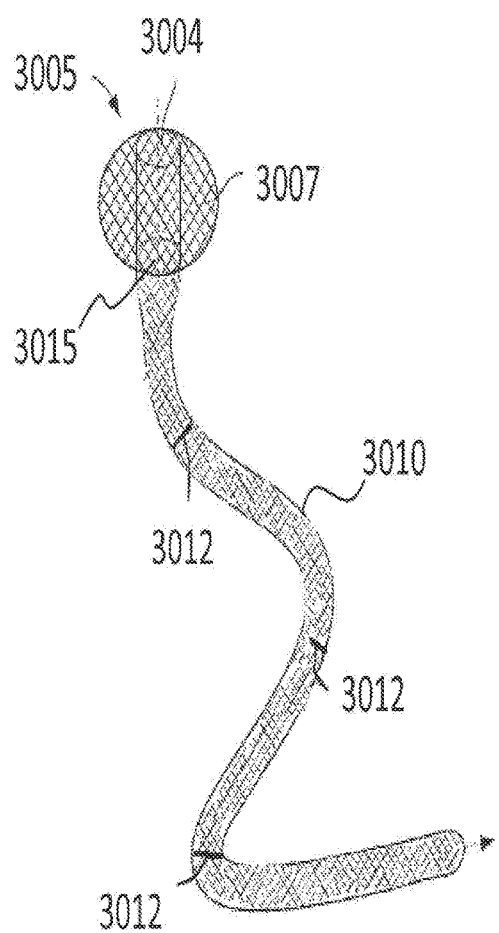
FIG. 30 is an illustration of another embodiment of an intragastric device in a post-deployment configuration with an attached device sleeve for implantation into the gastric pouch of a patient following a roux-en-y gastric bypass (RGB) procedure.

FIG. 30 is an illustration of another embodiment of an intragastric device 3005 in a post-deployment configuration with an attached device sleeve 3010 for implantation into the gastric pouch of a patient following a roux-en-y gastric bypass (RGB) procedure. In the embodiment depicted in FIG. 30, the device sleeve 3010 is attached to the proximal opening 3004 of the wire mesh structure 3007 and extends distally through the structure 3007 and into the jejunum. In one embodiment, the device sleeve 3010 extends at least 12 inches beyond the distal end of the wire mesh structure 3007. The wire mesh structure 3007 allows for anchoring of the device 3005 in the gastric pouch. Food passes from the esophagus into the proximal opening 3004 of the device 3005, through the device sleeve 3010, and into the small intestine. In one embodiment, the device sleeve 3010 includes one or more valves 3012 to prevent retrograde flow of food or small intestine contents. In various embodiments, a portion or whole of the wire mesh is covered by a membrane. FIG. 30 depicts a cross-section of an embodiment of the device 3005 where the spherical mesh 3007 is formed by the everted proximal end of the device 3005, creating the proximal opening 3004. The sleeve 3010 is attached to a distal opening 3015 of the mesh.

Figure 31:
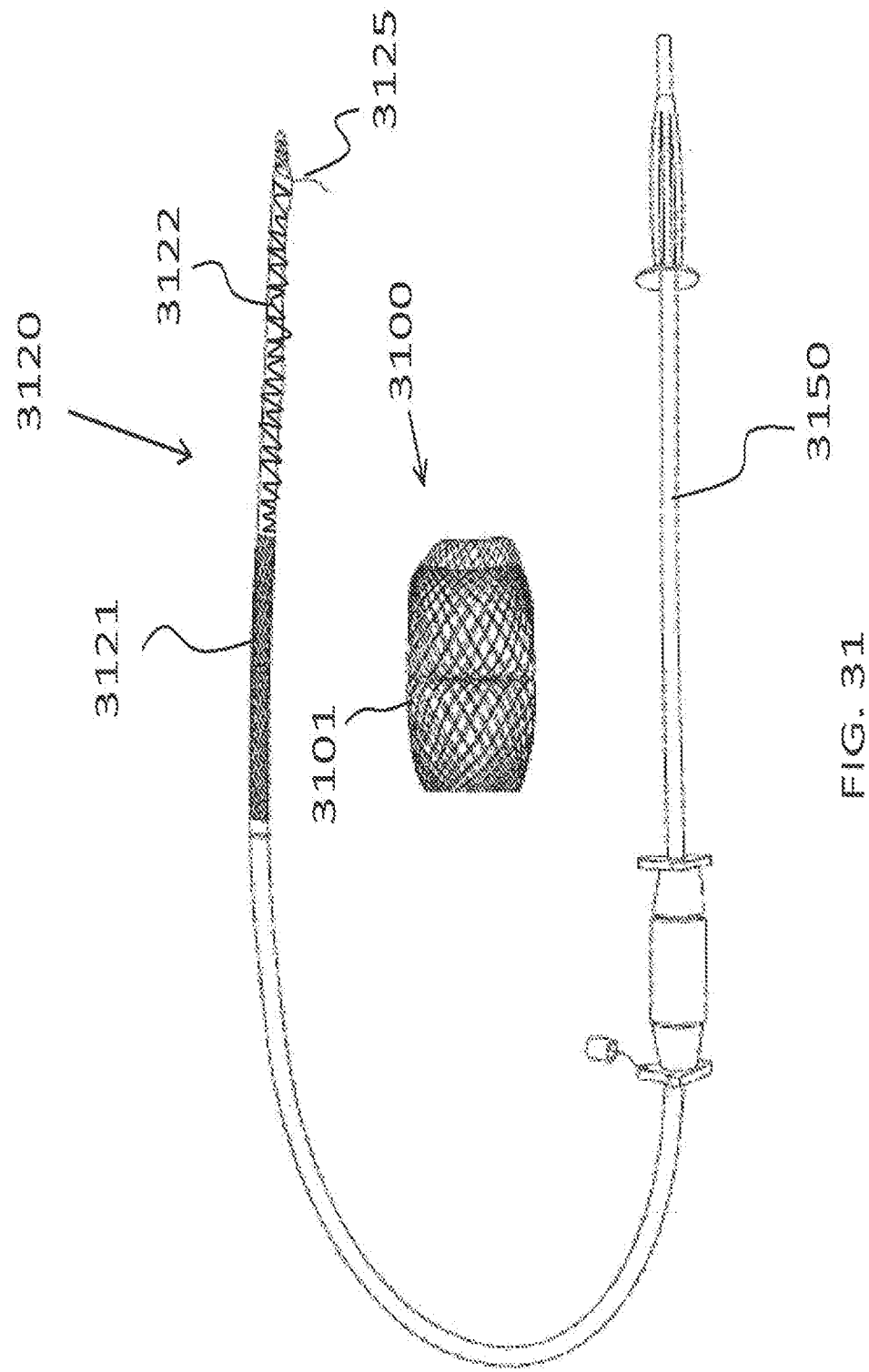
FIG. 31 is an illustration of an expanded wire mesh structure of a first intragastric device and a constricted wire mesh structure of a second intragastric device coupled to the distal end of an implantation catheter, in accordance with one embodiment of the present specification.

FIG. 31 is an illustration of an expanded wire mesh structure 3101 of a first intragastric device 3100 in a post-deployment configuration and a constricted wire mesh structure 3121 of a second intragastric device 3120 coupled to the distal end of an implantation catheter 3150, in accordance with one embodiment of the present specification. Second intragastric device 3120 also includes a sleeve 3122 coupled to the distal end of the wire mesh structure 3121. The wire mesh structure 3121 and sleeve 3122 of the second intragastric device 3120 have been compressed and slid coaxially onto the distal end of the implantation catheter 3150. In the pictured embodiment, the wire mesh structure 3121 and sleeve 3122 are maintained in their compressed configuration by a suture line or thread 3125 that has been wrapped about both the wire mesh structure 3121 and sleeve. Once the device 3120 has been positioned in the stomach and duodenum of a patient, the suture line or thread 3125 is unwound and the wire mesh structure 3121 and sleeve 3122 expand to their deployed configuration. As the device 3120 expands, it is released from the catheter 3150. The catheter 3150 is then removed from the patient. In another embodiment, the compressed wire mesh structure and sleeve are held in place over the implantation catheter via an overlaying coaxial sheath. Upon deployment, the sheath is either unzipped or torn in a vertical direction to release the device.

Figure 32:
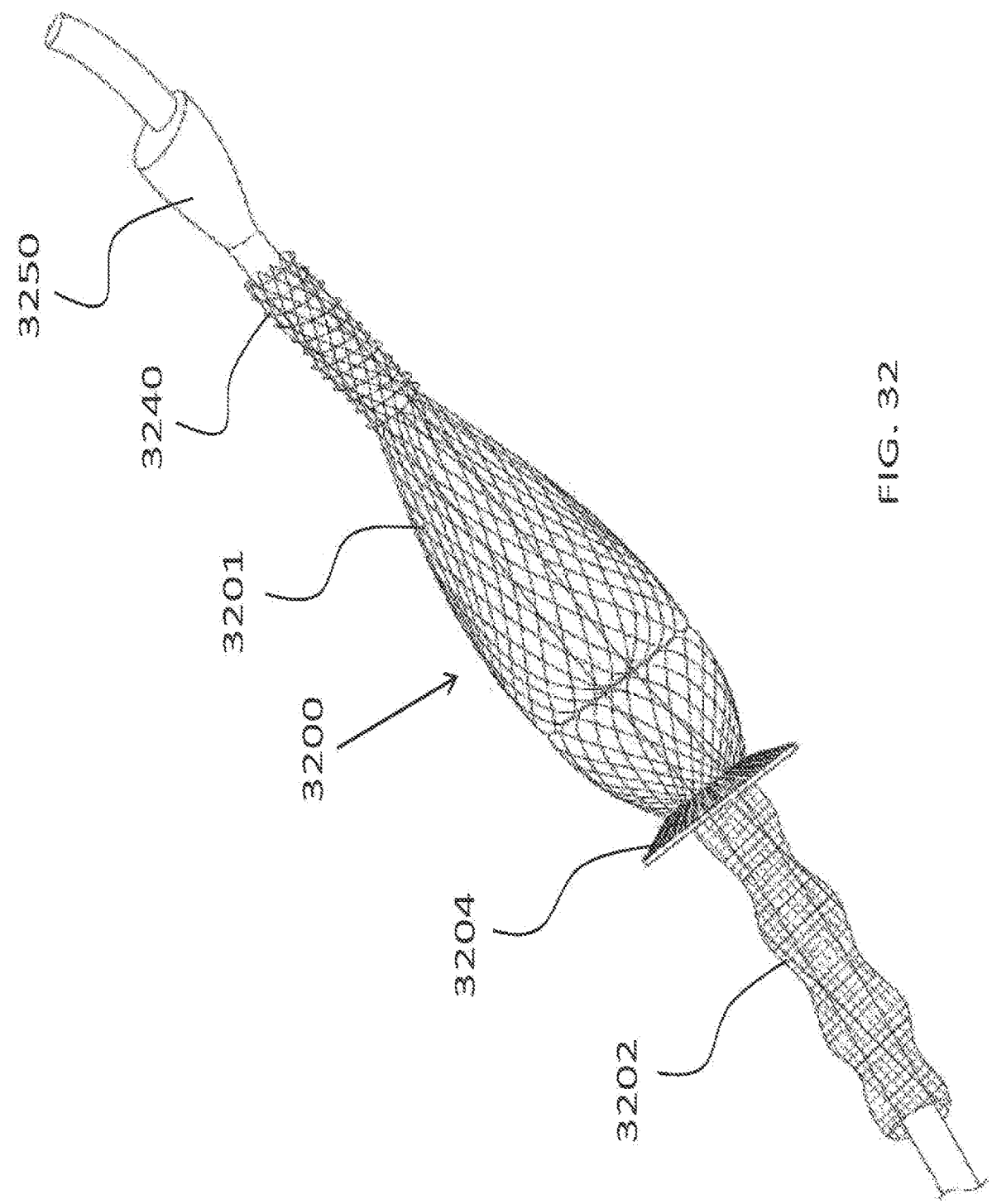
FIG. 32 is an illustration of an intragastric device with a partially constrained wire mesh structure on a delivery catheter, in accordance with one embodiment of the present specification.

FIG. 32 is an illustration of an intragastric device 3200 with a partially constrained wire mesh structure 3201 on a delivery catheter 3250, in accordance with one embodiment of the present specification. The device 3200 also includes a coupled sleeve 3202 and anti-migration component 3204. In the pictured embodiment, the proximal end of the wire mesh structure 3201 is still constricted by a suture or thread 3240. The sleeve 3202, anti-migration component 3204, and a portion of the wire mesh structure 3201 have begun to expand as the constricting suture or thread has already been removed from these components.

Figure 33A:
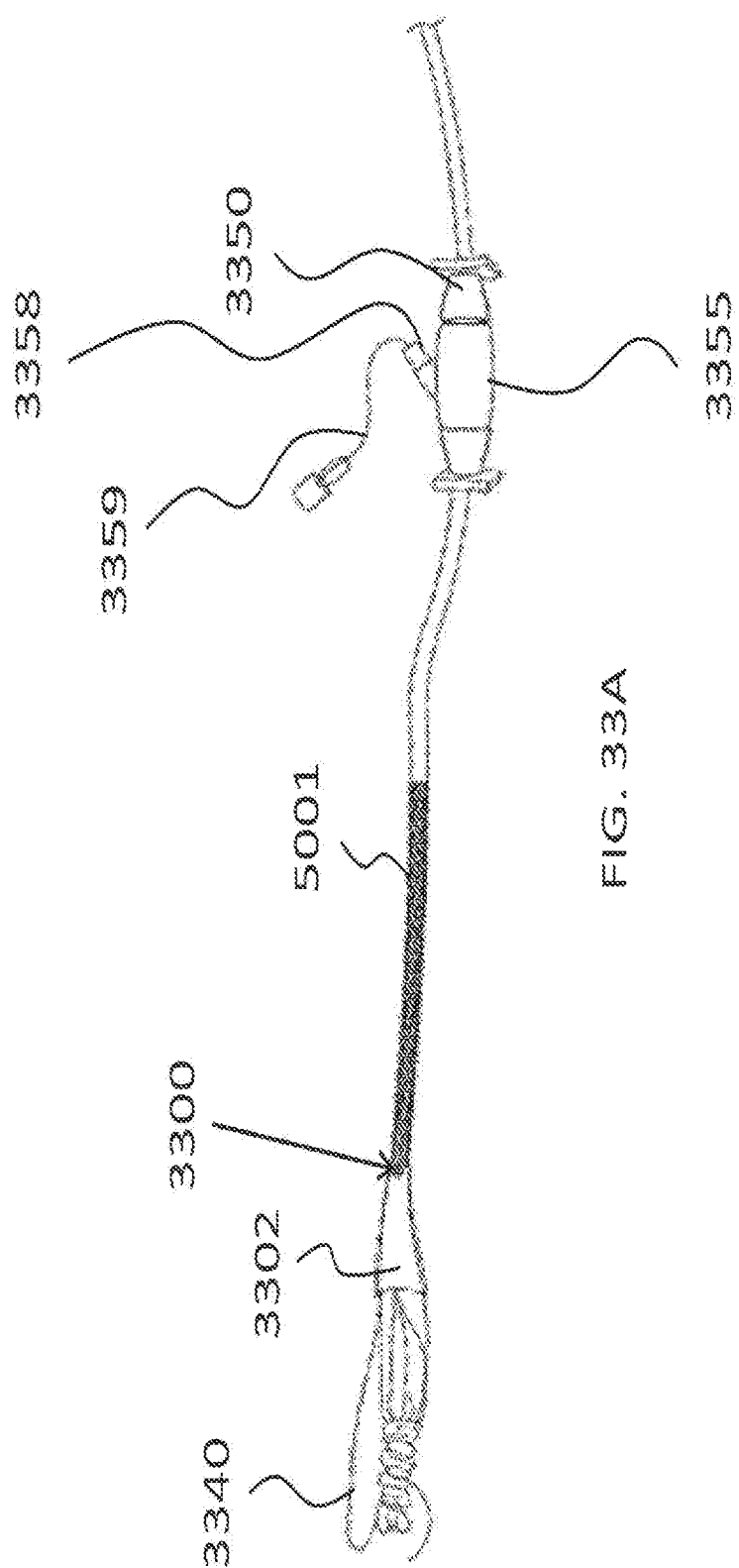
FIG. 33A is an illustration of a first exemplary delivery catheter for an intragastric device, in accordance with one embodiment of the present specification.

FIG. 33A is an illustration of a first exemplary delivery catheter 3350 for an intragastric device 3300, in accordance with one embodiment of the present specification. An intragastric device 3300, comprising a compressed wire mesh structure 3301 and sleeve 3302, is positioned coaxially about the distal end of the delivery catheter 3350. A suture or thread 3340 is wrapped about the device 3300, maintaining the device 3300 in its compressed configuration. The catheter 3350 further includes a thread port 3358 from which the suture or thread 3340 used to compress the intragastric device 3300 exits the proximal end of the catheter 3350. A physician pulls on the free end 3359 of the suture or thread 3340 to release the intragastric device 3300. In one embodiment, the catheter 3350 also includes a locking mechanism 3355 for locking the catheter 3350 in position.

Figure 33B:
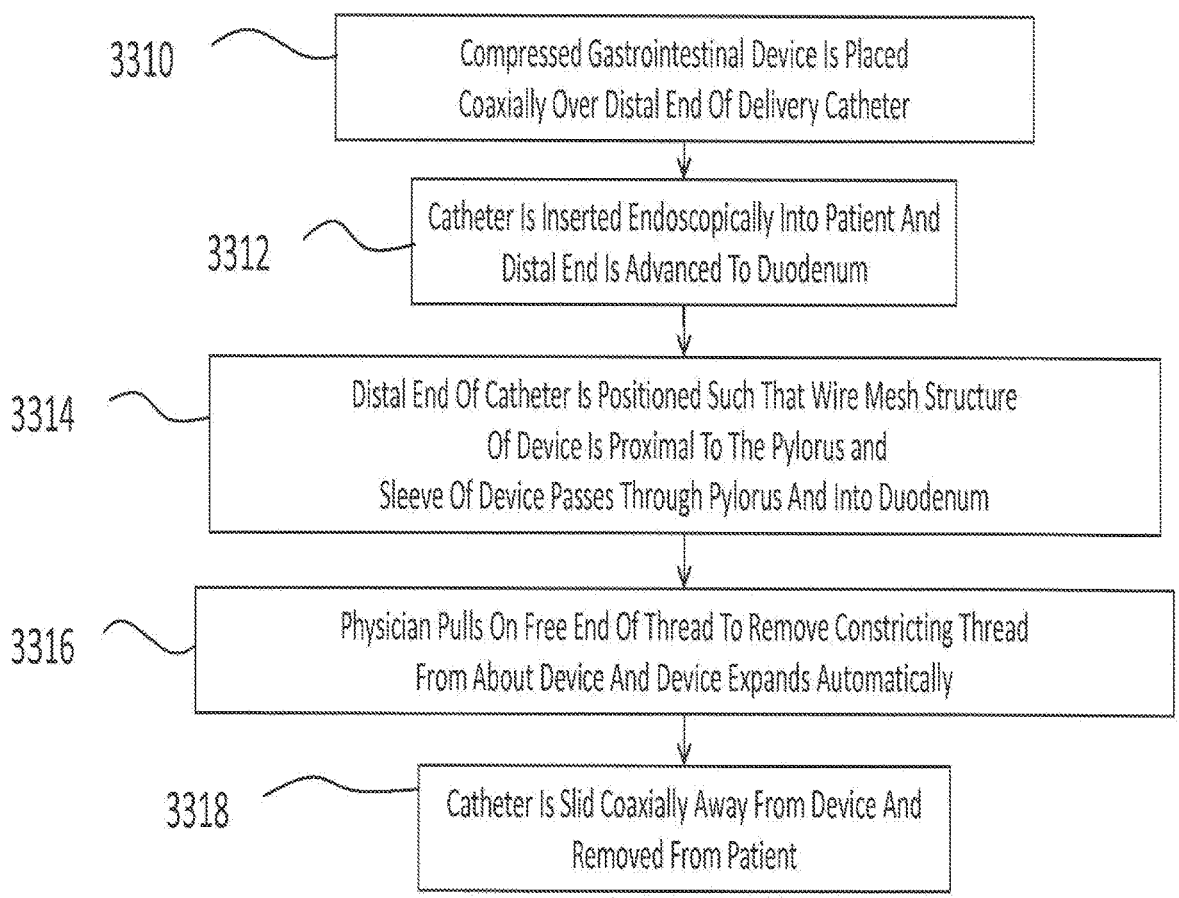
FIG. 33B is a flow chart illustrating the steps involved in delivering an intragastric device using the delivery catheter of FIG. 33A, in accordance with one embodiment of the present specification.

FIG. 33B is a flow chart illustrating the steps involved in delivering an intragastric device using the delivery catheter of FIG. 33A, in accordance with one embodiment of the present specification. At step 3310, a compressed intragastric device is placed coaxially over the distal end of the delivery catheter. The catheter is then inserted endoscopically into the patient and its distal end is advanced to the duodenum at step 3312. Then, at step 3314, the distal end of the catheter is positioned such that the wire mesh structure of the intragastric device is in the stomach just proximal to the pylorus and the sleeve of the device passes through the pylorus and into the duodenum. At step 3316, the physician pulls on the free end of the thread to remove the constricting thread from about the intragastric device, allowing the device to expand automatically. Finally, at step 3318, the catheter is slid coaxially away from the device and removed from the patient.

Figure 34A:
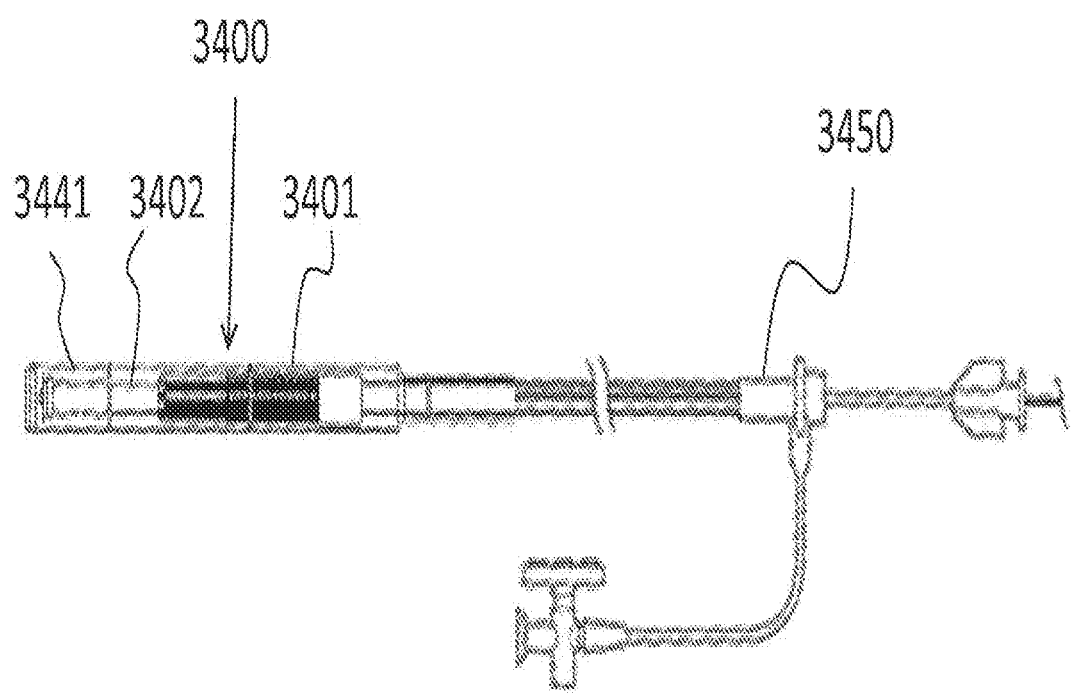
FIG. 34A is an illustration of a second exemplary delivery catheter for an intragastric device, in accordance with one embodiment of the present specification.

FIG. 34A is an illustration of a second exemplary delivery catheter 3450 for an intragastric device 3400, in accordance with one embodiment of the present specification. An intragastric device 3400, comprising a compressed wire mesh structure 3401 and sleeve 3402, is positioned coaxially about the distal end of the delivery catheter 3450. A zippered constraining sheath 3441 is coaxially positioned over the device 3400, maintaining the device 3400 in its compressed configuration.

Figure 34B:
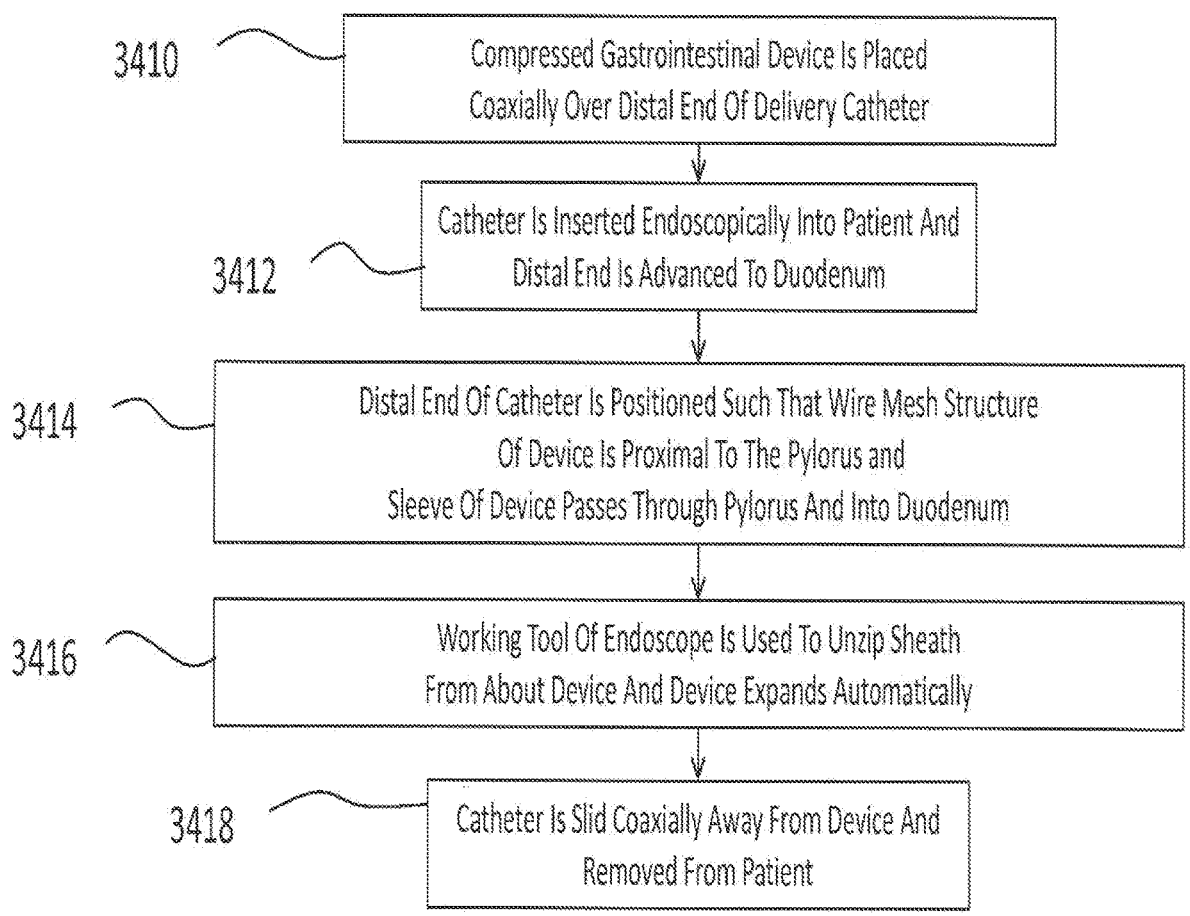
FIG. 34B is a flow chart illustrating the steps involved in delivering an intragastric device using the delivery catheter of FIG. 34A, in accordance with one embodiment of the present specification.

FIG. 34B is a flow chart illustrating the steps involved in delivering an intragastric device using the delivery catheter of FIG. 34A, in accordance with one embodiment of the present specification. At step 3410, a compressed intragastric device is placed coaxially over the distal end of the delivery catheter. The catheter is then inserted endoscopically into the patient and its distal end is advanced to the duodenum at step 3412. Then, at step 3414, the distal end of the catheter is positioned such that the wire mesh structure of the intragastric device is in the stomach just proximal to the pylorus and the sleeve of the device passes through the pylorus and into the duodenum. At step 3416, a working tool is used to unzip the compressing sheath from about the intragastric device, allowing the device to expand automatically. Finally, at step 3418, the catheter is slid coaxially away from the device and removed from the patient.

Alternatively, the sheath 3441 is a standard tubular sheath that is pulled off the wire-mesh device to release the wire-mesh device in the desired position.

Figure 35A:
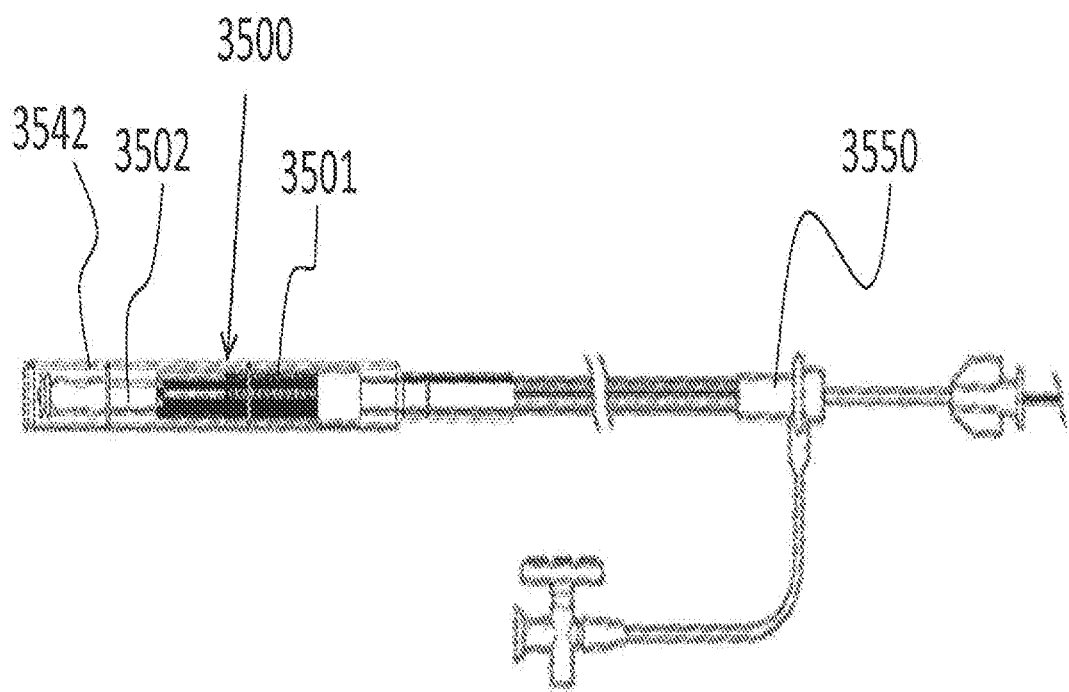
FIG. 35A is an illustration of a third exemplary delivery catheter for an intragastric device, in accordance with one embodiment of the present specification.

FIG. 35A is an illustration of a third exemplary delivery catheter 3550 for an intragastric device 3500, in accordance with one embodiment of the present specification. An intragastric device 3500, comprising a compressed wire mesh structure 3501 and sleeve 3502, is positioned coaxially about the distal end of the delivery catheter 3550. A tear-away constraining sheath 3542 is coaxially positioned over the device 3500, maintaining the device 3500 in its compressed configuration.

Figure 35B:
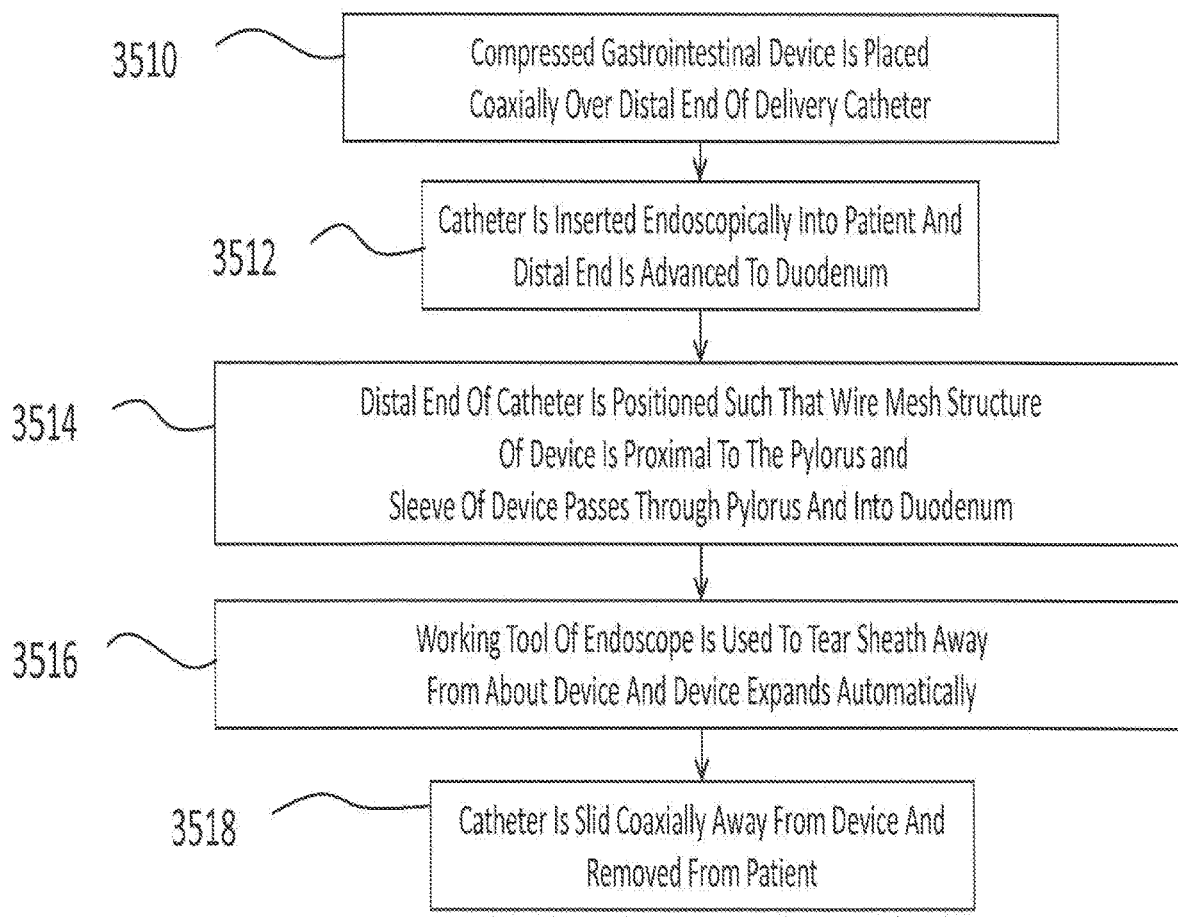
FIG. 35B is a flow chart illustrating the steps involved in delivering an intragastric device using the delivery catheter of FIG. 35A, in accordance with one embodiment of the present specification.

FIG. 35B is a flow chart illustrating the steps involved in delivering an intragastric device using the delivery catheter of FIG. 35A, in accordance with one embodiment of the present specification. At step 3510, a compressed intragastric device is placed coaxially over the distal end of the delivery catheter. The catheter is then inserted endoscopically into the patient and its distal end is advanced to the duodenum at step 3512. Then, at step 3514, the distal end of the catheter is positioned such that the wire mesh structure of the intragastric device is in the stomach just proximal to the pylorus and the sleeve of the device passes through the pylorus and into the duodenum. At step 3516, a working tool is used to tear away a compressing sheath from about the intragastric device, allowing the device to expand automatically. Finally, at step 3518, the catheter is slid coaxially away from the device and removed from the patient.

Figure 35C:
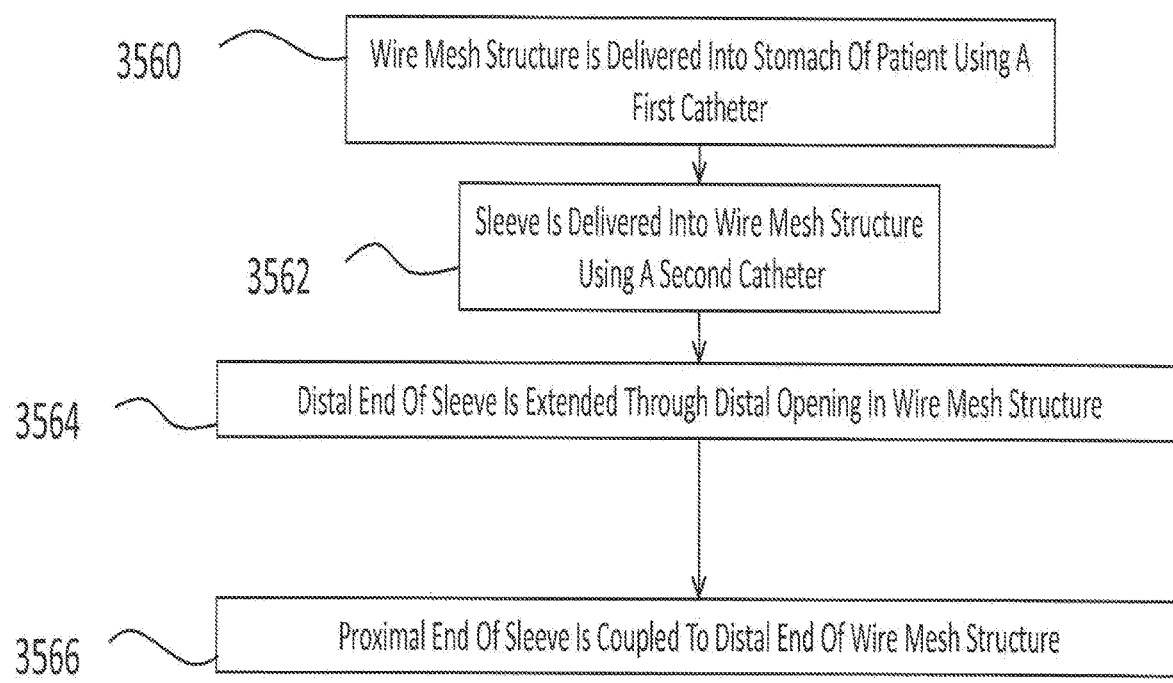
FIG. 35C is a flow chart illustrating the steps involved in delivering a wire mesh structure and sleeve separately and assembling an intragastric device within a patient's gastrointestinal tract.

FIG. 35C is a flow chart illustrating the steps involved in delivering a wire mesh structure and sleeve separately and assembling an intragastric device within a patient's gastrointestinal tract. At step 3560, the wire mesh structure is delivered into the stomach of a patient by a first catheter. Then, at step 3562, the sleeve is delivered into the wire mesh structure by a second catheter. The distal end of the sleeve is then extended through the distal opening in the wire mesh structure at step 3564. Finally, at step 3566, the proximal end of the sleeve is coupled to the distal end of the wire mesh structure.

FIG. 36 is an illustration of one embodiment of an intragastric device 3600 in a pre-deployment configuration. A catheter 3621 holds the compressed wire mesh structure 3622. The compressed wire mesh device is held in place by either a constraining catheter, sheath, or a silk suture or thread. The compressed wire mesh structure 3622 is made of vertical elements 3623 and horizontal elements 3624. Optionally the intragastric device can be a metal spiral that is cylindrical, comparable to a spring, in constrained positioned and a spiral metal sphere in the deployed shape. In one embodiment, the vertical elements 3623 and horizontal elements 3624 comprise a metal. In another embodiment, the vertical elements 3623 and horizontal elements 3624 comprise an alloy. In another embodiment, the vertical elements 3623 and horizontal elements 3624 comprise a polymer. In yet another embodiment, the vertical elements 3623 and horizontal elements 3624 comprise a shape memory metal. In yet another embodiment, the vertical elements 3623 and horizontal elements 3624 comprise a shape memory alloy. In yet another embodiment, the vertical elements 3623 and horizontal elements 3624 comprise a shape memory polymer. In one embodiment, a weight 3634 is positioned proximate to the bottom of the intragastric device. The weight serves to keep the intragastric device in the proper alignment when positioned in the stomach. Preferably, the weight is in a range of 1 to 500 grams, preferably between 10 and 50 grams. The catheter 3621 has optional ports for passage of wire, contrast or an endoscope located in the center of the catheter shaft. One of ordinary skill in the art would appreciate the structure and configuration of a compressed structure within a catheter that, after removing a constraining sheath, is permitted to expand at a treatment location.

Figure 37:
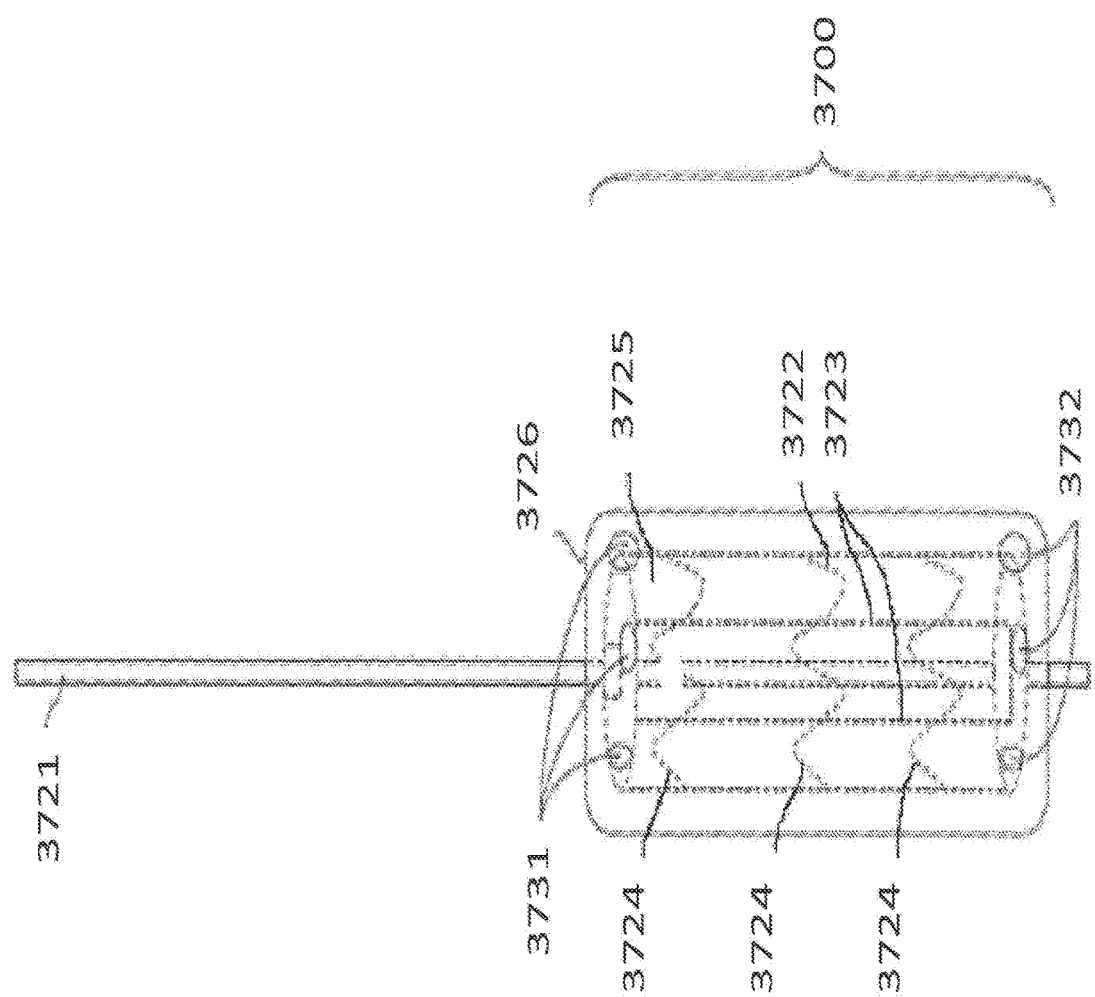
FIG. 37 is an illustration of another embodiment of an intragastric device in an exemplary pre-deployment configuration.

FIG. 37 is an illustration of another embodiment of an intragastric device 3700 in a pre-deployment configuration. A catheter 3721 holds the compressed wire mesh structure 3722. The compressed wire mesh structure 3722 is made of vertical elements 3723 and horizontal elements 3724. In one embodiment, the vertical elements 3723 and horizontal elements 3724 comprise metal. In another embodiment, the vertical elements 3723 and horizontal elements 3724 comprise an alloy. In another embodiment, the vertical elements 3723 and horizontal elements 3724 comprise a polymer. In yet another embodiment, the vertical elements 3723 and horizontal elements 3724 comprise a shape memory metal. In yet another embodiment, the vertical elements 3723 and horizontal elements 3724 comprise a shape memory alloy. In yet another embodiment, the vertical elements 3723 and horizontal elements 3724 comprise a shape memory polymer. In one embodiment, the compressed wire mesh structure 3722 is partially enveloped by a membrane 3726. The membrane 3726 is made up of a digestive resistance material.

In one embodiment, the membrane 3726 comprises latex. In another embodiment, the membrane 3726 comprises parylene. In another embodiment, the membrane 3726 comprises polyurethane. In another embodiment, the membrane 3726 comprises polytetrafluoroethylene (PTFE). In another embodiment, the membrane 3726 comprises fluorinated ethylene-propylene. In another embodiment, the membrane 3726 comprises Dacron. In yet another embodiment, the membrane 3726 comprises polyethylene terephthalate (PET). In one embodiment, the membrane 3726 comprises openings 3731 proximate the top of the intragastric device 3700 for receiving chyme and openings 3732 proximate the bottom of the intragastric device 3700 for slow release of the sequestered chyme.

Figure 38:
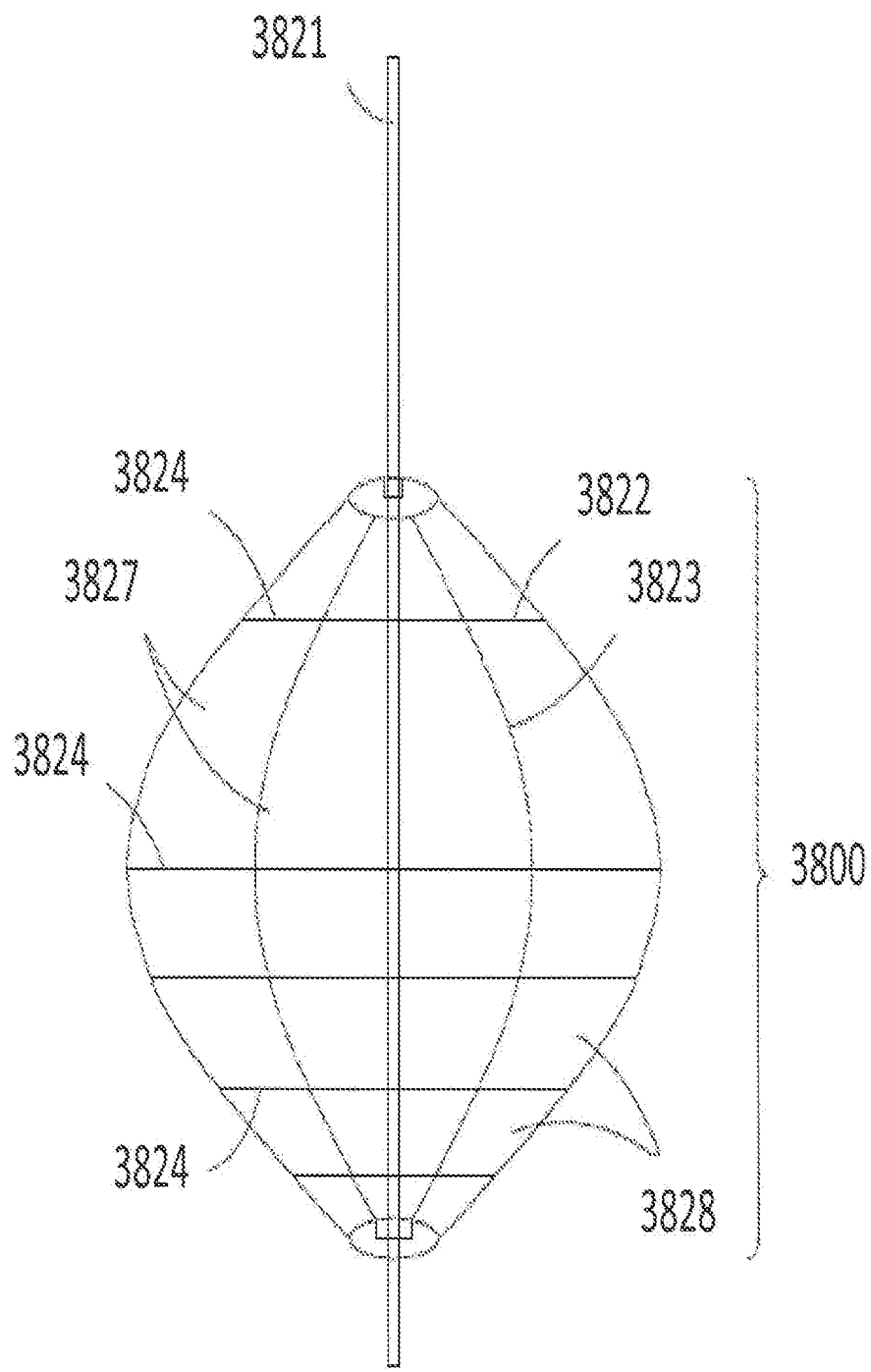

FIG. 38 is an illustration of one embodiment of an intragastric device 3800 in a post-deployment configuration. A catheter 3821 is positioned into the stomach and the compressed wire mesh structure 3822 is released. After deployment, the wire mesh structure 3822 assumes its expanded configuration. This is achieved through the use of shape memory technology as the vertical elements 3823 and horizontal elements 3824 expand to assume their pre-defined, post-deployment shapes. The expansion of the vertical elements 3823 and horizontal elements 3824 creates the spaces 3827 proximate the top of the intragastric device 3800 and the spaces 3828 proximate the bottom of the intragastric device 3800. These differing sized spaces slow gastric emptying and induce a longer period of satiety.

The spaces within the structure can range in size between 1 μm and 10 cm, preferably between 1 mm and 5 cm and most preferably between 5 mm and 10 mm. The spaces at the top of the structure can be same size as the spaces at the bottom of the structure. Alternatively, in various embodiments, the spaces at the bottom of the structure are smaller but no smaller than 50% of the larger openings at the top of the structure, otherwise food will accumulate in the device and interfere with its functionality. Alternatively, in one embodiment, the spaces or openings at the bottom of the structure are larger than the spaces or openings at the top of the structure. In one embodiment, the gastric emptying is achieved by having each opening at the top have the same surface area as each opening at the bottom. In this embodiment, the number of openings at the bottom of the structure will be less than the number of openings at the top of the structure. If one wished to delay gastric emptying by 50%, the number of openings in the bottom will be approximately 50% of the number of the openings in the top of the structure. In another embodiment, the number of openings at the bottom of the structure is greater than the number of openings at the top of the structure. Alternatively, the openings at the top can have a larger surface area than the openings at the bottom and, if one wished to delay gastric emptying by 50%, the total surface area of the openings in the bottom will be approximately 50% of the total surface area of the openings in the top of the structure. In another embodiment, the openings at the bottom have a larger surface area than the openings at the top.

After deployment, the catheter 3821 is removed, leaving the deployed intragastric device 3800 in the stomach. The post-deployment intragastric device 3800 occupies the gastric lumen thereby decreasing the effective volume available to accommodate ingested food. The post-deployment intragastric device 3800 presses upon the gastric wall, stimulating the stretch receptors and inducing the sensation of fullness or satiety. A sphere is the most effective embodiment of the device as it has the most volume for a given pre-deployment length and surface area.

In various possible embodiments, the pre and post-deployment configurations of the intragastric device contain the following attributes:

| Pre-deployment length (cm) | Post-deployment radius (cm) | Post-deployment volume (cc) |
| --- | --- | --- |
| 6 | 1.9 | 29 |
| 9 | 2.9 | 98 |
| 12 | 3.8 | 233 |
| 15 | 4.8 | 456 |
| 18 | 5.7 | 787 |
| 20 | 6.4 | 1080 |
| 25 | 8.0 | 2109 |
| 30 | 9.5 | 3645 |
| 40 | 12.7 | 8639 |
| 50 | 15.9 | 16873 |

The post-deployment radius (r) is equal to pre-deployment length (l) divided by pi ($\pi$) and the post-deployment volume (v) is equal to 4 l3/3 $\pi$2.

Figure 39:
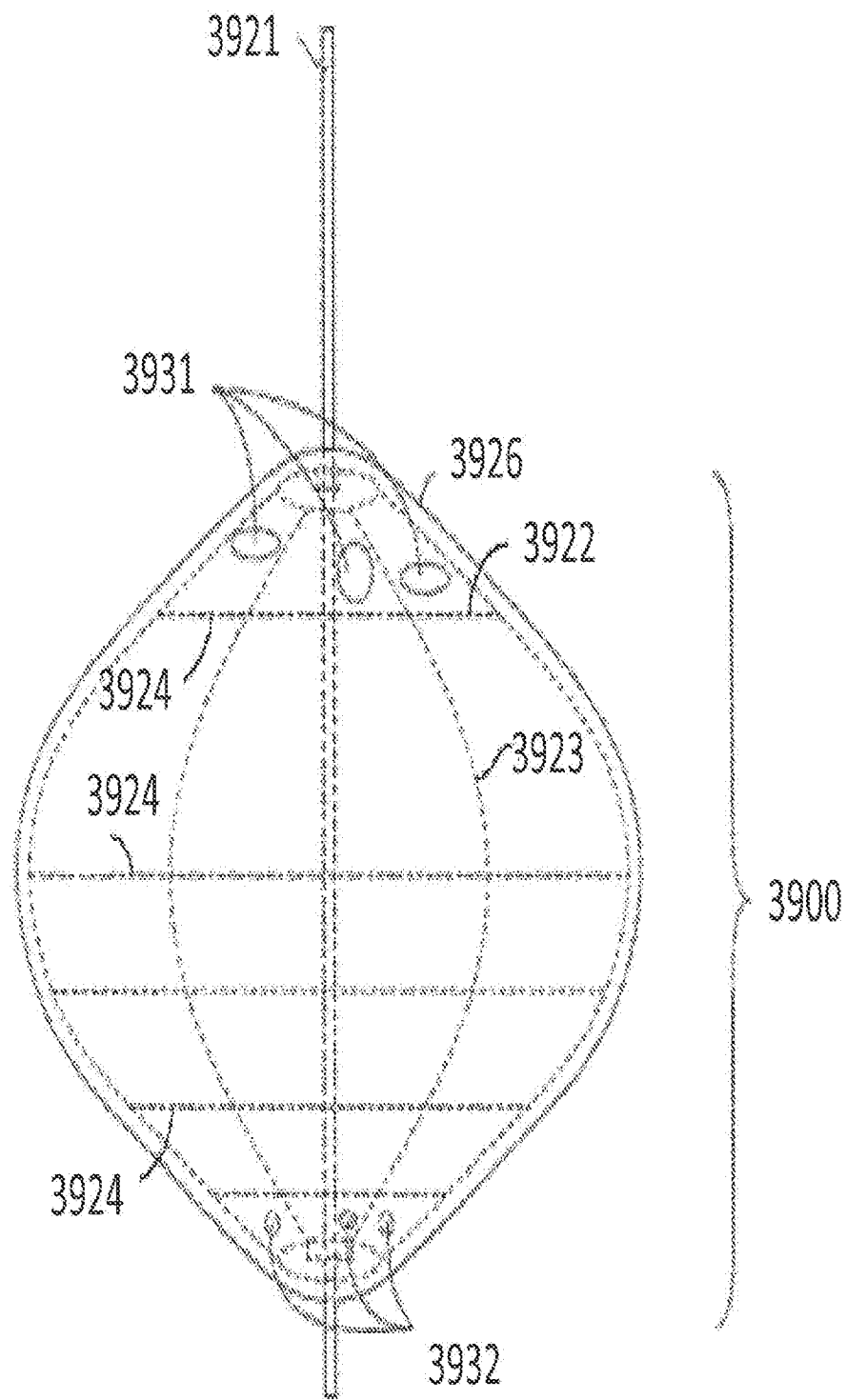

FIG. 39 is an illustration of another embodiment of an intragastric device 3900 in a post-deployment configuration. A catheter 3921 is positioned into the stomach and the compressed wire mesh structure 3922 is released. After deployment, the wire mesh structure 3922 assumes its expanded configuration. This is achieved through the use of shape memory technology as the vertical elements 3923 and horizontal elements 3924 expand to assume their pre-defined, post-deployment shapes. The enveloping membrane 3926 gives the intragastric device the quality of being partially permeable to gastric fluids. In the pictured embodiment, holes 3931 are positioned proximate the top of the intragastric device 3930 and holes 3932 are positioned proximate the bottom of the intragastric device 30. In one embodiment, the holes 3931 positioned proximate the top of the intragastric device 3930 are larger than the holes 3932 positioned proximate the bottom of the device 3930. These differing sized holes in the membrane 3926 allow for slowing of gastric emptying. After deployment, the catheter 3921 is removed, leaving the deployed intragastric device 3900 in the stomach. The post-deployment intragastric device 3900 occupies the gastric lumen thereby decreasing the effective volume available to accommodate ingested food. The post-deployment intragastric device 3900 presses upon the gastric wall, stimulating the stretch receptors and inducing the sensation of fullness or satiety.

Figure 40A:
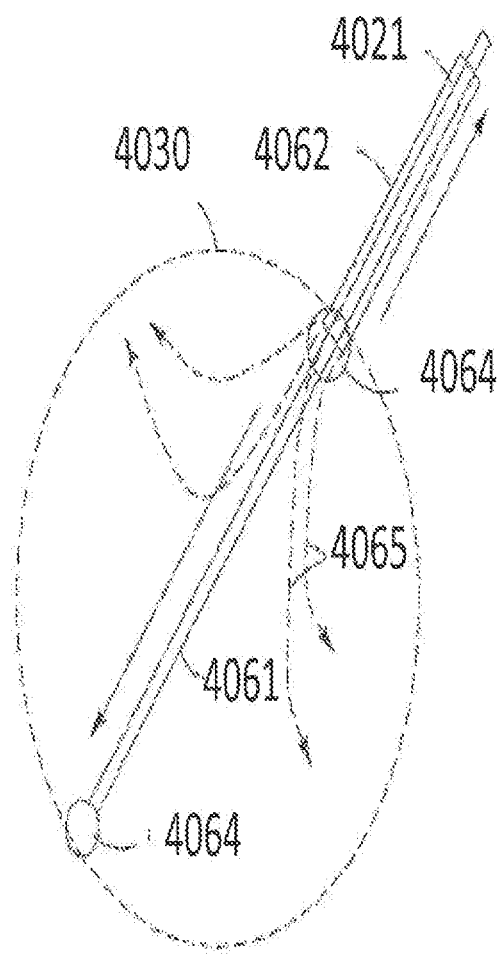

FIG. 40A is an illustration of a gastric device removal catheter 4021 attached to an intragastric device 4030 in an exemplary post-deployment configuration. The intragastric device 4030 is depicted in its expanded, spherical shape. A coaxial catheter 4021 is passed through the openings in the gastric device 4030 and the walls of the device 4030 are engaged by the expanded ends 4064 of the catheter 4021. An inner catheter 4061 and outer catheter 4062 are moved in opposite directions resulting in mechanical constriction of the device 4030 to its predominantly linear pre-deployment configuration. In one embodiment, cold fluid 4065 is instilled into the device 4030 via the catheter 4021 to lower the temperature of the shape memory structure and assist in further constriction of the device 4030 to its predominantly linear pre-deployment structure.

Figure 40B:
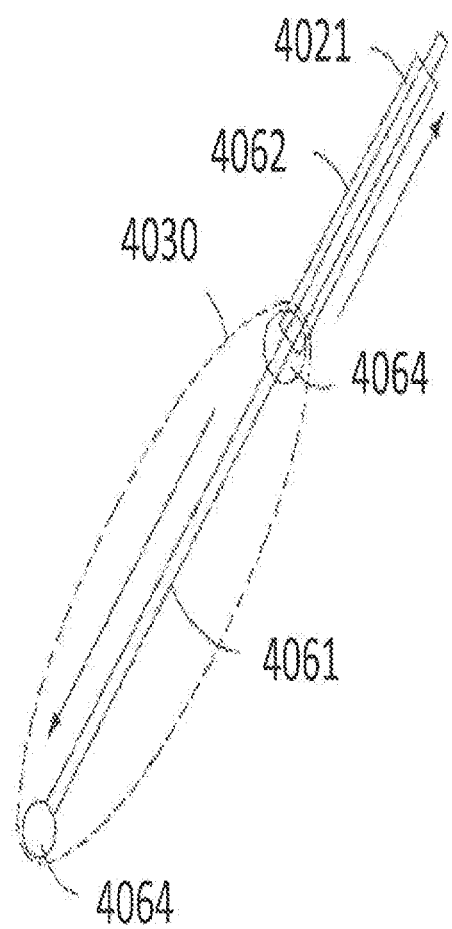

FIG. 40B is an illustration of a gastric device removal catheter 4021 attached to an intragastric device 4030 in an exemplary pre-deployment configuration. The intragastric device 4030 is depicted in its constricted, linear shape after constriction of the shape memory structure via use of the attached gastric device removal catheter 4021. The expanded ends 4064 of the catheter are depicted engaged with the ends of the linear intragastric device 4030. The inner catheter 4061 and outer catheter 4062 are depicted after having moved opposite one another in order to constrict the intragastric device 4030. The constricted, linear pre-deployment configuration facilitates in the removal of the device 4030 from a patient's gastric cavity.

Figure 41:
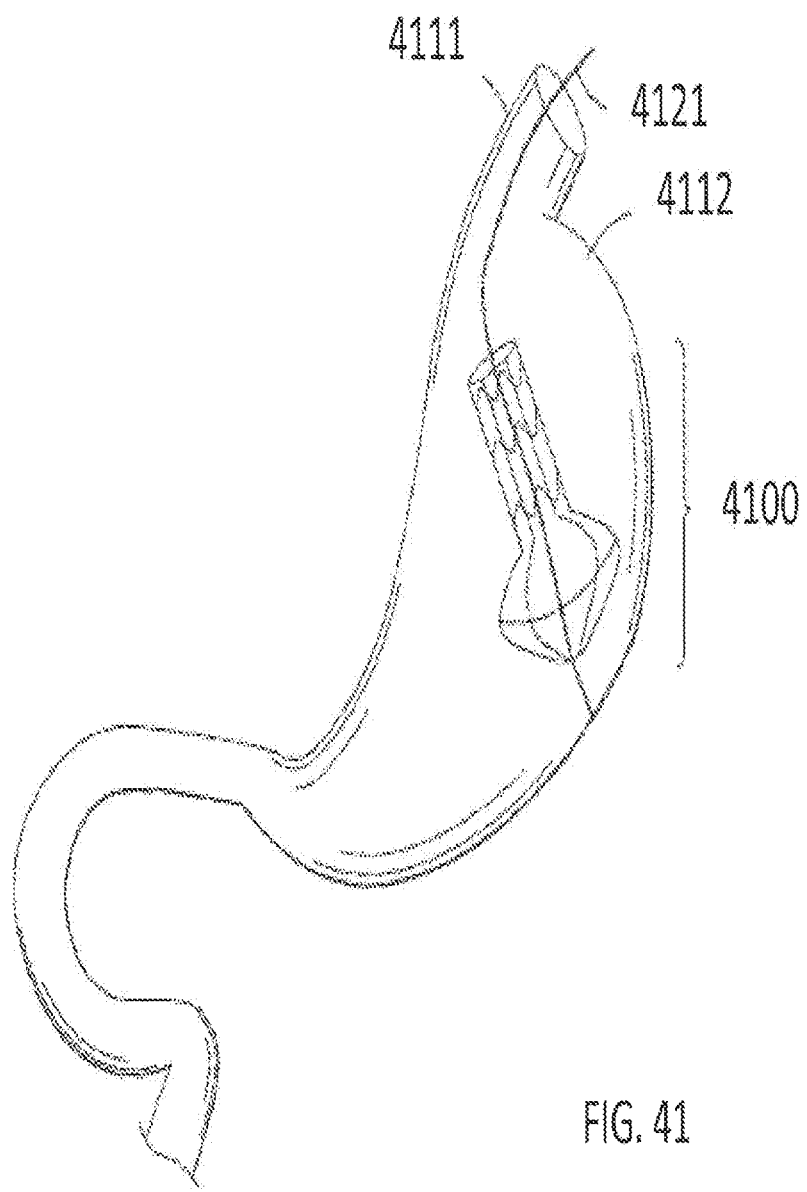

FIG. 41 is an illustration of an intragastric device 4100 being deployed in a stomach 4112. The catheter 4121 used to deliver the intragastric device 4100 is depicted as it traverses the esophagus 4111. The partially deployed device 4100 is shown in the stomach 4112.

Figure 42:
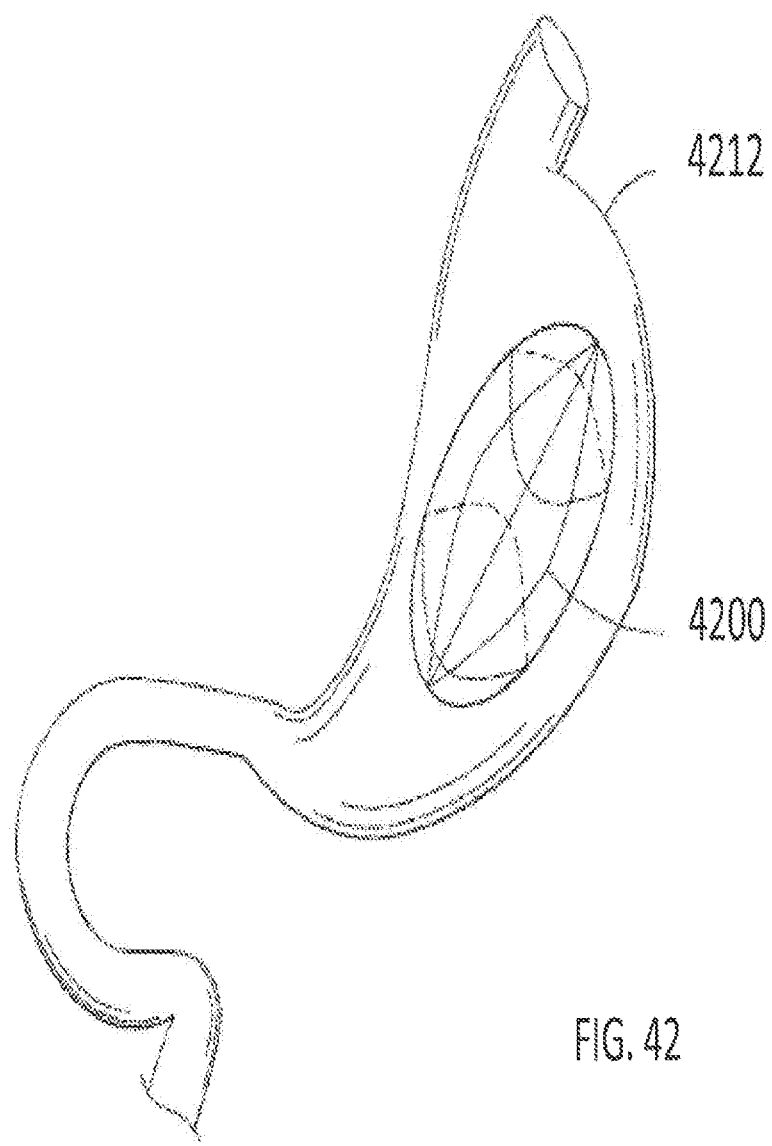

FIG. 42 is an illustration of a fully deployed intragastric device 4200 in a stomach 4212. The intragastric device 4200 occupies a significant portion of the stomach 4212, thereby limiting the available volume to accommodate ingested food. The catheter used for delivery has been removed.

Figures 43A, 43B:
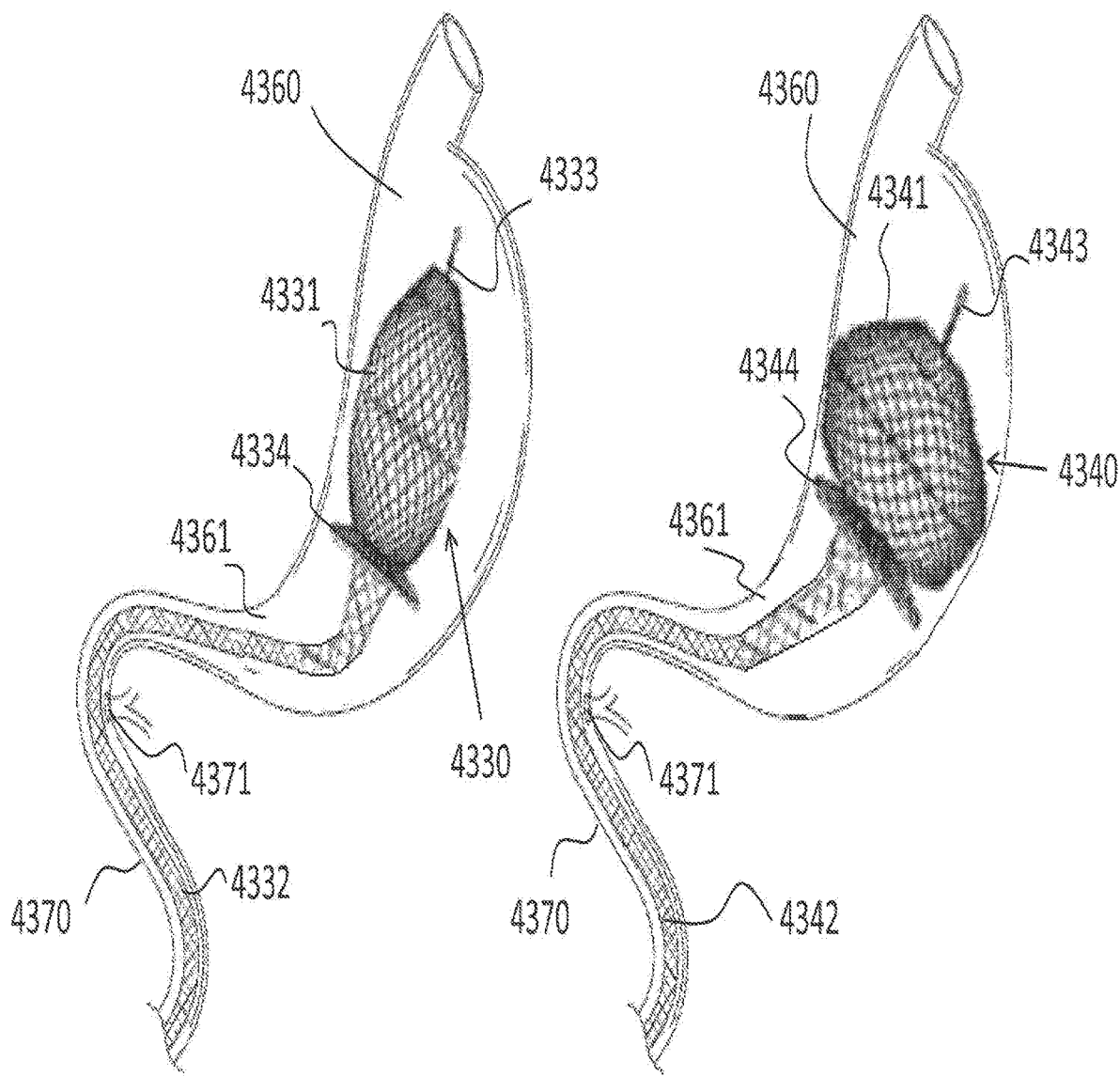

FIG. 43A is an illustration of an intragastric device 4330 having an oval shaped wire mesh structure 4331 deployed in the gastrointestinal tract of a patient, in accordance with one embodiment of the present specification. In the pictured embodiment, the device 4330 includes a wire mesh structure 4331 with a retrieval hook 4333, a coupled sleeve 4332, and an anti-migration disc 4334. The device 4330 is deployed such that the wire mesh structure 4331 resides in the stomach 4360 with the anti-migration disc 4334 positioned just proximal to the pylorus 4361 and the sleeve 4332 extending through the pylorus 4361 and the duodenum 4370. The distal end of the sleeve 4332 extends beyond the ampula of vater 4371. The device 4330 occupies a volume of the stomach 4360, does not move entirely past the pylorus 4361, and provides a bypass for food past the pylorus 4361, duodenum 4370, and ampula of vater 4371.

FIG. 43B is an illustration of an intragastric device 4340 having a football shaped wire mesh structure 4341 deployed in the gastrointestinal tract of a patient, in accordance with one embodiment of the present specification. In the pictured embodiment, the device 4340 includes a wire mesh structure 4341 with a retrieval mechanism 4343, a coupled sleeve 4342, and an anti-migration disc 4344. The device 4340 is deployed such that the wire mesh structure 4341 resides in the stomach 4360 with the anti-migration disc 4344 positioned just proximal to the pylorus 4361 and the sleeve 4342 extending through the pylorus 4361 and the duodenum 4370. The distal end of the sleeve 4342 extends beyond the ampula of vater 4371. The device 4340 occupies a volume of the stomach 4360, does not move entirely past the pylorus 4361, and provides a bypass for food past the pylorus 4361, duodenum 4370, and ampula of vater 4371.

Figure 44:
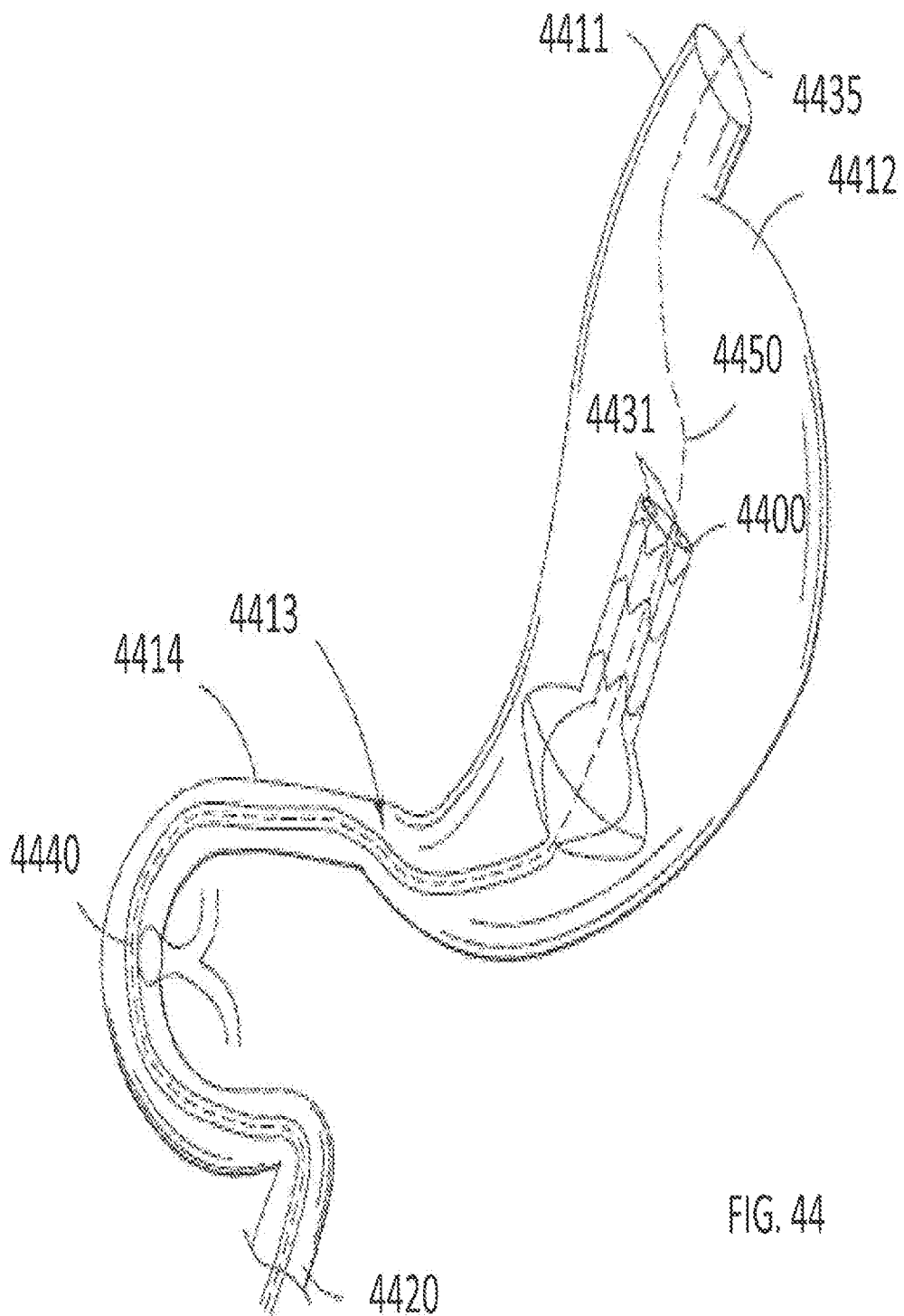

FIG. 44 is an illustration of an intragastric device 4400 with an attached sleeve 4440 being deployed over a guidewire 4435 in a gastrointestinal tract. The intragastric device 4400 is depicted in the stomach 4412. The attached sleeve 4440 is depicted traveling through the bottom portion of the stomach 4412, passing through the pylorus 4413 and duodenum 4414, and ending and opening up into the jejunum 4420. Food 4450 passes through the esophagus 4411 and into the stomach 4412. There it enters the intragastric device 4430 through the holes 4431 proximate the top of the intragastric device 4400. The food 4450 then travels from the intragastric device 4440, through the sleeve 4440, and into the middle portion of the jejunum 4420 without being exposed to the duodenum 4414 and proximal jejunum 4420.

Figure 45:
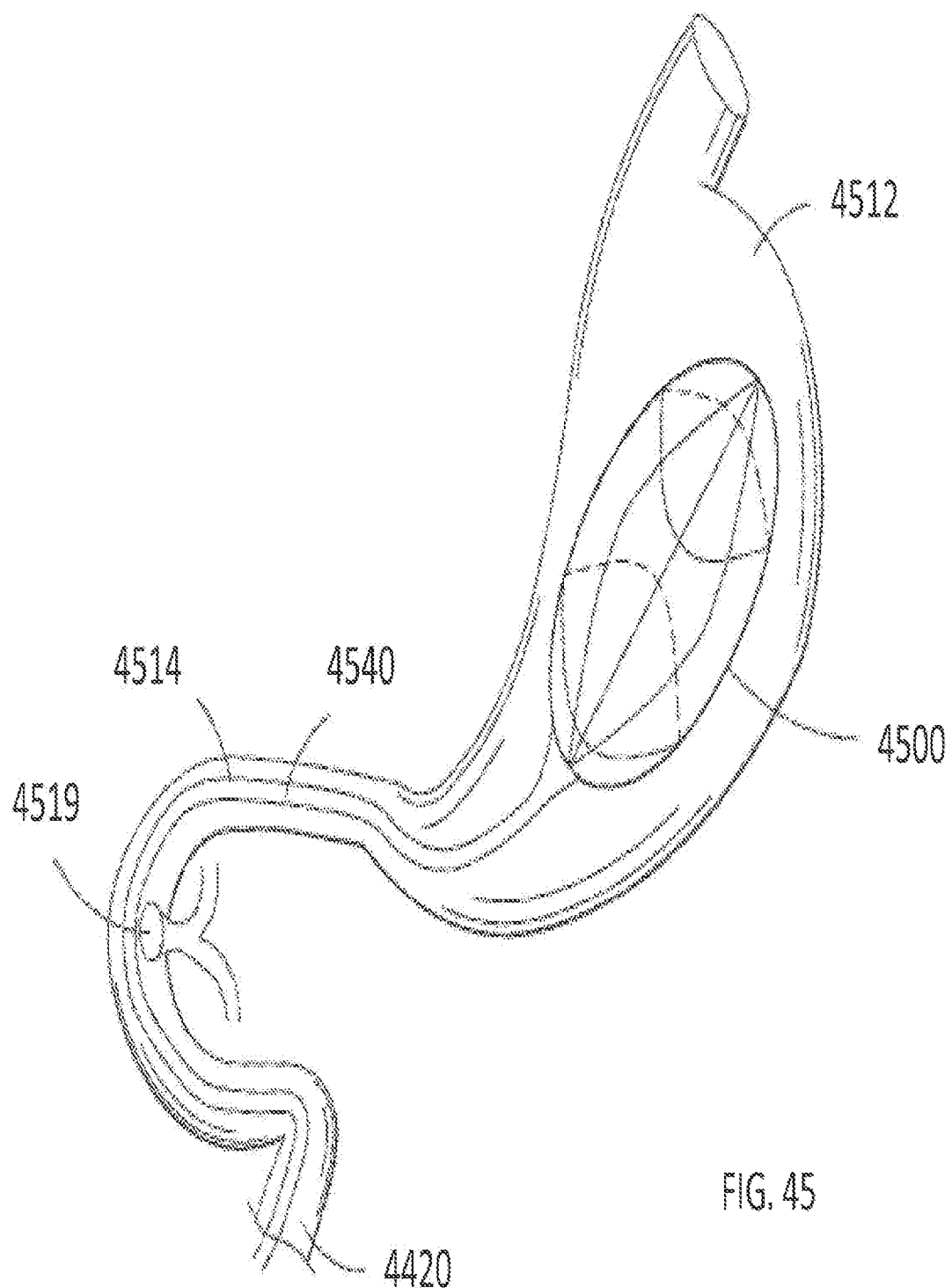

FIG. 45 is an illustration of a fully deployed intragastric device 4500 with an attached sleeve 4540 in a gastrointestinal tract. The intragastric device 4500 occupies a significant portion of the stomach 4512, thereby limiting the available volume to accommodate ingested food. The sleeve 4540 is depicted traveling through the duodenum 4514 and into the jejunum 4520, bypassing the duodenum 4514 and ampulla of vater 4519.

Figure 46:
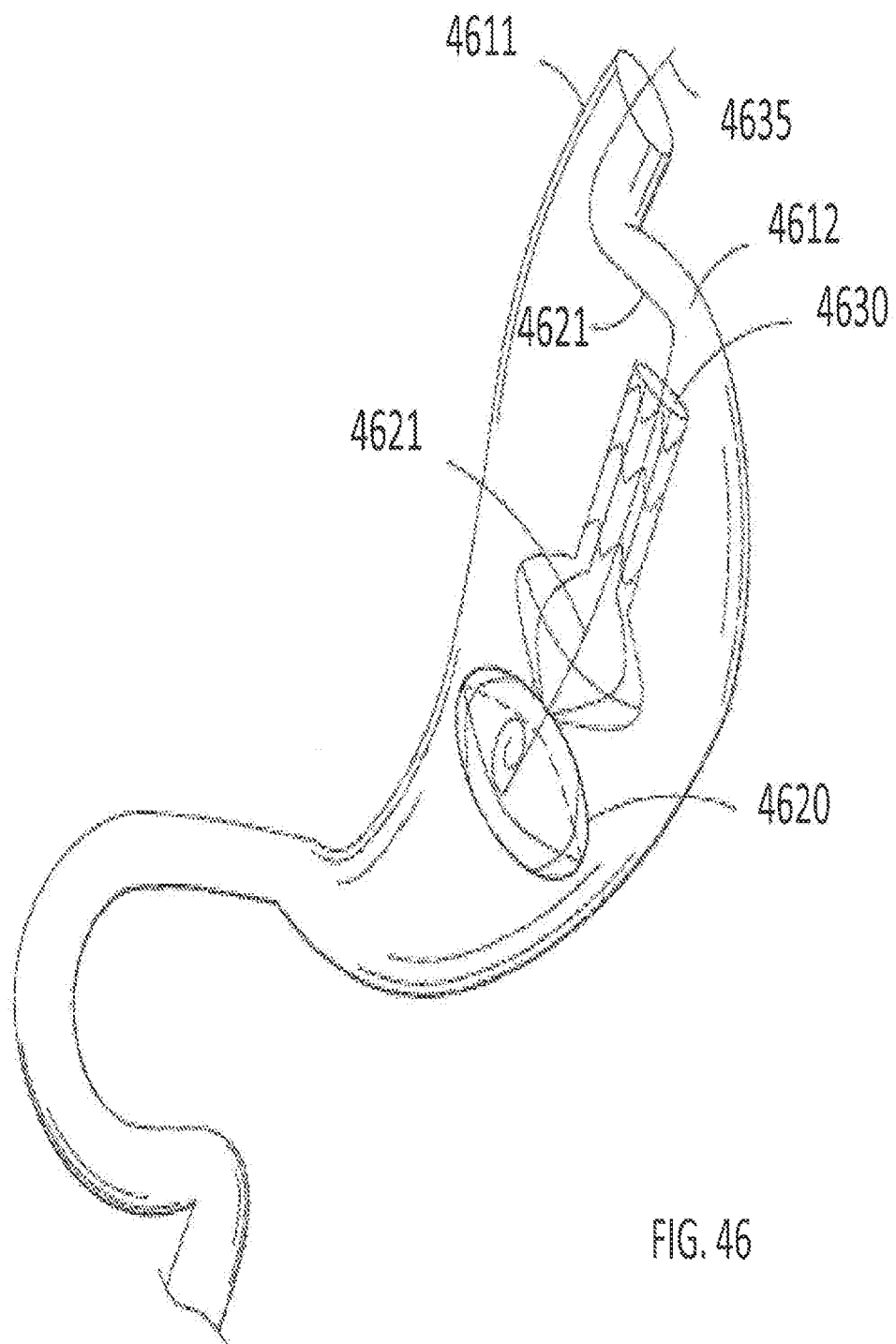

FIG. 46 is an illustration of one single intragastric device 4620 being passed over a guidewire 4635 and attached to a previously deployed single intragastric device 4630 in a stomach 4612. A catheter 4621 is depicted passing through the esophagus 4611 and into the stomach 4612. The catheter 4621 is deploying the second single intragastric device 4620 and assisting in its attachment to the previously deployed intragastric device 4630. Operationally, the catheter 4621 will be passed into an opening of the existing intragastric device 4630, preferably the opening used by the original catheter to deploy the device. The second device 4620 is then deployed with a portion of the second device, such as a neck, protrusion, or other member, fixedly attached to the first device 4630, thereby anchoring the two devices together.

Figure 47:
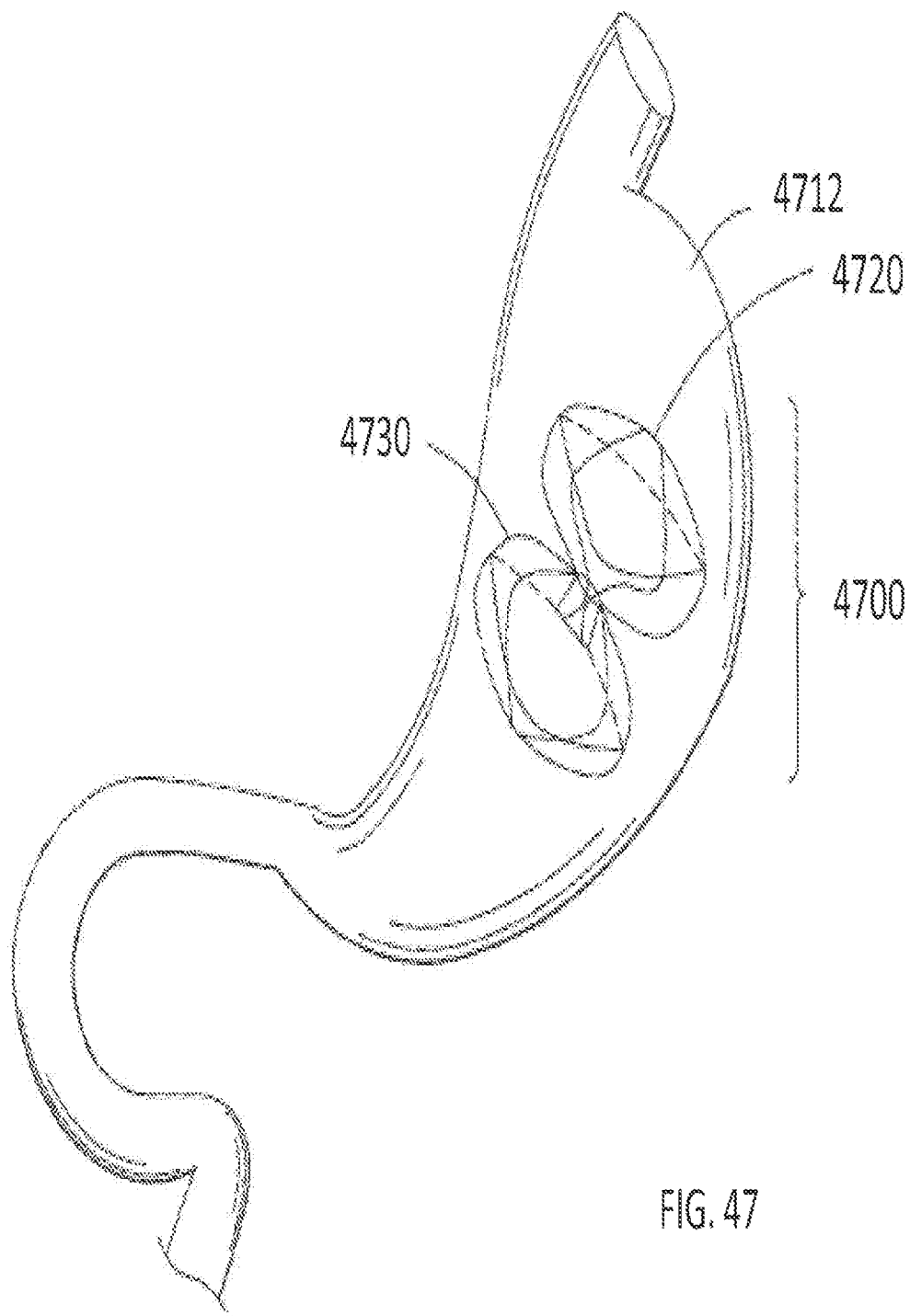

FIG. 47 is an illustration of a fully deployed combined intragastric device 4700 in a stomach 4812. The two single intragastric devices 4720, 4730 are depicted attached one on top of the other, occupying a greater stomach 4712 volume than one single intragastric device 4730.

FIGS. 48 and 49 are illustrations of embodiments of an intragastric device 4800, 4901 having a first type of circumferential constraining mechanism 4871 and a second type of circumferential constraining mechanism 4981, respectively, positioned on a wire mesh structure 4801, 4901. Referring to FIGS. 48 and 49 simultaneously, the devices 4800, 4900 each comprise a wire mesh structure 4801, 4901, a coupled sleeve 4802, 4902, a membrane 4805, 4905 covering the sleeve 4802, 4902 and a portion of the wire mesh structure 4801, 4901, and a plurality of circumferential constraining mechanisms 4871, 4981 positioned at different locations about the wire mesh structure 4801, 4901. The circumferential constraining mechanisms 4871, 4981 are composed of a material that is resistant to degradation by gastric secretions. The plurality of circumferential constraining mechanisms 4871, 4981 is used to constrict the wire mesh structure 4801, 4901 into its compressed configuration for removal. In one embodiment, an exposed free end of each circumferential constraining mechanism 4871, 4981 is pulled via a retrieval device, causing the diameter of each circumferential constraining mechanism 4871, 4981 and associated portion of wire mesh structure to decrease.

In one embodiment, each circumferential constraining mechanism comprises an elongate body having a plurality of pegs or tabs in series and a locking member having a central opening at one end. In one embodiment, the free end 4872, 4982 of each circumferential constraining mechanism 4871, 4981 is positioned outside of the wire mesh structure 4801, 4901. In another embodiment (not shown), the plurality of circumferential constricting mechanisms have their free ends positioned inside the wire mesh structure. Immediately before retrieval, as the free end 4872, 4982 of each circumferential constraining mechanism 4871, 4981 is pulled with the retrieval device, the pegs or tabs slide through the locking member and the diameter of the circumferential constraining mechanism 4871, 4981 is reduced. The locking member is designed such that pegs or tabs that have passed through the locking member cannot slide in the reverse direction. In one embodiment, the circumferential constraining mechanism 4871, 4981 is a zip tie. In another embodiment, the circumferential constraining mechanism 4871, 4981 is a silk suture. The silk suture includes a T-tag to maintain the wire mesh structure 4871, 4981 in a compressed configuration once constricted for easy removal. In another embodiment, a mechanism applies traction to the silk suture to constrain the wire mesh structure 4871, 4981 and then a clip or clamp is placed to prevent the silk suture from retracting and releasing the wire mesh structure 4871, 4981. As depicted, in one embodiment, the wire mesh structure 4801, 4901, includes a circumferential constraining mechanism 4871, 4981 around its proximal first opening. In one embodiment, the wire mesh structure 4801, 4901, also includes a circumferential constraining mechanism 4871, 4981 around its center. In another embodiment (not pictured), the wire mesh structure includes a circumferential constraining mechanism at its junction with the sleeve. In various embodiments, the wire mesh structure 4801, 4901 includes as few as one, two, or more than two circumferential constraining mechanisms 4871, 4981.

FIG. 50 is an illustration of an intragastric device 5000 being removed from a stomach 5012. A catheter 5021 is inserted through the esophagus 5011 and attaches to the intragastric device 5000 in the stomach 5012. The catheter 5021 is then used to introduce cold fluid into the intragastric device to lower the temperature of the intragastric device 5030, causing the intragastric device 5030 to return its shape back to its pre-deployment configuration. Additional mechanical force can be used to constrain the intragastric device 5030. Once returned to its initial compressed cylindrical shape, the intragastric device 5030 can be removed using the attached catheter 5021.

FIG. 51 is a flow chart illustrating the steps involved during retrieval of an intragastric device in accordance with one embodiment of the present specification. At step S102, a physician inserts an endoscope into the esophagus of a patient with an implanted intragastric device. A retrieval device, or forceps, is advanced through the working channel of the endoscope at step S104. Then, at step S106, the free end of a constricting mechanism is grabbed using the forceps. Gentle traction is applied slowly to draw the constricting mechanism tight and constrict the wire mesh structure to its compressed configuration at step S108. Steps S106 and S108 are repeated for each remaining constricting mechanism. Once all the constricting mechanisms have been pulled tight, the device is ready for removal. The forceps are used to grasp the proximal end of the device and the compressed device is removed through the working channel of the endoscope at step S110.

FIG. 52 is an illustration of one embodiment of a wire mesh component 5201a of an intragastric device in a post-deployment configuration being restrained by circumferential constricting mechanisms 5271 prior to removal. Pulling on the free ends 5272 of the circumferential constricting mechanisms 5271 causes them to constrict and lock in place, thereby reducing their diameters and the diameter of the wire mesh structure. Once the wire mesh structure has been constricted to its compressed configuration 5201b, it is ready for retrieval. In one embodiment, the free end 5272 of each circumferential constricting mechanism 5271 is grabbed by forceps or a grasper passed through the working channel of an endoscope. Gentle traction is applied slowly to constrict the wire mesh structure to its compressed configuration 5201b. The free ends 5272 of the constricting mechanisms 5271 are longer after compression and the wire mesh structure 5201b has an elongate tubular shape. In various embodiments, the locking mechanisms of the zip ties or the T-tags, clips or clamps of the silk sutures prevent the wire mesh structure 5201b from re-expanding such that the device can be removed without the need for constant traction to hold the wire mesh structure in the compressed configuration 5201b. The compressed wire mesh structure 5201b is then removed through the endoscope.

FIG. 53 is an illustration of one embodiment of a retrieval device 5380 and a portion of a wire mesh structure 5301 partially constrained by a circumferential constricting mechanism 5371. In the pictured embodiment, the retrieval device 5380 comprises an elongate body 5381 having a proximal end, a distal end, and a lumen within. An elongate metal wire 5383, having a proximal end and a distal end, is disposed within the lumen of the elongate body 5381. A hook 5382 is formed from the distal end of the wire 5383 and an actuator 5384 is attached to the proximal end of the wire 5383. In one embodiment, the actuator 5384 rests in a handle 5385. A physician manipulates the actuator 5384 to engage the hook 5382 at the distal end of the wire 5383 with the free end 5372 of a circumferential constricting member 5371 positioned on a wire mesh structure 5301. In the pictured embodiment, the circumferential constricting mechanism 5371 is a zip tie. The physician pulls on the actuator 5384 to draw the free end 5372 of the circumferential constricting mechanism 5371, reducing the diameter of the circumferential constricting mechanism 5371 and thereby constricting the wire mesh structure 5301, preparing it for retrieval.

FIG. 54 is an illustration of one embodiment of a grasping hook 5482 of a retrieval device 5480 engaging a tie 5488 that has been secured to the retrieval hook 5404 of a wire mesh structure 5401 of an intragastric device. In the pictured embodiment, the tie 5488 has been secured to the retrieval mechanism 5404 to facilitate engagement of the grasping hook 5482 with the wire mesh structure 5401. In one embodiment, the tie 5488 is secured to the retrieval mechanism 5404 prior to delivery of the intragastric device. In another embodiment, the tie 5488 is secured to the retrieval mechanism 5404 just prior to retrieval of the intragastric device. In another embodiment, the tie 5488 is not used and the grasping hook 5482 directly engages the retrieval mechanism 5404 during device retrieval.

FIG. 55A is an illustration of a wire mesh structure 5501 of an intragastric device 5500 partially drawn into the distal end of a retrieval device 5580, in accordance with one embodiment of the present specification. The intragastric device 5500 further includes a coupled sleeve 5502 and an anti-migration component 5504. In addition, a retrieval hook 5503 of the intragastric device 5500 is visible inside the distal end of the retrieval device 5580. The proximal end of the wire mesh structure 5501 also includes a circumferential constricting mechanism 5571 that has been used to compress the proximal end of the wire mesh structure 5501 to facilitate retrieval by the retrieval device 5580.

FIG. 55B is a flow chart illustrating the steps involved in retrieving a deployed intragastric device using the retrieval device of FIG. 54, in accordance with one embodiment of the present specification. At step S510, the retrieval device is inserted endoscopically into a patient and its distal end is advanced to the proximal end of the deployed intragastric device. Then, at step S512, a physician manipulates the grasping hook of the retrieval device to engage the free end of an automatically locking circumferential constricting mechanism that is positioned about the wire mesh structure of the intragastric device. At step S514, the physician pulls on the actuator of the retrieval device to constrict the automatically locking circumferential constricting mechanism and compress the wire mesh structure. The physician manipulates the grasping hook of the retrieval device to disengage from the free end of the circumferential constricting mechanism at step S516. If additional circumferential constricting mechanisms are included about the wire mesh structure, steps S512 through S516 are repeated to constrict each mechanism. Once all the circumferential constricting mechanisms have been constricted, the physician then manipulates the grasping hook of the retrieval device to engage the retrieval mechanism of the intragastric device at step S518. Then, at step S520, the physician pulls on the actuator to draw the proximal end of the intragastric device into the retrieval device. Finally, at step S522, the retrieval device and intragastric device are removed from the patient.

FIG. 56A is an illustration of a first exemplary circumferential constricting mechanism 5671 in accordance with one embodiment of the present specification. The circumferential constraining mechanism 5671 comprises an elongate body 5679 having a plurality of pegs or tabs 5675 in series, a free end 5672, and a locking member 5673 having a central opening 5674 at the opposite end.

FIG. 56B is an illustration of the first exemplary circumferential constricting mechanism 5671 of FIG. 56A, depicting the circumferential constricting mechanism 5671 wrapped about a portion of a wire mesh structure 5601. As the free end 5672 of the circumferential constraining mechanism 5671 is pulled with a retrieval device, the pegs or tabs 5675 slide through the locking member 5673 and the diameter of the circumferential constraining mechanism 5671 is reduced. The locking member 5673 is designed such that pegs or tabs 5675 that have passed through the locking member 5673 cannot slide in the reverse direction.

FIG. 57 is an illustration of a second exemplary circumferential constricting mechanism 5771 in accordance with one embodiment of the present specification. The circumferential constricting mechanism 5771 includes an elongate body 5779 having a free end 5772, pegs or tabs 5775, and a locking member 5773 having a pair of central openings 5774.

FIG. 58 is an illustration of a third exemplary circumferential constricting mechanism 5871 in accordance with one embodiment of the present specification. The circumferential constricting mechanism 5871 includes an elongate body 5879 having a free end 5872, a plurality of pairs of pegs or tabs 5875, and a plurality of openings 5874. The circumferential constricting mechanism 5871 is locked by passing one of said pairs of pegs or tabs 5875 through one of said openings 5874.

FIG. 59A is an illustration of a fourth exemplary circumferential constricting mechanism 5971 in accordance with one embodiment of the present specification. The circumferential constricting mechanism 5971 includes an elongate body 5979 having a free end 5972, pegs 5975, and a locking member 5973 having a central opening 5974. The circumferential constricting mechanism 5971 has an adjustable diameter. The central opening 5974 of the locking mechanism 5971 includes a first portion 5974a and a second portion 5974b wherein the diameter of the first portion 5974a is greater than the diameter of the second portion 5974b. A peg 5975 can slide freely through the first portion 5974a. The elongate body 5979 fits snugly in the second portion 5974b of the central opening 5974 and can be slid horizontally between the first portion 5974a and the second portion 5974b. The width of the pegs 5975 is greater than the diameter of the second portion 5974b. Therefore, once the elongate body 5979 has been slid horizontally into the second portion 5974b, the pegs 5975 prevent further sliding vertically of the free end 5972 within the central opening 5974. The elongate body 5979 can be slid horizontally back out of the second portion 5974b and the circumferential constricting mechanism 5971 can be resized.

FIG. 59B is an illustration of the exemplary circumferential constricting mechanism 5971 of FIG. 59A with a portion of the elongate body slid horizontally into the second section of the central opening 5974, thereby locking the circumferential constricting mechanism 5971.

FIG. 60 is an illustration of one embodiment of a retrieval device 6080 having a grasping hook 6082 and a grasper 6086 at its distal end. The retrieval device 6080 comprises an elongate body 6081 having a proximal end, a distal end, and a lumen within. An elongate metal wire 6083, having a proximal end and a distal end, is disposed within the lumen of the elongate body 6081. A hook 6082 is formed from the distal end of the wire 6083 and an actuator 6084 is attached to the proximal end of the wire 6083. In one embodiment, the actuator 6084 rests in a handle 6085. The grasper 6086 at the distal end of the retrieval device comprises a pair of opposing jaws. In various embodiments, the retrieval device 6080 is 5 cm or less in diameter and 50 cm or greater in length. The retrieval device 6080 is flexible enough to pass through an endoscope. A physician manipulates the actuator 6084 to engage the hook 6082 at the distal end of the wire 6083 with the free end of a circumferential constricting mechanism positioned on a wire mesh structure of an intragastric device (not shown).

FIG. 61 is an illustration of one embodiment of a retrieval device 6180 with a grasping hook 6182 engaging the free end 6172 of a circumferential constricting mechanism 6171 positioned about a wire mesh structure 6101. The wire mesh structure 6101 is viewed from above and still in its expanded configuration. In the pictured embodiment, the retrieval device 6180 comprises an elongate body 6181 having a proximal end, a distal end, and a lumen within. An elongate metal wire 6183, having a proximal end and a distal end, is disposed within the lumen of the elongate body 6181. A hook 6182 is formed from the distal end of the wire 6183 and an actuator 6184 is attached to the proximal end of the wire 6183. In one embodiment, the actuator 6184 rests in a handle 6185. A physician manipulates the actuator 6184 to engage the hook 6182 at the distal end of the wire 6183 with the free end 6172 of a circumferential constricting mechanism 6171 positioned on the wire mesh structure 6101. In the pictured embodiment, the circumferential constricting mechanism 6171 is a suture or thread. The physician pulls on the actuator 6184 to draw the free end 6172 of the circumferential constricting mechanism 6171, reducing the diameter of the circumferential constricting mechanism 6171 and thereby constricting the wire mesh structure 6101. The retrieval device depicted in FIG. 61 further includes a grasper 6186 having a pair of opposing jaws. A clamp 6187 is positioned between the jaws of the grasper 6186. Once the wire mesh structure 6101 has been constricted to its compressed configuration, the physician manipulates the actuator 6184 to close the jaws of the grasper 6186, thereby fixing the clamp 6187 about the free end of the circumferential constricting mechanism 6171 proximate the compressed wire mesh structure 6101. The circumferential constricting mechanism 6171 is held tightly by the clamp 6187 and cannot release so the wire mesh structure 6101 does not re-expand.

FIG. 62 is an illustration of one embodiment of a retrieval device 6280 applying a clamp 6287 to a circumferential constricting mechanism 6271 positioned about a wire mesh structure 6201 of an intragastric device. The wire mesh structure 6201 is viewed from above and has been constricted into its compressed configuration by the circumferential constricting mechanism 6271. In the pictured embodiment, the grasping hook 6282 of the retrieval device 6280 is engaged with the free end 6272 of the circumferential constricting mechanism 6271. A physician has pulled the actuator 6284 back from the handle 6285 of the retrieval device 6280, thereby withdrawing the wire 6283 and moving the grasping hook 6282 in a proximal direction within the lumen of the retrieval device body 6281. The free end 6272 of the circumferential constricting mechanism 6271 is pulled by the grasping hook 6282 into the lumen of the retrieval device body 6281, causing the circumferential constricting mechanism 6271 to constrict about the wire mesh structure 6201. At this point, the physician can manipulate the grasper 6286 at the distal end of the retrieval device 6280 to apply the clamp 6287 to a portion of the free end 6272 of the circumferential constricting mechanism 6271 that is closest to the wire mesh structure 6201. Application of the clamp 6287 will prevent release of the circumferential constricting mechanism 6271 and re-expansion of the wire mesh structure 6201.

FIG. 63 is an illustration of one embodiment of a restrained wire mesh structure 6301 with a clamp 6387 applied to the free end 6372 of a circumferential constricting mechanism 6371 positioned about the wire mesh structure 6301. The wire mesh structure 6301 is viewed from above and in its compressed configuration. A majority of the free end 6372 of the circumferential constricting mechanism 6371 has been pulled proximally, with respect to the clamp

6387, by a retrieval device as discussed with reference to FIG. 63. This has caused the portion of the circumferential constricting mechanism 6371 positioned around the wire mesh structure 6301 to decrease in diameter, thereby constricting the wire mesh structure 6301. The clamp 6387 has been applied to a portion of the free end 6372 of the circumferential constricting mechanism 6371 proximate the wire mesh structure 6301. The clamp 6387 holds the circumferential constricting mechanism 6371 in place, keeping the wire mesh structure 6301 compressed and ready for retrieval.

In another embodiment, rather than applying a clamp, the physician twists the free end of the circumferential constricting mechanism about itself until it holds the wire mesh structure in the compressed configuration. In this embodiment, the circumferential constricting mechanism comprises a flexible metal wire.

In another embodiment, rather than applying a clamp, the physician ties the free end of the circumferential constricting mechanism in a knot to hold the wire mesh structure in the compressed configuration. In this embodiment, the circumferential constricting mechanism comprises a silk suture.

FIG. 64 is a flow chart illustrating the steps involved in retrieving a deployed intragastric device using the retrieval device of FIG. 63, in accordance with one embodiment of the present specification. At step 6410, the retrieval device is inserted endoscopically into a patient and its distal end is advanced to the proximal end of the deployed intragastric device. Then, at step 6412, a physician manipulates the grasping hook of the retrieval device to engage the free end of a circumferential constricting mechanism that is positioned about the wire mesh structure of the intragastric device. At step 6414, the physician pulls on the actuator of the retrieval device to constrict the circumferential constricting mechanism and compress the wire mesh structure. Then, at step 6416, the physician manipulates the grasper of the retrieval device to apply a clamp to the free end of the circumferential constricting mechanism, proximate the wire mesh structure. At step 6418, the physician pulls on the actuator to draw the proximal end of the intragastric device into the retrieval device. Finally, at step 6420, the retrieval device and intragastric device are removed from the patient.

FIG. 65A is cross-section illustration of a retrieval device 6500 for removing an intragastric device in accordance with one embodiment of the present specification. The retrieval device 6500 includes a flexible catheter 6501 comprising an elongate wire 6505 covered coaxially by a sheath. The distal end of the wire 6505 is formed into a hook 6506 for grasping an intragastric device. The retrieval device 6500 also includes a handle at its proximal end comprising, in one embodiment, a first handle component 6514 and a second handle component 6515 that are joined with a screw 6520. The handle components 6514, 6515 can be disassembled for removal of the catheter 6501 from the endoscope or for passage of a flexible overtube 6530 over the wire 6505 and the sheath. The overtube 6530 comprises an elongate overtube body 6532 with proximal end, a distal end, and a lumen within, and is used for constraining the intragastric device for final removal out of the body. In one embodiment, the proximal end of the overtube 6530 includes an adapter 6533 configured to attach to component 6515 of the catheter handle. In one embodiment, wherein the intragastric device includes a wire mesh structure in accordance with the various embodiment of the present specification, the mesh is grasped with the wire hook 6506 and then the overtube 6530 is passed over the wire 6505 and sheath. The mesh is then pulled into the overtube 6530 using the wire hook 6506.

In various embodiments, the overtube 6530 includes an optional port 6537 at its proximal end for insufflation of an optional balloon 6536 at the distal end of the overtube body 6532. The balloon 6536 serves to further assist in compression of the intragastric device during removal. In one embodiment, the overtube 6530 includes a separate, additional lumen in fluid communication with port 6537 and with the balloon 6536 for insufflation of said balloon 6536. In one embodiment, the overtube body 6532 includes a compartment 6534 at its distal end for holding the balloon 6536 when the balloon is deflated. In various embodiments, the overtube 6530 includes an optional port 6538 at its proximal end for instillation of cold fluid to facilitate shape change of a temperature sensitive shape memory mesh. Fluid enters the port 6538, travels through the lumen of the overtube body 6532, and exits from the distal end of the overtube 6530.

FIGS. 65B and 65C are cross-section illustrations of an exploded view and assembled view respectively, of the catheter component 6501 of the retrieval device of FIG. 65A. Depicted are the first handle component 6514, second handle component 6515, and screw 6520 of the catheter handle. The handle components attach to the distal end of the wire 6505. The sheath 6510 coaxially covers the wire 6505 and restrains the hook 6506 at the distal end of the wire prior to operation of the retrieval device.

FIG. 65D is a cross-section illustration of the overtube 6530 of the retrieval device of FIG. 65A, depicting a deflated balloon 6536 at the distal end of the overtube 6530. In one embodiment, the overtube body 6532 includes a compartment 6534 at its distal end for holding the balloon 6536 prior to operation of the retrieval device. The overtube 6530 is configured to be slid over the catheter of the retrieval device after the user has grasped the intragastric device with the wire hook of the catheter. The user removes the handle of the catheter, slides the overtube 6530 over the catheter, and then reattaches the catheter handle. The catheter handle is configured to couple with an adapter 6533 on the proximal end of the overtube body 6532. The overtube 6530 includes an insufflation port 6537 for inflating the balloon 6536. In one embodiment, the overtube 6530 also includes a port 6538 for instillation of cold fluid to facilitate a shape change in a temperature sensitive shape memory intragastric device. FIG. 65E is a cross-section illustration of the overtube 6530 of the retrieval device of FIG. 65A, depicting an inflated balloon 6536 at the distal end of the overtube 6530. Air or cold saline has been provided at the insufflation port 6537, through the overtube body 6530, and into the balloon 6536. When inflated, the balloon 6536 emerges from compartment 6534 at the distal end of the overtube body 6530 and assists in compression of the intragastric device into a size manageable for removal from the patient. In one embodiment, the balloon 6536 comprises a thermally conducting material allowing for transfer of cooling energy of a cold fluid from within the balloon 6536 to the intragastric device. The cooling energy assists in the shape change of a temperature sensitive shape memory intragastric device. Once the intragastric device has been withdrawn into the overtube 6530, the balloon 6536 can be deflated and returned to compartment 6534 for removal.

FIG. 66 is a flow chart illustrating the steps involved in removing an intragastric device from a patient using the retrieval device of FIG. 65A, in accordance with one embodiment of the present specification. At step 6602, a physician inserts the catheter component of the retrieval device into the working channel of an endoscope that has been inserted into a patient. The distal end of the endoscope is positioned in the patient's stomach, proximate the intragastric device. The physician then manipulates the wire of the catheter to extend the wire hook beyond the distal end of the catheter sheath and grasps the intragastric device with the wire hook at step 6604. Then, at step 6606, the physician removes the catheter handle and slides the overtube component of the retrieval device over the catheter sheath and wire. With the overtube in place, the physician replaces the catheter handle at step 6608. Then, using the insufflation port, the physician inflates the balloon at the distal end of the overtube to assist in compression of the intragastric device at step 6610. Optionally, at step 6612, the physician installs cold water through the overtube, via the instillation port, to assist with the shape change of a temperature sensitive shape memory intragastric device. At step 6614, the physician pulls on the wire to retract the compressed intragastric device into the overtube. Finally, at step 6616, the retrieval device and intragastric device therein, are removed from the patient.

It should be appreciated that the present disclosure is intended to provide a teaching of several exemplary embodiments of the present invention and is should not be limited to the specific structures disclosed herein. Other variations of the disclosed embodiments, which would be understood by those of ordinary skill, are covered by the present application and are within the scope of the invention, as further defined by the claims.

I claim:

1. A medical device comprising:
    a porous mesh structure comprising a top, a bottom, and an interior and having a pre-deployment shape with a first volume and a substantially ovoid post-deployment shape with a second volume greater than said first volume, wherein, in said post-deployment shape, said porous structure includes at least one first opening proximate said top through which food is configured to enter and at least one second opening proximate said bottom through which the food is configured to exit, such that the food captured by the device is sequestered within the porous mesh structure for a period of time;
    an anti-migration component positioned proximate said bottom of said porous mesh structure, wherein said anti-migration component comprises a compressed pre-deployment configuration and an expanded post-deployment configuration, wherein said anti-migration component is an extension of said porous mesh structure, and wherein said anti-migration component has a bumper shape where the porous mesh extends distally, curls outward, and extends back proximally; and
    an elongate sleeve coupled to an outer edge of said anti-migration component.

2. The medical device of claim 1, wherein the elongate sleeve comprises a flexible elongate body, a proximal end with a third opening, a distal end with a fourth opening, and a sleeve interior, wherein said sleeve is coupled to said porous structure such that food exiting said at least one second opening enters said sleeve through said third opening, passes through said sleeve interior, and exits said sleeve through said fourth opening.

3. The medical device of claim 2, wherein said at least one first opening does not direct food into said sleeve interior such that food exiting said interior of said porous structure through said at least one first opening does not enter said sleeve and said at least one second opening does direct food into said sleeve interior such that food exiting said interior of said porous structure through said at least one second opening does enter said sleeve.

4. The medical device of claim 2, wherein a first surface area defined by said at least one first opening is greater than a second surface area defined by said at least one second opening.

5. The medical device of claim 2, wherein a first surface area defined by said at least one first opening is less than a second surface area defined by said at least one second opening.

6. The medical device of claim 1, wherein, when in said post-deployment configuration, the diameter of said porous structure is greater than the diameter of an open pylorus.

7. The medical device of claim 1, wherein the porous structure comprises a wire mesh structure.

8. The medical device of claim 1, wherein said porous structure is coated with a corrosion-resistant material preventing exposure of said porous structure to gastric acid, further wherein said corrosion-resistant material covers said porous structure and does not cover said openings of said porous structure.

9. The medical device of claim 8, wherein said corrosion-resistant material comprises any one or combination of silicone, polyester, polyether ether ketone (PEEK), a medical grade epoxy, ceramic, or metal.

10. The medical device of claim 1, wherein, when in said post-deployment configuration, said anti-migration component has a width that is greater than the diameter of the porous structure.

11. The medical device of claim 1, wherein, when in said post-deployment configuration, said anti-migration component has a radial strength that is greater than the compressive force of a patient's stomach.

12. The medical device of claim 1, wherein said anti-migration component is comprised of metal.

13. The medical device of claim 12, wherein said metal is a shape memory metal.

14. The medical device of claim 12, wherein said metal is temperature sensitive.

15. The medical device of claim 1, wherein said anti-migration component is coated with a corrosive resistant material.

16. The medical device of claim 15, wherein said corrosive resistant material is any one or combination of silicone, polyester, a medical grade epoxy, ceramic, or metal.

17. The medical device of claim 1, wherein the medical device is an intragastric device.

* * * * *